US011098126B2

(12) United States Patent
Michieli

(10) Patent No.: US 11,098,126 B2
(45) Date of Patent: Aug. 24, 2021

(54) ANTI-MET ANTIBODIES AND USES THEREOF

(71) Applicant: AGOMAB THERAPEUTICS BVBA, Ghent (BE)

(72) Inventor: Paolo Michieli, Rivalta di Torino (IT)

(73) Assignee: AGOMAB THERAPEUTICS BVBA, Ghent (BE)

( * ) Notice: Subject to any disclaimer, the term of this patent is extended or adjusted under 35 U.S.C. 154(b) by 144 days.

(21) Appl. No.: 16/313,710

(22) PCT Filed: Jun. 23, 2017

(86) PCT No.: PCT/EP2017/065599

§ 371 (c)(1),
(2) Date: Dec. 27, 2018

(87) PCT Pub. No.: WO2018/001909

PCT Pub. Date: Jan. 4, 2018

(65) Prior Publication Data

US 2019/0315873 A1 Oct. 17, 2019

(30) Foreign Application Priority Data

Jun. 27, 2016 (GB) .................................. 1611123.9

(51) Int. Cl.

| | |
|---|---|
| ***C07K 16/28*** | (2006.01) |
| ***A61P 1/16*** | (2006.01) |
| ***A61P 3/10*** | (2006.01) |
| ***A61P 13/12*** | (2006.01) |
| ***A61P 29/00*** | (2006.01) |
| ***A61P 1/04*** | (2006.01) |
| ***A61K 39/00*** | (2006.01) |

(52) U.S. Cl.

CPC ............ *C07K 16/2863* (2013.01); *A61P 1/04* (2018.01); *A61P 1/16* (2018.01); *A61P 3/10* (2018.01); *A61P 13/12* (2018.01); *A61P 29/00* (2018.01); *A61K 2039/505* (2013.01); *C07K 2317/21* (2013.01); *C07K 2317/22* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/522* (2013.01); *C07K 2317/524* (2013.01); *C07K 2317/526* (2013.01); *C07K 2317/528* (2013.01); *C07K 2317/53* (2013.01); *C07K 2317/55* (2013.01); *C07K 2317/565* (2013.01); *C07K 2317/567* (2013.01); *C07K 2317/74* (2013.01); *C07K 2317/75* (2013.01); *C07K 2317/92* (2013.01); *C07K 2317/94* (2013.01)

(58) Field of Classification Search

CPC ............ C07K 16/2863; C07K 2317/21; C07K 2317/34; C07K 2317/565; C07K 2317/75; C07K 2317/74; A61P 1/16; A61P 3/10; A61P 13/12; A61P 1/04; A61P 43/00; A61P 3/06; A61P 17/02; A61P 1/00

See application file for complete search history.

(56) References Cited

U.S. PATENT DOCUMENTS

| | | | |
|---|---|---|---|
| 5,686,292 | A | 11/1997 | Schwall et al. |
| 5,892,019 | A | 4/1999 | Schlom et al. |
| 6,099,841 | A | 8/2000 | Hillan et al. |
| 6,468,529 | B1 | 10/2002 | Schwall et al. |
| 7,476,724 | B2 | 1/2009 | Dennis et al. |
| 7,498,420 | B2 | 3/2009 | Michaud et al. |
| 7,556,804 | B2 | 7/2009 | Prat |
| 8,163,280 | B2 | 4/2012 | Michaud et al. |
| 8,388,958 | B2 | 3/2013 | Comoglio et al. |
| 8,562,985 | B2 | 10/2013 | Michaud |
| 8,729,043 | B2 | 5/2014 | Comoglio et al. |
| 8,821,869 | B2 | 9/2014 | Michaud et al. |
| 8,835,607 | B2 | 9/2014 | Dreier et al. |
| 9,150,613 | B2 | 10/2015 | Harding et al. |
| 9,169,329 | B2 | 10/2015 | Johns et al. |
| 9,540,437 | B2 | 1/2017 | Dreier et al. |
| 10,106,622 | B2 | 10/2018 | Yoo |
| 10,221,248 | B2 | 3/2019 | Tavazoie |
| 2005/0054019 | A1 | 3/2005 | Michaud et al. |
| 2009/0285807 | A1 | 11/2009 | Comoglio et al. |
| 2010/0040629 | A1 | 2/2010 | Michaud et al. |
| 2011/0165621 | A1 | 7/2011 | Dreier et al. |
| 2012/0134996 | A1 | 5/2012 | Comoglio et al. |
| 2012/0321614 | A1 | 12/2012 | Michaud et al. |
| 2014/0086914 | A1 | 3/2014 | Michaud et al. |

(Continued)

FOREIGN PATENT DOCUMENTS

| | | |
|---|---|---|
| AU | 2013201789 | 4/2013 |
| WO | 9638557 A1 | 12/1996 |

(Continued)

OTHER PUBLICATIONS

Ohashi, et al, "Sustained survival of human hepatocytes in mice: A model for in vivo infection with human hepatitis B and hepatitis delta virus", Mar. 2000, pp. 327-331, vol. 6, No. 3, Nature Medicine.

(Continued)

*Primary Examiner* — Ruixiang Li
(74) *Attorney, Agent, or Firm* — Patent Law Works, LLP

(57) ABSTRACT

The invention relates to agonistic anti-MET antibodies and uses thereof in the therapeutic treatment of disease. The antibodies bind with high affinity to the human and mouse hepatocyte growth factor (HGF) receptor, also known as MET, and are agonists of MET in both humans and mice, producing molecular and cellular effects resembling the effects of HGF binding.

3 Claims, 31 Drawing Sheets

Figure 1:
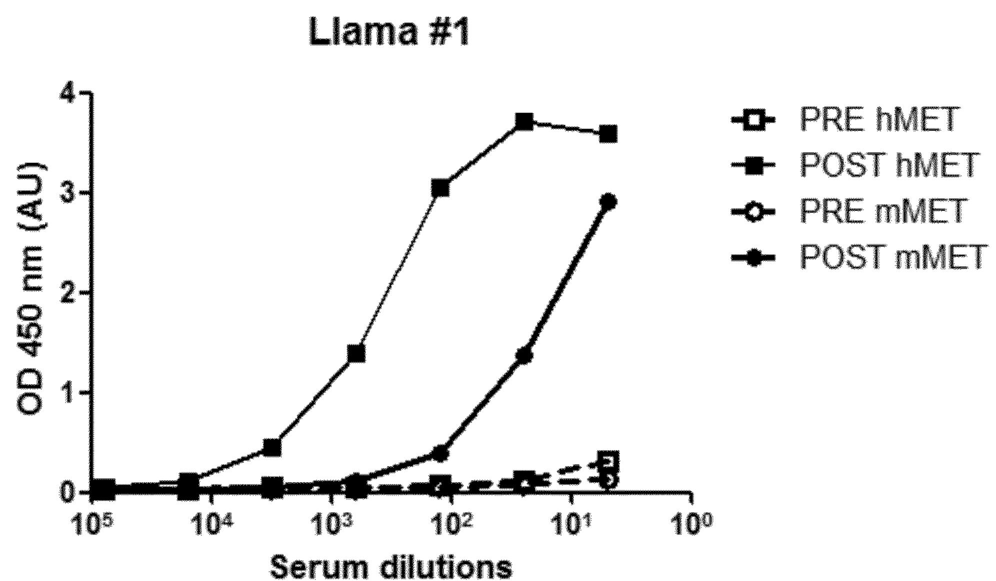
Figure 1:
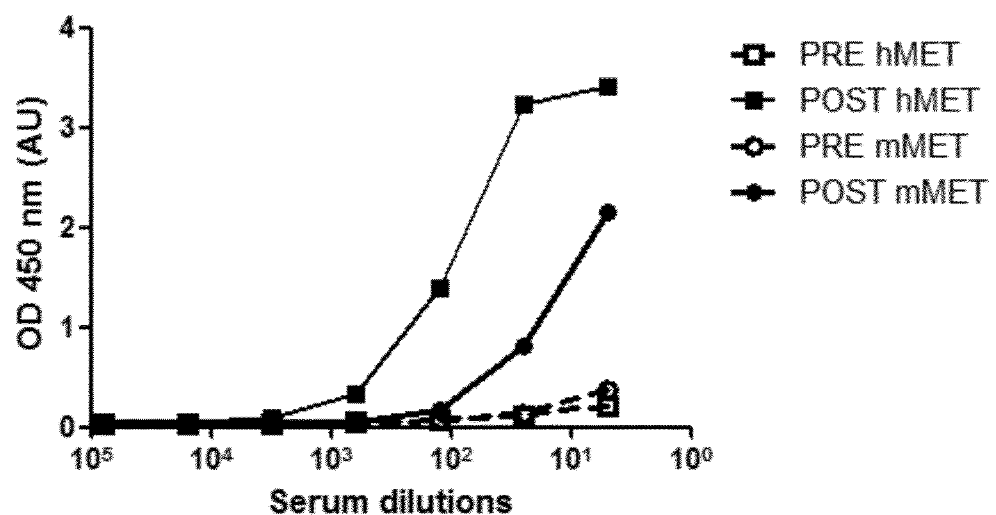

Specification includes a Sequence Listing.

(56) References Cited

U.S. PATENT DOCUMENTS

| | | | |
|---|---|---|---|
| 2014/0193431 | A1 | 7/2014 | Park et al. |
| 2015/0057436 | A1 | 2/2015 | Dreier et al. |
| 2017/0145088 | A1 | 5/2017 | Dreier et al. |
| 2018/0002444 | A1 | 1/2018 | Tavazoie et al. |
| 2019/0241676 | A1 | 8/2019 | Tavazoie et al. |
| 2019/0315872 | A1 | 10/2019 | Yu et al. |
| 2019/0315873 | A1 | 10/2019 | Michieli |

FOREIGN PATENT DOCUMENTS

| | | | |
|---|---|---|---|
| WO | 9800543 | A1 | 1/1998 |
| WO | WO-02088354 | | 11/2002 |
| WO | 2004108766 | A2 | 12/2004 |
| WO | 2005016382 | A1 | 2/2005 |
| WO | 2007090807 | A1 | 8/2007 |
| WO | WO-2010/001251 | | 1/2010 |
| WO | 2011080350 | A1 | 7/2011 |
| WO | 2011150454 | A1 | 12/2011 |
| WO | 2012138599 | A2 | 10/2012 |
| WO | 2016106221 | A1 | 6/2016 |
| WO | 2018001909 | A1 | 1/2018 |
| WO | 2019134927 | A1 | 7/2019 |
| WO | 2019134932 | A1 | 7/2019 |

OTHER PUBLICATIONS

Bardelli C et al: 11 Agonist Met antibodies define the signalling threshold required for a full mitogenic and invasive program of Kaposi's Sarcoma cells, Biochemical and Biophysical Research Communications, Elsevier, Amsterdam, NL, vol. 334, No. 4, Sep. 9, 2005 (Sep. 9, 2005), pp. 1172-1179, XP027459158, ISSN: 0006-291X, DOI: 10.1016/J.BBRC.2005.07.020 [retrieved on Jul. 29, 2005] the whole document.

Vargas GA et al: "Hepatocyte Growth Factor in Renal Failure: Promise and Reality" , Kidney International, Nature Publishing Group, London, GB, vol. 57, No. 4, Apr. 1, 2000 (Apr. 1, 2000), pp. 1426-1436, XP001181170, ISSN: 0085-2538, DOI: 10.1046/J.1523-1755.2000.00987.X title.

Kunio Matsumoto et al: "HGF-Met Pathway in Regeneration and Drug Discovery", Biomedicines, vol. 2, No. 4, Oct. 31, 2014 (Oct. 31, 2014), pp. 275-300, XP055412657, DOI: 10.3390/biomedicines2040275.

J. Mellado-Gil et al: "Disruption of Hepatocyte Growth Factor/c-Met Signaling Enhances Pancreatic-Cell Death and Accelerates the Onset of Diabetes", Diabetes,vol. 60, No. 2, Oct. 27, 2010 (Oct. 27, 2010), pp. 525-536, XP055412664, us ISSN: 0012-1797, DOI: 10.2337/db09-1305 title.

Giovanni Pacchiana et al: "Monovalency Unleashes the Full Therapeutic Potential of the DN-30 Anti-Met Antibody", Journal of Biological Chemistry, American Society for Biochemistry and Molecular Biology, vol. 285, No. 46, Nov. 12, 2010 (Nov. 12, 2010), pp. 36149-36157, XP002621766, ISSN: 0021-9258, DOI: 10.1074/JBC.M110.134031 [retrieved on Sep. 10, 2010] the whole document.

International Search Report for PCT/EP2017/065599, dated Oct. 10, 2017.

Written Opinion of the International Search Authority for PCT/EP2017/065599, dated Oct. 10, 2017.

Rudikoff, et al, "Single amino acid substitution altering antigen-binding specificity", Mar. 1982, pp. 1979-1983, vol. 79, Proc. Natl. Acad. Sci. USA.

Li, et al, "Anti-MET immunoPET for non-small cell lung cancer using novel fully human antibody fragments", Nov. 2014, pp. 2607-2617, vol. 13, No. 11, Mol Cancer Ther.

Ohno, et al, "Antigen-binding specificities of antibodies are primarily determined by sevel residues of $V_H$", May 1985, pp. 2945-2949, vol. 82, Proc. Natl. Acad. Sci. USA.

Diamond, et al, "Somatic mutation of the T15 heavy chain gives rise to an antibody with autoantibody specificity", Sep. 1984, pp. 5841-5844, vol. 81, Proc. Natl. Acad. Sci. USA.

Jin, Hongkui, et al. "MetMAb, the One-Armed 5D5 Anti-c-Met Antibody, Inhibits Orthotopic Pancreatic Tumor Growth and Improves Survival." Cancer Research, vol. 68, No. 11, pp. 4360-4368. doi:10.1158/0008-5472.CAN-07-5960. Accessed Jan. 26, 2021.

Oliveira, Alexandre G., et al. "The Role of Hepatocyte Growth Factor (HGF) in Insulin Resistance and Diabetes." Frontiers in Endocrinology, vol. 9, Aug. 2018. doi:10.3389/fendo.2018.00503.

PCT International Search Report and Written Opinion; Application No. PCT/EP2019/050084, Applicant AGOMAB Therapeutics BVBA, International filing date of Jan. 3, 2019, European Patent Office, dated Feb. 20, 2019, 15 pages.

Pothula, Srinivasa P., et al. "Targeting the HGF/c-MET pathway: stromal remodelling in pancreatic cancer." Oncotarget [Online], 8.44 (2017): 76722-76739. Web. Jan. 25, 2021.

Zhou, W., et al., PAK1 mediates pancreatic cancer cell migration and resistance to MET inhibition. J. Pathol., (2014) 234: 502-513. https://doi.org/10.1002/path.4412.

Kim, Ki-Hyun, and Hyori Kim. "Progress of Antibody-Based Inhibitors of the HGF-CMET Axis in Cancer Therapy." Experimental Molecular Medicine, vol. 49, No. 3, Mar. 2017, p. e307. doi:10.1038/emm.2017.17.

Koliaraki, Vasiliki et al., Tpl2 regulates intestinal myofibroblast HGF release to suppress colitis-associated tumorigenesis, Oct. 15, 2012, J Clin Invest. 2012;122(11):4231-4242. https://doi.org/10.1172/JCI63917.

Latella, Giovanni et al., Results of the 4th scientific workshop of the ECCO (I): Pathophysiology of intestinal fibrosis in IBD, Journal of Crohns and Colitis, vol. 8, Issue 10, Oct. 2014, pp. 1147-1165, https://doi.org/10.1016/j.crohns.2014.03.008.

Ohda, Y., et al. Effects of Hepatocyte Growth Factor on Rat Inflammatory Bowel Disease Models. Dig Dis Sci 50, 914-921 (2005). https://doi.org/10.1007/s10620-005-2664-z.

Owusu, Benjamin Yaw, et al. "Hepatocyte Growth Factor, a Key Tumor-Promoting Factor in the Tumor Microenvironment." Cancers, vol. 9, No. 4, Apr. 2017, p. 35. doi:10.3390/cancers9040035.

PCT International Search Report and Written Opinion; Application No. PCT/EP2019/050077, Applicant AGOMAB Therapeutics BVBA, International filing date of Jan. 3, 2019, European Patent Office, dated Mar. 25, 2019, 13 pages.

Prat, Maria, et al. "Monoclonal Antibodies against the MET/HGF Receptor and Its Ligand: Multitask Tools with Applications from Basic Research to Therapy." Biomedicines, vol. 2, No. 4, Dec. 2014, pp. 359-383. doi:10.3390/biomedicines2040359.

Seow H, Yip WK, Fifis T. "Advances in targeted and immunobased therapies for colorectal cancer in the genomic era." Onco Targets Therapy. 2016;9:1899-1920. https://doi.org/10.2147/OTT.S95101.

Van Der Horst, Edward Htun, et al. "Discovery of Fully Human Anti-MET Monoclonal Antibodies with Antitumor Activity against Colon Cancer Tumor Models In Vivo." Neoplasia, vol. 11, No. 4, Apr. 2009, p. 355. doi:10.1593/neo.81536.

Pietronave, Stefano et al. "Agonist Monoclonal Antibodies against Hgf Receptor Protect Cardiac Muscle Cells from Apoptosis." American Journal of Physiology—Heart and Circulatory Physiology 298.4 (2010).

Prat, Maria, et al. "Agonistic Monoclonal Antibodies against the Met Receptor Dissect the Biological Responses to Hgf." Journal of Cell Science. 111 2 (1998): 237-247.

Silvagno, Francesca et al. "In Vivo Activation of Met Tyrosine Kinase by Heterodimeric Hepatocyte Growth Factor Molecule Promotes Angiogenesis." Arteriosclerosis, Thrombosis, and Vascular Biology. 15.11 (1995): 1857-65.

LOC human kidney epithelial cells

MLP29 mouse liver precursor cells

A

B

Normal liver $CCl_4$ $CCl_4$

CCl4 + 71G3

CCl4 + 71D6

$CCl_4$ + 71G2

Normal liver $CCl_4$ $CCl_4$

CCl4 + 71G3

CCl4 + 71D6

$CCl_4$ + 71G2

Normal liver $CCl_4$ $CCl_4$

CCl4 + 71G3

CCl4 + 71D6

$CCl_4$ + 71G2

Normal kidney $HgCl_2$ $HgCl_2$ $HgCl_2$ + 71G3

$HgCl_2$ + 71D6

$HgCl_2$ + 71G2

A

B

C

CTR

Normal mucosa (200X)

TNBS

Lymphocytic aggregate (200X)

TNBS

Full depth ulcer (200X)

TNBS + 71G3 1 mg/kg

No sign of damage (200X)

TNBS + 71D6 1 mg/kg

No sign of damage (200X)

TNBS + 71G2 1 mg/kg

No sign of damage (200X)

A

B

C

D

NASH CTRL

NASH 71G3

NASH 71D6

NASH 71G2

NASH CTRL

NASH 71G3

NASH 71D6

NASH 71G2

Figure 30

A

```
                                                                        O
hMET   280 RFCSINSGLHSYMEMPLECILTEKRKKRSTKKEVFNILQAAYVSKPGAQL 329
mMET   279 RFCSVDSGLHSYMEMPLECILTEKRRKRSTREEVFNILQAAYVSKPGANL 328
rMET   281 RFCSVDSGLHSYMEMPLECILTEKRRKRSTREEVFNILQAAYVSKPGANL 330
cMET   299 RFCSLNSGLHSYMEMPLECILTEKRKKRSTKKEVFNILQAAYVSKPGAQL 348
lMET   279 RFCSVDSGLHSYMEMPLECILTEKRRRRSTKEEVFNILQAAYVSKPGSQL 328
           ****::******************::***::**************::*
                                                       1

            O     OO                                  S    S
hMET   330 ARQIGASLNDDILFGVFAQSKPDSAEPMDRSAMCAFPIKYVNDFFNKIVN 379
mMET   329 AKQIGASPSDDILFGVFAQSKPDSAEPVNRSAVCAFPIKYVNDFFNKIVN 378
rMET   331 AKQIGASPYDDILYGVFAQSKPDSAEPMNRSAVCAFPIKYVNDFFNKIVN 380
cMET   349 ARQIGASLNDDILFGVFAQSKPDSAEPMDRSAMCAFPIKYVNDFFNKIVN 398
lMET   329 AKQIGANLNDDILYGVFAQSKPDSAEPMNRSAVCAFPVKYVNEFFNKIVN 378
           *:****.  ****:************::***:****:****:*******
                 2     3                            4    5
```

B

```
                                           P
hMET   530 LSAPPFVQCGWCHDKCVRSEECLSGTWTQQICLPAIYKVFPNSAPLEGGT 579
mMET   529 LSAPYFIQCGWCHNQCVRFDECPSGTWTQEICLPAVYKVFPTSAPLEGGT 578
rMET   531 LSAPYFIQCGWCHNRCVHSNECPSGTWTQEICLPAVYKVFPTSAPLEGGT 580
cMET   549 LSAPPFVQCGWCHDKCVRSEECPSGTWTQQICLPAIYKVFPTSAPLEGGT 598
lMET   529 LSAPSFVQCGWCHDKCVQLEECSGGIWTQEICLPTIYKVLPTSAPLEGGT 578
           **** *:******::**: :** .* ***:****::***:*.********
                             6     7 8
```

```
* = single, fully conserved residue
: = conservation of strong groups
. = conservation of weak groups
  = no consensus

BLACK BOX = conserved in human and mouse but not llama MET

Regions scanned by mutagenesis underlined
progressive mutation number below

O = Residues crucial for interaction with Onartuzumab/5D5
S = Residues crucial for interaction with SEMA-binding mAbs
P = Residues crucial for interaction with PSI-binding mAbs
```

Figure 31

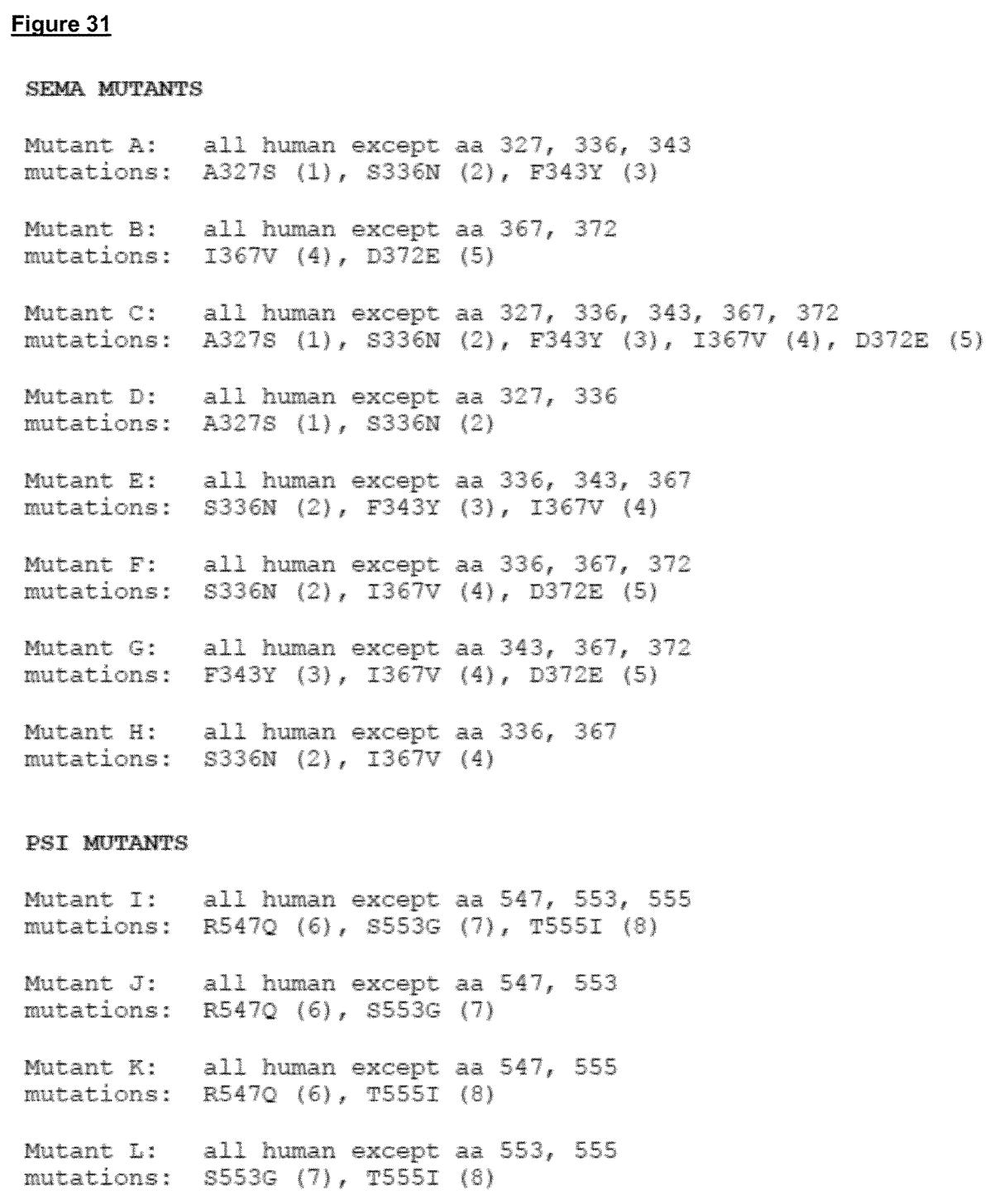

SEMA MUTANTS

Mutant A: all human except aa 327, 336, 343
mutations: A327S (1), S336N (2), F343Y (3)

Mutant B: all human except aa 367, 372
mutations: I367V (4), D372E (5)

Mutant C: all human except aa 327, 336, 343, 367, 372
mutations: A327S (1), S336N (2), F343Y (3), I367V (4), D372E (5)

Mutant D: all human except aa 327, 336
mutations: A327S (1), S336N (2)

Mutant E: all human except aa 336, 343, 367
mutations: S336N (2), F343Y (3), I367V (4)

Mutant F: all human except aa 336, 367, 372
mutations: S336N (2), I367V (4), D372E (5)

Mutant G: all human except aa 343, 367, 372
mutations: F343Y (3), I367V (4), D372E (5)

Mutant H: all human except aa 336, 367
mutations: S336N (2), I367V (4)

PSI MUTANTS

Mutant I: all human except aa 547, 553, 555
mutations: R547Q (6), S553G (7), T555I (8)

Mutant J: all human except aa 547, 553
mutations: R547Q (6), S553G (7)

Mutant K: all human except aa 547, 555
mutations: R547Q (6), T555I (8)

Mutant L: all human except aa 553, 555
mutations: S553G (7), T555I (8)

SEQUENCE LISTING

```
<160> NUMBER OF SEQ ID NOS: 248

<210> SEQ ID NO 1
<211> LENGTH: 30
<212> TYPE: PRT
<213> ORGANISM: Lama glama

<400> SEQUENCE: 1

Gln Leu Gln Leu Val Glu Ser Gly Gly Gly Leu Val Gln Pro Gly Gly
1               5                   10                  15

Ser Leu Arg Val Ser Cys Thr Ala Ser Gly Phe Thr Phe Asn
            20                  25                  30


<210> SEQ ID NO 2
<211> LENGTH: 5
<212> TYPE: PRT
<213> ORGANISM: Lama glama

<400> SEQUENCE: 2

Thr Tyr Tyr Met Thr
1               5


<210> SEQ ID NO 3
<211> LENGTH: 14
<212> TYPE: PRT
<213> ORGANISM: Lama glama

<400> SEQUENCE: 3

Trp Val Arg Gln Ala Pro Gly Lys Gly Leu Glu Trp Val Ser
1               5                   10


<210> SEQ ID NO 4
<211> LENGTH: 16
<212> TYPE: PRT
<213> ORGANISM: Lama glama

<400> SEQUENCE: 4

Asp Ile Asn Ser Gly Gly Gly Thr Tyr Tyr Ala Asp Ser Val Lys Gly
1               5                   10                  15


<210> SEQ ID NO 5
<211> LENGTH: 32
<212> TYPE: PRT
<213> ORGANISM: Lama glama

<400> SEQUENCE: 5
```

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Val Arg
            20                  25                  30


<210> SEQ ID NO 6
<211> LENGTH: 10
<212> TYPE: PRT
<213> ORGANISM: Lama glama

<400> SEQUENCE: 6

Val Arg Ile Trp Pro Val Gly Tyr Asp Tyr
1               5                   10


<210> SEQ ID NO 7
<211> LENGTH: 11
<212> TYPE: PRT
<213> ORGANISM: Lama glama

<400> SEQUENCE: 7

Trp Gly Gln Gly Thr Gln Val Thr Val Ser Ser
1               5                   10


<210> SEQ ID NO 8
<211> LENGTH: 30
<212> TYPE: PRT
<213> ORGANISM: Lama glama

<400> SEQUENCE: 8

Gln Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser
            20                  25                  30


<210> SEQ ID NO 9
<211> LENGTH: 5
<212> TYPE: PRT
<213> ORGANISM: Lama glama

<400> SEQUENCE: 9

Thr Tyr Tyr Met Ser
1               5


<210> SEQ ID NO 10
<211> LENGTH: 14
<212> TYPE: PRT
<213> ORGANISM: Lama glama

<400> SEQUENCE: 10

Trp Val Arg Gln Ala Pro Gly Lys Gly Leu Glu Trp Val Ser
1               5                   10


<210> SEQ ID NO 11
<211> LENGTH: 16
<212> TYPE: PRT
<213> ORGANISM: Lama glama

<400> SEQUENCE: 11

Asp Ile Arg Thr Asp Gly Gly Thr Tyr Tyr Ala Asp Ser Val Lys Gly
1               5                   10                  15


<210> SEQ ID NO 12
<211> LENGTH: 32
<212> TYPE: PRT
```

<213> ORGANISM: Lama glama

<400> SEQUENCE: 12

Arg Phe Thr Met Ser Arg Asp Asn Ala Lys Asn Thr Leu Tyr Leu Gln
1 5 10 15

Met Asn Ser Leu Lys Pro Glu Asp Thr Ala Leu Tyr Tyr Cys Ala Arg
20 25 30

<210> SEQ ID NO 13
<211> LENGTH: 10
<212> TYPE: PRT
<213> ORGANISM: Lama glama

<400> SEQUENCE: 13

Thr Arg Ile Phe Pro Ser Gly Tyr Asp Tyr
1 5 10

<210> SEQ ID NO 14
<211> LENGTH: 11
<212> TYPE: PRT
<213> ORGANISM: Lama glama

<400> SEQUENCE: 14

Trp Gly Gln Gly Thr Gln Val Thr Val Ser Ser
1 5 10

<210> SEQ ID NO 15
<211> LENGTH: 30
<212> TYPE: PRT
<213> ORGANISM: Lama glama

<400> SEQUENCE: 15

Gln Leu Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 16
<211> LENGTH: 5
<212> TYPE: PRT
<213> ORGANISM: Lama glama

<400> SEQUENCE: 16

Ser His Ala Met Ser
1 5

<210> SEQ ID NO 17
<211> LENGTH: 14
<212> TYPE: PRT
<213> ORGANISM: Lama glama

<400> SEQUENCE: 17

Trp Val Arg Gln Ala Pro Gly Lys Gly Leu Glu Trp Val Ser
1 5 10

<210> SEQ ID NO 18
<211> LENGTH: 17
<212> TYPE: PRT
<213> ORGANISM: Lama glama

<400> SEQUENCE: 18

Ala Ile Asn Ser Gly Gly Gly Ser Thr Ser Tyr Ala Asp Ser Val Lys
1 5 10 15

Gly

<210> SEQ ID NO 19
<211> LENGTH: 32
<212> TYPE: PRT
<213> ORGANISM: Lama glama

<400> SEQUENCE: 19

Arg Phe Thr Ile Ser Arg Asp Asn Ala Lys Asn Thr Leu Tyr Leu Gln
1 5 10 15

Met Asn Ser Leu Lys Pro Glu Asp Thr Ala Val Tyr Tyr Cys Ala Lys
20 25 30

<210> SEQ ID NO 20
<211> LENGTH: 17
<212> TYPE: PRT
<213> ORGANISM: Lama glama

<400> SEQUENCE: 20

Glu Leu Arg Phe Asp Leu Ala Arg Tyr Thr Asp Tyr Glu Ala Trp Asp
1 5 10 15

Tyr

<210> SEQ ID NO 21
<211> LENGTH: 11
<212> TYPE: PRT
<213> ORGANISM: Lama glama

<400> SEQUENCE: 21

Trp Gly Gln Gly Thr Gln Val Thr Val Ser Ser
1 5 10

<210> SEQ ID NO 22
<211> LENGTH: 30
<212> TYPE: PRT
<213> ORGANISM: Lama glama

<400> SEQUENCE: 22

Glu Leu Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 23
<211> LENGTH: 5
<212> TYPE: PRT
<213> ORGANISM: Lama glama

<400> SEQUENCE: 23

Gly Tyr Gly Met Ser
1 5

<210> SEQ ID NO 24
<211> LENGTH: 14
<212> TYPE: PRT
<213> ORGANISM: Lama glama

<400> SEQUENCE: 24

Trp Val Arg Gln Ala Pro Gly Lys Gly Leu Glu Trp Val Ser
1 5 10

<210> SEQ ID NO 25
<211> LENGTH: 17

<212> TYPE: PRT
<213> ORGANISM: Lama glama

<400> SEQUENCE: 25

```
Asp Ile Asn Ser Gly Gly Gly Ser Thr Ser Tyr Ala Asp Ser Val Lys
1               5                   10                  15

Gly
```

<210> SEQ ID NO 26
<211> LENGTH: 32
<212> TYPE: PRT
<213> ORGANISM: Lama glama

<400> SEQUENCE: 26

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30
```

<210> SEQ ID NO 27
<211> LENGTH: 17
<212> TYPE: PRT
<213> ORGANISM: Lama glama

<400> SEQUENCE: 27

```
Asp Met Arg Leu Tyr Leu Ala Arg Tyr Asn Asp Tyr Glu Ala Trp Asp
1               5                   10                  15

Tyr
```

<210> SEQ ID NO 28
<211> LENGTH: 11
<212> TYPE: PRT
<213> ORGANISM: Lama glama

<400> SEQUENCE: 28

```
Trp Gly Gln Gly Thr Gln Val Thr Val Ser Ser
1               5                   10
```

<210> SEQ ID NO 29
<211> LENGTH: 30
<212> TYPE: PRT
<213> ORGANISM: Lama glama

<400> SEQUENCE: 29

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 30
<211> LENGTH: 5
<212> TYPE: PRT
<213> ORGANISM: Lama glama

<400> SEQUENCE: 30

```
Ser Tyr Gly Met Ser
1               5
```

<210> SEQ ID NO 31
<211> LENGTH: 14
<212> TYPE: PRT
<213> ORGANISM: Lama glama

<400> SEQUENCE: 31

Trp Val Arg Gln Ala Pro Gly Lys Gly Leu Glu Trp Val Ser
1 5 10

<210> SEQ ID NO 32
<211> LENGTH: 17
<212> TYPE: PRT
<213> ORGANISM: Lama glama

<400> SEQUENCE: 32

Ala Ile Asn Ser Tyr Gly Gly Ser Thr Ser Tyr Ala Asp Ser Val Lys
1 5 10 15

Gly

<210> SEQ ID NO 33
<211> LENGTH: 32
<212> TYPE: PRT
<213> ORGANISM: Lama glama

<400> SEQUENCE: 33

Arg Phe Thr Ile Ser Arg Asp Asn Ala Lys Asn Thr Leu Tyr Leu Gln
1 5 10 15

Met Asn Ser Leu Lys Pro Glu Asp Thr Ala Val Tyr Tyr Cys Ala Lys
20 25 30

<210> SEQ ID NO 34
<211> LENGTH: 17
<212> TYPE: PRT
<213> ORGANISM: Lama glama

<400> SEQUENCE: 34

Glu Val Arg Ala Asp Leu Ser Arg Tyr Asn Asp Tyr Glu Ser Tyr Asp
1 5 10 15

Tyr

<210> SEQ ID NO 35
<211> LENGTH: 11
<212> TYPE: PRT
<213> ORGANISM: Lama glama

<400> SEQUENCE: 35

Trp Gly Gln Gly Thr Gln Val Thr Val Ser Ser
1 5 10

<210> SEQ ID NO 36
<211> LENGTH: 30
<212> TYPE: PRT
<213> ORGANISM: Lama glama

<400> SEQUENCE: 36

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Phe Lys
20 25 30

<210> SEQ ID NO 37
<211> LENGTH: 5
<212> TYPE: PRT
<213> ORGANISM: Lama glama

<400> SEQUENCE: 37

Asp Tyr Asp Ile Thr

```
1               5


<210> SEQ ID NO 38
<211> LENGTH: 14
<212> TYPE: PRT
<213> ORGANISM: Lama glama

<400> SEQUENCE: 38

Trp Val Arg Gln Ala Pro Gly Lys Gly Leu Glu Trp Val Ser
1               5                   10


<210> SEQ ID NO 39
<211> LENGTH: 17
<212> TYPE: PRT
<213> ORGANISM: Lama glama

<400> SEQUENCE: 39

Thr Ile Thr Ser Arg Ser Gly Ser Thr Ser Tyr Val Asp Ser Val Lys
1               5                   10                  15

Gly


<210> SEQ ID NO 40
<211> LENGTH: 32
<212> TYPE: PRT
<213> ORGANISM: Lama glama

<400> SEQUENCE: 40

Arg Phe Thr Ile Ser Gly Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30


<210> SEQ ID NO 41
<211> LENGTH: 17
<212> TYPE: PRT
<213> ORGANISM: Lama glama

<400> SEQUENCE: 41

Val Tyr Ala Thr Thr Trp Asp Val Gly Pro Leu Gly Tyr Gly Met Asp
1               5                   10                  15

Tyr


<210> SEQ ID NO 42
<211> LENGTH: 11
<212> TYPE: PRT
<213> ORGANISM: Lama glama

<400> SEQUENCE: 42

Trp Gly Lys Gly Thr Leu Val Thr Val Ser Ser
1               5                   10


<210> SEQ ID NO 43
<211> LENGTH: 30
<212> TYPE: PRT
<213> ORGANISM: Lama glama

<400> SEQUENCE: 43

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 44
<211> LENGTH: 5
<212> TYPE: PRT
<213> ORGANISM: Lama glama

<400> SEQUENCE: 44

```
Ile Tyr Asp Met Ser
1               5
```

<210> SEQ ID NO 45
<211> LENGTH: 14
<212> TYPE: PRT
<213> ORGANISM: Lama glama

<400> SEQUENCE: 45

```
Trp Val Arg Gln Ala Pro Gly Lys Gly Leu Glu Trp Val Ser
1               5                   10
```

<210> SEQ ID NO 46
<211> LENGTH: 17
<212> TYPE: PRT
<213> ORGANISM: Lama glama

<400> SEQUENCE: 46

```
Thr Ile Asn Ser Asp Gly Ser Ser Thr Ser Tyr Val Asp Ser Val Lys
1               5                   10                  15

Gly
```

<210> SEQ ID NO 47
<211> LENGTH: 32
<212> TYPE: PRT
<213> ORGANISM: Lama glama

<400> SEQUENCE: 47

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30
```

<210> SEQ ID NO 48
<211> LENGTH: 17
<212> TYPE: PRT
<213> ORGANISM: Lama glama

<400> SEQUENCE: 48

```
Val Tyr Gly Ser Thr Trp Asp Val Gly Pro Met Gly Tyr Gly Met Asp
1               5                   10                  15

Tyr
```

<210> SEQ ID NO 49
<211> LENGTH: 11
<212> TYPE: PRT
<213> ORGANISM: Lama glama

<400> SEQUENCE: 49

```
Trp Gly Lys Gly Thr Leu Val Thr Val Ser Ser
1               5                   10
```

<210> SEQ ID NO 50
<211> LENGTH: 30
<212> TYPE: PRT
<213> ORGANISM: Lama glama

<400> SEQUENCE: 50

```
Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser
            20                  25                  30


<210> SEQ ID NO 51
<211> LENGTH: 5
<212> TYPE: PRT
<213> ORGANISM: Lama glama

<400> SEQUENCE: 51

Asn Tyr Tyr Met Ser
1               5


<210> SEQ ID NO 52
<211> LENGTH: 14
<212> TYPE: PRT
<213> ORGANISM: Lama glama

<400> SEQUENCE: 52

Trp Val Arg Gln Ala Pro Gly Lys Gly Leu Glu Trp Val Ser
1               5                   10


<210> SEQ ID NO 53
<211> LENGTH: 17
<212> TYPE: PRT
<213> ORGANISM: Lama glama

<400> SEQUENCE: 53

Asp Ile Tyr Ser Asp Gly Ser Thr Thr Trp Tyr Ser Asp Ser Val Lys
1               5                   10                  15

Gly


<210> SEQ ID NO 54
<211> LENGTH: 32
<212> TYPE: PRT
<213> ORGANISM: Lama glama

<400> SEQUENCE: 54

Arg Phe Thr Ile Ser Arg Asp Asn Ala Lys Asn Thr Leu Ser Leu Gln
1               5                   10                  15

Met Asn Ser Leu Lys Ser Glu Asp Thr Ala Val Tyr Tyr Cys Ala Arg
            20                  25                  30


<210> SEQ ID NO 55
<211> LENGTH: 10
<212> TYPE: PRT
<213> ORGANISM: Lama glama

<400> SEQUENCE: 55

Val Lys Ile Tyr Pro Gly Gly Tyr Asp Ala
1               5                   10


<210> SEQ ID NO 56
<211> LENGTH: 11
<212> TYPE: PRT
<213> ORGANISM: Lama glama

<400> SEQUENCE: 56

Trp Gly Gln Gly Thr Gln Val Thr Val Ser Ser
1               5                   10
```

```
<210> SEQ ID NO 57
<211> LENGTH: 30
<212> TYPE: PRT
<213> ORGANISM: Lama glama

<400> SEQUENCE: 57

Gln Val Gln Leu Gln Glu Ser Gly Gly Asp Leu Val Gln Pro Gly Gly
1               5                   10                  15

Ser Leu Arg Val Ser Cys Val Val Ser Gly Phe Thr Phe Ser
            20                  25                  30


<210> SEQ ID NO 58
<211> LENGTH: 5
<212> TYPE: PRT
<213> ORGANISM: Lama glama

<400> SEQUENCE: 58

Arg Tyr Tyr Met Ser
1               5


<210> SEQ ID NO 59
<211> LENGTH: 14
<212> TYPE: PRT
<213> ORGANISM: Lama glama

<400> SEQUENCE: 59

Trp Val Arg Gln Ala Pro Gly Lys Gly Leu Glu Trp Val Ser
1               5                   10


<210> SEQ ID NO 60
<211> LENGTH: 17
<212> TYPE: PRT
<213> ORGANISM: Lama glama

<400> SEQUENCE: 60

Ser Ile Asp Ser Tyr Gly Tyr Ser Thr Tyr Tyr Thr Asp Ser Val Lys
1               5                   10                  15

Gly


<210> SEQ ID NO 61
<211> LENGTH: 32
<212> TYPE: PRT
<213> ORGANISM: Lama glama

<400> SEQUENCE: 61

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Arg
            20                  25                  30


<210> SEQ ID NO 62
<211> LENGTH: 9
<212> TYPE: PRT
<213> ORGANISM: Lama glama

<400> SEQUENCE: 62

Ala Lys Thr Thr Trp Ser Tyr Asp Tyr
1               5


<210> SEQ ID NO 63
<211> LENGTH: 11
<212> TYPE: PRT
<213> ORGANISM: Lama glama
```

<400> SEQUENCE: 63

Trp Gly Gln Gly Thr Gln Val Thr Val Ser Ser
1               5                   10

<210> SEQ ID NO 64
<211> LENGTH: 30
<212> TYPE: PRT
<213> ORGANISM: Lama glama

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg
            20                  25                  30

<210> SEQ ID NO 65
<211> LENGTH: 5
<212> TYPE: PRT
<213> ORGANISM: Lama glama

<400> SEQUENCE: 65

Asn Tyr His Met Ser
1               5

<210> SEQ ID NO 66
<211> LENGTH: 14
<212> TYPE: PRT
<213> ORGANISM: Lama glama

<400> SEQUENCE: 66

Trp Val Arg Gln Val Pro Gly Lys Gly Phe Glu Trp Ile Ser
1               5                   10

<210> SEQ ID NO 67
<211> LENGTH: 17
<212> TYPE: PRT
<213> ORGANISM: Lama glama

<400> SEQUENCE: 67

Asp Ile Asn Ser Ala Gly Gly Ser Thr Tyr Tyr Ala Asp Ser Val Lys
1               5                   10                  15

Gly

<210> SEQ ID NO 68
<211> LENGTH: 32
<212> TYPE: PRT
<213> ORGANISM: Lama glama

<400> SEQUENCE: 68

Arg Phe Thr Ile Ser Arg Asp Asn Ala Lys Asn Thr Leu Tyr Leu Glu
1               5                   10                  15

Met Asn Ser Leu Lys Pro Glu Asp Thr Ala Leu Tyr Tyr Cys Ala Arg
            20                  25                  30

<210> SEQ ID NO 69
<211> LENGTH: 8
<212> TYPE: PRT
<213> ORGANISM: Lama glama

<400> SEQUENCE: 69

Val Asn Val Trp Gly Val Asn Tyr
1               5

<210> SEQ ID NO 70
<211> LENGTH: 11
<212> TYPE: PRT
<213> ORGANISM: Lama glama

<400> SEQUENCE: 70

Trp Gly Lys Gly Thr Leu Val Ser Val Ser Ser
1 5 10

<210> SEQ ID NO 71
<211> LENGTH: 30
<212> TYPE: PRT
<213> ORGANISM: Lama glama

<400> SEQUENCE: 71

Glu Leu Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 72
<211> LENGTH: 5
<212> TYPE: PRT
<213> ORGANISM: Lama glama

<400> SEQUENCE: 72

Asn Tyr Val Met Ser
1 5

<210> SEQ ID NO 73
<211> LENGTH: 14
<212> TYPE: PRT
<213> ORGANISM: Lama glama

<400> SEQUENCE: 73

Trp Val Arg Gln Ala Pro Gly Lys Gly Leu Glu Trp Val Ser
1 5 10

<210> SEQ ID NO 74
<211> LENGTH: 16
<212> TYPE: PRT
<213> ORGANISM: Lama glama

<400> SEQUENCE: 74

Asp Thr Asn Ser Gly Gly Ser Thr Ser Tyr Ala Asp Ser Val Lys Gly
1 5 10 15

<210> SEQ ID NO 75
<211> LENGTH: 32
<212> TYPE: PRT
<213> ORGANISM: Lama glama

<400> SEQUENCE: 75

Arg Phe Thr Ile Ser Arg Asp Asn Ala Lys Asn Thr Leu Tyr Leu Gln
1 5 10 15

Met Asn Ser Leu Lys Pro Glu Asp Thr Ala Leu Tyr Tyr Cys Ala Arg
20 25 30

<210> SEQ ID NO 76
<211> LENGTH: 8
<212> TYPE: PRT
<213> ORGANISM: Lama glama

<400> SEQUENCE: 76

Ser Phe Phe Tyr Gly Met Asn Tyr
1 5

<210> SEQ ID NO 77
<211> LENGTH: 11
<212> TYPE: PRT
<213> ORGANISM: Lama glama

<400> SEQUENCE: 77

Trp Gly Lys Gly Thr Gln Val Thr Val Ser Ser
1 5 10

<210> SEQ ID NO 78
<211> LENGTH: 22
<212> TYPE: PRT
<213> ORGANISM: Lama glama

<400> SEQUENCE: 78

Gln Ala Val Val Thr Gln Glu Pro Ser Leu Ser Val Ser Pro Gly Gly
1 5 10 15

Thr Val Thr Leu Thr Cys
20

<210> SEQ ID NO 79
<211> LENGTH: 14
<212> TYPE: PRT
<213> ORGANISM: Lama glama

<400> SEQUENCE: 79

Gly Leu Ser Ser Gly Ser Val Thr Thr Ser Asn Tyr Pro Gly
1 5 10

<210> SEQ ID NO 80
<211> LENGTH: 15
<212> TYPE: PRT
<213> ORGANISM: Lama glama

<400> SEQUENCE: 80

Trp Phe Gln Gln Thr Pro Gly Gln Ala Pro Arg Thr Leu Ile Tyr
1 5 10 15

<210> SEQ ID NO 81
<211> LENGTH: 7
<212> TYPE: PRT
<213> ORGANISM: Lama glama

<400> SEQUENCE: 81

Asn Thr Asn Asn Arg His Ser
1 5

<210> SEQ ID NO 82
<211> LENGTH: 32
<212> TYPE: PRT
<213> ORGANISM: Lama glama

<400> SEQUENCE: 82

Gly Val Pro Ser Arg Phe Ser Gly Ser Ile Ser Gly Asn Lys Ala Ala
1 5 10 15

Leu Thr Ile Thr Gly Ala Gln Pro Glu Asp Glu Ala Asp Tyr Tyr Cys
20 25 30

<210> SEQ ID NO 83
<211> LENGTH: 10

<212> TYPE: PRT
<213> ORGANISM: Lama glama

<400> SEQUENCE: 83

Ser Leu Tyr Thr Gly Ser Tyr Thr Thr Val
1 5 10

<210> SEQ ID NO 84
<211> LENGTH: 10
<212> TYPE: PRT
<213> ORGANISM: Lama glama

<400> SEQUENCE: 84

Phe Gly Gly Gly Thr His Leu Thr Val Leu
1 5 10

<210> SEQ ID NO 85
<211> LENGTH: 22
<212> TYPE: PRT
<213> ORGANISM: Lama glama

<400> SEQUENCE: 85

Gln Ala Val Val Thr Gln Glu Pro Ser Leu Ser Val Ser Pro Gly Gly
1 5 10 15

Thr Val Thr Leu Thr Cys
20

<210> SEQ ID NO 86
<211> LENGTH: 14
<212> TYPE: PRT
<213> ORGANISM: Lama glama

<400> SEQUENCE: 86

Gly Leu Ser Ser Gly Ser Val Thr Thr Ser Asn Tyr Pro Gly
1 5 10

<210> SEQ ID NO 87
<211> LENGTH: 15
<212> TYPE: PRT
<213> ORGANISM: Lama glama

<400> SEQUENCE: 87

Trp Phe Gln Gln Thr Pro Gly Gln Ala Pro Arg Thr Leu Ile Tyr
1 5 10 15

<210> SEQ ID NO 88
<211> LENGTH: 7
<212> TYPE: PRT
<213> ORGANISM: Lama glama

<400> SEQUENCE: 88

Asn Thr Asn Ser Arg His Ser
1 5

<210> SEQ ID NO 89
<211> LENGTH: 32
<212> TYPE: PRT
<213> ORGANISM: Lama glama

<400> SEQUENCE: 89

Gly Val Pro Ser Arg Phe Ser Gly Ser Ile Ser Gly Asn Lys Ala Ala
1 5 10 15

Leu Thr Ile Met Gly Ala Gln Pro Glu Asp Glu Ala Asp Tyr Tyr Cys
20 25 30

<210> SEQ ID NO 90
<211> LENGTH: 9
<212> TYPE: PRT
<213> ORGANISM: Lama glama

<400> SEQUENCE: 90

Ser Leu Tyr Pro Gly Ser Thr Thr Val
1 5

<210> SEQ ID NO 91
<211> LENGTH: 10
<212> TYPE: PRT
<213> ORGANISM: Lama glama

<400> SEQUENCE: 91

Phe Gly Gly Gly Thr His Leu Thr Val Leu
1 5 10

<210> SEQ ID NO 92
<211> LENGTH: 22
<212> TYPE: PRT
<213> ORGANISM: Lama glama

<400> SEQUENCE: 92

Ser Tyr Glu Leu Thr Gln Pro Ser Ala Leu Ser Val Thr Leu Gly Gln
1 5 10 15

Thr Ala Lys Ile Thr Cys
20

<210> SEQ ID NO 93
<211> LENGTH: 11
<212> TYPE: PRT
<213> ORGANISM: Lama glama

<400> SEQUENCE: 93

Gln Gly Gly Ser Leu Gly Ser Ser Tyr Ala His
1 5 10

<210> SEQ ID NO 94
<211> LENGTH: 15
<212> TYPE: PRT
<213> ORGANISM: Lama glama

<400> SEQUENCE: 94

Trp Tyr Gln Gln Lys Pro Gly Gln Ala Pro Val Leu Val Ile Tyr
1 5 10 15

<210> SEQ ID NO 95
<211> LENGTH: 7
<212> TYPE: PRT
<213> ORGANISM: Lama glama

<400> SEQUENCE: 95

Asp Asp Asp Ser Arg Pro Ser
1 5

<210> SEQ ID NO 96
<211> LENGTH: 32
<212> TYPE: PRT
<213> ORGANISM: Lama glama

<400> SEQUENCE: 96

Gly Ile Pro Glu Arg Phe Ser Gly Ser Ser Ser Gly Gly Thr Ala Thr

```
1               5                   10                  15

Leu Thr Ile Ser Gly Ala Gln Ala Glu Asp Glu Gly Asp Tyr Tyr Cys
            20                  25                  30


<210> SEQ ID NO 97
<211> LENGTH: 11
<212> TYPE: PRT
<213> ORGANISM: Lama glama

<400> SEQUENCE: 97

Gln Ser Ala Asp Ser Ser Gly Asn Ala Ala Val
1               5                   10


<210> SEQ ID NO 98
<211> LENGTH: 10
<212> TYPE: PRT
<213> ORGANISM: Lama glama

<400> SEQUENCE: 98

Phe Gly Gly Gly Thr His Leu Thr Val Leu
1               5                   10


<210> SEQ ID NO 99
<211> LENGTH: 22
<212> TYPE: PRT
<213> ORGANISM: Lama glama

<400> SEQUENCE: 99

Ser Ser Ala Leu Thr Gln Pro Ser Ala Leu Ser Val Thr Leu Gly Gln
1               5                   10                  15

Thr Ala Lys Ile Thr Cys
            20


<210> SEQ ID NO 100
<211> LENGTH: 11
<212> TYPE: PRT
<213> ORGANISM: Lama glama

<400> SEQUENCE: 100

Gln Gly Gly Ser Leu Gly Ser Ser Tyr Ala His
1               5                   10


<210> SEQ ID NO 101
<211> LENGTH: 15
<212> TYPE: PRT
<213> ORGANISM: Lama glama

<400> SEQUENCE: 101

Trp Tyr Gln Gln Lys Pro Gly Gln Ala Pro Val Leu Val Ile Tyr
1               5                   10                  15


<210> SEQ ID NO 102
<211> LENGTH: 7
<212> TYPE: PRT
<213> ORGANISM: Lama glama

<400> SEQUENCE: 102

Asp Asp Asp Ser Arg Pro Ser
1               5


<210> SEQ ID NO 103
<211> LENGTH: 32
<212> TYPE: PRT
<213> ORGANISM: Lama glama
```

<400> SEQUENCE: 103

Gly Ile Pro Glu Arg Phe Ser Gly Ser Ser Ser Gly Gly Thr Ala Thr
1 5 10 15

Leu Thr Ile Ser Gly Ala Gln Ala Glu Asp Glu Gly Asp Tyr Tyr Cys
20 25 30

<210> SEQ ID NO 104
<211> LENGTH: 11
<212> TYPE: PRT
<213> ORGANISM: Lama glama

<400> SEQUENCE: 104

Gln Ser Ala Asp Ser Ser Gly Asn Ala Ala Val
1 5 10

<210> SEQ ID NO 105
<211> LENGTH: 10
<212> TYPE: PRT
<213> ORGANISM: Lama glama

<400> SEQUENCE: 105

Phe Gly Gly Gly Thr His Leu Thr Val Leu
1 5 10

<210> SEQ ID NO 106
<211> LENGTH: 22
<212> TYPE: PRT
<213> ORGANISM: Lama glama

<400> SEQUENCE: 106

Gln Pro Val Leu Asn Gln Pro Ser Ala Leu Ser Val Thr Leu Gly Gln
1 5 10 15

Thr Ala Lys Ile Thr Cys
20

<210> SEQ ID NO 107
<211> LENGTH: 11
<212> TYPE: PRT
<213> ORGANISM: Lama glama

<400> SEQUENCE: 107

Gln Gly Gly Ser Leu Gly Ala Arg Tyr Ala His
1 5 10

<210> SEQ ID NO 108
<211> LENGTH: 15
<212> TYPE: PRT
<213> ORGANISM: Lama glama

<400> SEQUENCE: 108

Trp Tyr Gln Gln Lys Pro Gly Gln Ala Pro Val Leu Val Ile Tyr
1 5 10 15

<210> SEQ ID NO 109
<211> LENGTH: 7
<212> TYPE: PRT
<213> ORGANISM: Lama glama

<400> SEQUENCE: 109

Asp Asp Asp Ser Arg Pro Ser
1 5

<210> SEQ ID NO 110
<211> LENGTH: 32
<212> TYPE: PRT
<213> ORGANISM: Lama glama

<400> SEQUENCE: 110

Gly Ile Pro Glu Arg Phe Ser Gly Ser Ser Ser Gly Gly Thr Ala Thr
1 5 10 15

Leu Thr Ile Ser Gly Ala Gln Ala Glu Asp Glu Gly Asp Tyr Tyr Cys
20 25 30

<210> SEQ ID NO 111
<211> LENGTH: 9
<212> TYPE: PRT
<213> ORGANISM: Lama glama

<400> SEQUENCE: 111

Gln Ser Ala Asp Ser Ser Gly Ser Val
1 5

<210> SEQ ID NO 112
<211> LENGTH: 10
<212> TYPE: PRT
<213> ORGANISM: Lama glama

<400> SEQUENCE: 112

Phe Gly Gly Gly Thr His Leu Thr Val Leu
1 5 10

<210> SEQ ID NO 113
<211> LENGTH: 22
<212> TYPE: PRT
<213> ORGANISM: Lama glama

<400> SEQUENCE: 113

Ser Tyr Glu Leu Thr Gln Pro Ser Ala Leu Ser Val Thr Leu Gly Gln
1 5 10 15

Thr Ala Lys Ile Thr Cys
20

<210> SEQ ID NO 114
<211> LENGTH: 11
<212> TYPE: PRT
<213> ORGANISM: Lama glama

<400> SEQUENCE: 114

Gln Gly Gly Ser Leu Gly Ser Ser Tyr Ala His
1 5 10

<210> SEQ ID NO 115
<211> LENGTH: 15
<212> TYPE: PRT
<213> ORGANISM: Lama glama

<400> SEQUENCE: 115

Trp Tyr Gln Gln Lys Pro Gly Gln Ala Pro Val Leu Val Ile Tyr
1 5 10 15

<210> SEQ ID NO 116
<211> LENGTH: 7
<212> TYPE: PRT
<213> ORGANISM: Lama glama

<400> SEQUENCE: 116

```
Asp Asp Asp Ser Arg Pro Ser
1               5


<210> SEQ ID NO 117
<211> LENGTH: 32
<212> TYPE: PRT
<213> ORGANISM: Lama glama

<400> SEQUENCE: 117

Gly Ile Pro Glu Arg Phe Ser Gly Ser Ser Ser Gly Gly Thr Ala Thr
1               5                   10                  15

Leu Thr Ile Ser Gly Ala Gln Ala Glu Asp Glu Gly Asp Tyr Tyr Cys
            20                  25                  30


<210> SEQ ID NO 118
<211> LENGTH: 11
<212> TYPE: PRT
<213> ORGANISM: Lama glama

<400> SEQUENCE: 118

Gln Ser Ala Asp Ser Ser Gly Asn Ala Ala Val
1               5                   10


<210> SEQ ID NO 119
<211> LENGTH: 10
<212> TYPE: PRT
<213> ORGANISM: Lama glama

<400> SEQUENCE: 119

Phe Gly Gly Gly Thr His Leu Thr Val Leu
1               5                   10


<210> SEQ ID NO 120
<211> LENGTH: 22
<212> TYPE: PRT
<213> ORGANISM: Lama glama

<400> SEQUENCE: 120

Ser Ser Ala Leu Thr Gln Pro Ser Ala Leu Ser Val Ser Leu Gly Gln
1               5                   10                  15

Thr Ala Arg Ile Thr Cys
            20


<210> SEQ ID NO 121
<211> LENGTH: 11
<212> TYPE: PRT
<213> ORGANISM: Lama glama

<400> SEQUENCE: 121

Gln Gly Gly Ser Leu Gly Ser Ser Tyr Ala His
1               5                   10


<210> SEQ ID NO 122
<211> LENGTH: 15
<212> TYPE: PRT
<213> ORGANISM: Lama glama

<400> SEQUENCE: 122

Trp Tyr Gln Gln Lys Pro Gly Gln Ala Pro Val Leu Val Ile Tyr
1               5                   10                  15


<210> SEQ ID NO 123
<211> LENGTH: 7
<212> TYPE: PRT
```

<213> ORGANISM: Lama glama

<400> SEQUENCE: 123

Gly Asp Asp Ser Arg Pro Ser
1               5

<210> SEQ ID NO 124
<211> LENGTH: 32
<212> TYPE: PRT
<213> ORGANISM: Lama glama

<400> SEQUENCE: 124

Gly Ile Pro Glu Arg Phe Ser Gly Ser Ser Ser Gly Gly Thr Ala Thr
1               5                   10                  15

Leu Thr Ile Ser Gly Ala Gln Ala Glu Asp Glu Asp Asp Tyr Tyr Cys
            20                  25                  30

<210> SEQ ID NO 125
<211> LENGTH: 10
<212> TYPE: PRT
<213> ORGANISM: Lama glama

<400> SEQUENCE: 125

Gln Ser Thr Asp Ser Ser Gly Asn Thr Val
1               5                   10

<210> SEQ ID NO 126
<211> LENGTH: 10
<212> TYPE: PRT
<213> ORGANISM: Lama glama

<400> SEQUENCE: 126

Phe Gly Gly Gly Thr Arg Leu Thr Val Leu
1               5                   10

<210> SEQ ID NO 127
<211> LENGTH: 22
<212> TYPE: PRT
<213> ORGANISM: Lama glama

<400> SEQUENCE: 127

Gln Ala Gly Leu Thr Gln Pro Pro Ser Val Ser Gly Ser Pro Gly Lys
1               5                   10                  15

Thr Val Thr Ile Ser Cys
            20

<210> SEQ ID NO 128
<211> LENGTH: 14
<212> TYPE: PRT
<213> ORGANISM: Lama glama

<400> SEQUENCE: 128

Ala Gly Asn Ser Ser Asp Val Gly Tyr Gly Asn Tyr Val Ser
1               5                   10

<210> SEQ ID NO 129
<211> LENGTH: 15
<212> TYPE: PRT
<213> ORGANISM: Lama glama

<400> SEQUENCE: 129

Trp Tyr Gln Gln Phe Pro Gly Met Ala Pro Lys Leu Leu Ile Tyr
1               5                   10                  15

<210> SEQ ID NO 130
<211> LENGTH: 7
<212> TYPE: PRT
<213> ORGANISM: Lama glama

<400> SEQUENCE: 130

Leu Val Asn Lys Arg Ala Ser
1               5

<210> SEQ ID NO 131
<211> LENGTH: 32
<212> TYPE: PRT
<213> ORGANISM: Lama glama

<400> SEQUENCE: 131

Gly Ile Thr Asp Arg Phe Ser Gly Ser Lys Ser Gly Asn Thr Ala Ser
1               5                   10                  15

Leu Thr Ile Ser Gly Leu Gln Ser Glu Asp Glu Ala Asp Tyr Tyr Cys
            20                  25                  30

<210> SEQ ID NO 132
<211> LENGTH: 10
<212> TYPE: PRT
<213> ORGANISM: Lama glama

<400> SEQUENCE: 132

Ala Ser Tyr Thr Gly Ser Asn Asn Ile Val
1               5                   10

<210> SEQ ID NO 133
<211> LENGTH: 10
<212> TYPE: PRT
<213> ORGANISM: Lama glama

<400> SEQUENCE: 133

Phe Gly Gly Gly Thr His Leu Thr Val Leu
1               5                   10

<210> SEQ ID NO 134
<211> LENGTH: 23
<212> TYPE: PRT
<213> ORGANISM: Lama glama

<400> SEQUENCE: 134

Glu Ile Val Leu Thr Gln Ser Pro Ser Ser Val Thr Ala Ser Val Gly
1               5                   10                  15

Gly Lys Val Thr Ile Asn Cys
            20

<210> SEQ ID NO 135
<211> LENGTH: 17
<212> TYPE: PRT
<213> ORGANISM: Lama glama

<400> SEQUENCE: 135

Lys Ser Ser Gln Ser Val Phe Ile Ala Ser Asn Gln Lys Thr Tyr Leu
1               5                   10                  15

Asn

<210> SEQ ID NO 136
<211> LENGTH: 15
<212> TYPE: PRT
<213> ORGANISM: Lama glama

<400> SEQUENCE: 136

Trp Tyr Gln Gln Arg Pro Gly Gln Ser Pro Arg Leu Val Ile Ser
1               5                   10                  15

<210> SEQ ID NO 137
<211> LENGTH: 7
<212> TYPE: PRT
<213> ORGANISM: Lama glama

<400> SEQUENCE: 137

Tyr Ala Ser Thr Arg Glu Ser
1               5

<210> SEQ ID NO 138
<211> LENGTH: 32
<212> TYPE: PRT
<213> ORGANISM: Lama glama

<400> SEQUENCE: 138

Gly Ile Pro Asp Arg Phe Ser Gly Ser Gly Ser Thr Thr Asp Phe Thr
1               5                   10                  15

Leu Thr Ile Ser Ser Val Gln Pro Glu Asp Ala Ala Val Tyr Tyr Cys
            20                  25                  30

<210> SEQ ID NO 139
<211> LENGTH: 8
<212> TYPE: PRT
<213> ORGANISM: Lama glama

<400> SEQUENCE: 139

Gln Gln Ala Tyr Ser His Pro Thr
1               5

<210> SEQ ID NO 140
<211> LENGTH: 10
<212> TYPE: PRT
<213> ORGANISM: Lama glama

<400> SEQUENCE: 140

Phe Gly Gln Gly Thr Lys Val Glu Leu Lys
1               5                   10

<210> SEQ ID NO 141
<211> LENGTH: 22
<212> TYPE: PRT
<213> ORGANISM: Lama glama

<400> SEQUENCE: 141

Gln Thr Val Val Thr Gln Glu Pro Ser Leu Ser Val Ser Pro Gly Gly
1               5                   10                  15

Thr Val Thr Leu Thr Cys
            20

<210> SEQ ID NO 142
<211> LENGTH: 14
<212> TYPE: PRT
<213> ORGANISM: Lama glama

<400> SEQUENCE: 142

Gly Leu Ser Ser Gly Ser Val Thr Thr Ser Asn Tyr Pro Gly
1               5                   10

<210> SEQ ID NO 143
<211> LENGTH: 15
<212> TYPE: PRT
<213> ORGANISM: Lama glama

<400> SEQUENCE: 143

Trp Phe Gln Gln Thr Pro Gly Gln Ala Pro Arg Thr Leu Ile Tyr
1 5 10 15

<210> SEQ ID NO 144
<211> LENGTH: 7
<212> TYPE: PRT
<213> ORGANISM: Lama glama

<400> SEQUENCE: 144

Asn Thr Asn Ser Arg His Ser
1 5

<210> SEQ ID NO 145
<211> LENGTH: 32
<212> TYPE: PRT
<213> ORGANISM: Lama glama

<400> SEQUENCE: 145

Gly Val Pro Ser Arg Phe Ser Gly Ser Ile Ser Gly Asn Lys Ala Ala
1 5 10 15

Leu Thr Ile Thr Gly Ala Gln Pro Glu Asp Glu Ala Asp Tyr Tyr Cys
20 25 30

<210> SEQ ID NO 146
<211> LENGTH: 10
<212> TYPE: PRT
<213> ORGANISM: Lama glama

<400> SEQUENCE: 146

Ser Leu Tyr Pro Gly Ser Tyr Thr Asn Val
1 5 10

<210> SEQ ID NO 147
<211> LENGTH: 10
<212> TYPE: PRT
<213> ORGANISM: Lama glama

<400> SEQUENCE: 147

Phe Gly Gly Gly Thr His Leu Thr Val Leu
1 5 10

<210> SEQ ID NO 148
<211> LENGTH: 22
<212> TYPE: PRT
<213> ORGANISM: Lama glama

<400> SEQUENCE: 148

Gln Ser Ala Leu Thr Gln Pro Pro Ser Leu Ser Ala Ser Pro Gly Ser
1 5 10 15

Ser Val Arg Leu Thr Cys
20

<210> SEQ ID NO 149
<211> LENGTH: 14
<212> TYPE: PRT
<213> ORGANISM: Lama glama

<400> SEQUENCE: 149

Thr Leu Ser Ser Gly Asn Asn Ile Gly Ser Tyr Asp Ile Ser
1 5 10

<210> SEQ ID NO 150
<211> LENGTH: 15
<212> TYPE: PRT
<213> ORGANISM: Lama glama

<400> SEQUENCE: 150

Trp Tyr Gln Gln Lys Ala Gly Ser Pro Pro Arg Tyr Leu Leu Asn
1 5 10 15

<210> SEQ ID NO 151
<211> LENGTH: 11
<212> TYPE: PRT
<213> ORGANISM: Lama glama

<400> SEQUENCE: 151

Tyr Tyr Thr Asp Ser Arg Lys His Gln Asp Ser
1 5 10

<210> SEQ ID NO 152
<211> LENGTH: 34
<212> TYPE: PRT
<213> ORGANISM: Lama glama

<400> SEQUENCE: 152

Gly Val Pro Ser Arg Phe Ser Gly Ser Lys Asp Ala Ser Ala Asn Ala
1 5 10 15

Gly Leu Leu Leu Ile Ser Gly Leu Gln Pro Glu Asp Glu Ala Asp Tyr
20 25 30

Tyr Cys

<210> SEQ ID NO 153
<211> LENGTH: 11
<212> TYPE: PRT
<213> ORGANISM: Lama glama

<400> SEQUENCE: 153

Ser Ala Tyr Lys Ser Gly Ser Tyr Arg Trp Val
1 5 10

<210> SEQ ID NO 154
<211> LENGTH: 10
<212> TYPE: PRT
<213> ORGANISM: Lama glama

<400> SEQUENCE: 154

Phe Gly Gly Gly Thr His Val Thr Val Leu
1 5 10

<210> SEQ ID NO 155
<211> LENGTH: 118
<212> TYPE: PRT
<213> ORGANISM: Lama glama

<400> SEQUENCE: 155

Gln Leu Gln Leu Val Glu Ser Gly Gly Gly Leu Val Gln Pro Gly Gly
1 5 10 15

Ser Leu Arg Val Ser Cys Thr Ala Ser Gly Phe Thr Phe Asn Thr Tyr
20 25 30

Tyr Met Thr Trp Val Arg Gln Ala Pro Gly Lys Gly Leu Glu Trp Val
35 40 45

```
Ser Asp Ile Asn Ser Gly Gly Gly Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Leu Tyr Tyr Cys Val
                85                  90                  95

Arg Val Arg Ile Trp Pro Val Gly Tyr Asp Tyr Trp Gly Gln Gly Thr
            100                 105                 110

Gln Val Thr Val Ser Ser
        115


<210> SEQ ID NO 156
<211> LENGTH: 110
<212> TYPE: PRT
<213> ORGANISM: Lama glama

<400> SEQUENCE: 156

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Asn Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ser Leu Tyr Thr Gly Ser
                85                  90                  95

Tyr Thr Thr Val Phe Gly Gly Gly Thr His Leu Thr Val Leu
            100                 105                 110


<210> SEQ ID NO 157
<211> LENGTH: 118
<212> TYPE: PRT
<213> ORGANISM: Lama glama

<400> SEQUENCE: 157

Gln Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Thr Tyr
            20                  25                  30

Tyr Met Ser Trp Val Arg Gln Ala Pro Gly Lys Gly Leu Glu Trp Val
        35                  40                  45

Ser Asp Ile Arg Thr Asp Gly Gly Thr Tyr Tyr Ala Asp Ser Val Lys
    50                  55                  60

Gly Arg Phe Thr Met Ser Arg Asp Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Arg Thr Arg Ile Phe Pro Ser Gly Tyr Asp Tyr Trp Gly Gln Gly Thr
            100                 105                 110

Gln Val Thr Val Ser Ser
        115


<210> SEQ ID NO 158
```

<211> LENGTH: 109
<212> TYPE: PRT
<213> ORGANISM: Lama glama

<400> SEQUENCE: 158

```
Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Met Gly Ala
65                  70                  75                  80

Gln Pro Glu Asp Glu Ala Asp Tyr Tyr Cys Ser Leu Tyr Pro Gly Ser
                85                  90                  95

Thr Thr Val Phe Gly Gly Gly Thr His Leu Thr Val Leu
            100                 105
```

<210> SEQ ID NO 159
<211> LENGTH: 126
<212> TYPE: PRT
<213> ORGANISM: Lama glama

<400> SEQUENCE: 159

```
Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Leu Arg Phe Asp Leu Ala Arg Tyr Thr Asp Tyr Glu Ala
            100                 105                 110

Trp Asp Tyr Trp Gly Gln Gly Thr Gln Val Thr Val Ser Ser
        115                 120                 125
```

<210> SEQ ID NO 160
<211> LENGTH: 108
<212> TYPE: PRT
<213> ORGANISM: Lama glama

<400> SEQUENCE: 160

```
Ser Tyr Glu Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60
```

```
Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu
            100                 105


<210> SEQ ID NO 161
<211> LENGTH: 126
<212> TYPE: PRT
<213> ORGANISM: Lama glama

<400> SEQUENCE: 161

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ser Asp Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Met Arg Leu Tyr Leu Ala Arg Tyr Asn Asp Tyr Glu Ala
            100                 105                 110

Trp Asp Tyr Trp Gly Gln Gly Thr Gln Val Thr Val Ser Ser
        115                 120                 125


<210> SEQ ID NO 162
<211> LENGTH: 108
<212> TYPE: PRT
<213> ORGANISM: Lama glama

<400> SEQUENCE: 162

Ser Ser Ala Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu
            100                 105


<210> SEQ ID NO 163
<211> LENGTH: 126
<212> TYPE: PRT
<213> ORGANISM: Lama glama

<400> SEQUENCE: 163

Glu Leu Gln Leu Val Glu Ser Gly Gly Gly Leu Val Gln Pro Gly Gly
```

```
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ala Ile Asn Ser Tyr Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Val Arg Ala Asp Leu Ser Arg Tyr Asn Asp Tyr Glu Ser
            100                 105                 110

Tyr Asp Tyr Trp Gly Gln Gly Thr Gln Val Thr Val Ser Ser
        115                 120                 125


<210> SEQ ID NO 164
<211> LENGTH: 106
<212> TYPE: PRT
<213> ORGANISM: Lama glama

<400> SEQUENCE: 164

Gln Pro Val Leu Asn Gln Pro Ser Ala Leu Ser Val Thr Leu Gly Gln
1               5                   10                  15

Thr Ala Lys Ile Thr Cys Gln Gly Gly Ser Leu Gly Ala Arg Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Ser Val
                85                  90                  95

Phe Gly Gly Gly Thr His Leu Thr Val Leu
            100                 105


<210> SEQ ID NO 165
<211> LENGTH: 126
<212> TYPE: PRT
<213> ORGANISM: Lama glama

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Lys Asp Tyr
            20                  25                  30

Asp Ile Thr Trp Val Arg Gln Ala Pro Gly Lys Gly Leu Glu Trp Val
        35                  40                  45

Ser Thr Ile Thr Ser Arg Ser Gly Ser Thr Ser Tyr Val Asp Ser Val
    50                  55                  60

Lys Gly Arg Phe Thr Ile Ser Gly Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Val Tyr Ala Thr Thr Trp Asp Val Gly Pro Leu Gly Tyr Gly
```

```
            100                 105                 110

Met Asp Tyr Trp Gly Lys Gly Thr Leu Val Thr Val Ser Ser
        115                 120                 125


<210> SEQ ID NO 166
<211> LENGTH: 108
<212> TYPE: PRT
<213> ORGANISM: Lama glama

<400> SEQUENCE: 166

Ser Tyr Glu Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu
            100                 105


<210> SEQ ID NO 167
<211> LENGTH: 126
<212> TYPE: PRT
<213> ORGANISM: Lama glama

<400> SEQUENCE: 167

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met Ser Trp Val Arg Gln Ala Pro Gly Lys Gly Leu Glu Trp Val
        35                  40                  45

Ser Thr Ile Asn Ser Asp Gly Ser Ser Thr Ser Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Val Tyr Gly Ser Thr Trp Asp Val Gly Pro Met Gly Tyr Gly
            100                 105                 110

Met Asp Tyr Trp Gly Lys Gly Thr Leu Val Thr Val Ser Ser
        115                 120                 125


<210> SEQ ID NO 168
<211> LENGTH: 107
<212> TYPE: PRT
<213> ORGANISM: Lama glama

<400> SEQUENCE: 168

Ser Ser Ala Leu Thr Gln Pro Ser Ala Leu Ser Val Ser Leu Gly Gln
1               5                   10                  15

Thr Ala Arg Ile Thr Cys Gln Gly Gly Ser Leu Gly Ser Ser Tyr Ala
            20                  25                  30
```

```
His Trp Tyr Gln Gln Lys Pro Gly Gln Ala Pro Val Leu Val Ile Tyr
        35                  40                  45

Gly Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Asp Asp Tyr Tyr Cys Gln Ser Thr Asp Ser Ser Gly Asn Thr
                85                  90                  95

Val Phe Gly Gly Gly Thr Arg Leu Thr Val Leu
            100                 105


<210> SEQ ID NO 169
<211> LENGTH: 119
<212> TYPE: PRT
<213> ORGANISM: Lama glama

<400> SEQUENCE: 169

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Asp Ile Tyr Ser Asp Gly Ser Thr Thr Trp Tyr Ser Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Ser Glu Asp Thr Ala Val Tyr Tyr Cys
                85                  90                  95

Ala Arg Val Lys Ile Tyr Pro Gly Gly Tyr Asp Ala Trp Gly Gln Gly
            100                 105                 110

Thr Gln Val Thr Val Ser Ser
        115


<210> SEQ ID NO 170
<211> LENGTH: 110
<212> TYPE: PRT
<213> ORGANISM: Lama glama

<400> SEQUENCE: 170

Gln Ala Gly Leu Thr Gln Pro Pro Ser Val Ser Gly Ser Pro Gly Lys
1               5                   10                  15

Thr Val Thr Ile Ser Cys Ala Gly Asn Ser Ser Asp Val Gly Tyr Gly
            20                  25                  30

Asn Tyr Val Ser Trp Tyr Gln Gln Phe Pro Gly Met Ala Pro Lys Leu
        35                  40                  45

Leu Ile Tyr Leu Val Asn Lys Arg Ala Ser Gly Ile Thr Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Thr Gly Ser
                85                  90                  95

Asn Asn Ile Val Phe Gly Gly Gly Thr His Leu Thr Val Leu
            100                 105                 110


<210> SEQ ID NO 171
```

<211> LENGTH: 118
<212> TYPE: PRT
<213> ORGANISM: Lama glama

<400> SEQUENCE: 171

```
Gln Val Gln Leu Gln Glu Ser Gly Gly Asp Leu Val Gln Pro Gly Gly
1               5                   10                  15

Ser Leu Arg Val Ser Cys Val Val Ser Gly Phe Thr Phe Ser Arg Tyr
            20                  25                  30

Tyr Met Ser Trp Val Arg Gln Ala Pro Gly Lys Gly Leu Glu Trp Val
        35                  40                  45

Ser Ser Ile Asp Ser Tyr Gly Tyr Ser Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Ala Lys Thr Thr Trp Ser Tyr Asp Tyr Trp Gly Gln Gly Thr
            100                 105                 110

Gln Val Thr Val Ser Ser
        115
```

<210> SEQ ID NO 172
<211> LENGTH: 112
<212> TYPE: PRT
<213> ORGANISM: Lama glama

<400> SEQUENCE: 172

```
Glu Ile Val Leu Thr Gln Ser Pro Ser Ser Val Thr Ala Ser Val Gly
1               5                   10                  15

Gly Lys Val Thr Ile Asn Cys Lys Ser Ser Gln Ser Val Phe Ile Ala
            20                  25                  30

Ser Asn Gln Lys Thr Tyr Leu Asn Trp Tyr Gln Gln Arg Pro Gly Gln
        35                  40                  45

Ser Pro Arg Leu Val Ile Ser Tyr Ala Ser Thr Arg Glu Ser Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser His Pro Thr Phe Gly Gln Gly Thr Lys Val Glu Leu Lys
            100                 105                 110
```

<210> SEQ ID NO 173
<211> LENGTH: 117
<212> TYPE: PRT
<213> ORGANISM: Lama glama

<400> SEQUENCE: 173

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

His Met Ser Trp Val Arg Gln Val Pro Gly Lys Gly Phe Glu Trp Ile
        35                  40                  45

Ser Asp Ile Asn Ser Ala Gly Gly Ser Thr Tyr Tyr Ala Asp Ser Val
    50                  55                  60
```

```
Lys Gly Arg Phe Thr Ile Ser Arg Asp Asn Ala Lys Asn Thr Leu Tyr
65                  70                  75                  80

Leu Glu Met Asn Ser Leu Lys Pro Glu Asp Thr Ala Leu Tyr Tyr Cys
                85                  90                  95

Ala Arg Val Asn Val Trp Gly Val Asn Tyr Trp Gly Lys Gly Thr Leu
            100                 105                 110

Val Ser Val Ser Ser
        115
```

```
<210> SEQ ID NO 174
<211> LENGTH: 110
<212> TYPE: PRT
<213> ORGANISM: Lama glama

<400> SEQUENCE: 174

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ser Leu Tyr Pro Gly Ser
                85                  90                  95

Tyr Thr Asn Val Phe Gly Gly Gly Thr His Leu Thr Val Leu
            100                 105                 110
```

```
<210> SEQ ID NO 175
<211> LENGTH: 116
<212> TYPE: PRT
<213> ORGANISM: Lama glama

<400> SEQUENCE: 175

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Val Met Ser Trp Val Arg Gln Ala Pro Gly Lys Gly Leu Glu Trp Val
        35                  40                  45

Ser Asp Thr Asn Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Arg Ser Phe Phe Tyr Gly Met Asn Tyr Trp Gly Lys Gly Thr Gln Val
            100                 105                 110

Thr Val Ser Ser
        115
```

```
<210> SEQ ID NO 176
<211> LENGTH: 117
<212> TYPE: PRT
<213> ORGANISM: Lama glama
```

<400> SEQUENCE: 176

```
Gln Ser Ala Leu Thr Gln Pro Pro Ser Leu Ser Ala Ser Pro Gly Ser
1               5                   10                  15

Ser Val Arg Leu Thr Cys Thr Leu Ser Ser Gly Asn Asn Ile Gly Ser
            20                  25                  30

Tyr Asp Ile Ser Trp Tyr Gln Gln Lys Ala Gly Ser Pro Pro Arg Tyr
        35                  40                  45

Leu Leu Asn Tyr Tyr Thr Asp Ser Arg Lys His Gln Asp Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ser Ala Tyr Lys Ser Gly Ser Tyr Arg Trp Val Phe Gly Gly Gly Thr
            100                 105                 110

His Val Thr Val Leu
        115
```

<210> SEQ ID NO 177
<211> LENGTH: 354
<212> TYPE: DNA
<213> ORGANISM: Lama glama

<400> SEQUENCE: 177

```
cagttgcagc tggtggagtc tgggggaggc ttggtgcagc ctggggggtc tctgagagtt     60

tcctgtacag cctctggatt caccttcaat acctactaca tgacctgggt ccgccaggct    120

ccagggaagg ggctcgagtg ggtctcagat attaatagtg gtggtggtac atactatgca    180

gactccgtga agggccgatt caccatctcc agagacaacg ccaagaacac gctatatctg    240

caaatgaaca gcctgaaacc tgaggacacg gccctgtatt actgtgtaag agttcgtatt    300

tggccagtgg gatatgacta ctggggccag gggacccagg tcaccgtttc ctca          354
```

<210> SEQ ID NO 178
<211> LENGTH: 330
<212> TYPE: DNA
<213> ORGANISM: Lama glama

<400> SEQUENCE: 178

```
caggctgtgg tgacccagga gccgtccctg tcagtgtctc caggagggac ggtcacactc     60

acctgcggcc tcagctctgg gtctgtcact accagtaact accctggttg gttccagcag    120

acaccgggcc aggctccacg cactcttatc tacaacacaa acaaccgcca ctctggggtc    180

cccagtcgct tctccggatc catctctggg aacaaagccg ccctcaccat cacgggggcc    240

cagcccgagg acgaggccga ctattactgt tctctatata ctggcagtta cactactgtg    300

ttcggcggag ggacccatct gaccgtcctg                                     330
```

<210> SEQ ID NO 179
<211> LENGTH: 354
<212> TYPE: DNA
<213> ORGANISM: Lama glama

<400> SEQUENCE: 179

```
caggtgcagc tcgtggagtc tgggggaggc ttggtgcagc ctggggggtc tctgagagtc     60

tcctgtgcag cctctggatt caccttcagt acctactaca tgagctgggt ccgccaggct    120

ccagggaagg ggctcgagtg ggtctcagat attcgtactg atggtggcac atactatgca    180
```

```
gactccgtga agggccgatt caccatgtcc agagacaacg ccaagaacac gctgtatcta    240

caaatgaaca gcctgaaacc tgaggacacg gccctgtatt actgtgcaag aactcgaatt    300

ttcccctcgg ggtatgacta ctggggccag gggacccagg tcaccgtctc ctca          354


<210> SEQ ID NO 180
<211> LENGTH: 327
<212> TYPE: DNA
<213> ORGANISM: Lama glama

<400> SEQUENCE: 180

caggctgtgg tgacccagga gccgtccctg tcagtgtctc caggagggac ggtcacactc     60

acctgcggcc tcagctctgg gtctgtcact accagtaact accctggttg gttccagcag    120

acaccaggcc aggctccgcg cactcttatc tacaacacaa acagccgcca ctctggggtc    180

cccagtcgct tctccggatc catctctggg aacaaagccg ccctcaccat catgggggcc    240

cagcccgagg acgaggccga ctattactgt tctctgtacc ctggtagtac cactgtgttc    300

ggcggaggga cccatctgac cgtcctg                                        327


<210> SEQ ID NO 181
<211> LENGTH: 378
<212> TYPE: DNA
<213> ORGANISM: Lama glama

<400> SEQUENCE: 181

cagttgcagc tggtggagtc tgggggaggc ttggtgcagc ctggggggtc tctgagactc     60

tcctgtgcag cctctggatt caccttcagt agccatgcca tgagctgggt ccgccaggct    120

ccaggaaagg ggctcgagtg ggtctcagct attaatagtg gtggtggtag cacaagctat    180

gcagactccg tgaagggccg attcaccatc tccagagaca acgccaagaa cacgctgtac    240

ctgcaaatga acagcctgaa acctgaggac acggccgtgt attactgtgc aaaagagctg    300

agattcgacc tagcaaggta taccgactat gaggcctggg actactgggg ccaggggacc    360

caggtcaccg tctcctca                                                  378


<210> SEQ ID NO 182
<211> LENGTH: 324
<212> TYPE: DNA
<213> ORGANISM: Lama glama

<400> SEQUENCE: 182

tcctatgagc tgactcagcc ctccgcgctg tccgtaacct tgggacagac ggccaagatc     60

acctgccaag gtggcagctt aggtagcagt tatgctcact ggtaccagca gaagccaggc    120

caggcccctg tgctggtcat ctatgatgat gacagcaggc cctcagggat ccctgagcgg    180

ttctctggct ccagctctgg gggcacagcc accctgacca tcagcggggc ccaggccgag    240

gacgagggtg actattactg tcagtcagca gacagcagtg gtaatgctgc tgtgttcggc    300

ggagggaccc atctgaccgt cctg                                           324


<210> SEQ ID NO 183
<211> LENGTH: 378
<212> TYPE: DNA
<213> ORGANISM: Lama glama

<400> SEQUENCE: 183

gagttgcagc tggtggagtc tgggggaggc ttggtgcagc ctggggggtc tctgagactc     60
```

```
tcctgtgcag cctctggatt caccttcagt ggctatggca tgagctgggt ccgccaggct    120

ccaggaaagg ggctcgagtg ggtctcagat attaatagtg gtggtggtag cacaagctat    180

gcagactccg tgaagggccg attcaccatc tccagagaca acgccaagaa cacgctgtat    240

ctgcaaatga acagcctgaa acctgaggac acggccgtgt attactgtgc aaaagatatg    300

agattatacc tagcaaggta taacgactat gaggcctggg actactgggg ccaggggacc    360

caggtcaccg tctcctca                                                  378


<210> SEQ ID NO 184
<211> LENGTH: 324
<212> TYPE: DNA
<213> ORGANISM: Lama glama

<400> SEQUENCE: 184

tcctctgcac tgactcagcc ctccgcgctg tccgtaacct tgggacagac ggccaagatc     60

acctgccaag gtggcagctt aggtagcagt tatgctcact ggtaccagca gaagccaggc    120

caggcccctg tgctggtcat ctatgatgat gacagcaggc cctcagggat ccctgagcgg    180

ttctctggct ccagctctgg gggcacagcc accctgacca tcagcggggc ccaggccgag    240

gacgagggtg actattactg tcagtcagca gacagcagtg gtaatgctgc tgtgttcggc    300

ggagggaccc atctgaccgt cctg                                           324


<210> SEQ ID NO 185
<211> LENGTH: 378
<212> TYPE: DNA
<213> ORGANISM: Lama glama

<400> SEQUENCE: 185

gagttgcagc tggtggagtc tgggggaggc ttggtgcagc ctggggggtc tctgagactc     60

tcctgtgcag cctctggatt caccttcagt agctatggca tgagctgggt ccgccaggct    120

ccaggaaagg ggctcgagtg ggtctcagct attaatagtt atggtggtag cacaagctat    180

gcagactccg tgaagggccg attcaccatc tccagagaca acgccaagaa cacgctgtat    240

ctgcaaatga acagcctgaa acctgaggac acggccgtgt attactgtgc aaaagaagtg    300

cgggccgacc taagccgcta taacgactat gagtcgtatg actactgggg ccaggggacc    360

caggtcaccg tctcctca                                                  378


<210> SEQ ID NO 186
<211> LENGTH: 318
<212> TYPE: DNA
<213> ORGANISM: Lama glama

<400> SEQUENCE: 186

cagccggtgc tgaatcagcc ctccgcgctg tccgtaacct tgggacagac ggccaagatc     60

acctgccaag gtggcagctt aggtgcgcgt tatgctcact ggtaccagca gaagccaggc    120

caggcccctg tgctggtcat ctatgatgat gacagcaggc cctcagggat ccctgagcgg    180

ttctctggct ccagctctgg gggcacagcc accctgacca tcagcggggc ccaggccgag    240

gacgagggtg actattactg tcagtcagca gacagcagtg gttctgtgtt cggcggaggg    300

acccatctga ccgtcctg                                                  318


<210> SEQ ID NO 187
<211> LENGTH: 378
<212> TYPE: DNA
<213> ORGANISM: Lama glama
```

<400> SEQUENCE: 187
gaggtgcagc tcgtggagtc tgggggaggc ttggtgcagc ctggggggtc tctgagactc 60
tcctgtgcag cctctggatt cagcttcaag gactatgaca taacctgggt ccgccaggct 120
ccgggaaagg ggctcgagtg ggtctcaact attactagtc gtagtggtag cacaagctat 180
gtagactccg taaagggccg attcaccatc tccggagaca acgccaagaa cacgctgtat 240
ctgcaaatga acagcctgaa acctgaggac acggccgtgt attactgtgc aaaagtttac 300
gcgactacct gggacgtcgg ccctctgggc tacggcatgg actactgggg caaggggacc 360
ctggtcaccg tctcctca 378

<210> SEQ ID NO 188
<211> LENGTH: 324
<212> TYPE: DNA
<213> ORGANISM: Lama glama

<400> SEQUENCE: 188
tcctatgagc tgactcagcc ctccgcgctg tccgtaacct tgggacagac ggccaagatc 60
acctgccaag gtggcagctt aggtagcagt tatgctcact ggtaccagca gaagccaggc 120
caggcccctg tgctggtcat ctatgatgat gacagcaggc cctcagggat ccctgagcgg 180
ttctctggct ccagctctgg gggcacagcc accctgacca tcagcggggc ccaggccgag 240
gacgagggtg actattactg tcagtcagca gacagcagtg gtaatgctgc tgtgttcggc 300
ggagggaccc atctgaccgt cctg 324

<210> SEQ ID NO 189
<211> LENGTH: 378
<212> TYPE: DNA
<213> ORGANISM: Lama glama

<400> SEQUENCE: 189
gaggtgcagc tgcaggagtc ggggggaggc ttggtgcagc ctggggggtc tctgagactc 60
tcctgtgcag cctctggatt caccttcagt atatatgaca tgagctgggt ccgccaggct 120
ccaggaaagg ggctcgagtg ggtctcaact attaatagtg atggtagtag cacaagctat 180
gtagactccg tgaagggccg attcaccatc tccagagaca acgccaagaa cacgctgtat 240
ctgcaaatga acagcctgaa acctgaggac acggccgtgt attactgtgc gaaagtttac 300
ggtagtacct gggacgtcgg ccctatgggc tacggcatgg actactgggg caaagggacc 360
ctggtcactg tctcctca 378

<210> SEQ ID NO 190
<211> LENGTH: 321
<212> TYPE: DNA
<213> ORGANISM: Lama glama

<400> SEQUENCE: 190
tcctctgcac tgactcagcc ctccgcgctg tccgtgtcct tgggacagac ggccaggatc 60
acctgccaag gtggcagctt aggtagcagt tatgctcact ggtaccagca gaagccaggc 120
caggcccctg tgctggtcat ctatggtgat gacagcaggc cctcagggat ccctgagcgg 180
ttctctggct ccagctctgg gggcacagcc accctgacca tcagcggggc ccaggccgag 240
gacgaggatg actattactg tcagtcaaca gacagcagtg gtaatactgt gttcggcgga 300
gggacccgac tgaccgtcct g 321

<210> SEQ ID NO 191
<211> LENGTH: 357
<212> TYPE: DNA
<213> ORGANISM: Lama glama

<400> SEQUENCE: 191
caggtgcagc tggtggagtc tgggggaaac ttggtgcagc ctgggggttc tctgagactc 60
tcctgtgcag cctctggatt caccttcagt aactactaca tgagctgggt ccgccaggct 120
ccagggaagg ggctggaatg ggtgtccgat atttatagtg acggtagtac cacatggtat 180
tcagactccg tcaagggccg attcaccatc tccagagaca acgccaagaa cacgctgtct 240
ctgcaaatga acagtctgaa atctgaggac acggccgtct attactgtgc gcgcgtgaag 300
atctatccgg gggggtatga cgcctggggc caggggaccc aggtcaccgt ctcctca 357

<210> SEQ ID NO 192
<211> LENGTH: 330
<212> TYPE: DNA
<213> ORGANISM: Lama glama

<400> SEQUENCE: 192
caggcagggc tgactcagcc tccctccgtg tctgggtctc caggaaagac ggtcaccatc 60
tcctgtgcag gaaacagcag tgatgttggg tatggaaact atgtctcctg gtaccagcag 120
ttcccaggaa tggcccccaa actcctgata tatctcgtca ataaacgggc ctcagggatc 180
actgatcgct tctctggctc caagtcaggc aacacggcct ccctgaccat ctctgggctc 240
cagtctgagg acgaggctga ttattactgt gcctcatata caggtagcaa caatatcgtg 300
ttcggcggag ggacccatct aaccgtcctc 330

<210> SEQ ID NO 193
<211> LENGTH: 354
<212> TYPE: DNA
<213> ORGANISM: Lama glama

<400> SEQUENCE: 193
caggtgcagc tgcaggagtc ggggggagac ttggtgcagc ctggggggtc tctgagagtc 60
tcctgtgtag tctctggatt caccttcagt cgctactaca tgagctgggt ccgccaggct 120
ccagggaagg ggctcgagtg ggtctcatct attgatagtt atggttacag cacatactat 180
acagactccg tgaagggccg attcaccatc tccagagaca acgccaagaa cacgctgtat 240
ctgcaaatga acagcctgaa acctgaggac acggccctgt attactgtgc aagagcgaaa 300
acgacttgga gttatgacta ctggggccag gggacccagg tcaccgtctc ctca 354

<210> SEQ ID NO 194
<211> LENGTH: 336
<212> TYPE: DNA
<213> ORGANISM: Lama glama

<400> SEQUENCE: 194
gaaattgtgt tgacgcagtc tcccagctcc gtgactgcat ctgtaggagg gaaggtcact 60
atcaactgta agtccagcca gagcgtcttc atagcttcta atcagaaaac ctacttaaac 120
tggtaccagc agagacctgg acagtctccg aggttggtca tcagctatgc gtccacccgt 180
gaatcgggga tccctgatcg attcagcggc agtgggtcca caacagattt cactctcacg 240
atcagcagtg tccagcctga agatgcggcc gtgtattact gtcagcaggc ttatagccat 300
ccaacgttcg gccaggggac caaggtggaa ctcaaa 336

<210> SEQ ID NO 195
<211> LENGTH: 351
<212> TYPE: DNA
<213> ORGANISM: Lama glama

<400> SEQUENCE: 195
gaggtgcagc tcgtggagtc tgggggaggc ttggtgcaac ctggggggttc tctgagactc 60 tcctgtgcag cctctggatt caccttcagg aattaccaca tgagttgggt ccgccaggtt 120
ccagggaagg ggttcgagtg gatctcagat attaatagtg caggtggtag cacatactat 180
gcagactccg tgaagggccg attcaccatc tccagagaca acgccaagaa cacgctgtat 240
ctggaaatga acagcctgaa acctgaggac acggccctgt attactgtgc aagagtcaac 300
gtctgggggg tgaactactg gggcaaaggg accctggtca gcgtctcctc a 351

<210> SEQ ID NO 196
<211> LENGTH: 330
<212> TYPE: DNA
<213> ORGANISM: Lama glama

<400> SEQUENCE: 196
cagactgtgg tgactcagga gccgtccctg tcagtgtctc caggagggac ggtcacactc 60
acctgcggcc tcagctctgg gtctgtcact accagtaact accctggttg gttccagcag 120
acaccaggcc aggctccacg cactcttatc tacaacacaa acagccgcca ctctggggtc 180
cccagtcgct tctccggatc catctctggg aacaaagccg ccctcaccat cacgggggcc 240
cagcccgagg acgaggccga ctattactgt tctctgtacc ctggtagtta cactaatgtg 300
ttcggcggag ggacccatct gaccgtcctg 330

<210> SEQ ID NO 197
<211> LENGTH: 348
<212> TYPE: DNA
<213> ORGANISM: Lama glama

<400> SEQUENCE: 197
gagttgcagc tggtggagtc tgggggaggc ttggtgcagc ctggggggtc tctgagactc 60
tcctgtgcag cctctggatt caccttcagc aactatgtca tgagctgggt ccgccaggct 120
ccaggaaagg ggctcgagtg ggtctcagat actaatagtg gtggtagcac aagctatgca 180
gactccgtga agggccgatt caccatctct agagacaacg ccaagaacac gctgtatttg 240
caaatgaaca gcctgaaacc tgaggacacg gcattgtatt actgtgcgag atcatttttc 300
tacggcatga actactgggg caaagggacc caggtcaccg tgtcctca 348

<210> SEQ ID NO 198
<211> LENGTH: 351
<212> TYPE: DNA
<213> ORGANISM: Lama glama

<400> SEQUENCE: 198
cagtctgccc tgactcagcc gccctccctc tctgcatctc cgggatcatc tgtcagactc 60
acctgcaccc tgagcagtgg aaacaatatt ggcagctatg acataagttg gtaccagcag 120
aaggcaggga gccctccccg gtacctcctg aactactaca ccgactcacg caagcaccag 180
gactccgggg tcccgagccg cttctctggg tccaaagatg cctcggccaa cgcagggctt 240
ctgctcatct ctgggcttca gcccgaggac gaggctgact attactgttc tgcatacaag 300

```
agtggttctt accgttgggt gttcggcgga gggacgcacg tgaccgtcct g           351


<210> SEQ ID NO 199
<211> LENGTH: 450
<212> TYPE: PRT
<213> ORGANISM: Lama glama

<400> SEQUENCE: 199

Gln Leu Gln Leu Val Glu Ser Gly Gly Gly Leu Val Gln Pro Gly Gly
1               5                   10                  15

Ser Leu Arg Val Ser Cys Thr Ala Ser Gly Phe Thr Phe Asn Thr Tyr
            20                  25                  30

Tyr Met Thr Trp Val Arg Gln Ala Pro Gly Lys Gly Leu Glu Trp Val
        35                  40                  45

Ser Asp Ile Asn Ser Gly Gly Gly Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Leu Tyr Tyr Cys Val
                85                  90                  95

Arg Val Arg Ile Trp Pro Val Gly Tyr Asp Tyr Trp Gly Gln Gly Thr
            100                 105                 110

Gln Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Ser Glu Val Phe Val Pro Gln Ser Arg Lys
        435                 440                 445

Val Ile
    450


<210> SEQ ID NO 200
<211> LENGTH: 215
<212> TYPE: PRT
<213> ORGANISM: Lama glama

<400> SEQUENCE: 200

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Asn Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ser Leu Tyr Thr Gly Ser
                85                  90                  95

Tyr Thr Thr Val Phe Gly Gly Gly Thr His Leu Thr Val Leu Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 201
<211> LENGTH: 450
<212> TYPE: PRT
<213> ORGANISM: Lama glama

<400> SEQUENCE: 201

Gln Val Gln Leu Val Glu Ser Gly Gly Gly Leu Val Gln Pro Gly Gly
1               5                   10                  15
```

```
Ser Leu Arg Val Ser Cys Ala Ala Ser Gly Phe Thr Phe Ser Thr Tyr
            20                  25                  30

Tyr Met Ser Trp Val Arg Gln Ala Pro Gly Lys Gly Leu Glu Trp Val
        35                  40                  45

Ser Asp Ile Arg Thr Asp Gly Gly Thr Tyr Tyr Ala Asp Ser Val Lys
    50                  55                  60

Gly Arg Phe Thr Met Ser Arg Asp Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Arg Thr Arg Ile Phe Pro Ser Gly Tyr Asp Tyr Trp Gly Gln Gly Thr
            100                 105                 110

Gln Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Ser Glu Val Phe Val Pro Gln Ser Arg Lys
```

```
        435                 440                 445

Val Ile
    450


<210> SEQ ID NO 202
<211> LENGTH: 214
<212> TYPE: PRT
<213> ORGANISM: Lama glama

<400> SEQUENCE: 202

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Met Gly Ala
65                  70                  75                  80

Gln Pro Glu Asp Glu Ala Asp Tyr Tyr Cys Ser Leu Tyr Pro Gly Ser
                85                  90                  95

Thr Thr Val Phe Gly Gly Gly Thr His Leu Thr Val Leu Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 203
<211> LENGTH: 458
<212> TYPE: PRT
<213> ORGANISM: Lama glama

<400> SEQUENCE: 203

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
```

```
                85                  90                  95

Ala Lys Glu Leu Arg Phe Asp Leu Ala Arg Tyr Thr Asp Tyr Glu Ala
            100                 105                 110

Trp Asp Tyr Trp Gly Gln Gly Thr Gln Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Ser Glu
        435                 440                 445

Val Phe Val Pro Gln Ser Arg Lys Val Ile
    450                 455
```

<210> SEQ ID NO 204
<211> LENGTH: 213
<212> TYPE: PRT
<213> ORGANISM: Lama glama

<400> SEQUENCE: 204

```
Ser Tyr Glu Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210


<210> SEQ ID NO 205
<211> LENGTH: 458
<212> TYPE: PRT
<213> ORGANISM: Lama glama

<400> SEQUENCE: 205

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ser Asp Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Met Arg Leu Tyr Leu Ala Arg Tyr Asn Asp Tyr Glu Ala
            100                 105                 110

Trp Asp Tyr Trp Gly Gln Gly Thr Gln Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160
```

```
Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Ser Glu
        435                 440                 445

Val Phe Val Pro Gln Ser Arg Lys Val Ile
    450                 455


<210> SEQ ID NO 206
<211> LENGTH: 213
<212> TYPE: PRT
<213> ORGANISM: Lama glama

<400> SEQUENCE: 206

Ser Ser Ala Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
```

```
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210


<210> SEQ ID NO 207
<211> LENGTH: 458
<212> TYPE: PRT
<213> ORGANISM: Lama glama

<400> SEQUENCE: 207

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ala Ile Asn Ser Tyr Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Val Arg Ala Asp Leu Ser Arg Tyr Asn Asp Tyr Glu Ser
            100                 105                 110

Tyr Asp Tyr Trp Gly Gln Gly Thr Gln Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220
```

```
Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Ser Glu
        435                 440                 445

Val Phe Val Pro Gln Ser Arg Lys Val Ile
    450                 455
```

<210> SEQ ID NO 208
<211> LENGTH: 211
<212> TYPE: PRT
<213> ORGANISM: Lama glama

<400> SEQUENCE: 208

```
Gln Pro Val Leu Asn Gln Pro Ser Ala Leu Ser Val Thr Leu Gly Gln
1               5                   10                  15

Thr Ala Lys Ile Thr Cys Gln Gly Gly Ser Leu Gly Ala Arg Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Ser Val
                85                  90                  95

Phe Gly Gly Gly Thr His Leu Thr Val Leu Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140
```

```
Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210


<210> SEQ ID NO 209
<211> LENGTH: 458
<212> TYPE: PRT
<213> ORGANISM: Lama glama

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Lys Asp Tyr
            20                  25                  30

Asp Ile Thr Trp Val Arg Gln Ala Pro Gly Lys Gly Leu Glu Trp Val
        35                  40                  45

Ser Thr Ile Thr Ser Arg Ser Gly Ser Thr Ser Tyr Val Asp Ser Val
    50                  55                  60

Lys Gly Arg Phe Thr Ile Ser Gly Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Val Tyr Ala Thr Thr Trp Asp Val Gly Pro Leu Gly Tyr Gly
            100                 105                 110

Met Asp Tyr Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
```

```
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Ser Glu
        435                 440                 445

Val Phe Val Pro Gln Ser Arg Lys Val Ile
    450                 455


<210> SEQ ID NO 210
<211> LENGTH: 213
<212> TYPE: PRT
<213> ORGANISM: Lama glama

<400> SEQUENCE: 210

Ser Tyr Glu Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205
```

```
Pro Thr Glu Cys Ser
    210


<210> SEQ ID NO 211
<211> LENGTH: 458
<212> TYPE: PRT
<213> ORGANISM: Lama glama

<400> SEQUENCE: 211

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met Ser Trp Val Arg Gln Ala Pro Gly Lys Gly Leu Glu Trp Val
        35                  40                  45

Ser Thr Ile Asn Ser Asp Gly Ser Ser Thr Ser Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Val Tyr Gly Ser Thr Trp Asp Val Gly Pro Met Gly Tyr Gly
            100                 105                 110

Met Asp Tyr Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365
```

```
Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Ser Glu
        435                 440                 445

Val Phe Val Pro Gln Ser Arg Lys Val Ile
    450                 455


<210> SEQ ID NO 212
<211> LENGTH: 212
<212> TYPE: PRT
<213> ORGANISM: Lama glama

<400> SEQUENCE: 212

Ser Ser Ala Leu Thr Gln Pro Ser Ala Leu Ser Val Ser Leu Gly Gln
1               5                   10                  15

Thr Ala Arg Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Gly Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Asp Asp Tyr Tyr Cys Gln Ser Thr Asp Ser Ser Gly Asn Thr
                85                  90                  95

Val Phe Gly Gly Gly Thr Arg Leu Thr Val Leu Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210


<210> SEQ ID NO 213
<211> LENGTH: 451
<212> TYPE: PRT
<213> ORGANISM: Lama glama

<400> SEQUENCE: 213

Gln Val Gln Leu Val Glu Ser Gly Gly Asn Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Asp Ile Tyr Ser Asp Gly Ser Thr Thr Trp Tyr Ser Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Ser Glu Asp Thr Ala Val Tyr Tyr Cys
                85                  90                  95

Ala Arg Val Lys Ile Tyr Pro Gly Gly Tyr Asp Ala Trp Gly Gln Gly
            100                 105                 110

Thr Gln Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Ser Glu Val Phe Val Pro Gln Ser Arg
        435                 440                 445

Lys Val Ile
    450


<210> SEQ ID NO 214
<211> LENGTH: 215
<212> TYPE: PRT
<213> ORGANISM: Lama glama

<400> SEQUENCE: 214

Gln Ala Gly Leu Thr Gln Pro Pro Ser Val Ser Gly Ser Pro Gly Lys
1               5                   10                  15

Thr Val Thr Ile Ser Cys Ala Gly Asn Ser Ser Asp Val Gly Tyr Gly
            20                  25                  30

Asn Tyr Val Ser Trp Tyr Gln Gln Phe Pro Gly Met Ala Pro Lys Leu
        35                  40                  45

Leu Ile Tyr Leu Val Asn Lys Arg Ala Ser Gly Ile Thr Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Thr Gly Ser
                85                  90                  95

Asn Asn Ile Val Phe Gly Gly Gly Thr His Leu Thr Val Leu Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 215
<211> LENGTH: 450
<212> TYPE: PRT
<213> ORGANISM: Lama glama

<400> SEQUENCE: 215

Gln Val Gln Leu Gln Glu Ser Gly Gly Asp Leu Val Gln Pro Gly Gly
1               5                   10                  15

Ser Leu Arg Val Ser Cys Val Val Ser Gly Phe Thr Phe Ser Arg Tyr
            20                  25                  30

Tyr Met Ser Trp Val Arg Gln Ala Pro Gly Lys Gly Leu Glu Trp Val
        35                  40                  45

Ser Ser Ile Asp Ser Tyr Gly Tyr Ser Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Lys Pro Glu Asp Thr Ala Leu Tyr Tyr Cys
                85                  90                  95

Ala Arg Ala Lys Thr Thr Trp Ser Tyr Asp Tyr Trp Gly Gln Gly Thr
            100                 105                 110

Gln Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Ser Glu Val Phe Val Pro Gln Ser Arg Lys
        435                 440                 445

Val Ile
    450
```

<210> SEQ ID NO 216
<211> LENGTH: 219
<212> TYPE: PRT
<213> ORGANISM: Lama glama

<400> SEQUENCE: 216

```
Glu Ile Val Leu Thr Gln Ser Pro Ser Ser Val Thr Ala Ser Val Gly
1               5                   10                  15

Gly Lys Val Thr Ile Asn Cys Lys Ser Ser Gln Ser Val Phe Ile Ala
            20                  25                  30

Ser Asn Gln Lys Thr Tyr Leu Asn Trp Tyr Gln Gln Arg Pro Gly Gln
        35                  40                  45

Ser Pro Arg Leu Val Ile Ser Tyr Ala Ser Thr Arg Glu Ser Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser His Pro Thr Phe Gly Gln Gly Thr Lys Val Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 217
<211> LENGTH: 449
<212> TYPE: PRT
<213> ORGANISM: Lama glama

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

His Met Ser Trp Val Arg Gln Val Pro Gly Lys Gly Phe Glu Trp Ile
        35                  40                  45

Ser Asp Ile Asn Ser Ala Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Glu Met Asn Ser Leu Lys Pro Glu Asp Thr Ala Leu Tyr Tyr Cys
                85                  90                  95

Ala Arg Val Asn Val Trp Gly Val Asn Tyr Trp Gly Lys Gly Thr Leu
            100                 105                 110

Val Ser Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
```

```
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Ser Glu Val Phe Val Pro Gln Ser Arg Lys Val
        435                 440                 445

Ile
```

<210> SEQ ID NO 218
<211> LENGTH: 215
<212> TYPE: PRT
<213> ORGANISM: Lama glama

<400> SEQUENCE: 218

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
```

```
65                  70                  75                  80

Gln Pro Glu Asp Glu Ala Asp Tyr Tyr Cys Ser Leu Tyr Pro Gly Ser
                85                  90                  95

Tyr Thr Asn Val Phe Gly Gly Gly Thr His Leu Thr Val Leu Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 219
<211> LENGTH: 448
<212> TYPE: PRT
<213> ORGANISM: Lama glama

<400> SEQUENCE: 219

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Val Met Ser Trp Val Arg Gln Ala Pro Gly Lys Gly Leu Glu Trp Val
        35                  40                  45

Ser Asp Thr Asn Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Arg Ser Phe Phe Tyr Gly Met Asn Tyr Trp Gly Lys Gly Thr Gln Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Ser Glu Val Phe Val Pro Gln Ser Arg Lys Val Ile
        435                 440                 445


<210> SEQ ID NO 220
<211> LENGTH: 222
<212> TYPE: PRT
<213> ORGANISM: Lama glama

<400> SEQUENCE: 220

Gln Ser Ala Leu Thr Gln Pro Pro Ser Leu Ser Ala Ser Pro Gly Ser
1               5                   10                  15

Ser Val Arg Leu Thr Cys Thr Leu Ser Ser Gly Asn Asn Ile Gly Ser
            20                  25                  30

Tyr Asp Ile Ser Trp Tyr Gln Gln Lys Ala Gly Ser Pro Pro Arg Tyr
        35                  40                  45

Leu Leu Asn Tyr Tyr Thr Asp Ser Arg Lys His Gln Asp Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ser Ala Tyr Lys Ser Gly Ser Tyr Arg Trp Val Phe Gly Gly Gly Thr
            100                 105                 110

His Val Thr Val Leu Gln Pro Lys Ala Ala Pro Ser Val Thr Leu Phe
        115                 120                 125

Pro Pro Ser Ser Glu Glu Leu Gln Ala Asn Lys Ala Thr Leu Val Cys
    130                 135                 140

Leu Ile Ser Asp Phe Tyr Pro Gly Ala Val Thr Val Ala Trp Lys Ala
145                 150                 155                 160
```

```
Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Cys Ser
    210                 215                 220


<210> SEQ ID NO 221
<211> LENGTH: 442
<212> TYPE: PRT
<213> ORGANISM: Lama glama

<400> SEQUENCE: 221

Gln Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Thr Tyr
            20                  25                  30

Tyr Met Ser Trp Val Arg Gln Ala Pro Gly Lys Gly Leu Glu Trp Val
        35                  40                  45

Ser Asp Ile Arg Thr Asp Gly Gly Thr Tyr Tyr Ala Asp Ser Val Lys
    50                  55                  60

Gly Arg Phe Thr Met Ser Arg Asp Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Arg Thr Arg Ile Phe Pro Ser Gly Tyr Asp Tyr Trp Gly Gln Gly Thr
            100                 105                 110

Gln Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Pro
            180                 185                 190

Arg Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
```

```
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asn Thr Asn Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440


<210> SEQ ID NO 222
<211> LENGTH: 219
<212> TYPE: PRT
<213> ORGANISM: Lama glama

<400> SEQUENCE: 222

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Met Gly Ala
65                  70                  75                  80

Gln Pro Glu Asp Glu Ala Asp Tyr Tyr Cys Ser Leu Tyr Pro Gly Ser
                85                  90                  95

Thr Thr Val Phe Gly Gly Gly Thr His Leu Thr Val Leu Gly Gln Pro
            100                 105                 110

Lys Ser Ser Pro Ser Val Thr Leu Phe Pro Pro Ser Ser Glu Glu Leu
        115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Glu Thr Thr Gln Pro Ser Lys Gln Ser Asn Asn Lys
                165                 170                 175

Tyr Met Glu Thr Ala Ser Ser Tyr Leu Thr Leu Thr Ala Arg Ala Trp
            180                 185                 190

Glu Arg His Ser Ser Tyr Ser Cys Gln Val Thr His Glu Gly His Thr
        195                 200                 205

Val Glu Lys Ser Leu Ser Arg Ala Asp Cys Ser
    210                 215


<210> SEQ ID NO 223
<211> LENGTH: 450
```

<212> TYPE: PRT
<213> ORGANISM: Lama glama

<400> SEQUENCE: 223

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ala Ile Asn Ser Tyr Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Val Arg Ala Asp Leu Ser Arg Tyr Asn Asp Tyr Glu Ser
            100                 105                 110

Tyr Asp Tyr Trp Gly Gln Gly Thr Gln Val Thr Val Ser Ser Ala Lys
        115                 120                 125

Thr Thr Pro Pro Ser Val Tyr Pro Leu Ala Pro Gly Ser Ala Ala Gln
    130                 135                 140

Thr Asn Ser Met Val Thr Leu Gly Cys Leu Val Lys Gly Tyr Phe Pro
145                 150                 155                 160

Glu Pro Val Thr Val Thr Trp Asn Ser Gly Ser Leu Ser Ser Gly Val
                165                 170                 175

His Thr Phe Pro Ala Val Leu Gln Ser Asp Leu Tyr Thr Leu Ser Ser
            180                 185                 190

Ser Val Thr Val Pro Ser Ser Pro Arg Pro Ser Glu Thr Val Thr Cys
        195                 200                 205

Asn Val Ala His Pro Ala Ser Ser Thr Lys Val Asp Lys Lys Ile Val
    210                 215                 220

Pro Arg Asp Cys Gly Cys Lys Pro Cys Ile Cys Thr Val Pro Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Lys Asp
            260                 265                 270

Asp Pro Glu Val Gln Phe Ser Trp Phe Val Asp Asp Val Glu Val His
        275                 280                 285

Thr Ala Gln Thr Gln Pro Arg Glu Glu Gln Phe Asn Ser Thr Phe Arg
    290                 295                 300

Ser Val Ser Glu Leu Pro Ile Met His Gln Asp Trp Leu Asn Gly Lys
305                 310                 315                 320

Glu Phe Lys Cys Arg Val Asn Ser Ala Ala Phe Pro Ala Pro Ile Glu
                325                 330                 335

Lys Thr Ile Ser Lys Thr Lys Gly Arg Pro Lys Ala Pro Gln Val Tyr
            340                 345                 350

Thr Ile Pro Pro Pro Lys Glu Gln Met Ala Lys Asp Lys Val Ser Leu
        355                 360                 365

Thr Cys Met Ile Thr Asp Phe Phe Pro Glu Asp Ile Thr Val Glu Trp
    370                 375                 380

Gln Trp Asn Gly Gln Pro Ala Glu Asn Tyr Lys Asn Thr Gln Pro Ile
385                 390                 395                 400
```

Met Asn Thr Asn Gly Ser Tyr Phe Val Tyr Ser Lys Leu Asn Val Gln
405 410 415

Lys Ser Asn Trp Glu Ala Gly Asn Thr Phe Thr Cys Ser Val Leu His
420 425 430

Glu Gly Leu His Asn His His Thr Glu Lys Ser Leu Ser His Ser Pro
435 440 445

Gly Lys
450

<210> SEQ ID NO 224
<211> LENGTH: 216
<212> TYPE: PRT
<213> ORGANISM: Lama glama

<400> SEQUENCE: 224

Gln Pro Val Leu Asn Gln Pro Ser Ala Leu Ser Val Thr Leu Gly Gln
1 5 10 15

Thr Ala Lys Ile Thr Cys Gln Gly Gly Ser Leu Gly Ala Arg Tyr Ala
20 25 30

His Trp Tyr Gln Gln Lys Pro Gly Gln Ala Pro Val Leu Val Ile Tyr
35 40 45

Asp Asp Asp Ser Arg Pro Ser Gly Ile Pro Glu Arg Phe Ser Gly Ser
50 55 60

Ser Ser Gly Gly Thr Ala Thr Leu Thr Ile Ser Gly Ala Gln Ala Glu
65 70 75 80

Asp Glu Gly Asp Tyr Tyr Cys Gln Ser Ala Asp Ser Ser Gly Ser Val
85 90 95

Phe Gly Gly Gly Thr His Leu Thr Val Leu Gly Gln Pro Lys Ser Ser
100 105 110

Pro Ser Val Thr Leu Phe Pro Pro Ser Ser Glu Glu Leu Glu Thr Asn
115 120 125

Lys Ala Thr Leu Val Cys Thr Ile Thr Asp Phe Tyr Pro Gly Val Val
130 135 140

Thr Val Asp Trp Lys Val Asp Gly Thr Pro Val Thr Gln Gly Met Glu
145 150 155 160

Thr Glu Thr Thr Gln Pro Ser Lys Gln Ser Asn Asn Lys Tyr Met Glu
165 170 175

Thr Ala Ser Ser Tyr Leu Thr Leu Thr Ala Arg Ala Trp Glu Arg His
180 185 190

Ser Ser Tyr Ser Cys Gln Val Thr His Glu Gly His Thr Val Glu Lys
195 200 205

Ser Leu Ser Arg Ala Asp Cys Ser
210 215

<210> SEQ ID NO 225
<211> LENGTH: 450
<212> TYPE: PRT
<213> ORGANISM: Lama glama

<400> SEQUENCE: 225

Glu Val Gln Leu Gln Glu Ser Gly Gly Gly Leu Val Gln Pro Gly Gly
1 5 10 15

Ser Leu Arg Leu Ser Cys Ala Ala Ser Gly Phe Thr Phe Ser Ile Tyr
20 25 30

Asp Met Ser Trp Val Arg Gln Ala Pro Gly Lys Gly Leu Glu Trp Val
35 40 45

```
Ser Thr Ile Asn Ser Asp Gly Ser Ser Thr Ser Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Val Tyr Gly Ser Thr Trp Asp Val Gly Pro Met Gly Tyr Gly
            100                 105                 110

Met Asp Tyr Trp Gly Lys Gly Thr Leu Val Thr Val Ser Ser Ala Lys
        115                 120                 125

Thr Thr Pro Pro Ser Val Tyr Pro Leu Ala Pro Gly Ser Ala Ala Gln
    130                 135                 140

Thr Asn Ser Met Val Thr Leu Gly Cys Leu Val Lys Gly Tyr Phe Pro
145                 150                 155                 160

Glu Pro Val Thr Val Thr Trp Asn Ser Gly Ser Leu Ser Ser Gly Val
                165                 170                 175

His Thr Phe Pro Ala Val Leu Gln Ser Asp Leu Tyr Thr Leu Ser Ser
            180                 185                 190

Ser Val Thr Val Pro Ser Ser Pro Arg Pro Ser Glu Thr Val Thr Cys
        195                 200                 205

Asn Val Ala His Pro Ala Ser Ser Thr Lys Val Asp Lys Lys Ile Val
    210                 215                 220

Pro Arg Asp Cys Gly Cys Lys Pro Cys Ile Cys Thr Val Pro Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Lys Asp
            260                 265                 270

Asp Pro Glu Val Gln Phe Ser Trp Phe Val Asp Asp Val Glu Val His
        275                 280                 285

Thr Ala Gln Thr Gln Pro Arg Glu Glu Gln Phe Asn Ser Thr Phe Arg
    290                 295                 300

Ser Val Ser Glu Leu Pro Ile Met His Gln Asp Trp Leu Asn Gly Lys
305                 310                 315                 320

Glu Phe Lys Cys Arg Val Asn Ser Ala Ala Phe Pro Ala Pro Ile Glu
                325                 330                 335

Lys Thr Ile Ser Lys Thr Lys Gly Arg Pro Lys Ala Pro Gln Val Tyr
            340                 345                 350

Thr Ile Pro Pro Pro Lys Glu Gln Met Ala Lys Asp Lys Val Ser Leu
        355                 360                 365

Thr Cys Met Ile Thr Asp Phe Phe Pro Glu Asp Ile Thr Val Glu Trp
    370                 375                 380

Gln Trp Asn Gly Gln Pro Ala Glu Asn Tyr Lys Asn Thr Gln Pro Ile
385                 390                 395                 400

Met Asn Thr Asn Gly Ser Tyr Phe Val Tyr Ser Lys Leu Asn Val Gln
                405                 410                 415

Lys Ser Asn Trp Glu Ala Gly Asn Thr Phe Thr Cys Ser Val Leu His
            420                 425                 430

Glu Gly Leu His Asn His His Thr Glu Lys Ser Leu Ser His Ser Pro
        435                 440                 445

Gly Lys
    450
```

```
<210> SEQ ID NO 226
<211> LENGTH: 217
<212> TYPE: PRT
<213> ORGANISM: Lama glama

<400> SEQUENCE: 226

Ser Ser Ala Leu Thr Gln Pro Ser Ala Leu Ser Val Ser Leu Gly Gln
1               5                   10                  15

Thr Ala Arg Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Gly Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Asp Asp Tyr Tyr Cys Gln Ser Thr Asp Ser Ser Gly Asn Thr
                85                  90                  95

Val Phe Gly Gly Gly Thr Arg Leu Thr Val Leu Gly Gln Pro Lys Ser
            100                 105                 110

Ser Pro Ser Val Thr Leu Phe Pro Pro Ser Ser Glu Glu Leu Glu Thr
        115                 120                 125

Asn Lys Ala Thr Leu Val Cys Thr Ile Thr Asp Phe Tyr Pro Gly Val
    130                 135                 140

Val Thr Val Asp Trp Lys Val Asp Gly Thr Pro Val Thr Gln Gly Met
145                 150                 155                 160

Glu Thr Glu Thr Thr Gln Pro Ser Lys Gln Ser Asn Asn Lys Tyr Met
                165                 170                 175

Glu Thr Ala Ser Ser Tyr Leu Thr Leu Thr Ala Arg Ala Trp Glu Arg
            180                 185                 190

His Ser Ser Tyr Ser Cys Gln Val Thr His Glu Gly His Thr Val Glu
        195                 200                 205

Lys Ser Leu Ser Arg Ala Asp Cys Ser
    210                 215


<210> SEQ ID NO 227
<211> LENGTH: 10
<212> TYPE: PRT
<213> ORGANISM: Homo sapiens

<400> SEQUENCE: 227

Glu Pro Lys Ser Cys Asp Lys Thr His Thr
1               5                   10


<210> SEQ ID NO 228
<211> LENGTH: 5
<212> TYPE: PRT
<213> ORGANISM: Homo sapiens

<400> SEQUENCE: 228

Cys Pro Pro Cys Pro
1               5


<210> SEQ ID NO 229
<211> LENGTH: 8
<212> TYPE: PRT
<213> ORGANISM: Homo sapiens

<400> SEQUENCE: 229
```

Ala Pro Glu Leu Leu Gly Gly Pro
1               5

<210> SEQ ID NO 230
<211> LENGTH: 12
<212> TYPE: PRT
<213> ORGANISM: Homo sapiens

<400> SEQUENCE: 230

Glu Leu Lys Thr Pro Leu Gly Asp Thr Thr His Thr
1               5                   10

<210> SEQ ID NO 231
<211> LENGTH: 5
<212> TYPE: PRT
<213> ORGANISM: Homo sapiens

<400> SEQUENCE: 231

Cys Pro Arg Cys Pro
1               5

<210> SEQ ID NO 232
<211> LENGTH: 8
<212> TYPE: PRT
<213> ORGANISM: Homo sapiens

<400> SEQUENCE: 232

Ala Pro Glu Leu Leu Gly Gly Pro
1               5

<210> SEQ ID NO 233
<211> LENGTH: 7
<212> TYPE: PRT
<213> ORGANISM: Homo sapiens

<400> SEQUENCE: 233

Glu Ser Lys Tyr Gly Pro Pro
1               5

<210> SEQ ID NO 234
<211> LENGTH: 5
<212> TYPE: PRT
<213> ORGANISM: Homo sapiens

<400> SEQUENCE: 234

Cys Pro Ser Cys Pro
1               5

<210> SEQ ID NO 235
<211> LENGTH: 8
<212> TYPE: PRT
<213> ORGANISM: Homo sapiens

<400> SEQUENCE: 235

Ala Pro Glu Phe Leu Gly Gly Pro
1               5

<210> SEQ ID NO 236
<211> LENGTH: 3
<212> TYPE: PRT
<213> ORGANISM: Homo sapiens

<400> SEQUENCE: 236

Glu Arg Lys

1

<210> SEQ ID NO 237
<211> LENGTH: 10
<212> TYPE: PRT
<213> ORGANISM: Homo sapiens

<400> SEQUENCE: 237

Cys Cys Val Glu Cys Pro Pro Pro Cys Pro
1 5 10

<210> SEQ ID NO 238
<211> LENGTH: 7
<212> TYPE: PRT
<213> ORGANISM: Homo sapiens

<400> SEQUENCE: 238

Ala Pro Pro Val Ala Gly Pro
1 5

<210> SEQ ID NO 239
<211> LENGTH: 100
<212> TYPE: PRT
<213> ORGANISM: Homo sapiens

<400> SEQUENCE: 239

Arg Phe Cys Ser Ile Asn Ser Gly Leu His Ser Tyr Met Glu Met Pro
1 5 10 15

Leu Glu Cys Ile Leu Thr Glu Lys Arg Lys Lys Arg Ser Thr Lys Lys
20 25 30

Glu Val Phe Asn Ile Leu Gln Ala Ala Tyr Val Ser Lys Pro Gly Ala
35 40 45

Gln Leu Ala Arg Gln Ile Gly Ala Ser Leu Asn Asp Asp Ile Leu Phe
50 55 60

Gly Val Phe Ala Gln Ser Lys Pro Asp Ser Ala Glu Pro Met Asp Arg
65 70 75 80

Ser Ala Met Cys Ala Phe Pro Ile Lys Tyr Val Asn Asp Phe Phe Asn
85 90 95

Lys Ile Val Asn
100

<210> SEQ ID NO 240
<211> LENGTH: 100
<212> TYPE: PRT
<213> ORGANISM: Mus musculus

<400> SEQUENCE: 240

Arg Phe Cys Ser Val Asp Ser Gly Leu His Ser Tyr Met Glu Met Pro
1 5 10 15

Leu Glu Cys Ile Leu Thr Glu Lys Arg Arg Lys Arg Ser Thr Arg Glu
20 25 30

Glu Val Phe Asn Ile Leu Gln Ala Ala Tyr Val Ser Lys Pro Gly Ala
35 40 45

Asn Leu Ala Lys Gln Ile Gly Ala Ser Pro Ser Asp Asp Ile Leu Phe
50 55 60

Gly Val Phe Ala Gln Ser Lys Pro Asp Ser Ala Glu Pro Val Asn Arg
65 70 75 80

Ser Ala Val Cys Ala Phe Pro Ile Lys Tyr Val Asn Asp Phe Phe Asn
85 90 95

```
Lys Ile Val Asn
            100


<210> SEQ ID NO 241
<211> LENGTH: 100
<212> TYPE: PRT
<213> ORGANISM: Rattus norvegicus

<400> SEQUENCE: 241

Arg Phe Cys Ser Val Asp Ser Gly Leu His Ser Tyr Met Glu Met Pro
1               5                   10                  15

Leu Glu Cys Ile Leu Thr Glu Lys Arg Arg Lys Arg Ser Thr Arg Glu
            20                  25                  30

Glu Val Phe Asn Ile Leu Gln Ala Ala Tyr Val Ser Lys Pro Gly Ala
        35                  40                  45

Asn Leu Ala Lys Gln Ile Gly Ala Ser Pro Tyr Asp Asp Ile Leu Tyr
    50                  55                  60

Gly Val Phe Ala Gln Ser Lys Pro Asp Ser Ala Glu Pro Met Asn Arg
65                  70                  75                  80

Ser Ala Val Cys Ala Phe Pro Ile Lys Tyr Val Asn Asp Phe Phe Asn
                85                  90                  95

Lys Ile Val Asn
            100


<210> SEQ ID NO 242
<211> LENGTH: 100
<212> TYPE: PRT
<213> ORGANISM: Macaca fascicularis

<400> SEQUENCE: 242

Arg Phe Cys Ser Leu Asn Ser Gly Leu His Ser Tyr Met Glu Met Pro
1               5                   10                  15

Leu Glu Cys Ile Leu Thr Glu Lys Arg Lys Lys Arg Ser Thr Lys Lys
            20                  25                  30

Glu Val Phe Asn Ile Leu Gln Ala Ala Tyr Val Ser Lys Pro Gly Ala
        35                  40                  45

Gln Leu Ala Arg Gln Ile Gly Ala Ser Leu Asn Asp Asp Ile Leu Phe
    50                  55                  60

Gly Val Phe Ala Gln Ser Lys Pro Asp Ser Ala Glu Pro Met Asp Arg
65                  70                  75                  80

Ser Ala Met Cys Ala Phe Pro Ile Lys Tyr Val Asn Asp Phe Phe Asn
                85                  90                  95

Lys Ile Val Asn
            100


<210> SEQ ID NO 243
<211> LENGTH: 100
<212> TYPE: PRT
<213> ORGANISM: Lama glama

<400> SEQUENCE: 243

Arg Phe Cys Ser Val Asp Ser Gly Leu His Ser Tyr Met Glu Met Pro
1               5                   10                  15

Leu Glu Cys Ile Leu Thr Glu Lys Arg Arg Arg Arg Ser Thr Lys Glu
            20                  25                  30

Glu Val Phe Asn Ile Leu Gln Ala Ala Tyr Val Ser Lys Pro Gly Ser
        35                  40                  45

Gln Leu Ala Lys Gln Ile Gly Ala Asn Leu Asn Asp Asp Ile Leu Tyr
```

```
    50                  55                  60

Gly Val Phe Ala Gln Ser Lys Pro Asp Ser Ala Glu Pro Met Asn Arg
65                  70                  75                  80

Ser Ala Val Cys Ala Phe Pro Val Lys Tyr Val Asn Glu Phe Phe Asn
                85                  90                  95

Lys Ile Val Asn
            100


<210> SEQ ID NO 244
<211> LENGTH: 50
<212> TYPE: PRT
<213> ORGANISM: Homo sapiens

<400> SEQUENCE: 244

Leu Ser Ala Pro Pro Phe Val Gln Cys Gly Trp Cys His Asp Lys Cys
1               5                   10                  15

Val Arg Ser Glu Glu Cys Leu Ser Gly Thr Trp Thr Gln Gln Ile Cys
            20                  25                  30

Leu Pro Ala Ile Tyr Lys Val Phe Pro Asn Ser Ala Pro Leu Glu Gly
        35                  40                  45

Gly Thr
    50


<210> SEQ ID NO 245
<211> LENGTH: 50
<212> TYPE: PRT
<213> ORGANISM: Mus musculus

<400> SEQUENCE: 245

Leu Ser Ala Pro Tyr Phe Ile Gln Cys Gly Trp Cys His Asn Gln Cys
1               5                   10                  15

Val Arg Phe Asp Glu Cys Pro Ser Gly Thr Trp Thr Gln Glu Ile Cys
            20                  25                  30

Leu Pro Ala Val Tyr Lys Val Phe Pro Thr Ser Ala Pro Leu Glu Gly
        35                  40                  45

Gly Thr
    50


<210> SEQ ID NO 246
<211> LENGTH: 50
<212> TYPE: PRT
<213> ORGANISM: Rattus norvegicus

<400> SEQUENCE: 246

Leu Ser Ala Pro Tyr Phe Ile Gln Cys Gly Trp Cys His Asn Arg Cys
1               5                   10                  15

Val His Ser Asn Glu Cys Pro Ser Gly Thr Trp Thr Gln Glu Ile Cys
            20                  25                  30

Leu Pro Ala Val Tyr Lys Val Phe Pro Thr Ser Ala Pro Leu Glu Gly
        35                  40                  45

Gly Thr
    50


<210> SEQ ID NO 247
<211> LENGTH: 50
<212> TYPE: PRT
<213> ORGANISM: Macaca fascicularis

<400> SEQUENCE: 247
```

-continued

```
Leu Ser Ala Pro Pro Phe Val Gln Cys Gly Trp Cys His Asp Lys Cys
1               5                   10                  15

Val Arg Ser Glu Glu Cys Pro Ser Gly Thr Trp Thr Gln Gln Ile Cys
            20                  25                  30

Leu Pro Ala Ile Tyr Lys Val Phe Pro Thr Ser Ala Pro Leu Glu Gly
        35                  40                  45

Gly Thr
    50


<210> SEQ ID NO 248
<211> LENGTH: 50
<212> TYPE: PRT
<213> ORGANISM: Lama glama

<400> SEQUENCE: 248

Leu Ser Ala Pro Ser Phe Val Gln Cys Gly Trp Cys His Asp Lys Cys
1               5                   10                  15

Val Gln Leu Glu Glu Cys Ser Gly Gly Ile Trp Thr Gln Glu Ile Cys
            20                  25                  30

Leu Pro Thr Ile Tyr Lys Val Leu Pro Thr Ser Ala Pro Leu Glu Gly
        35                  40                  45

Gly Thr
    50
```

ANTI-MET ANTIBODIES AND USES THEREOF

FIELD OF THE INVENTION

The present invention relates to antibodies and antigen binding fragments that bind with high affinity to the human and mouse hepatocyte growth factor (HGF) receptor, also known as MET. The antibodies and antigen binding fragments are agonists of MET in both humans and mice, resulting in molecular and cellular effects resembling the effects of HGF binding. The invention further relates to therapeutic uses of antibodies and antigen binding fragments that are agonists of MET.

BACKGROUND

HGF is a pleiotropic cytokine of mesenchymal origin that mediates a characteristic array of biological functions including cell proliferation, motility, differentiation and survival. The HGF receptor, also known as MET, is expressed by a variety of tissues including all epithelia, the endothelium, muscle cells, neuronal cells, osteoblasts, hematopoietic cells and various components of the immune system.

HGF and MET signalling plays an essential role during embryo development, where it guides migration of precursor cells and determines cell survival or death. In adults, HGF/MET signalling is ordinarily quiescent and is resumed during wound healing and tissue regeneration. Some cancers and tumours usurp HGF/MET signalling in order to promote the survival and proliferation of the tumour in the host organism. Therefore, inhibiting the HGF-MET axis has become a popular target for anti-cancer treatment, though with limited success.

Due to its role in tissue healing and regeneration, recombinant HGF has also been investigated as a treatment for a number of conditions, including degenerative diseases, inflammatory diseases, auto-immune diseases, metabolic diseases, and transplantation-related disorders. However, recombinant HGF has poor pharmacological properties: it requires proteolytic activation in order to become biologically active; once activated, it has an extremely short half-life in vivo; and its industrial manufacture is complex and expensive.

Agonistic anti-MET antibodies which activate MET in a manner mimicking that of HGF have been proposed as alternatives.

The following antibodies that mimic HGF activity, at least partially, have been described: (i) the 3D6 mouse anti-human MET antibody (U.S. Pat. No. 6,099,841); (ii) the 5D5 mouse anti-human MET antibody (U.S. Pat. No. 5,686,292); (iii) the NO-23 mouse anti-human MET antibody (U.S. Pat. No. 7,556,804B2); (iv) the B7 human naïve anti-human MET antibody (U.S. Patent Application No. 2014/0193431 A1); (v) the DO-24 mouse anti-human MET antibody (Prat et al., Mol Cell Biol. 11, 5954-5962, 1991; Prat et al., J Cell Sci. 111, 237-247, 1998); and (vi) the DN-30 mouse anti-human MET antibody (Prat et al., Mol Cell Biol. 11, 5954-5962, 1991; Prat et al., J Cell Sci. 111, 237-247, 1998).

SUMMARY OF INVENTION

Agonistic anti-MET antibodies generated to date, for example those described in the Background section, are frequently obtained as by-products from processes intending to identify antagonistic molecules and are not designed explicitly to become agonistic molecules for therapeutic use. Moreover, the most manifest limit of the prior art anti-MET antibodies is that they have been generated in a mouse system (except for B7 that was identified using a human naïve phage library); as a result, it is unlikely that these antibodies will display cross-reactivity with mouse MET. Even if a minor cross-reactivity with self-antigens is in principle possible, these interactions have normally a very low affinity.

While the absence of cross-reactivity is not a concern for mouse models of cancer (as they employ human xenografts), cross-reactivity of antibodies between human and mouse MET is an important requirement for pre-clinical mouse models of regenerative medicine or non-oncological human diseases, which require the antibody to function on mouse tissues and cells.

Not only is it necessary for an agonistic anti-MET antibody to cross-react with mouse MET in order for the antibody to be evaluated in pre-clinical models, but it is desirable that the antibody binds to mouse MET with an affinity the same or similar to its affinity for human MET, and also that the antibody elicits effects in mouse systems the same or similar to the effects which it evokes in human systems—otherwise the experiments conducted in pre-clinical models will not be predictive of the human situation. As demonstrated in the Examples, none of the prior art anti-MET agonistic antibodies exhibit affinity for mouse MET, and certainly none of the prior art antibodies exhibit the same or similar binding and agonistic effects in both mouse and human systems.

The present application provides anti-MET agonistic antibodies made by design to bind to both human and mouse MET with high affinities. These antibodies: (i) display agonistic activity in both human and mouse MET biological systems—that is they induce MET signalling—some with a potency similar or superior to that of HGF; (ii) elicit the full spectrum of HGF-induced biological activities, thus representing valid substitutes for recombinant HGF; (iii) exhibit superior binding to mouse MET when directly compared to prior art antibodies; (iv) display biologically significant agonistic activity at concentrations as low as 1 pM; (v) display a plasma half-life of several days in mice, reaching pharmacologically saturating concentrations already at a dose of 1 μg/kg, which is very low for a therapeutic antibody; (vi) preserve renal function and kidney integrity in a mouse model of acute kidney injury; (vii) prevent liver failure and antagonize hepatocyte damage in a mouse model of acute liver injury; (viii) display anti-fibrotic, anti-inflammatory and pro-regenerative activity in a mouse model of chronic liver damage; (ix) prevent weight loss, attenuate intestinal bleeding, preserve colon integrity, suppress inflammation and promote epithelial regeneration in a mouse model of ulcerative colitis and a mouse model of inflammatory bowel disease; (x) promote insulin-independent uptake of glucose in a mouse model of type I diabetes; (xi) overcome insulin resistance in a mouse model of type II diabetes; (xii) ameliorate fatty liver, suppress fibrosis and restore liver function in a mouse model of non-alcoholic steatohepatitis (NASH); (xiii) accelerate wound healing in a mouse model of diabetic ulcer; (xiv) cross-react with *Rattus norvegicus* MET and *Macaca fascicularis* MET, thus allowing to conduct toxicological and pharmacological studies in these two vertebrates, required prior to applying for first-in-human trials; (xv) recognise epitopes conserved across human, mouse, rat and cynomolgus macaque, thereby providing greater utility across animal models.

Therefore, in a first aspect, the present invention provides an antibody, or an antigen binding fragment thereof, which binds human MET protein (hMET) with high affinity and binds mouse MET protein (mMET) with high affinity, wherein the antibody or an antigen binding fragment thereof is a hMET agonist and a mMET agonist. In certain embodiments, the antibody or antigen binding fragment thereof comprises at least one heavy chain variable domain (VH) and at least one light chain variable domain (VL), wherein said VH and VL domain, when tested as a Fab fragment, exhibit an off-rate ($k_{off}$ measured by Biacore) for hMET in the range of from $1\times10^{-3}$ $s^{-1}$ to $1\times10^{-2}$ $s^{-1}$, optionally $1\times10^{-3}$ $s^{-1}$ to $6\times10^{-3}$ $s^{-1}$, and exhibit an off-rate ($k_{off}$ measured by Biacore) for mMET in the range of from $1\times10^{-3}$ $s^{-1}$ to $1\times10^{-2}$ $s^{-1}$, optionally $1\times10^{-3}$ $s^{-1}$ to $6\times10^{-3}$ $s^{-1}$. In certain embodiments, the antibody or antigen binding fragment thereof has equivalent affinity for hMET and mMET.

In certain embodiments, the antibody or antigen binding fragment thereof induces phosphorylation of hMET and induces phosphorylation of mMET. In certain embodiments, the antibody or antigen binding fragment induces phosphorylation of hMET with an $EC_{50}$ (as measured by phospho-MET ELISA) of less than 3.0 nM, optionally less than 2.0 nM and induces phosphorylation of mMET with an $EC_{50}$ (as measured by phospho-MET ELISA) of less than 3.0 nM, optionally less than 2.0 nM. In certain embodiments, the antibody or antigen binding fragment thereof induces phosphorylation of hMET and mMET equivalently.

In certain embodiments, the antibody or antigen binding fragment thereof exhibits high phosphorylation potency for hMET and exhibits high phosphorylation potency for mMET. In certain embodiments, the antibody or antigen binding fragment thereof induces phosphorylation of hMET with an $EC_{50}$ of less than 1 nM and/or an $E_{max}$ (as a percentage of HGF-induced activation in a phospho-MET ELISA) of at least 80% and induces phosphorylation of mMET with an $EC_{50}$ of less than 1 nM and/or an $E_{max}$ (as a percentage of HGF-induced activation in a phospho-MET ELISA) of at least 80%. In certain alternative embodiments, the antibody or antigen binding fragment thereof exhibits low phosphorylation potency for hMET and exhibits low phosphorylation potency for mMET. In certain such embodiments, the antibody or antigen binding fragment thereof induces phosphorylation of hMET with $EC_{50}$ of 1 nM-5 nM and/or an $E_{max}$ (as a percentage of HGF-induced activation in a phospho-MET ELISA) of 60-80% and induces phosphorylation of mMET with $EC_{50}$ of 1 nM-5 nM and/or an $E_{max}$ (as a percentage of HGF-induced activation in a phospho-MET ELISA) of 60-80%.

In certain embodiments, the antibody or antigen binding fragment thereof induces an HGF-like cellular response when contacted with a human cell and induces an HGF-like cellular response when contacted with a mouse cell. In certain embodiments, the antibody or antigen binding fragment thereof fully induces an HGF-like cellular response when contacted with a human cell and when contacted with a mouse cell. In certain embodiments, full induction of HGF-like cellular response is measurable as one, any two, or all of:

(i) in a cell scattering assay, the antibody or antigen binding fragment thereof induces cell scattering comparable to maximal HGF-induced scattering when the antibody or antigen binding fragment thereof is at a concentration of 0.1-1.0 nM;

(ii) in an anti-apoptotic cell assay, the antibody or antigen binding fragment thereof exhibits an $EC_{50}$ of less than 1.1× that of HGF, and/or with an $E_{max}$ (measured as a of total ATP content of non-apoptotic control cells) of greater than 90% that observed for HGF; and/or (iii) in a branching morphogenesis assay, cells treated with the antibody exhibit greater than 90% of the number of branches per spheroid induced by the same (non-zero) concentration of HGF.

In certain embodiments, the antibody or antigen binding fragment thereof partially induces an HGF-like cellular response when contacted with a human cell and when contacted with a mouse cell. In certain embodiments, partial induction of an HGF-like cellular response is measurable as:

(i) in a cell scattering assay, the antibody or antigen binding fragment thereof induces cell scattering of at least 25% that induced by 0.1 nM homologous HGF when the antibody concentration is 1 nM or lower;

(ii) in anti-apoptotic cell assay, the antibody or antigen binding fragment thereof exhibits an $EC_{50}$ no more than 7.0× that of HGF and/or an $E_{max}$ cellular viability of at least 50% that observed for HGF; and/or (ii) in a branching morphogenesis assay, cells treated with the antibody exhibit at least 25% the number of branches per spheroid induced by the same (non-zero) concentration of HGF;

and the antibody or antigen binding fragment does not fully induce an HGF-like cellular response.

In certain embodiments, the antibody or antigen binding fragment thereof is a HGF competitor. In certain embodiments, the antibody or antigen binding fragment thereof competes with hHGF binding to hMET with an $IC_{50}$ of no more than 5 nM and/or an $I_{max}$ of at least 50% and competes with mHGF binding to mMET with an $IC_{50}$ of no more than 5 nM and/or an $I_{max}$ of at least 50%. In certain embodiments, the antibody or antigen binding fragment thereof competes with hHGF and mHGF equivalently. In certain embodiments, the antibody or antigen binding fragment thereof is a full HGF competitor. In certain such embodiments, the antibody or antigen binding fragment thereof competes with hHGF with an $IC_{50}$ of less than 2 nM and/or an $I_{max}$ of greater than 90% and competes with mHGF with an $IC_{50}$ of less than 2 nM and/or an $I_{max}$ of greater than 90%. In certain embodiments, the antibody or antigen binding fragment thereof is a partial HGF competitor. In certain such embodiments, the antibody or antigen binding fragment thereof competes with hHGF with an $IC_{50}$ of 2-5 nM and/or an $I_{max}$ of 50%-90% and competes with mHGF with an $IC_{50}$ of 2-5 nM and/or an $I_{max}$ of 50%-90%.

Antibodies or antigen binding fragment thereof of the invention may exhibit cross-reactivity with MET of simian origin, such as cynomolgus monkey (*Macaca* cynomolgus) MET, and may exhibit cross-reactivity with MET of rat origin (*Rattus norvegicus*).

Antibodies or antigen binding fragment thereof of the invention may bind an epitope of human MET from amino acid residue 123 to 223 of human MET (throughout the document, numbering of human MET refers to GenBank sequence #X54559). Also provided are antibodies or antigen binding fragment thereof of the invention which may bind an epitope of human MET between amino acids 224-311 of human MET. Also provided are antibodies or antigen binding fragment thereof of the invention which may bind an epitope of human MET between amino acids 314-372 of human MET. Also provided are antibodies or antigen binding fragment thereof of the invention which may bind an epitope of human MET between amino acids 546-562 of human MET.

Also provided are antibodies or antigen binding fragment thereof of the invention which may bind an epitope of human MET comprising the amino acid residue Ile367. Also provided are antibodies or antigen binding fragment thereof of the invention which may bind an epitope of human MET comprising the amino acid residue Asp372 of human MET. In certain embodiments, the antibody or antigen binding fragment thereof binds an epitope of human MET comprising the amino acid residues Ile367 and Asp372 of human MET.

Also provided are antibodies or antigen binding fragment thereof of the invention which may bind an epitope of human MET comprising the amino acid residue Thr555 of human MET.

The invention further provides an antibody or antigen binding fragment thereof which comprises a heavy chain variable domain comprising H-CDR1, H-CDR2 and H-CDR3, and a light chain variable domain comprising L-CDR1, L-CDR2 and L-CDR3, wherein:

H-CDR1 comprises an amino acid sequence selected from SEQ ID NO:2, 9, 16, 23, 30, 37, 44, 51, 58, 65, and 72;

H-CDR2 comprises an amino acid sequence selected from SEQ ID NO:4, 11, 18, 25, 32, 39, 46, 53, 60, 67, and 74;

H-CDR3 comprises an amino acid sequence selected from SEQ ID NO:6, 13, 20, 27, 34, 41, 48, 55, 62, 69, and 76, L-CDR1 comprises an amino acid sequence selected from SEQ ID NO:79, 86, 93, 100, 107, 114, 121, 128, 135, 142, and 149;

L-CDR2 comprises an amino acid sequence selected from SEQ ID NO:81, 88, 95, 102, 109, 116, 123, 130, 137, 144, and 151; and L-CDR3 comprises an amino acid sequence selected from SEQ ID NO:83, 90, 97, 104, 111, 118, 125, 132, 139, 146, and 153.

[71G2] In one embodiment, the invention provides an antibody or antigen binding fragment which comprises a heavy chain variable domain comprising H-CDR1, H-CDR2 and H-CDR3, and a light chain variable domain comprising L-CDR1, L-CDR2 and L-CDR3, wherein:

H-CDR1 comprises the amino acid sequence shown as SEQ ID NO:44, H-CDR2 comprises the amino acid sequence shown as SEQ ID NO:46, H-CDR3 comprises the amino acid sequence shown as SEQ ID NO:48, L-CDR1 comprises the amino acid sequence shown as SEQ ID NO:121, L-CDR2 comprises the amino acid sequence shown as SEQ ID NO:123, and L-CDR3 comprises the amino acid sequence shown as SEQ ID NO:125.

[71G2] In certain such embodiments, the heavy chain variable domain of the antibody or fragment comprises the amino acid sequence of SEQ ID NO:167, or a sequence at least 90%, 95%, 97% or 99% identical thereto, and the light chain variable domain comprises the amino acid sequence of SEQ ID NO:168, or a sequence at least 90%, 95%, 97% or 99% identical thereto.

[71D6] In another embodiment, the invention provides an antibody or antigen binding fragment which comprises a heavy chain variable domain comprising H-CDR1, H-CDR2 and H-CDR3, and a light chain variable domain comprising L-CDR1, L-CDR2 and L-CDR3, wherein:

H-CDR1 comprises the amino acid sequence shown as SEQ ID NO:30,

H-CDR2 comprises the amino acid sequence shown as SEQ ID NO:32,

H-CDR3 comprises the amino acid sequence shown as SEQ ID NO:34,

L-CDR1 comprises the amino acid sequence shown as SEQ ID NO:107,

L-CDR2 comprises the amino acid sequence shown as SEQ ID NO:109, and

L-CDR3 comprises the amino acid sequence shown as SEQ ID NO:111.

[71 D6] In certain such embodiments, the heavy chain variable domain of the antibody or antigen binding fragment comprises the amino acid sequence of SEQ ID NO:163, or a sequence at least 90%, 95%, 97% or 99% identical thereto, and the light chain variable domain comprises the amino acid sequence of SEQ ID NO:164, or a sequence at least 90%, 95%, 97% or 99% identical thereto.

[71G3] In a further embodiment, the invention provides an antibody or antigen binding fragment which comprises a heavy chain variable domain comprising H-CDR1, H-CDR2 and H-CDR3, and a light chain variable domain comprising L-CDR1, L-CDR2 and L-CDR3, wherein:

H-CDR1 comprises the amino acid sequence shown as SEQ ID NO:9,

H-CDR2 comprises the amino acid sequence shown as SEQ ID NO:11,

H-CDR3 comprises the amino acid sequence shown as SEQ ID NO:13,

L-CDR1 comprises the amino acid sequence shown as SEQ ID NO:86,

L-CDR2 comprises the amino acid sequence shown as SEQ ID NO:88, and

L-CDR3 comprises the amino acid sequence shown as SEQ ID NO:90.

[71G3] In certain such embodiments, the heavy chain variable domain of the antibody or antigen binding fragment comprises the amino acid sequence of SEQ ID NO:157, or a sequence at least 90%, 95%, 97% or 99% identical thereto, and the light chain variable domain comprises the amino acid sequence of SEQ ID NO:158, or a sequence at least 90%, 95%, 97% or 99% identical thereto.

In further embodiments, the invention provides an antibody or antigen binding fragment comprising a heavy chain variable domain comprising H-CDR1, H-CDR2 and H-CDR3, and a light chain variable domain comprising L-CDR1, L-CDR2 and L-CDR3, wherein H-CDR1, H-CDR2 and H-CDR3 are selected from a set of CDRs (CDR1, CDR2 and CDR3) for a Fab shown in Table 3, and L-CDR1, L-CDR2 and L-CDR3 are the corresponding CDRs (CDR1, CDR2 and CDR3) for the same Fab shown in Table 4.

In certain embodiments, the heavy chain variable domain of the antibody or antigen binding fragment comprises a VH amino acid sequence from Table 5 or a sequence at least 90%, 95%, 97% or 99% identical thereto, and the light chain variable domain comprises the corresponding VL amino acid sequence in Table 5 or a sequence at least 90%, 95%, 97% or 99% identical thereto.

Embodiments wherein the amino acid sequence of the VH domain exhibits less than 100% sequence identity with a defined VH domain amino acid sequence (e.g. SEQ ID NO: x) may nevertheless comprise heavy chain CDRs which are identical to the HCDR1, HCDR2 and HCDR3 of the VH of SEQ ID NO: x whilst exhibiting amino acid sequence variation within the framework regions. For example, one or more amino acid residues of the framework region may be substituted by an amino acid residue which occurs in the equivalent position in a human VH domain encoded by the human germline. Likewise, embodiments wherein the amino acid sequence of the VL domain exhibits less than 100% sequence identity with a defined VL domain amino acid sequence (e.g. SEQ ID NO:y) may nevertheless comprise light chain CDRs which are identical to the LCDR1, LCDR2 and LCDR3 of the VL of SEQ ID NO:y, whilst exhibiting amino acid sequence variation within the framework regions. For example, one or more amino acid residues of the framework region may be substituted by an amino acid residue which occurs in the equivalent position in a human VL domain encoded by the human germline.

The invention also provides antibodies and antigen binding fragments comprising humanised/germlined variants of VH and VL domains of the foregoing antibodies, plus affinity variants and variants containing conservative amino acid substitutions, as defined herein. Specifically provided are chimeric antibodies containing VH and VL domains of the llama-derived Fabs described above, or human germlined variants thereof, fused to constant domains of human antibodies, in particular human IgG1, IgG2, IgG3 or IgG4. The heavy and light chain variable domains of the foregoing antibodies, or germlined variants, affinity variants or conserved variants thereof, may be included within a conventional four-chain antibody or other antigen binding proteins, such as for example Fab, Fab', F(ab')2, bi-specific Fabs, and Fv fragments, diabodies, linear antibodies, single-chain antibody molecules, a single chain variable fragment (scFv) and multispecific antibodies. The heavy chain variable domains, or germlined variant, affinity variant or conserved variant thereof, can also be utilised as single domain antibodies.

In further aspects, the invention also provides an isolated polynucleotide which encodes an antibody or antigen binding fragment of the invention, an expression vector comprising said polynucleotide operably linked to regulatory sequences which permit expression of the antibody or antigen binding fragment thereof in a host cell or cell-free expression system, and a host cell or cell free expression system containing said expression vector. The invention further provides a method of producing a recombinant antibody or antigen binding fragment thereof which comprises culturing said host cell or cell free expression system under conditions which permit expression of the antibody or antigen binding fragment and recovering the expressed antibody or antigen binding fragment.

In a further aspect, the invention provides a pharmaceutical composition comprising an antibody or antigen binding fragment of the invention and at least one pharmaceutically acceptable carrier or excipient.

In a further aspect, the invention provides an antibody or antigen binding fragment of the invention, or the pharmaceutical composition of the invention, for use in therapy.

In a further aspect, the invention provides a method of treating or preventing liver damage in a human patient, optionally acute liver damage or chronic liver damage, which comprises administering to a patient in need thereof a therapeutically effective amount of a MET agonist antibody. In certain embodiments, the MET agonist antibody is an antibody or antigen binding fragment according to the invention.

In a further aspect, the invention provides a method of treating or preventing kidney damage in a human patient, optionally acute kidney damage, which comprises administering to a patient in need thereof a therapeutically effective amount of a MET agonist antibody. In certain embodiments, the MET agonist antibody is an antibody or antigen binding fragment according to the invention.

In a further aspect, the invention provides a method of treating or preventing inflammatory bowel disease in a human patient, optionally ulcerative colitis, which comprises administering to a patient in need thereof a therapeutically effective amount of a MET agonist antibody. In certain embodiments, the MET agonist antibody is an antibody or antigen binding fragment according to the invention.

In a further aspect, the invention provides a method of treating or preventing diabetes in a human patient, optionally type I or type II diabetes, which comprises administering to a patient in need thereof a therapeutically effective amount of a MET agonist antibody.

In certain embodiments, the MET agonist antibody is an antibody or antigen binding fragment according to the invention.

In a further aspect, the invention provides a method of treating or preventing non-alcoholic steatohepatitis in a human patient, which comprises administering to a patient in need thereof a therapeutically effective amount of a MET agonist antibody. In certain embodiments, the MET agonist antibody is an antibody or antigen binding fragment according to the invention.

In a further aspect, the invention provides a method of treating or promoting wound healing in a human patient, optionally a patient having diabetes, which comprises administering to a patient in need thereof a therapeutically effective amount of a MET agonist antibody. In certain embodiments, the MET agonist antibody is an antibody or antigen binding fragment according to the invention.

DRAWINGS

FIG. 1. Immune response of llamas immunized with human MET-Fc as determined by ELISA. Human MET ECD (hMET) or mouse MET ECD (mMET) recombinant protein was immobilized in solid phase and exposed to serial dilutions of sera from llamas before (PRE) or after (POST) immunization. Binding was revealed using a mouse anti-llama IgG1 and a HRP-conjugated donkey anti-mouse antibody. OD, optical density; AU, arbitrary units.

Figure 2:
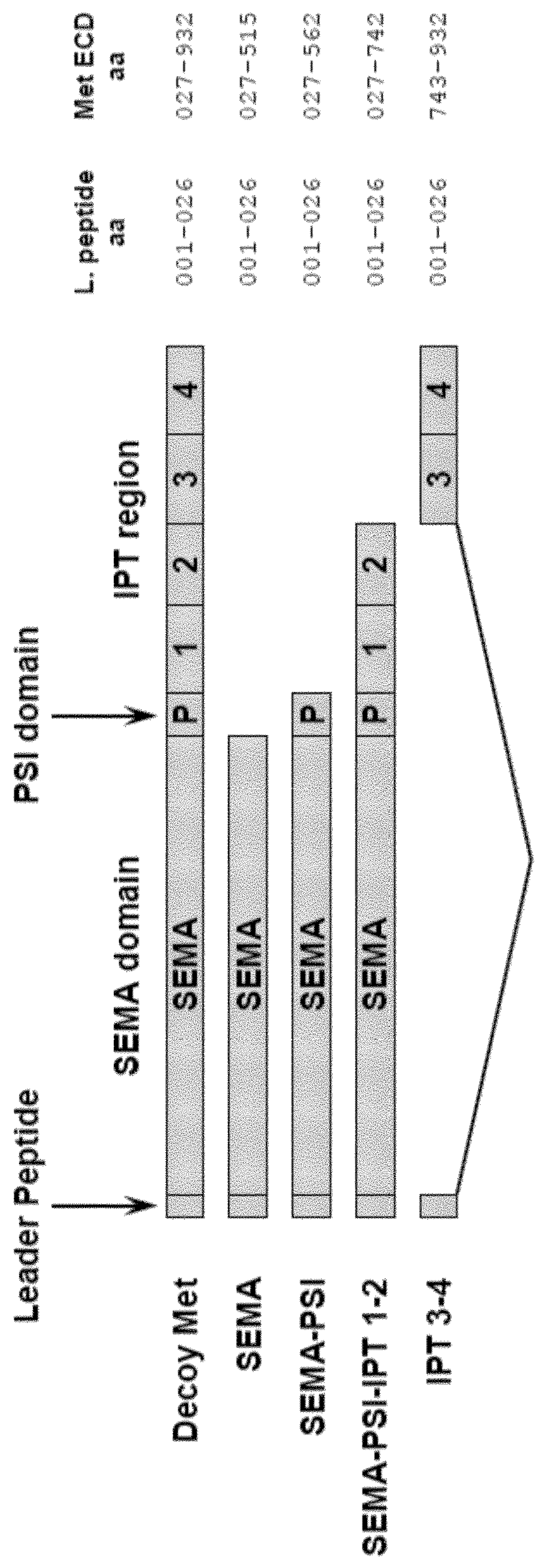

FIG. 2. Schematic drawing of the human MET deletion mutants used for identifying the domains of MET responsible for mAb binding. ECD, extra-cellular domain; aa, amino acid; L. peptide, leader peptide; SEMA, semaphorin homology domain; PSI or P, plexin-semaphorin-integrin homology domain; IPT, Immunoglobulin-transcription factor-plexin homology domain. On the right, the corresponding residues of human MET are reported according to UniProtKB #P08581.

Figure 3:
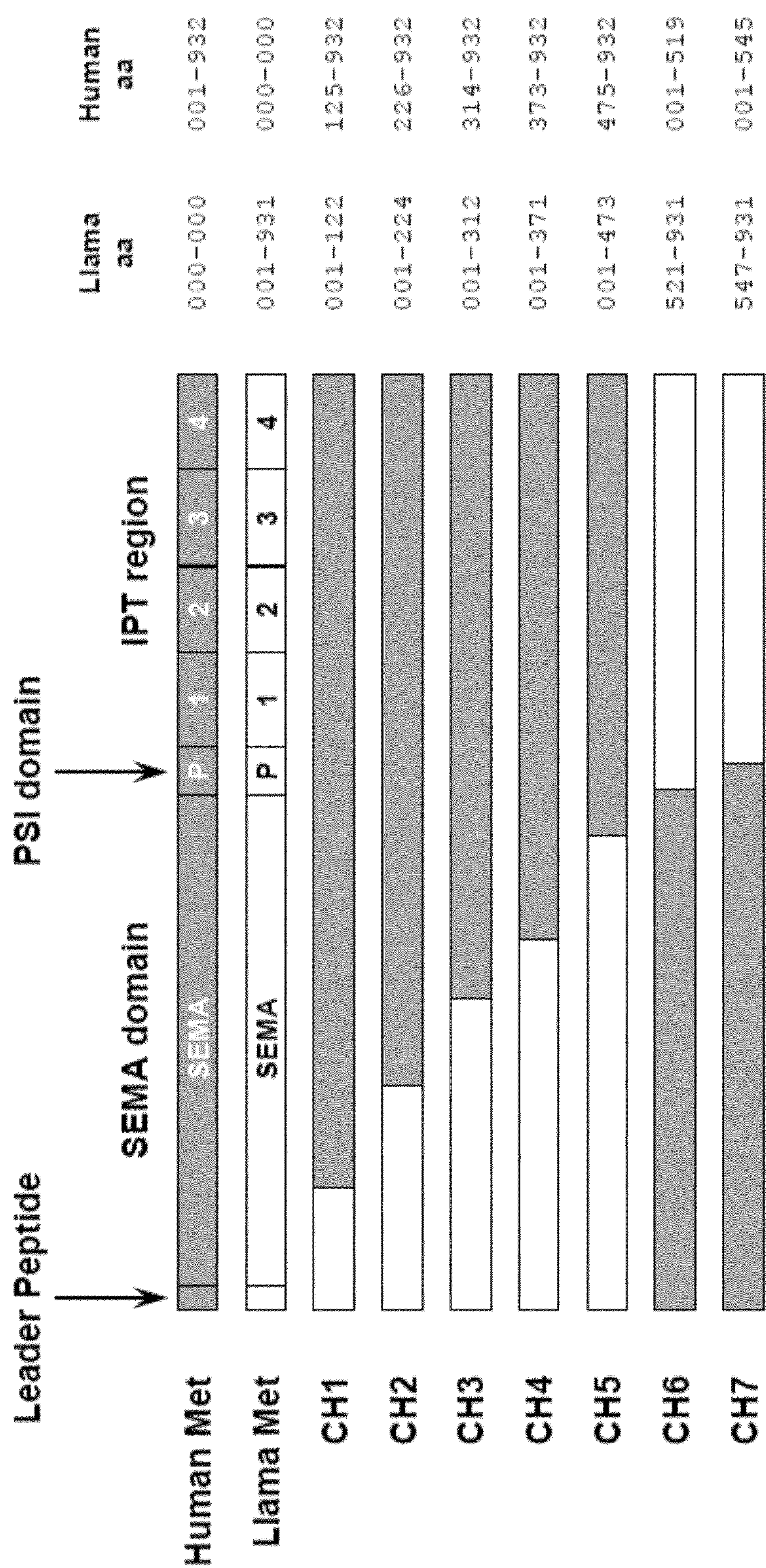

FIG. 3. Schematic drawing of the llama-human chimeric MET proteins used for finely mapping the epitopes recognized by anti-MET antibodies. The extracellular portions of llama MET and human MET are composed of 931 and 932 amino acids (aa), respectively (llama MET has a 2 aa shorter leader peptide but has an insertion after aa 163). Both receptor ectodomains comprise a leader peptide, a semaphorin homology domain (SEMA), a plexin-semaphorin-integrin homology domain (PSI or P) and four immunoglobulin-transcription factor-plexin homology domains (IPT). Chimeras CH1-5 have a N-terminal llama portion followed by a C-terminal human portion. Chimeras CH6-7 have an N-terminal human portion followed by a C-terminal llama portion.

Figure 4:
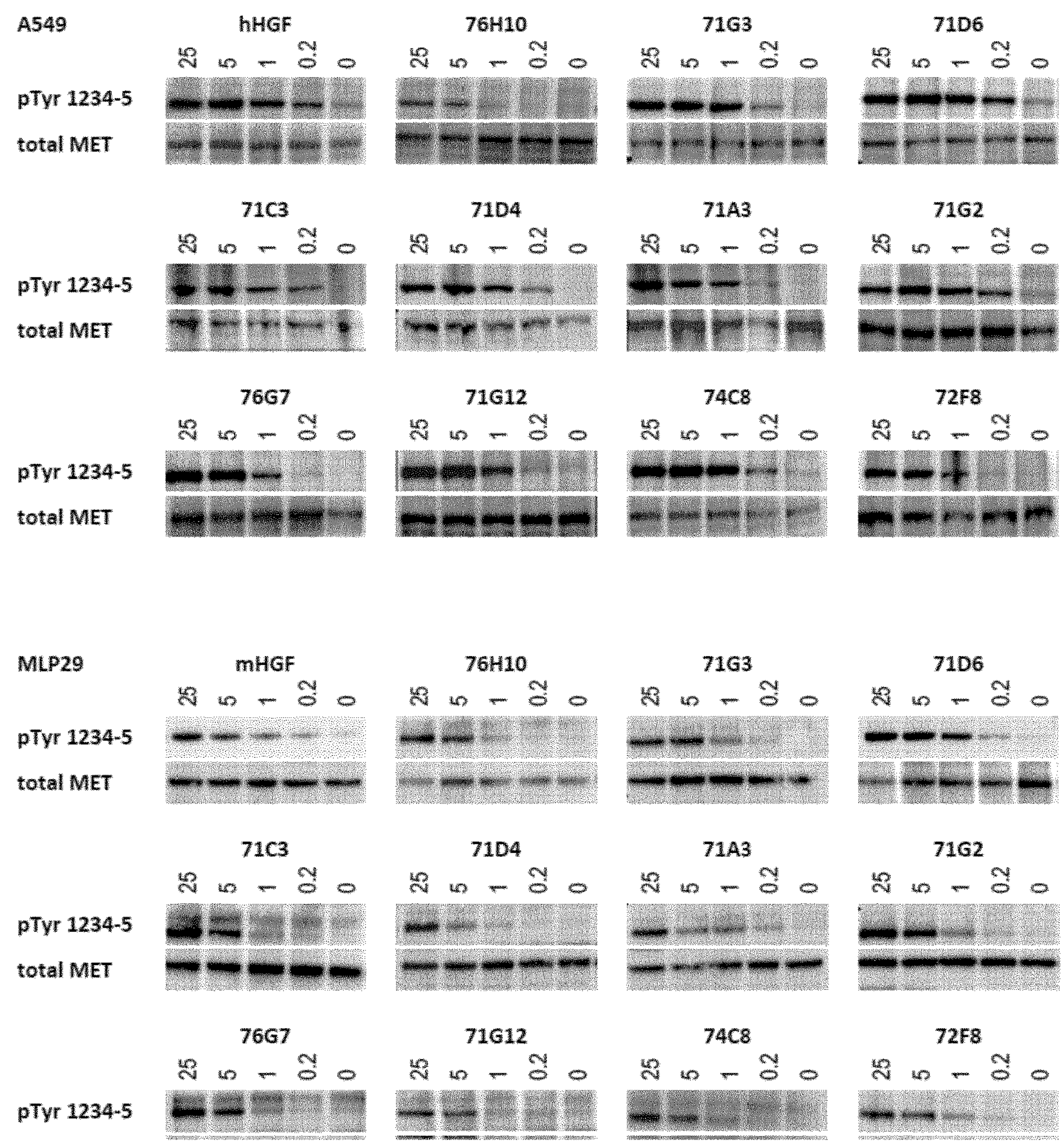

FIG. 4. Agonistic activity of human/mouse equivalent anti-MET antibodies in human and mouse cells as measured by Western blotting. A549 human lung carcinoma cells and MLP29 mouse liver precursor cells were serum-starved and then stimulated with increasing concentrations of mAbs or recombinant human HGF (hHGF; A549) or mouse HGF (mHGF; MLP29). MET auto-phosphorylation was determined by Western blotting using anti-phospho-MET antibodies (tyrosines 1234-1235). The same cell lysates were also analysed by Western blotting using anti-total human MET antibodies (A549) or anti-total mouse MET antibodies (MLP29).

Figure 5:
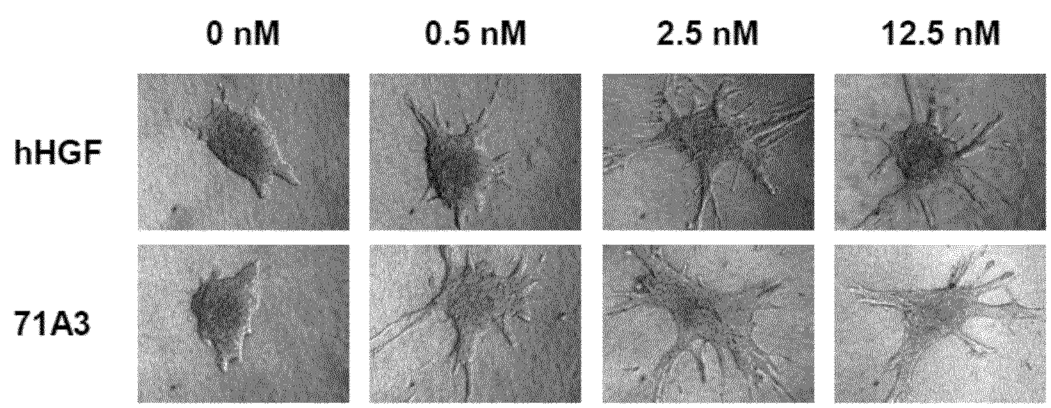
Figure 5:
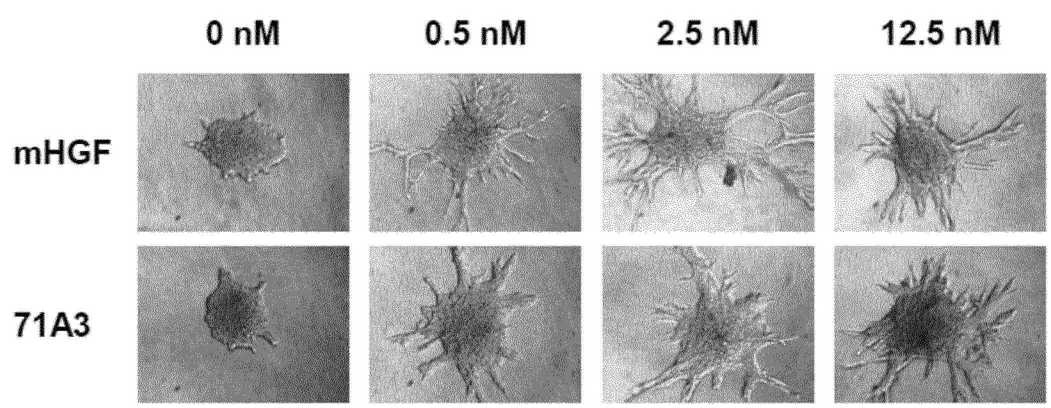

FIG. 5. Biological activity of human/mouse equivalent anti-MET antibodies as measured by a branching morphogenesis assay using LOC human kidney epithelial cells and MLP29 mouse liver precursor cells. Cell spheroids were seeded inside a collagen layer and then exposed to increasing concentrations of mAbs or recombinant human HGF (LOC) or mouse HGF (MLP29). Branching morphogenesis was followed over time by microscopy, and colonies were photographed after 5 days.

Figure 6:
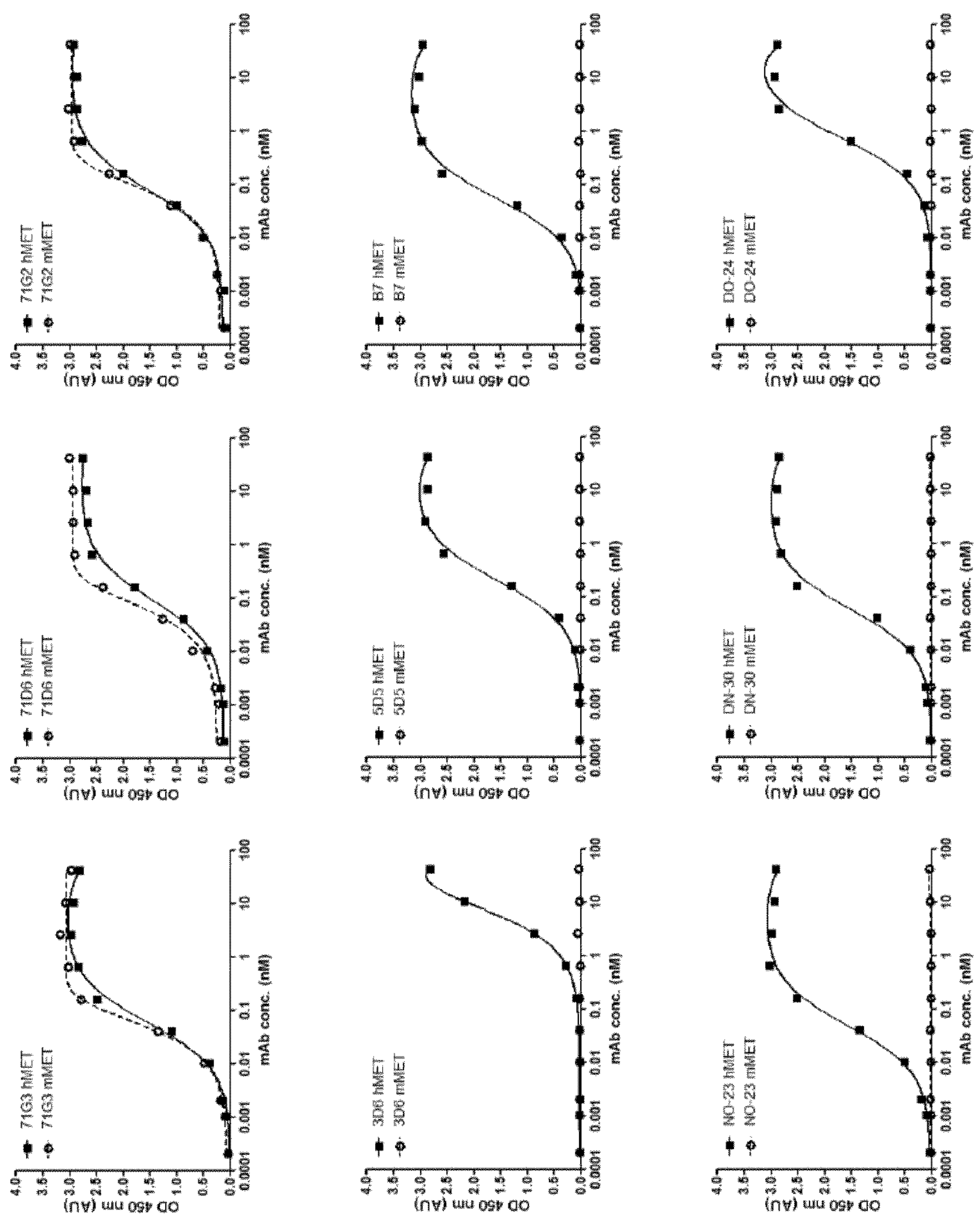

FIG. 6. Comparison with prior art antibodies: human-mouse cross-reactivity. Human or mouse MET ECD was immobilized in solid phase and exposed to increasing concentrations of antibodies (all in a mouse IgG/A format) in solution. Binding was revealed by ELISA using HRP-conjugated anti-mouse Fc antibodies.

Figure 7:
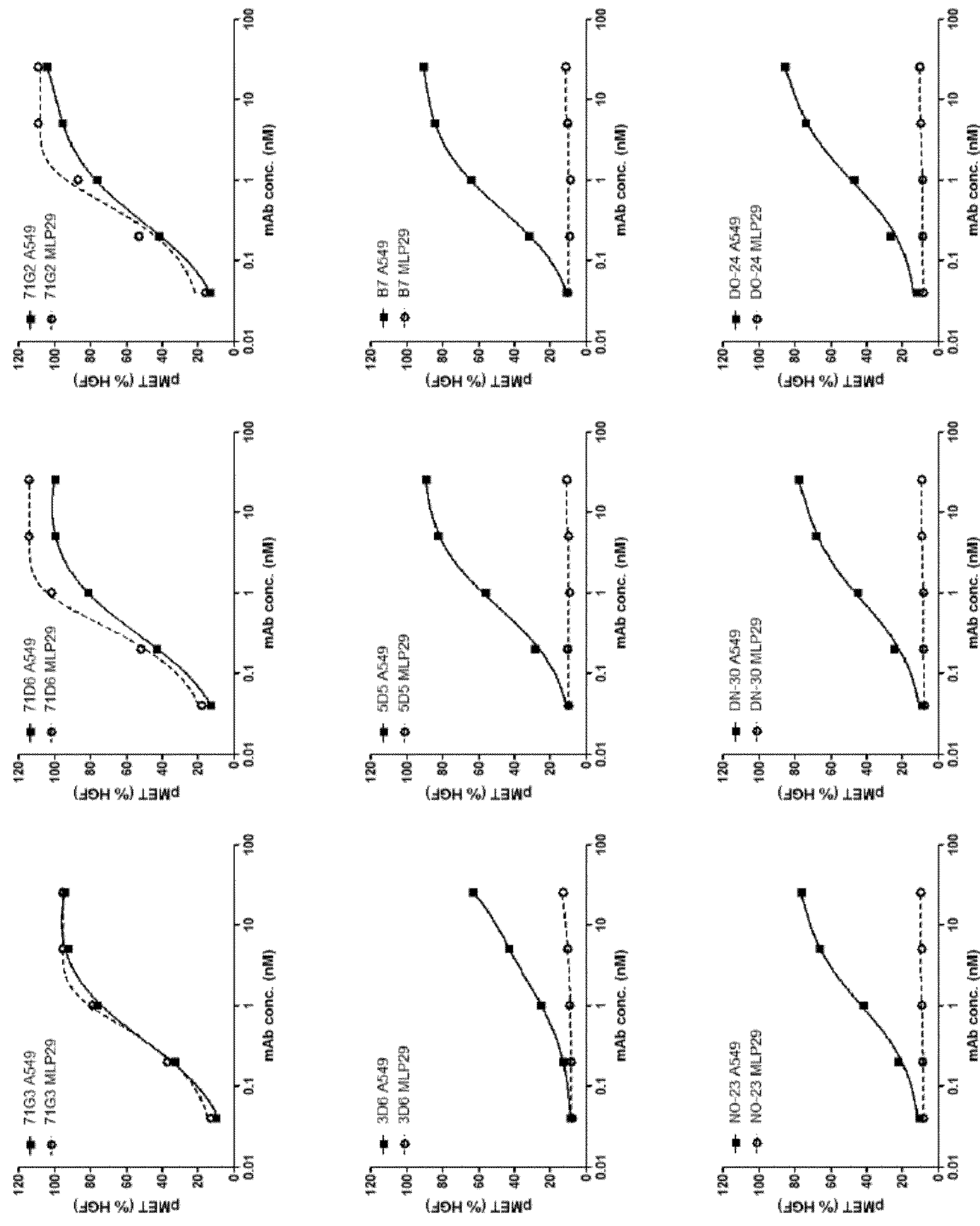

FIG. 7. Comparison with prior art antibodies: MET autophosphorylation. A549 human lung carcinoma cells and MLP29 mouse liver precursor cells were deprived of serum growth factors for 48 hours and then stimulated with increasing concentrations of antibodies. After 15 minutes of stimulation, cells were lysed, and phospho-MET levels were determined by ELISA using anti-MET antibodies for capture and anti-phospho-tyrosine antibodies for revealing.

Figure 8:
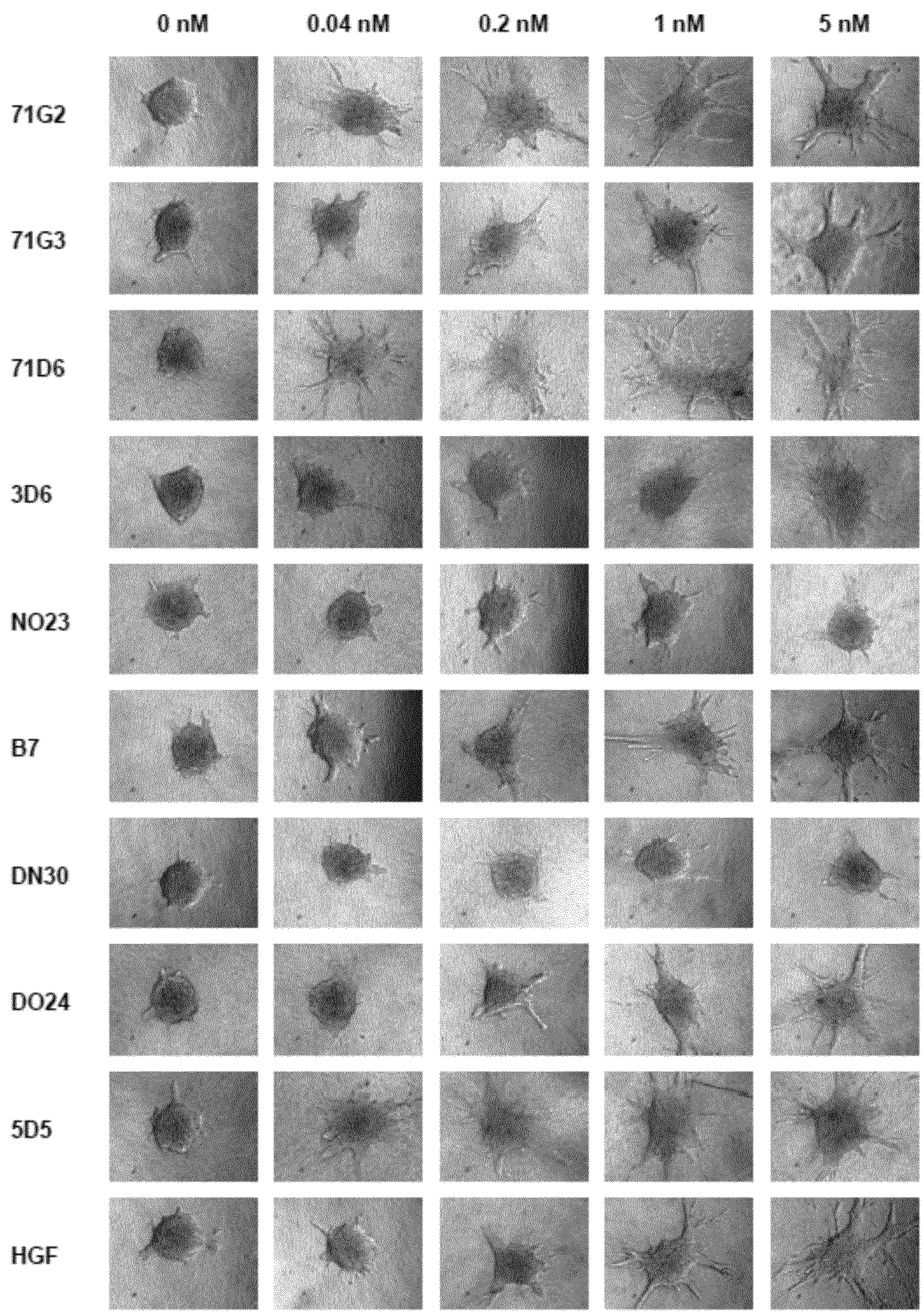

FIG. 8. Comparison with prior art antibodies: branching morphogenesis. LOC human kidney epithelial cell spheroids were seeded in a collagen layer and then incubated with increasing concentrations of mAbs. Branching morphogenesis was followed over time by microscopy, and colonies were photographed after 5 days.

Figure 9:
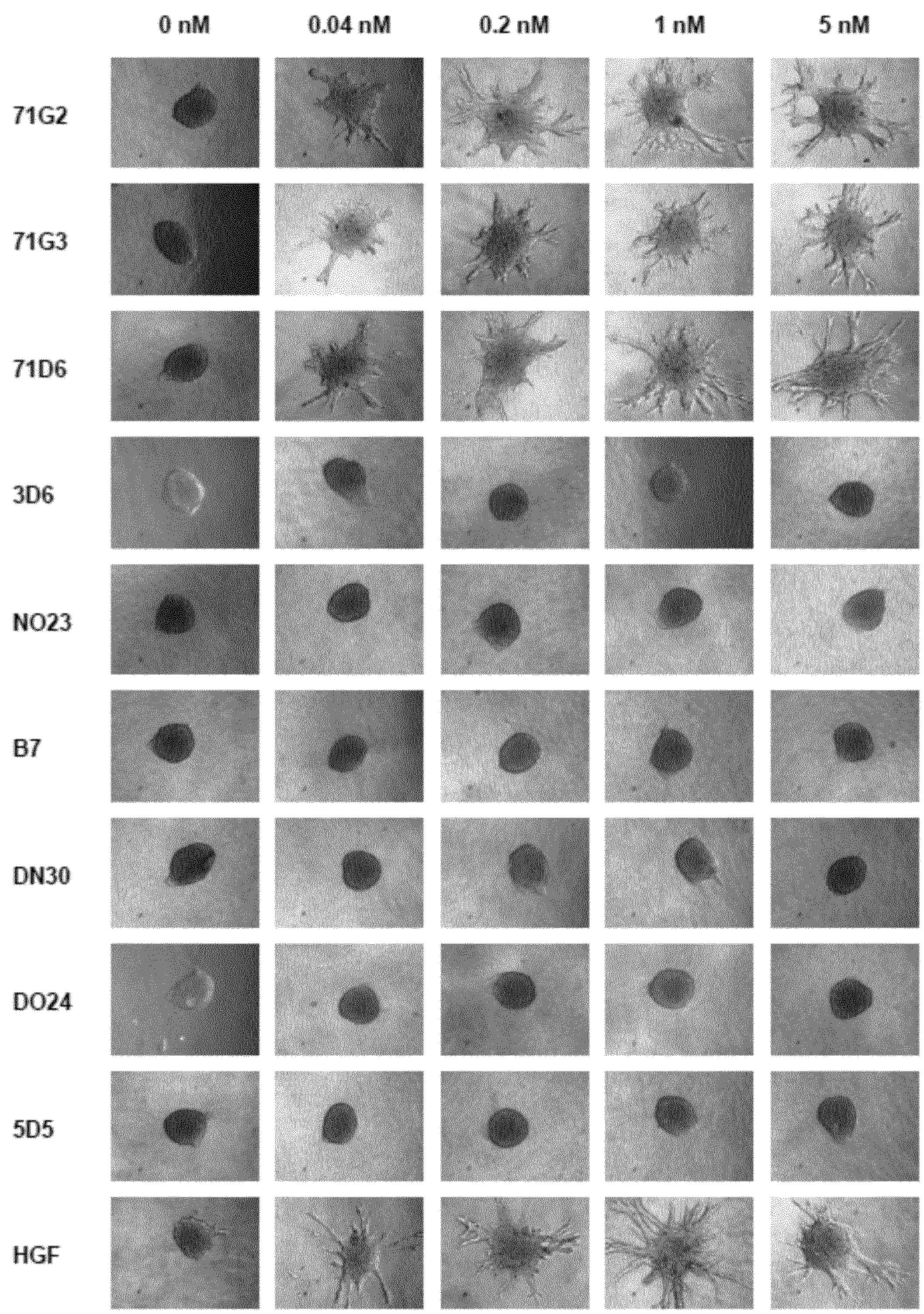

FIG. 9. Comparison with prior art antibodies: branching morphogenesis. MLP29 mouse liver precursor cell spheroids were seeded in a collagen layer and then incubated with increasing concentrations of mAbs. Branching morphogenesis was followed over time by microscopy, and colonies were photographed after 5 days.

Figure 10:
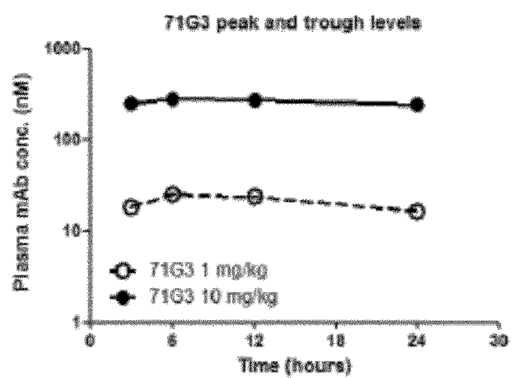
Figure 10:
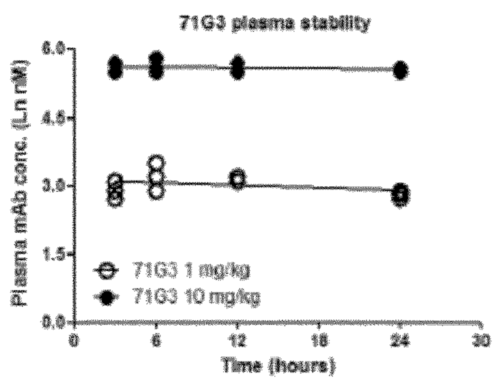
Figure 10:
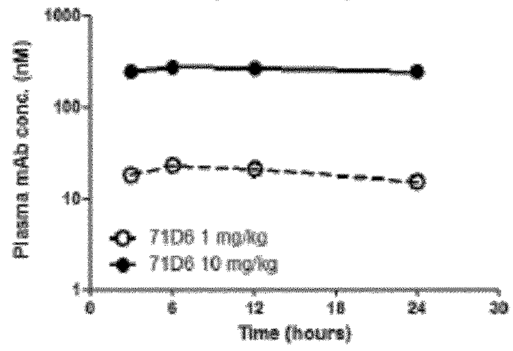
Figure 10:
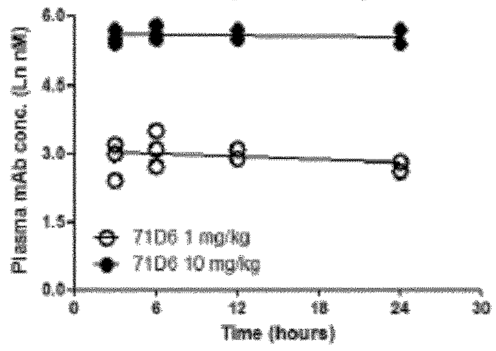
Figure 10:
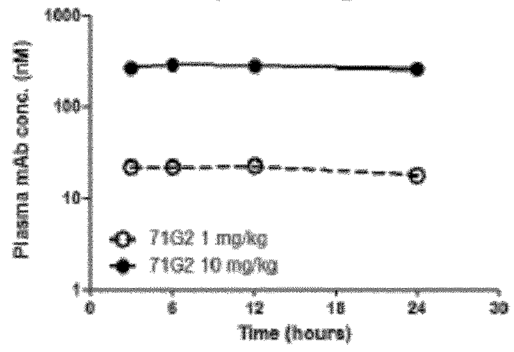
Figure 10:
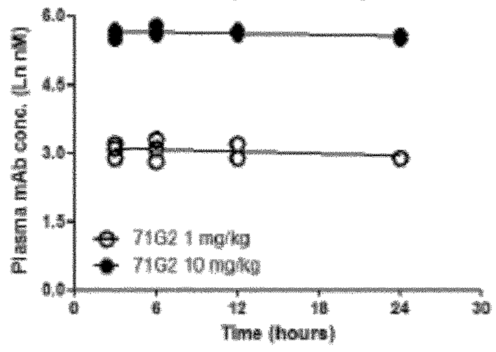

FIG. 10. Plasma stability of human/mouse equivalent anti-MET antibodies. A single bolus of 1 mg/kg or 10 mg/kg antibody was injected i.p. and blood samples were taken from the tail vein at 3, 6, 12 and 24 hours post-injection. Blood samples were processed and antibody concentration in plasma was determined by ELISA. (A) Peak and trough levels of injected antibodies. (B) Antibody plasma half-life was calculated by linear fitting of the antibody concentration Ln transforms.

Figure 11:
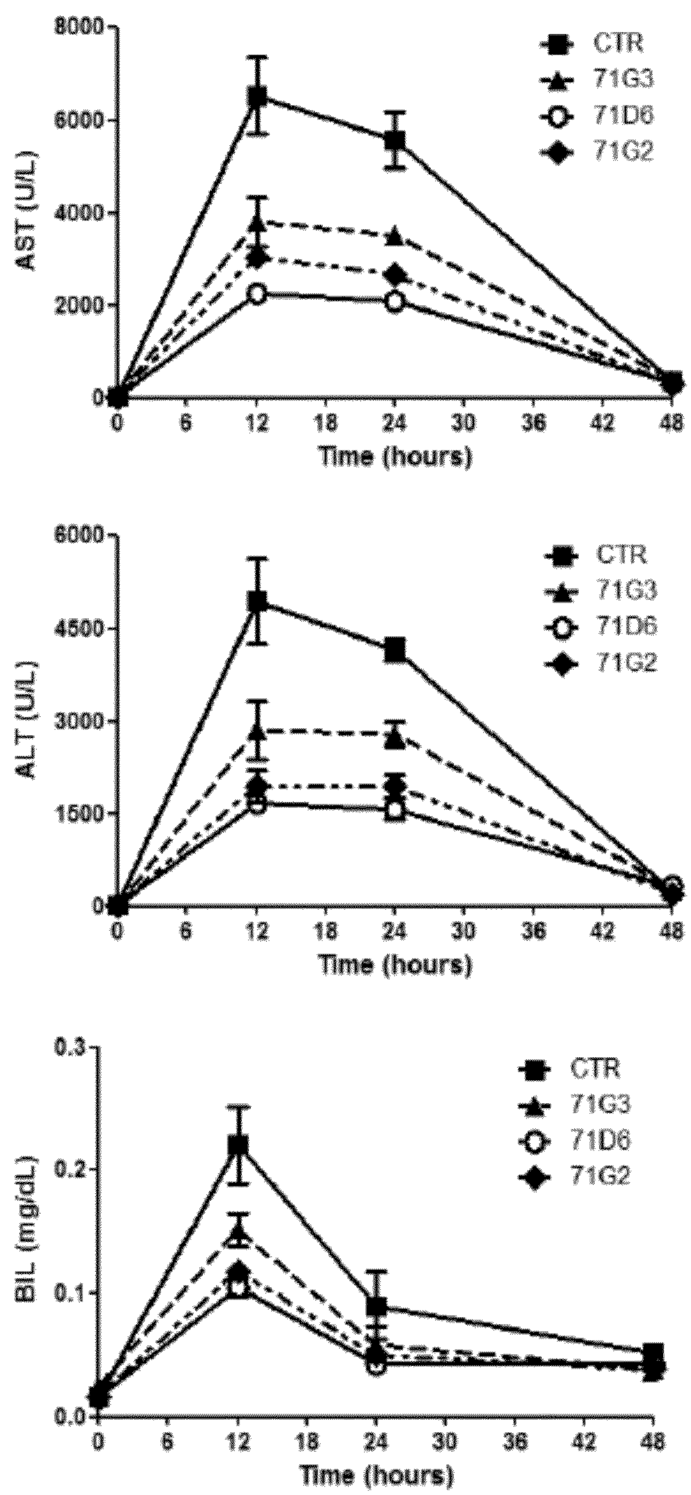

FIG. 11. Acute liver failure model: plasma concentration of liver function markers. Acute liver damage was induced in BALB/c mice by subcutaneous injection of a $CCl_4$ solution. Soon after intoxication, mice were randomized into 4 arms which received a single bolus of 71G3, 71 D6, 71G2 or vehicle only (PBS). Antibodies were administered by i.p. injection at a dose of 5 mg/kg. Each arm comprised three groups of mice that were sacrificed at different times post-intoxication (12, 24 and 48 hours). Blood samples were taken at different times post-injection (0, 12, 24 and 48 hours). At autopsy, blood and livers were collected for analysis. Plasma levels of the hepatic markers aspartate transaminase (AST), alanine aminotransferase (ALT) and bilirubin (BIL) was determined by standard clinical biochemistry methods.

Figure 12:
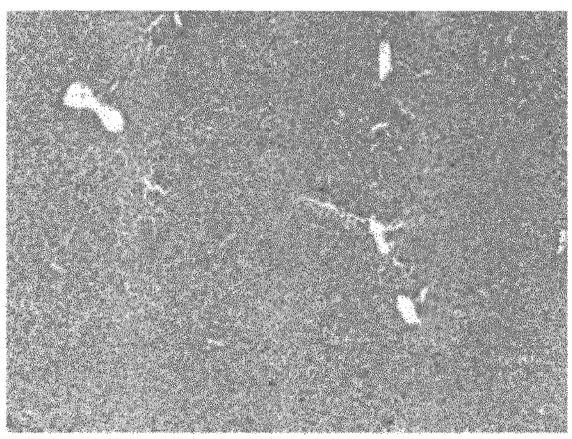
Figure 12:
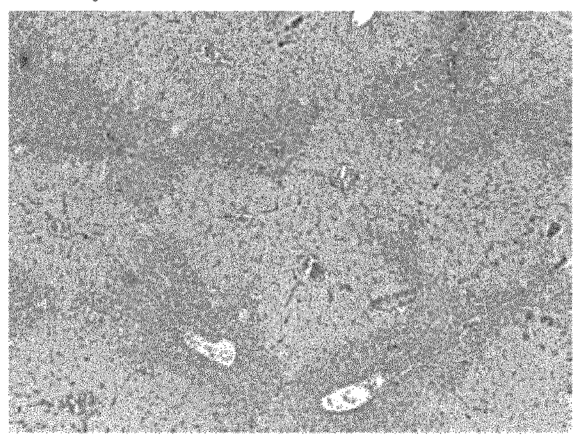
Figure 12:
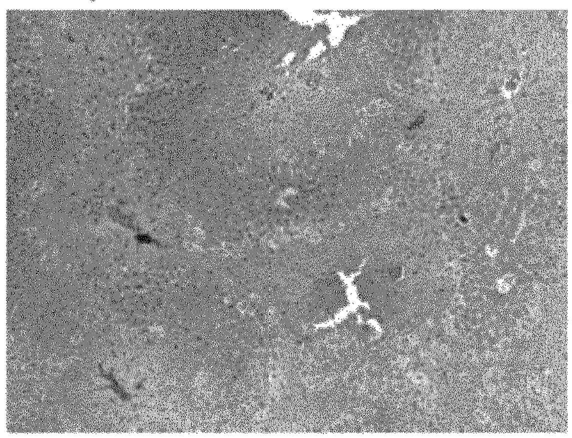
Figure 12:
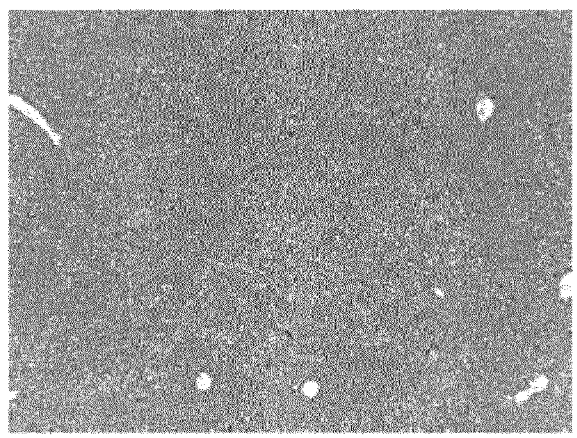
Figure 12:
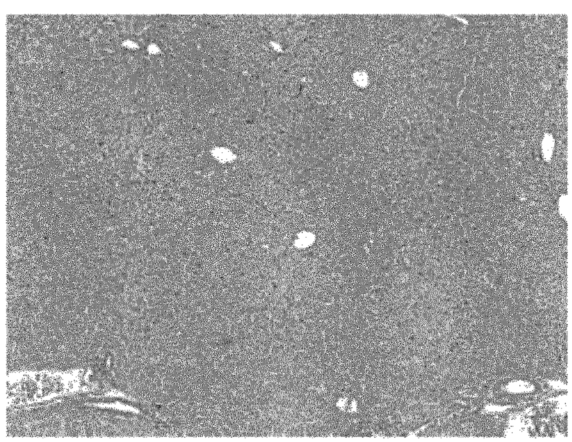

FIG. 12. Acute liver failure model: histological examination of liver sections. Acute liver damage was induced in BALB/c mice as described in FIG. 11 legend. At autopsy, livers were extracted and embedded in paraffin for histological analysis. Sections were stained with hematoxylin and eosin and examined by microscopy. A representative image for each treatment arm is shown. Magnification: 100×.

Figure 13:
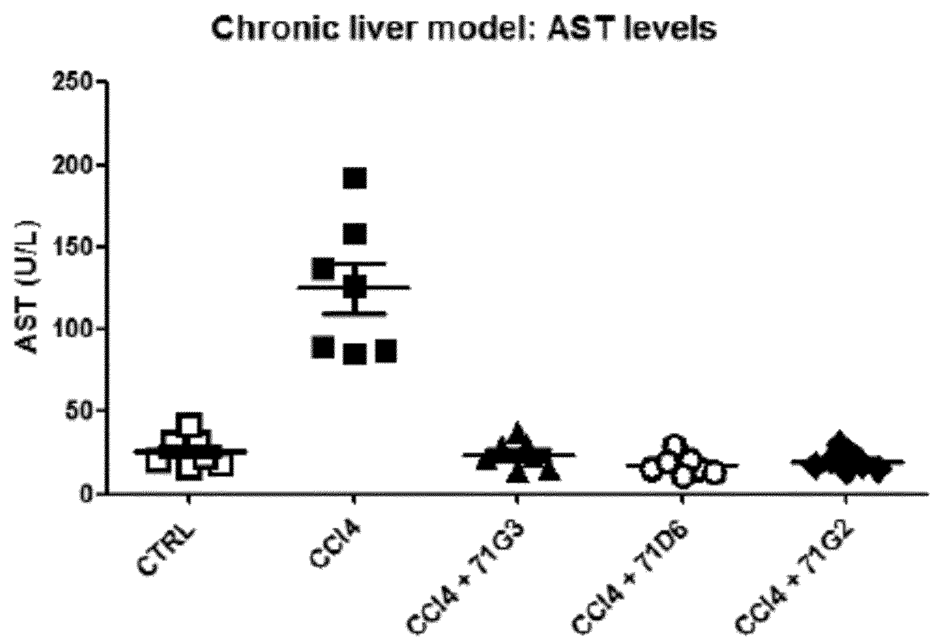
Figure 13:
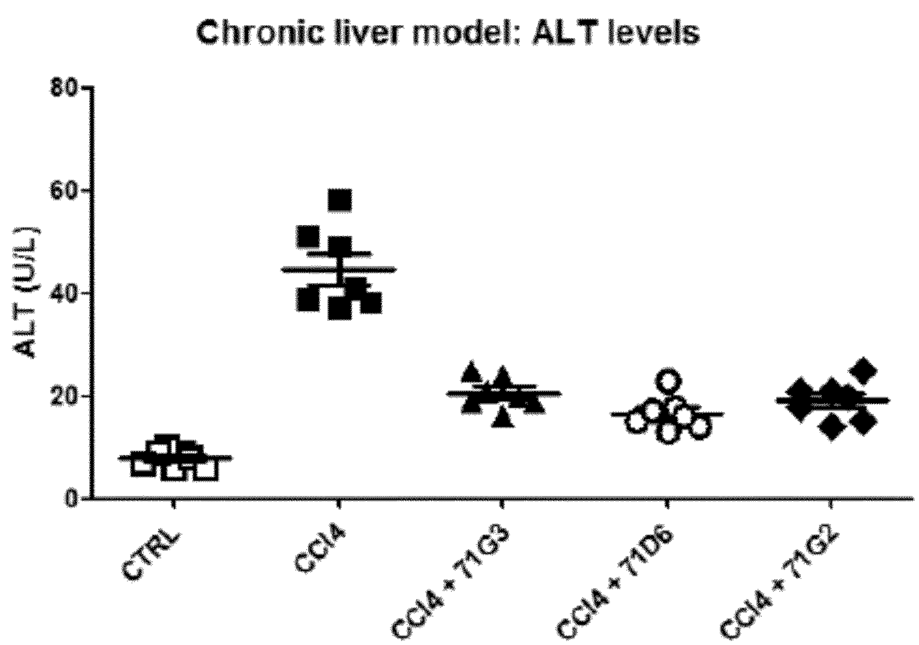

FIG. 13. Chronic liver damage model: plasma concentration of liver function markers. Liver injury and fibrosis in BALB/c mice was induced by chronic exposure to $CCl_4$ for several weeks. Soon after the first $CCl_4$ injection, mice were randomized into 4 arms which received treatment with 71G3, 71D6, 71G2 or vehicle only (PBS), respectively. Antibodies were administered three times a week by i.p. injection at a dose of 1 mg/kg. An additional, fifth control arm received no $CCl_4$ or antibody and served as healthy control. Mice were sacrificed after 6 weeks of chronic $CCl_4$ intoxication. At autopsy, blood and livers were collected for analysis. Plasma levels of the hepatic markers aspartate transaminase (AST) and alanine aminotransferase (ALT) were determined by standard clinical biochemistry methods.

Figure 14:
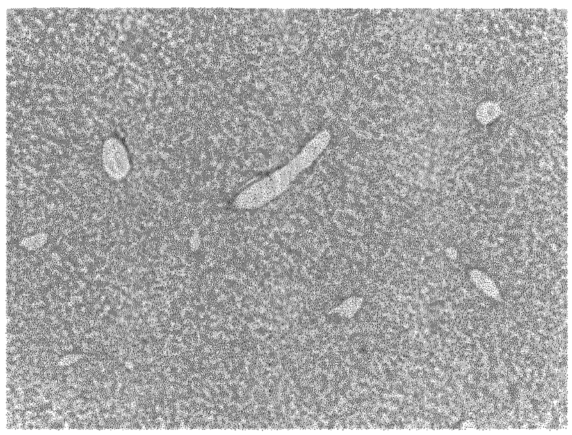
Figure 14:
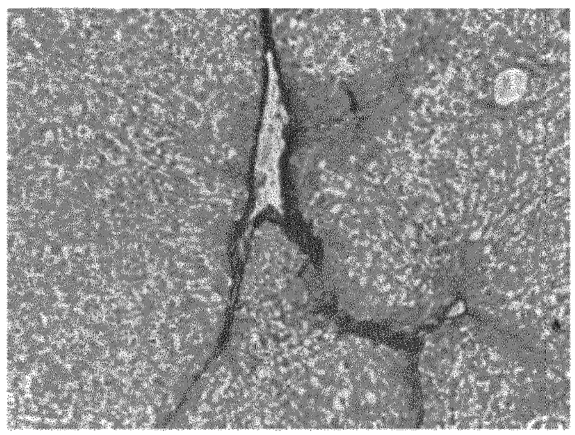
Figure 14:
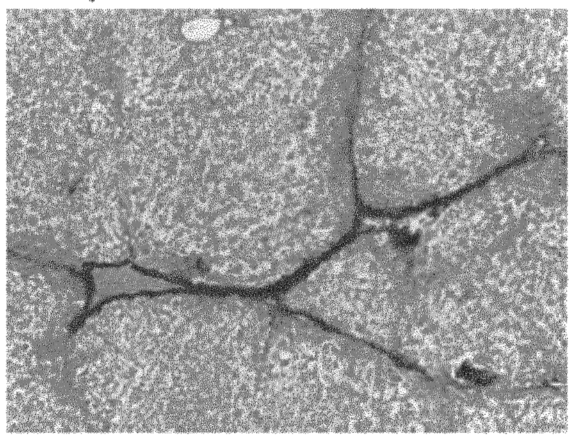
Figure 14:
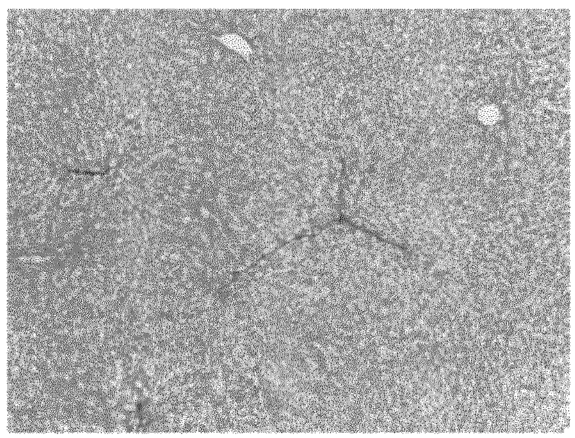
Figure 14:
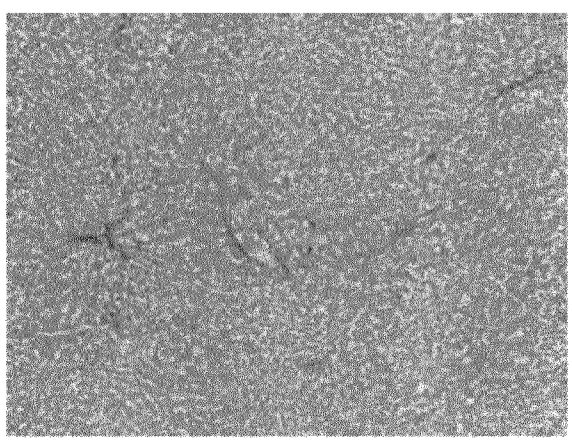
Figure 14:
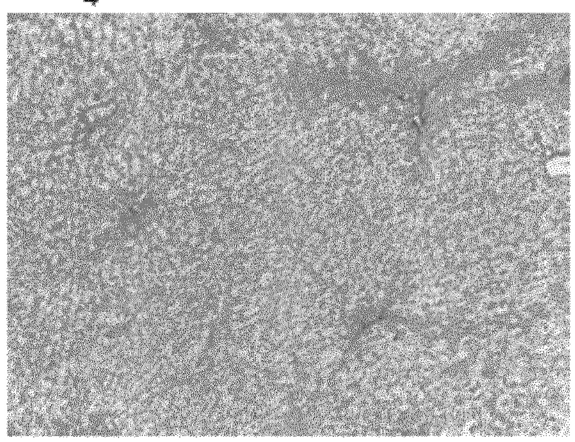

FIG. 14. Chronic liver damage model: histological examination of liver sections stained with Picro Sirius red. Liver injury and fibrosis in BALB/c mice were induced by chronic exposure to $CCl_4$ as described in FIG. 13 legend. At autopsy, livers were extracted and embedded in paraffin for immunohistochemical analysis. Sections were stained with Picro Sirius red. A representative image for each treatment arm is shown. Magnification: 100×.

Figure 15:
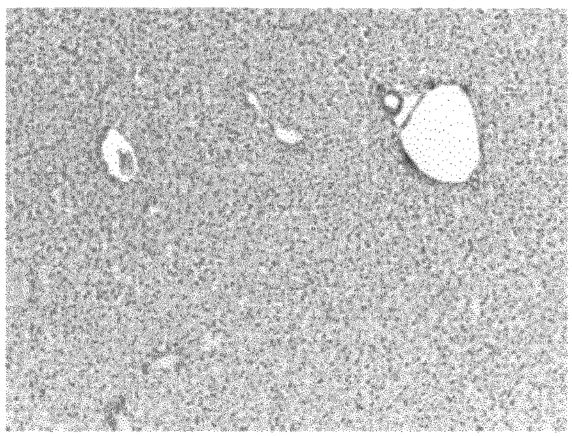
Figure 15:
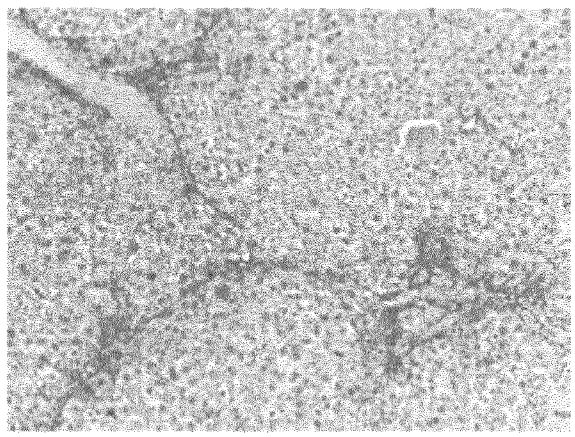
Figure 15:
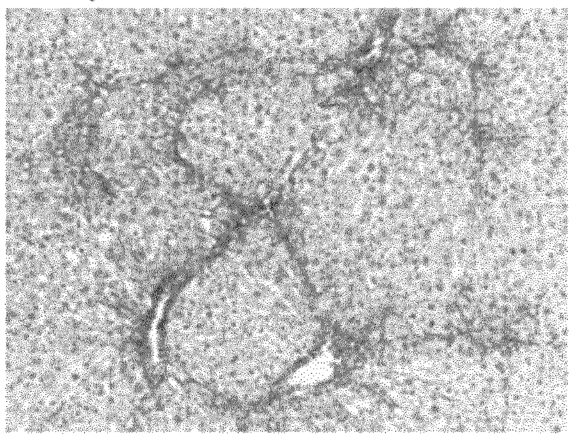
Figure 15:
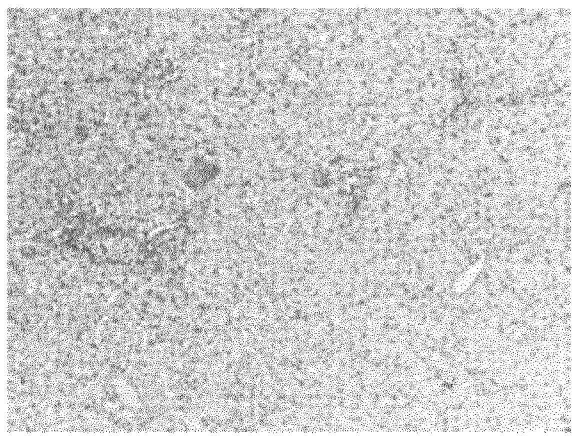
Figure 15:
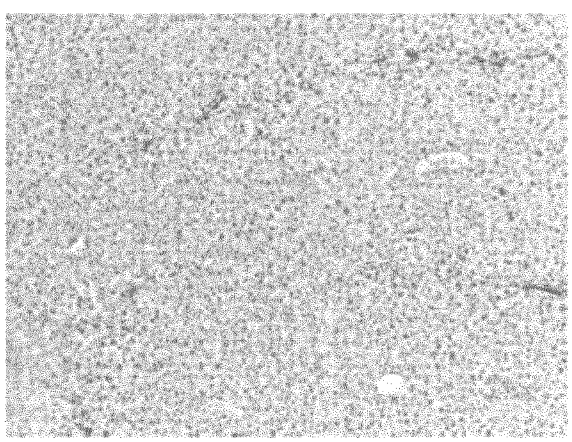
Figure 15:
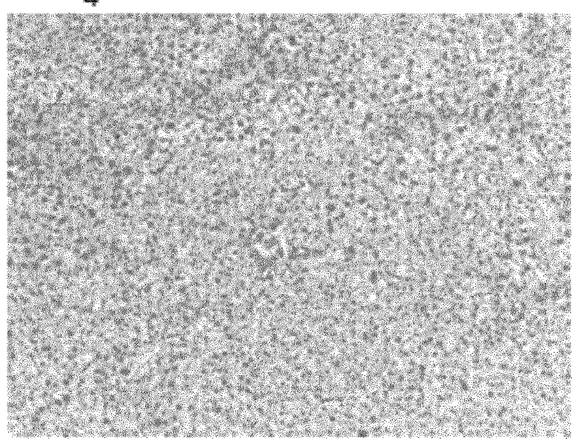

FIG. 15. Chronic liver damage model: histological examination of liver sections stained with anti-alpha smooth muscle actin (α-SMA) antibodies. Liver injury and fibrosis in BALB/c mice were induced by chronic exposure to $CCl_4$ as described in FIG. 13 legend. At autopsy, livers were extracted and embedded in paraffin for immuno-histochemical analysis. Sections were stained with anti-alpha smooth muscle actin (α-SMA) antibodies. A representative image for each treatment arm is shown. Magnification: 100×.

Figure 16:
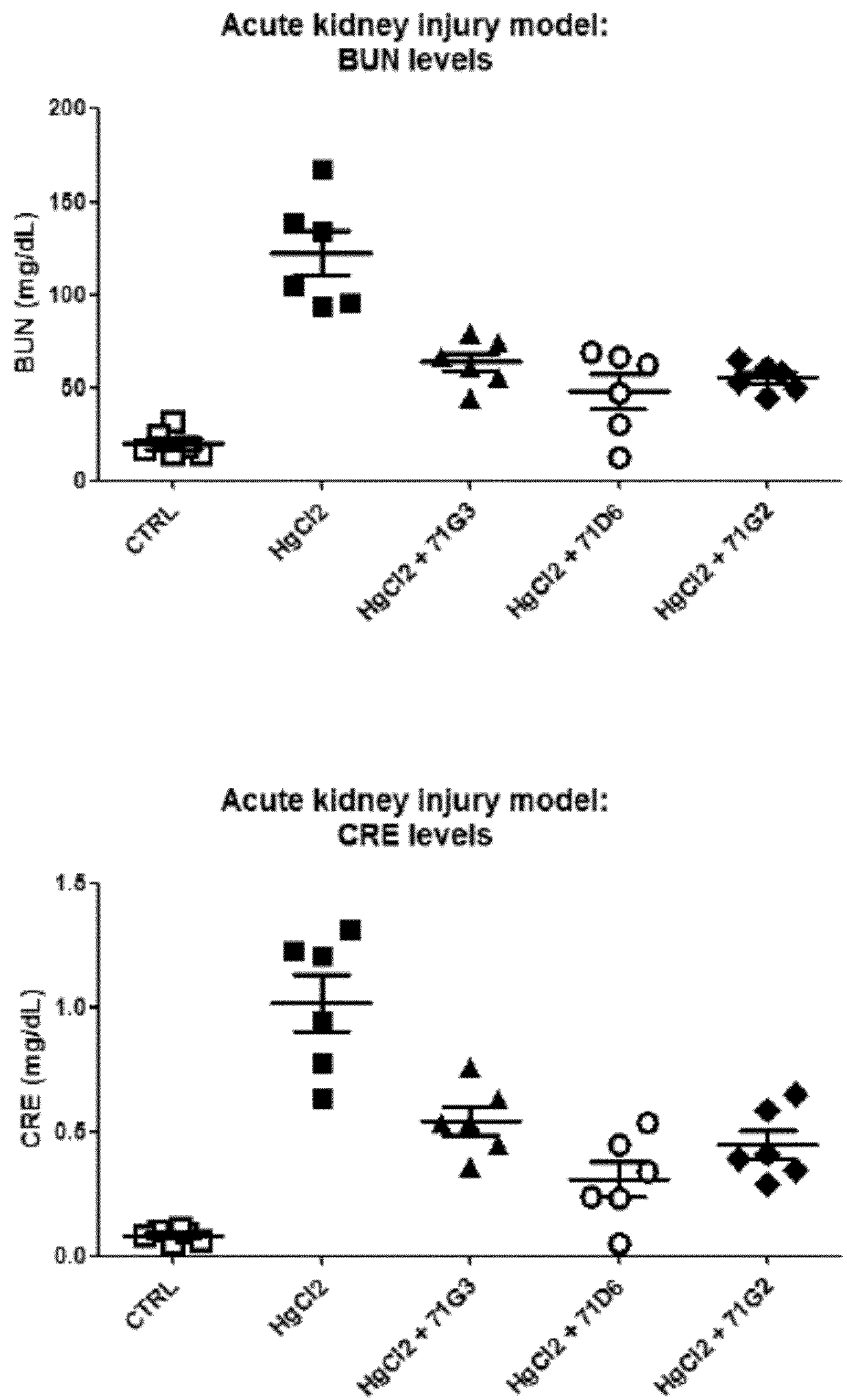

FIG. 16. Acute kidney injury model: plasma levels of renal function markers. Acute renal failure was induced in BALB/c mice by i.p. injection of a single bolus of $HgCl_2$. Soon after $HgCl_2$ intoxication, mice were randomized into 4 arms which were subjected to treatment with 71G3, 71D6, 71G2 or vehicle only (PBS). Antibodies were administered by i.p. injection every 24 hours at a dose of 5 mg/kg. Mice were sacrificed 72 hours after $HgCl_2$ injection. At autopsy, blood and kidneys were collected for analysis. Blood urea nitrogen (BUN) and creatinine (CRE) plasma levels were determined by standard clinical biochemistry methods.

Figure 17:
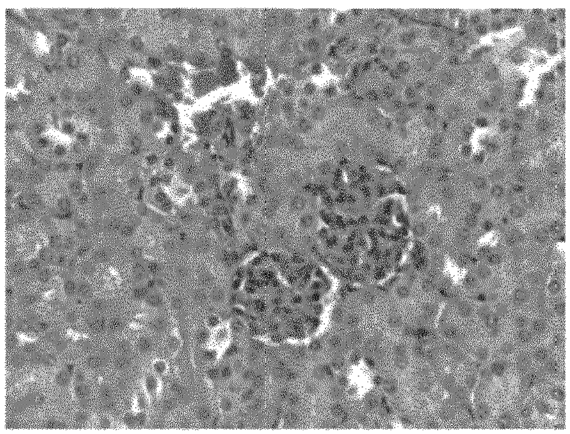
Figure 17:
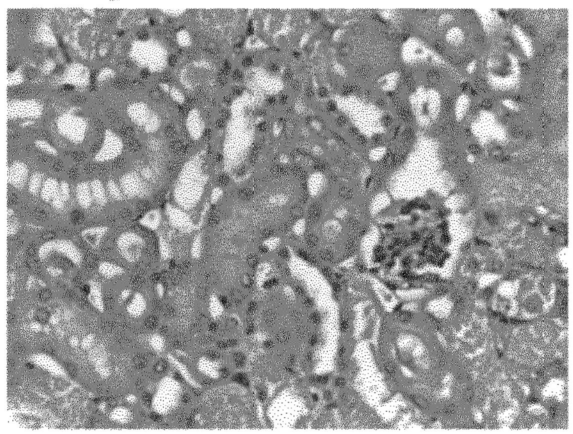
Figure 17:
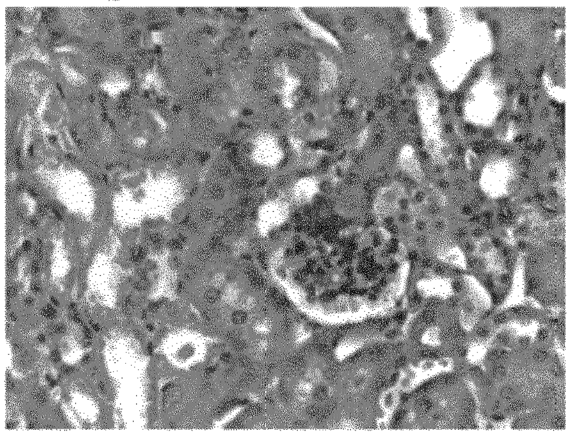
Figure 17:
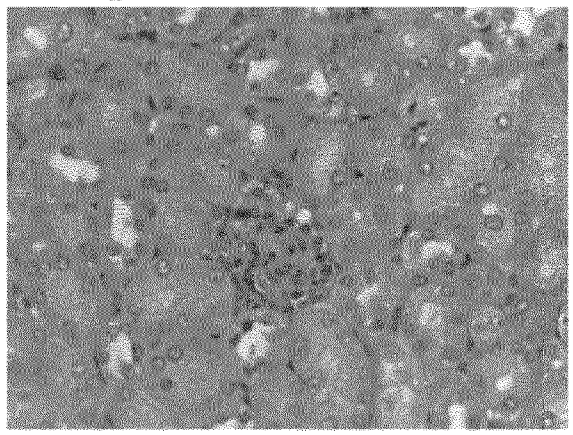
Figure 17:
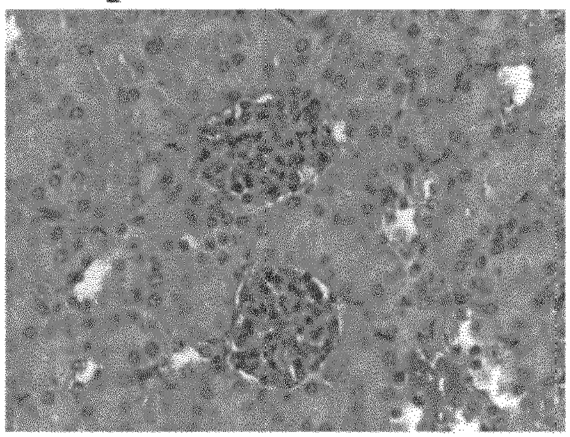
Figure 17:
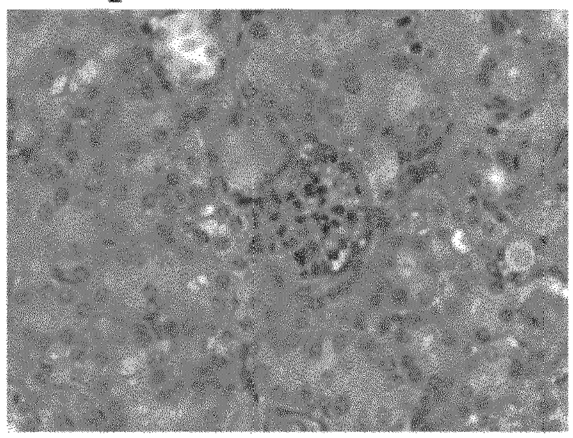

FIG. 17. Acute kidney injury model: histological analysis of kidney sections. Acute renal failure was induced in BALB/c mice by $HgCl_2$ injection as described in FIG. 16 legend. At autopsy, kidneys were extracted and embedded in paraffin for histological analysis. Kidney sections were stained with hematoxylin and eosin. A representative image for each treatment arm is shown. Magnification: 400×.

Figure 18:
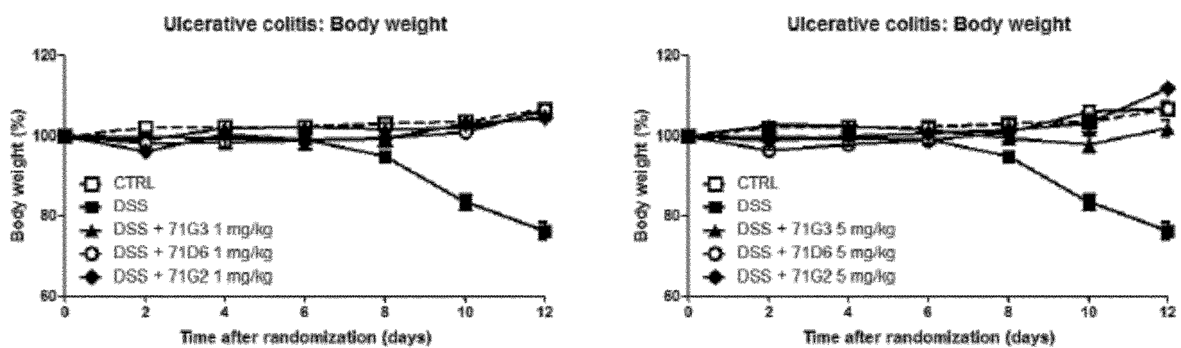
Figure 18:
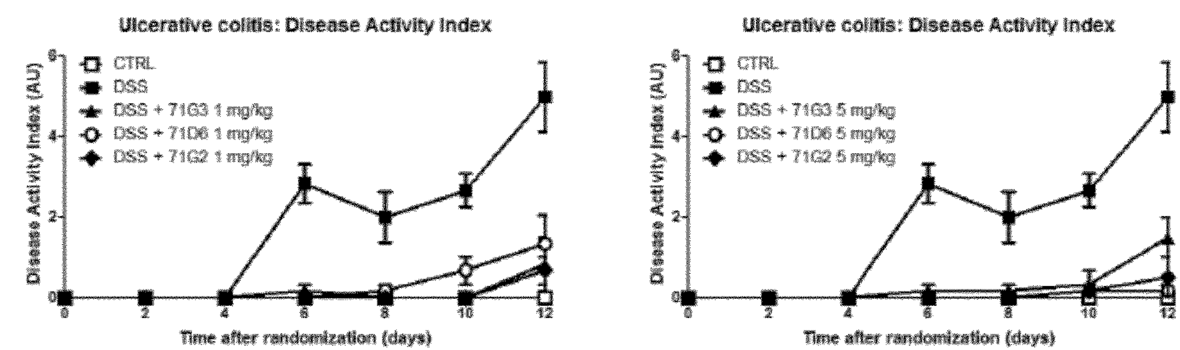
Figure 18:
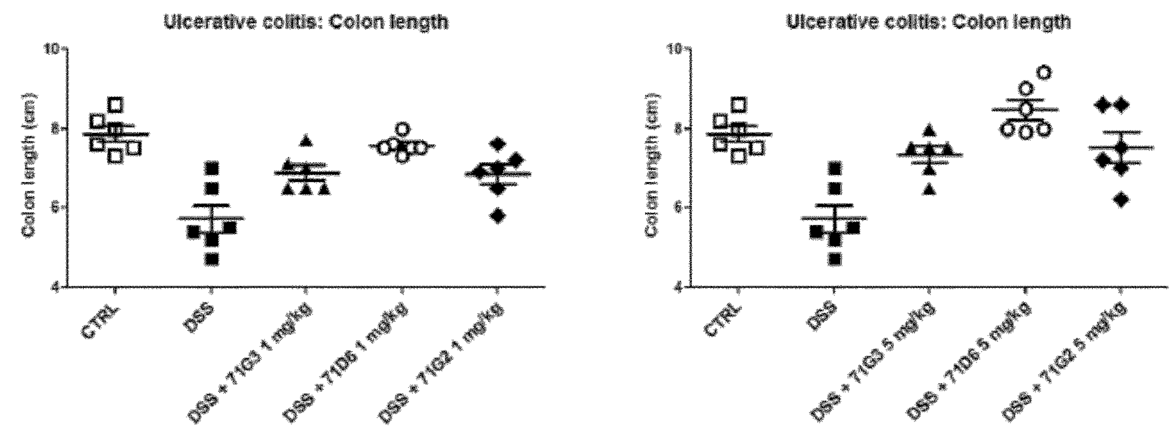

FIG. 18. Ulcerative colitis model: body weight, Disease Activity Index (DAI), and colon length. Ulcerative colitis was induced in BALB/c mice by addition of dextran sodium sulphate (DSS) to the drinking water for 10 days. On day 10, DSS treatment was interrupted and mice were put back on normal water. Starting from day 1, mice were randomized into 7 arms which received treatment with 71G3, 71D6, 71G2 (at a dose of 1 mg/kg or 5 mg/kg) or vehicle only (PBS). An additional, eighth control arm received no DSS or antibody and served as healthy control. Mice were sacrificed on day 12, i.e. 2 days after DSS administration was interrupted. At autopsy, colons were collected, washed through, and their length was determined using a ruler. Following measurement, colons were embedded in paraffin and processed for histological analysis. During the whole course of the experiment, mouse weight was monitored on a regular basis, and the clinical symptoms of ulcerative colitis were assessed by determining faecal blood, rectal bleeding and stool consistency. Each parameter was given a score from 0 (absence of the symptom) to 3 (maximal manifestation of the symptom). Scores relative to the single parameters were summed together to give rise to the DAI ranging from 0 to 9. (A) Body weight over time (% relative to time 0). (B) DAI over time. (C) Colon length at autopsy. Data of the 1 mg/kg arms and of the 5 mg/kg arms are shown in separate graphs for clarity.

Figure 19:
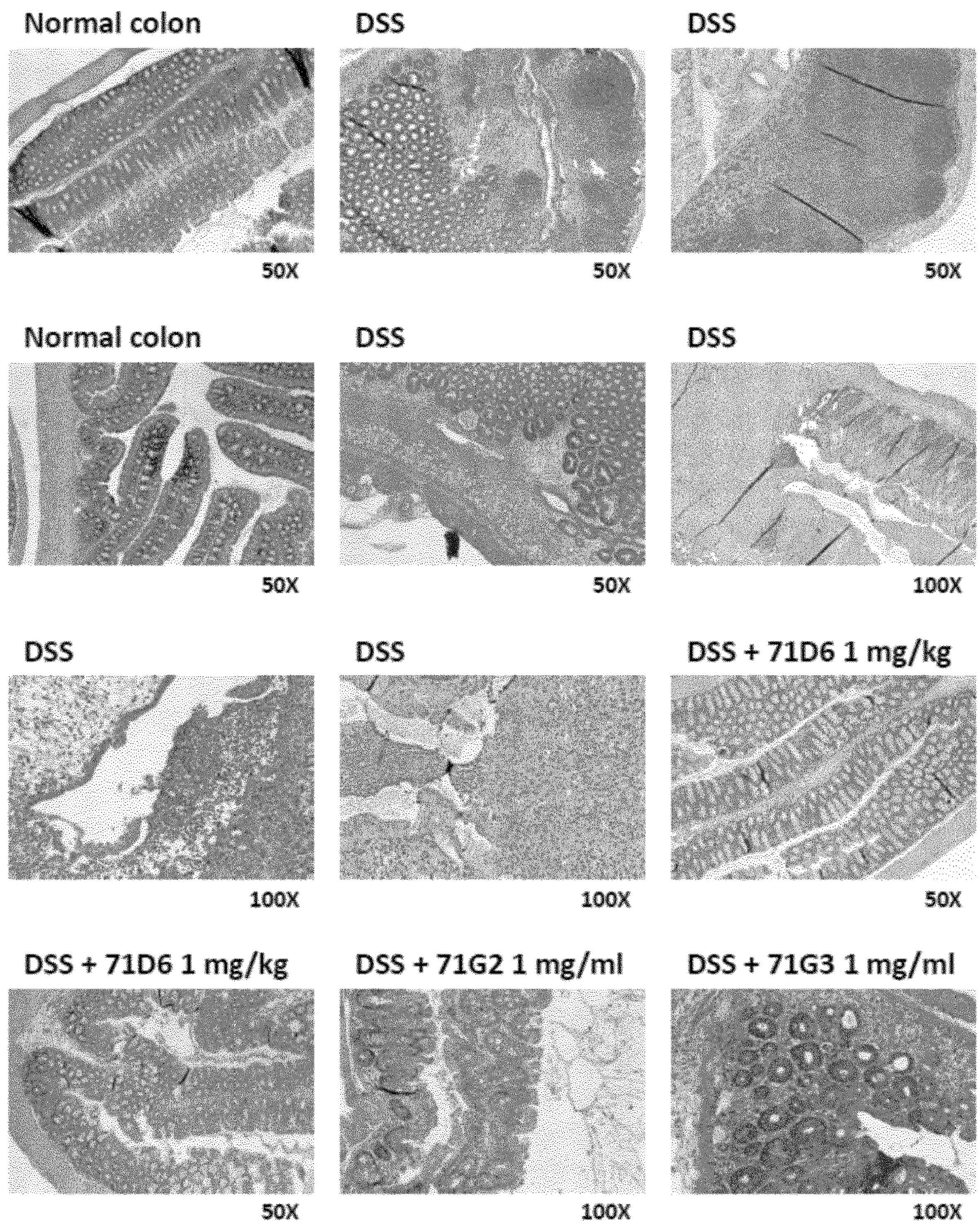

FIG. 19. Ulcerative colitis model: histological analysis of colon sections. Ulcerative colitis was induced in BALB/c mice by exposure to dextran sodium sulphate (DSS) as described in FIG. 18 legend. At autopsy, colons were collected, measured, and then embedded in paraffin and processed for histological analysis. Colon sections were stained with hematoxylin and eosin, examined by microscopy, and photographed. Experimental arm, antibody dose and magnification are indicated close to each image. Please refer to the main text for image analysis.

Figure 20:
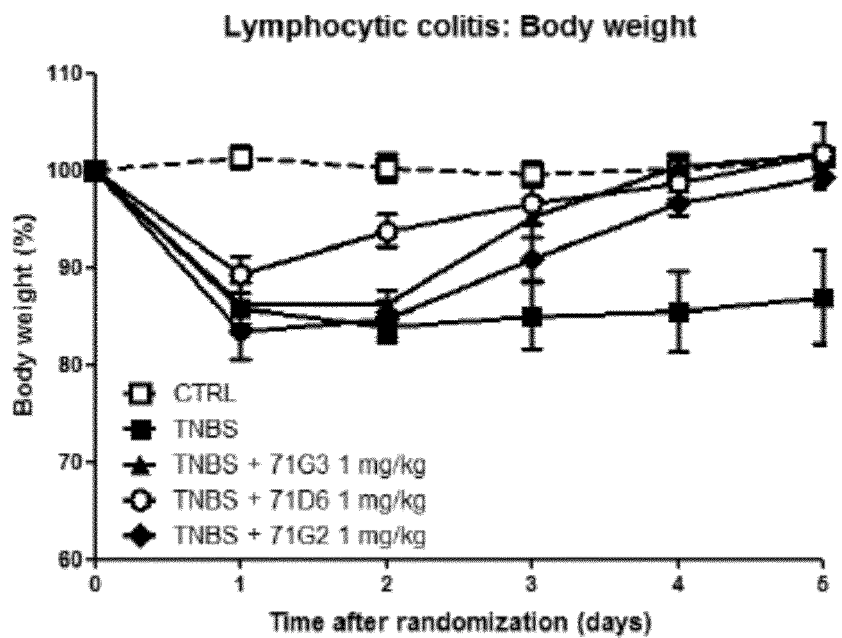
Figure 20:
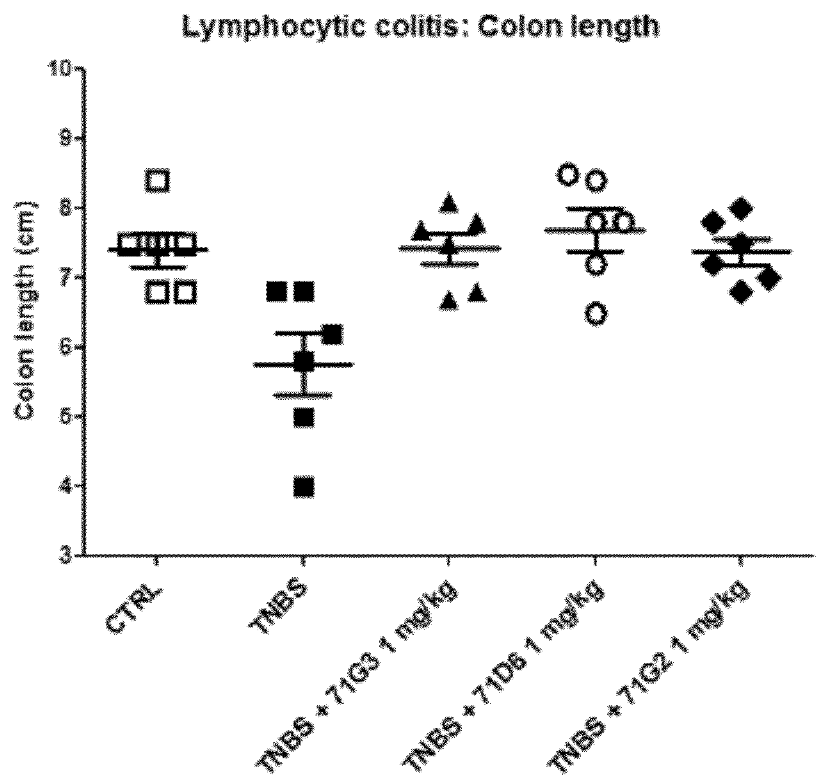

FIG. 20. Inflammatory bowel disease model: body weight and colon length. Colon injury and inflammation was induced in C57BLKS/J mice by intra-rectal injection of 2,4,6-trinitrobenzenesulfonic acid (TNBS) dissolved in ethanol. Soon after TNBS administration, mice were randomized into 4 arms which received treatment with 71G3, 71D6, 71G2 or vehicle only (PBS). An additional, fifth control arm received no TNBS or antibody and served as healthy control. Mice were sacrificed 5 days after TNBS administration. At autopsy, colons were collected and measured. Following measurement, colons were embedded in paraffin and processed for histological analysis. During the whole course of the experiment, mouse weight was measured every day. (A) Body weight over time (% relative to time 0). (B) Colon length at autopsy.

Figure 21:
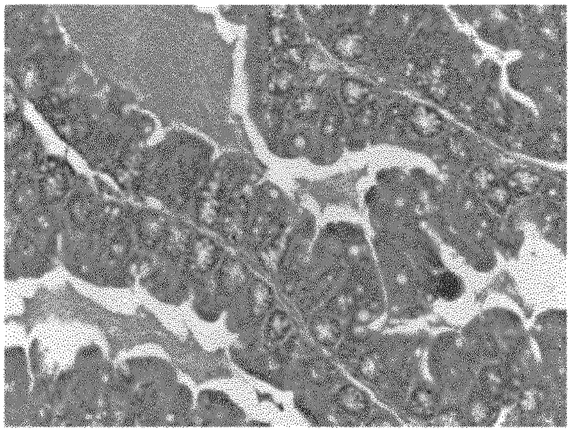
Figure 21:
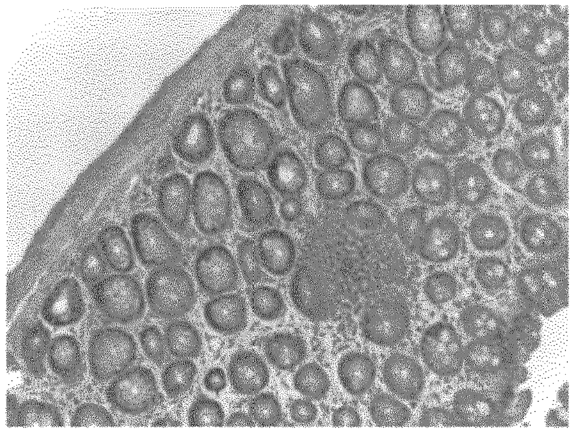
Figure 21:
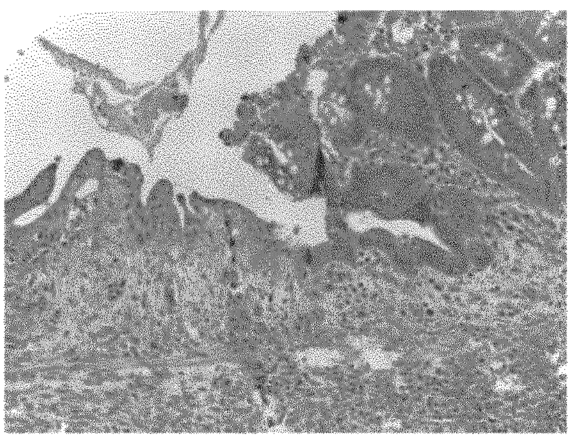
Figure 21:
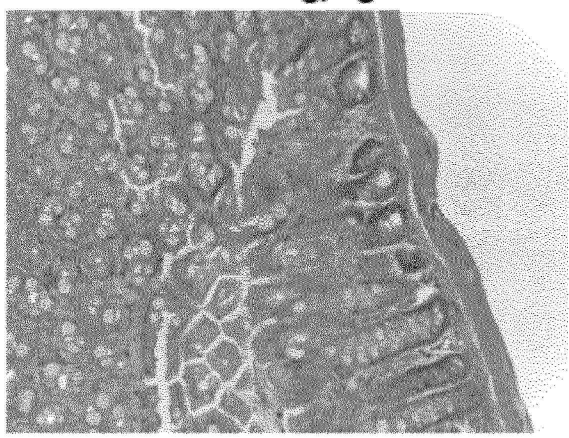
Figure 21:
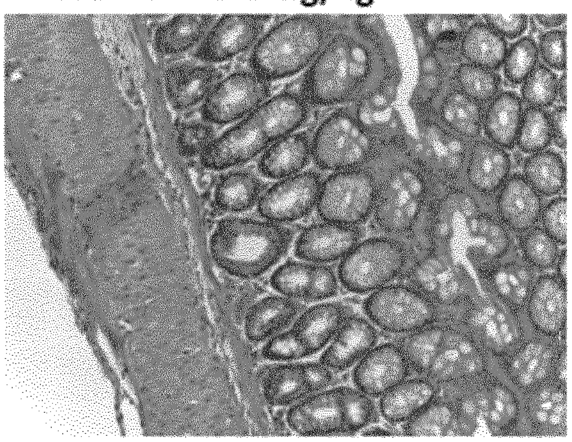
Figure 21:
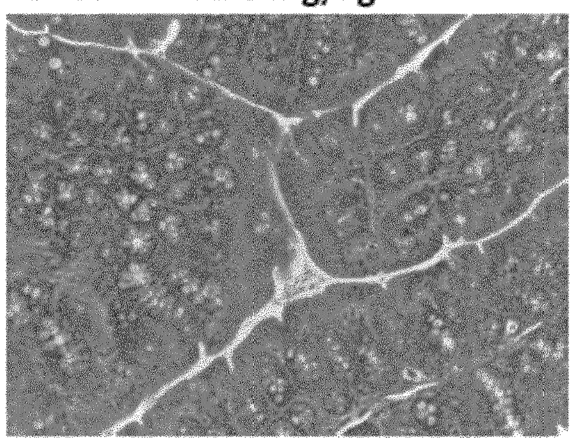

FIG. 21. Inflammatory bowel disease model: histological analysis of colon sections. Colon injury and inflammation was induced in BALB/c mice by intra-rectal injection of 2,4,6-trinitrobenzenesulfonic acid (TNBS) as described in FIG. 20 legend. At autopsy, colons were collected and measured. Following measurement, colons were embedded in paraffin and processed for histological analysis. Colon sections were stained with hematoxylin and eosin, examined by microscopy, and photographed. Please refer to the main text for image analysis.

Figure 22:
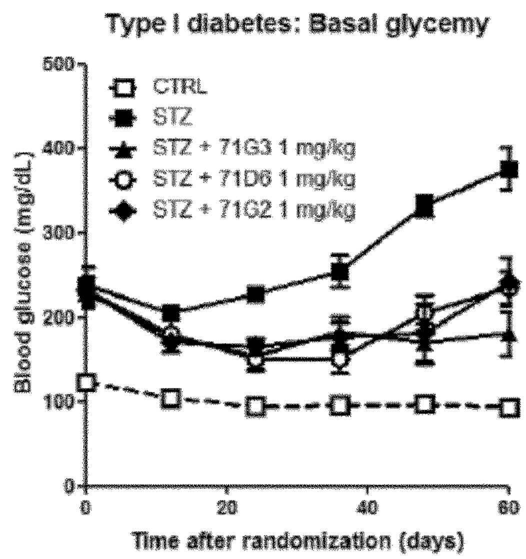
Figure 22:
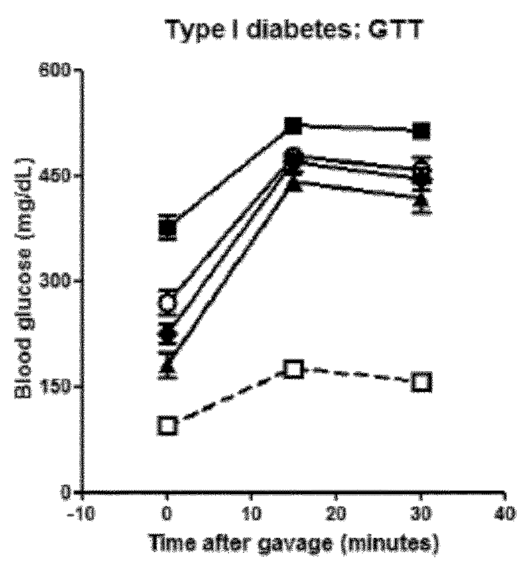
Figure 22:
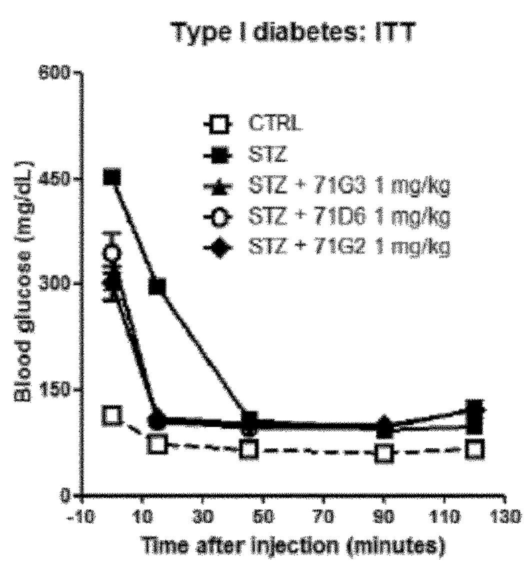
Figure 22:
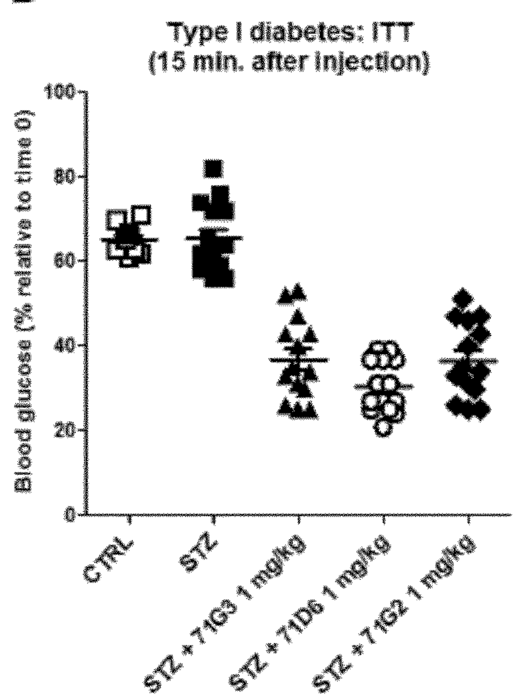

FIG. 22. Type I diabetes model: promotion of glucose uptake and cooperation with insulin in diabetic mice. Pancreatic β-cell degeneration was induced in BALB/c mice by i.p. injection of streptozotocin (STZ). STZ-treated mice displayed a mean basal glycemy two times higher compared to untreated mice. STZ-treated mice were randomized into 4 arms, which received treatment with 71G3, 71D6, 71G2 or vehicle only (PBS), respectively. An additional, fifth control arm received no STZ or antibody and served as healthy control. Blood glucose concentration in fasting conditions was monitored over time for 5 weeks. At the end of week 5, a glucose tolerance test (GTT) and an insulin tolerance test (ITT) were performed. (A) Analysis over time of basal blood glucose levels in fasting conditions. (B) GTT: following oral administration of glucose to a fasting animal, blood glucose levels are monitored over time. (C) ITT: following i.p. injection of insulin to a partially fasting animal, blood glucose levels are monitored over time.

Figure 23:
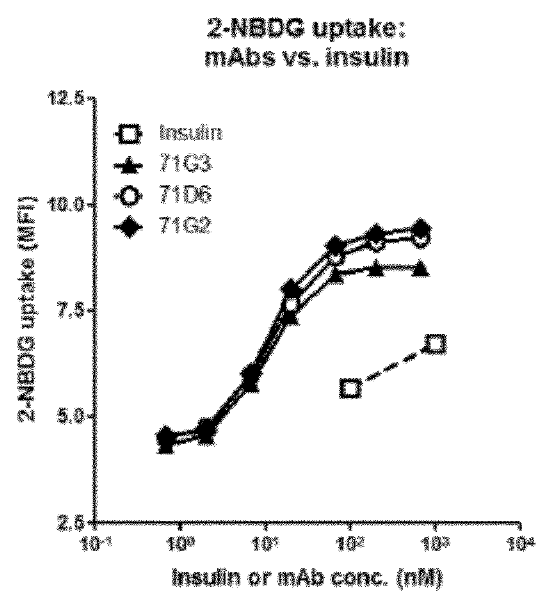
Figure 23:
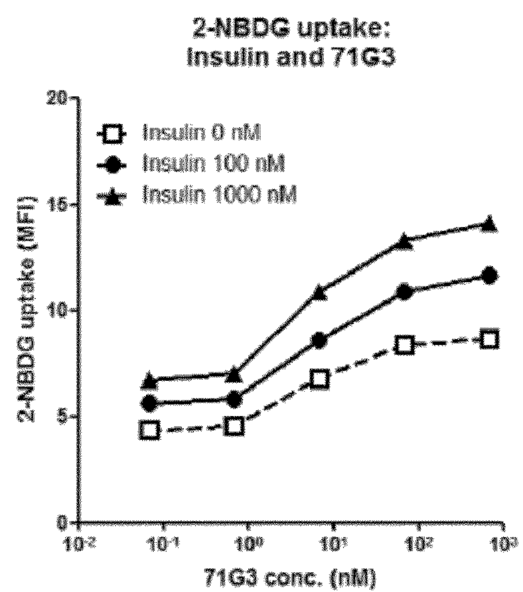
Figure 23:
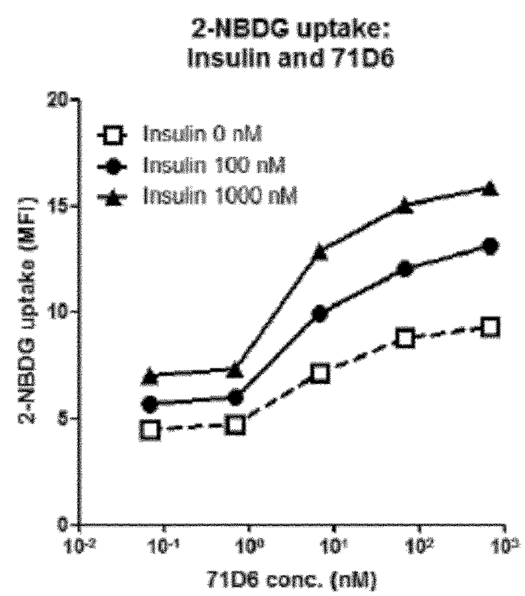
Figure 23:
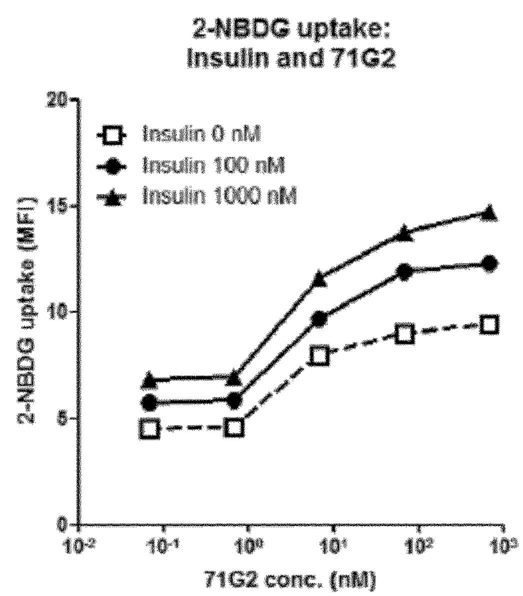

FIG. 23. Type I diabetes model: promotion of glucose uptake and co-operation with insulin in cultured cells. C2C12 mouse myoblast cells were induced to differentiate into myocytes and then incubated with human/mouse equivalent agonistic anti-MET antibodies (71G3, 71D6, 71G2). After 24 hours, antibody-treated cells were divided into 3 arms, which were subjected to acute stimulation with 0 nM, 100 nM or 1000 nM human recombinant insulin for 1 hour in the presence of the fluorescent glucose analogue 2-(N-(7-Nitrobenz-2-oxa-1,3-diazol-4-yl)Amino)-2-Deoxy-glucose (2-NBDG). 2-NBDG uptake was determined by flow cytometry. (A) Induction of 2-NBDG uptake by human/mouse equivalent agonistic anti-MET antibodies or insulin. (B) Induction of 2-NBDG uptake by 71G3 in the absence or presence of insulin. (C) Induction of 2-NBDG uptake by 71D6 in the absence or presence of insulin. (D) Induction of 2-NBDG uptake by 71G2 in the absence or presence of insulin.

Figure 24:
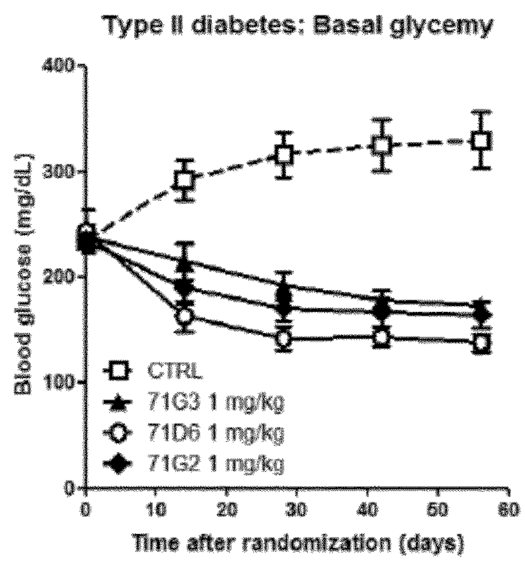
Figure 24:
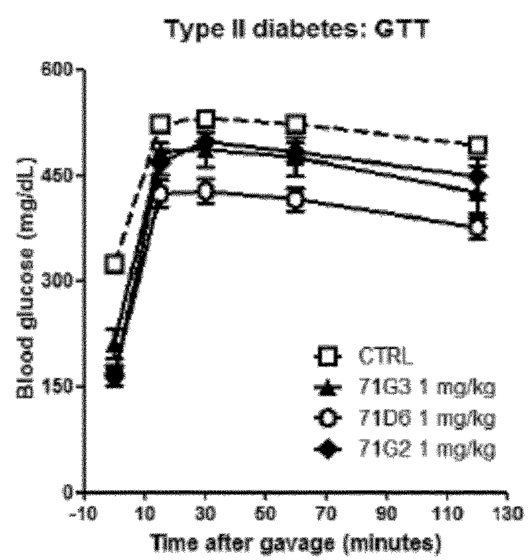
Figure 24:
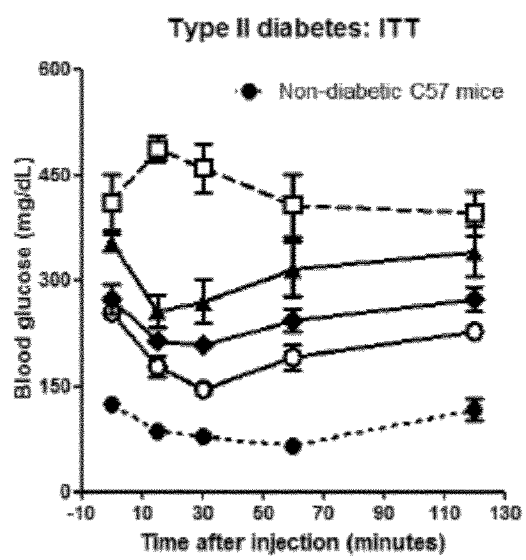
Figure 24:
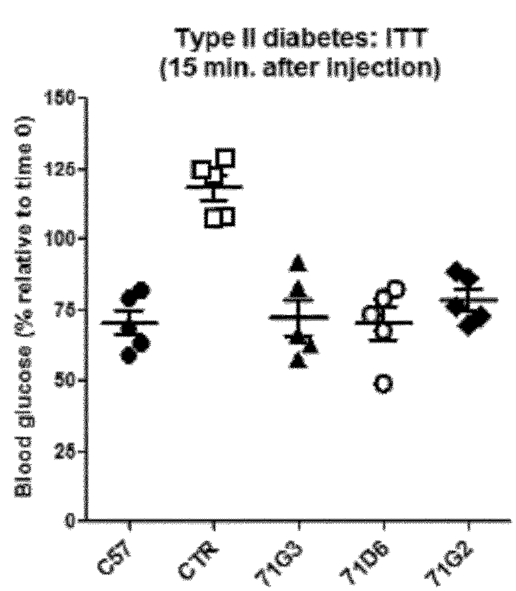

FIG. 24. Type II diabetes model: blood glucose level normalization and insulin resistance overcoming in db/db mice. At the age of 8 weeks, female db/db mice (a C57BLKS/J variant bearing a point mutation in the leptin receptor gene lepr) were randomized into 4 arms that received treatment with 71G3, 71D6, 71G2 or vehicle only (PBS), respectively. Antibodies were administered two times a week by i.p. injection at a dose of 1 mg/kg. Blood glucose concentration in fasting conditions was monitored every 10 days for 7 weeks. At the end of the treatment, i.e. when mice were 15 weeks old, a glucose tolerance test (GTT) and an insulin tolerance test (ITT) were performed using age-matched wild-type C57BLKS/J mice as control. (A) Blood glucose concentration overtime. (B) GTT: following oral administration of glucose to a fasting animal, blood glucose levels are monitored over time. (C) ITT: following i.p. injection of insulin to a partially fasting animal, blood glucose levels are monitored over time.

Figure 25:
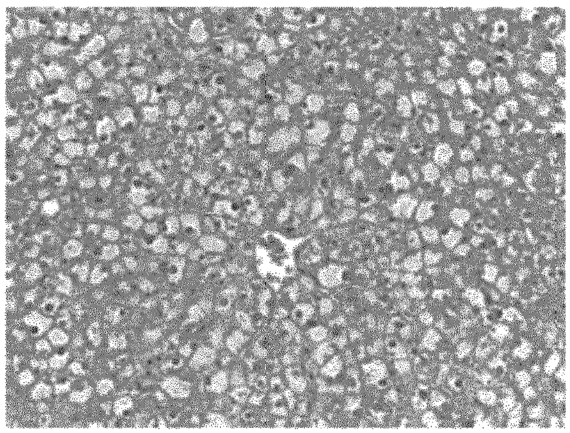
Figure 25:
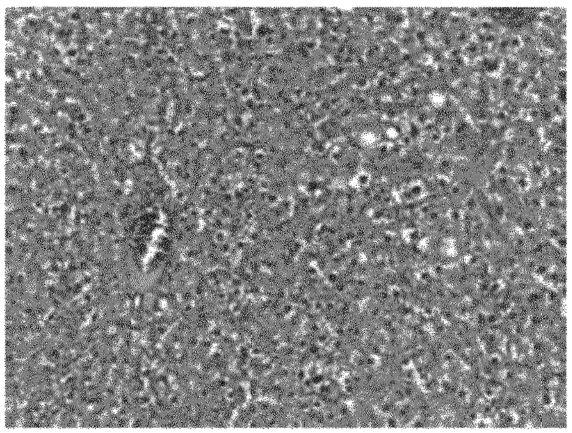
Figure 25:
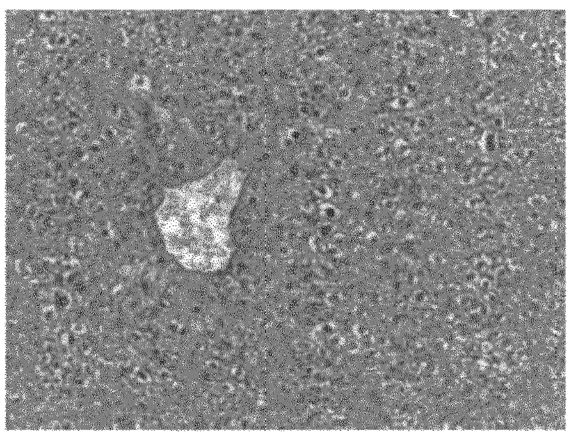
Figure 25:
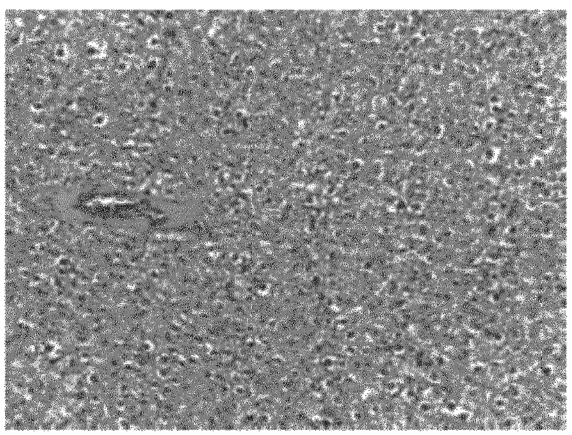

FIG. 25. Mouse model of non-alcoholic steatohepatitis (NASH): fatty liver amelioration as determined by histology. Eight week-old female db/db mice were randomized into 4 arms that received treatment with 71G3, 71D6, 71G2 or vehicle only (PBS), respectively. Antibodies were administered two times a week by i.p. injection at a dose of 1 mg/kg. After 8 weeks of treatment, mice were sacrificed and subjected to autopsy. Blood was collected for analysis of hepatic function markers. Livers were extracted, embedded in paraffin and processed for histological examination. Liver sections were stained with hematoxylin and eosin. The cytoplasm of fatty cells appears empty and white because lipids are washed away during alcohol processing of the specimen. A representative image for each treatment arm is shown. Magnification: 200×.

Figure 26:
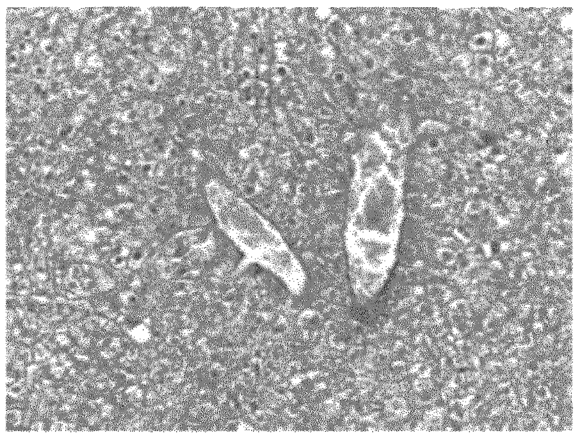
Figure 26:
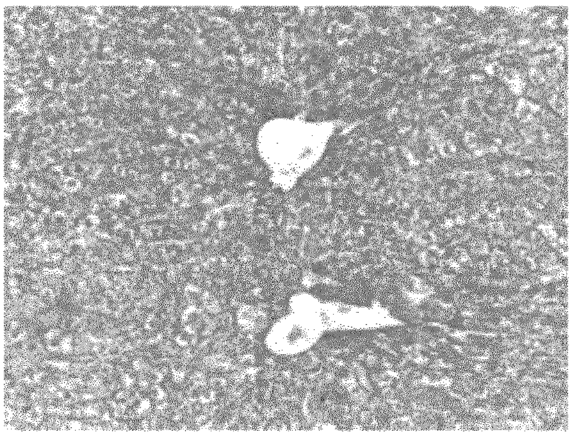
Figure 26:
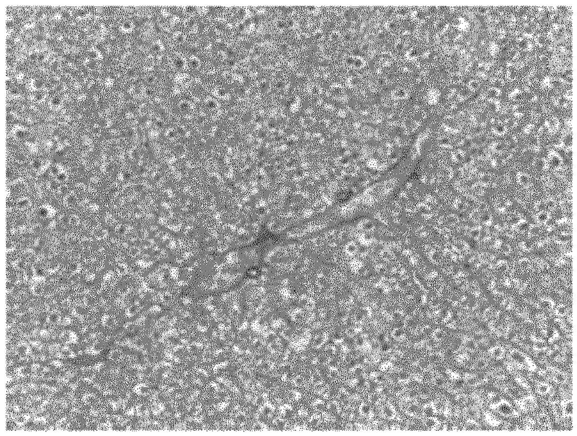

FIG. 26. Mouse model of non-alcoholic steatohepatitis (NASH): suppression of fibrosis as determined by Picro Sirius red staining. Eight week-old female db/db mice were randomized and treated as described in FIG. 25 legend. At autopsy, livers were processed for histological examination. Liver sections were stained with Sirius red to highlight fibrosis. A representative image for each treatment arm is shown. Magnification: 200×.

Figure 27:
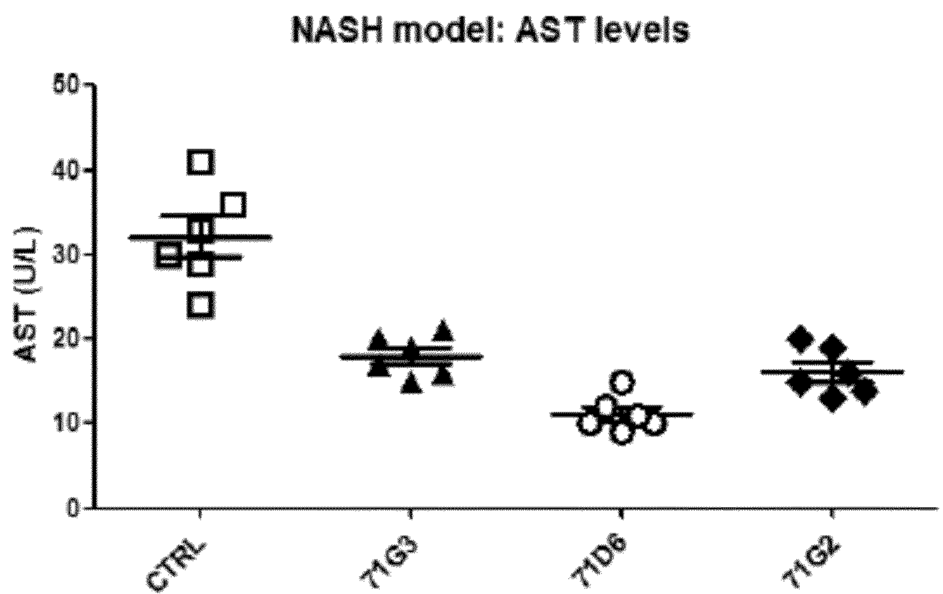
Figure 27:
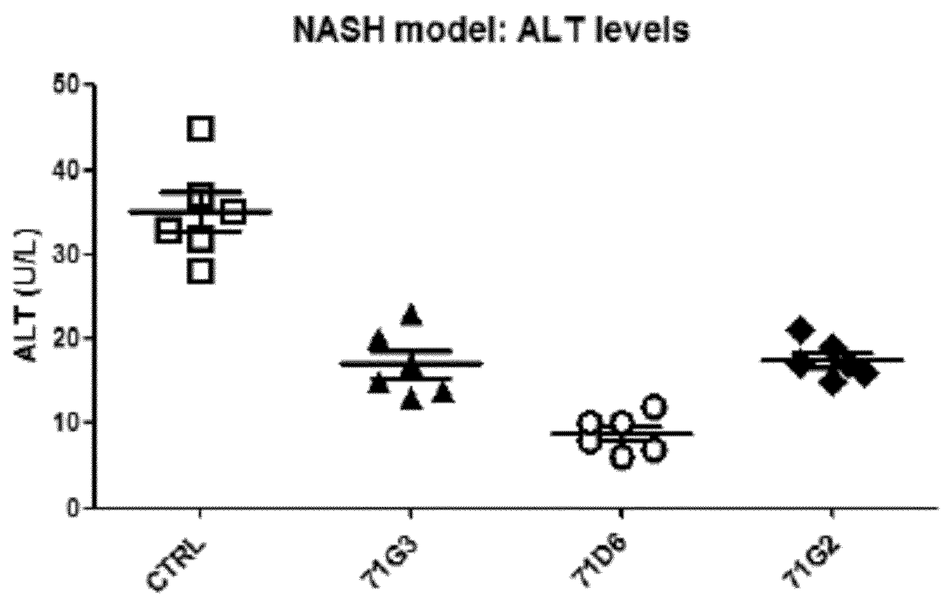

FIG. 27. Mouse model of non-alcoholic steatohepatitis (NASH): normalization of liver function markers. Eight week-old female db/db mice were treated with purified 71G3, 71D6, 71G2 or vehicle only as described in FIG. 25 legend. After 7 weeks of treatment, blood was collected for analysis of the hepatic function markers. (A) Plasma levels of aspartate transaminase (AST). (B) Plasma levels of alanine aminotransferase (ALT).

Figure 28:
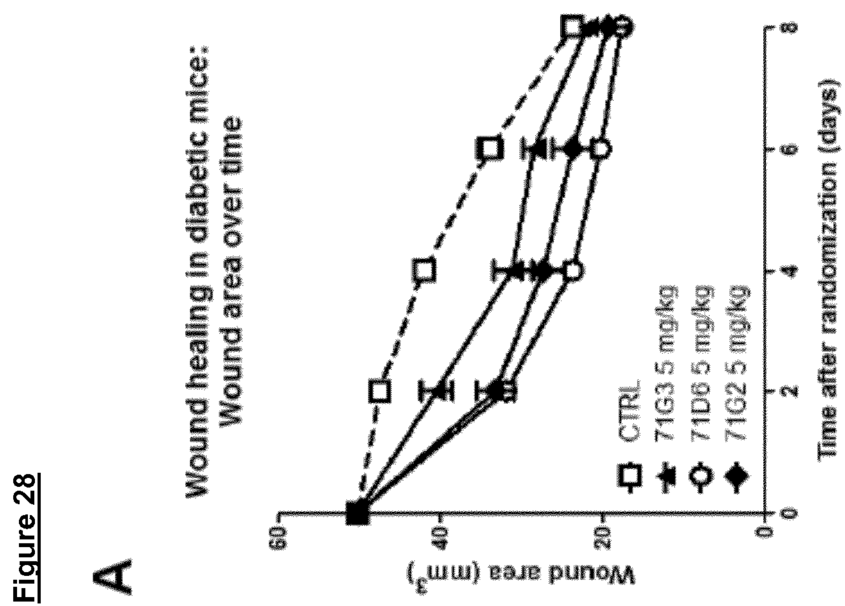
Figure 28:
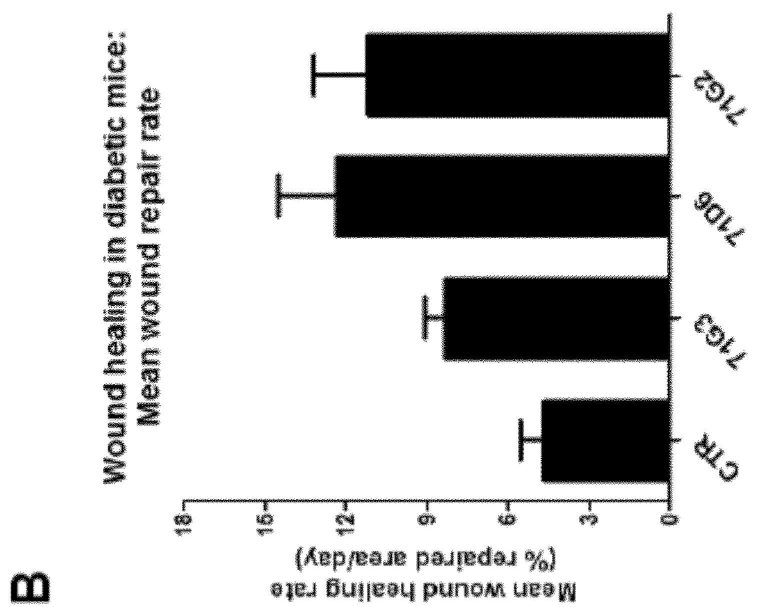

FIG. 28. Mouse model of diabetic ulcers: accelerated healing of wounds. Eight week-old db/db diabetic mice were subjected to anaesthesia and then cut with a 0.8 cm-wide circular punch blade for skin biopsies to create a round wound in the right posterior flank. The entire epidermal layer was removed. The day after surgery, mice were randomized into 4 arms that received treatment with purified 71G3, 71D6 and 71G2 or vehicle only (PBS). Antibodies were delivered every second day by i.p injection at a dose of 5 mg/kg. Wound diameter was measured every day using a caliper. (A) Wound area over time. (B) Mean re-epithelization rate as determined by averaging the daily % of wound closure.

Figure 29:
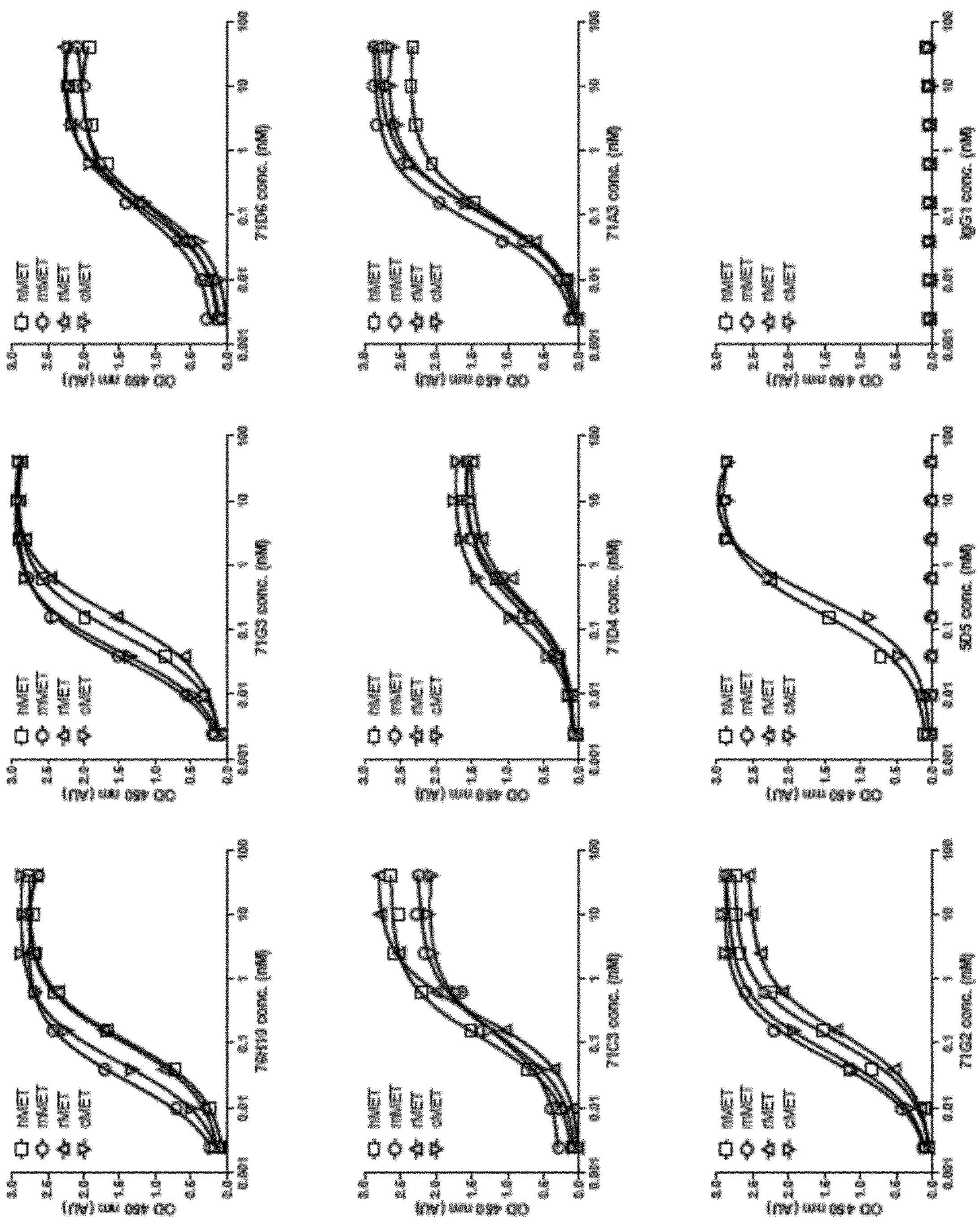

FIG. 29. *Rattus norvegicus* and *Macaca fascicularis* cross-reactivity as determined by ELISA. In order to test pan-species cross-reactivity, a restricted panel of antibodies representative of both SEMA binders (71D6, 71C3, 71D4, 71A3, 71G2) and PSI binders (76H10, 71G3) was selected. The 5D5 prior art antibody was used as control. Human, mouse, rat or monkey MET ECD was immobilized in solid phase and exposed to increasing concentrations of mAbs (in their human IgG1/A format) in solution. Binding was revealed using HRP-conjugated anti-human Fc antibodies.

FIG. 30. Amino acid sequence alignment among the MET ECD domains of from *H. sapiens, M. musculus, R. norvegicus, M. fascicularis* and *L. glama*. (A) Sequence alignment relative to the region recognized by the SEMA-binding antibodies (71 D6, 71C3, 71D4, 71A3 and 71G2) (human MET sequence SEQ ID NO: 239; mouse MET sequence SEQ ID NO: 240; rat MET sequence SEQ ID NO: 241, cyno MET sequence SEQ ID NO: 242, Llama MET sequence SEQ ID NO: 243). The amino acids identified by the human-llama chimera approach shown in Table 12 are underlined. Within this region there are five residues that are conserved in human and mouse MET but not in llama MET (Ala 327, Ser 336, Phe 343, Ile 367, Asp 372). These amino acids are indicated with a black box and the progressive numbers 1-5. Of these, four residues are also conserved in rat and cynomolgus monkey MET (Ala 327, Ser 336, Ile 367, Asp 372). Amino acids responsible for binding to the SEMA-binding antibodies are indicated with an "S" (for SEMA). Amino acids responsible for binding to 5D5/Onartuzumab are indicated with an "O" (for Onartuzumab). (B) Sequence alignment relative to the region recognized by the PSI-binding antibodies 76H10 and 71G3 (human MET sequence SEQ ID NO: 244; mouse MET sequence SEQ ID NO: 245; rat MET sequence SEQ ID NO: 246, cyno MET sequence SEQ ID NO: 247, Llama MET sequence SEQ ID NO: 248). The amino acids identified by the human-llama chimera approach shown in Table 12 are underlined. Within this region there are three residues that are conserved in human and mouse MET but not in llama MET (Arg 547, Ser 553, Thr 555). These amino acids are indicated with a black box and the progressive numbers 6-8. Of these, two residues are also conserved in rat and cynomolgus monkey MET (Ser 553 and Thr 555). The amino acid responsible for binding to the PSI-binding antibodies is indicated with a "P" (for PSI).

FIG. 31. Schematic representation of the MET mutants used for fine epitope mapping. Using human MET ECD as a template, the key residues indicated with the progressive numbers 1-8 in FIG. 30 were mutagenized in different permutations, generating mutants A-L. Each of these mutants is fully human except for the indicated residues, which are llama.

DETAILED DESCRIPTION

As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. MET). The term "MET antibodies" or "anti-MET antibodies" are used herein to refer to antibodies which exhibit immunological specificity for MET protein. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. Although all five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated by B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

As used herein, the terms "MET protein" or "MET antigen" or "MET" are used interchangeably and refer to the receptor tyrosine kinase that, in its wild-type form, binds Hepatocyte Growth Factor (HGF). The terms "human MET protein" or "human MET receptor" or "human MET" or "hMET" are used interchangeably to refer to human MET (GenBank accession number: X54559), including the native human MET protein naturally expressed in the human host and/or on the surface of human cultured cell lines, as well as recombinant forms and fragments thereof and also naturally occurring mutant forms. The terms "mouse MET protein" or "mouse MET receptor" or "mouse MET" or "mMET" are used interchangeably to refer to mouse MET (GenBank accession number: NM_008591), including the native mouse MET protein naturally expressed in the mouse host and/or on the surface of mouse cultured cell lines, as well as recombinant forms and fragments thereof and also naturally occurring mutant forms.

As used herein, the term "binding site" comprises a region of a polypeptide which is responsible for selectively binding to a target antigen of interest (e.g. hMET). Binding domains comprise at least one binding site. Exemplary binding domains include an antibody variable domain. The antibody molecules of the invention may comprise a single binding site or multiple (e.g., two, three or four) binding sites.

As used herein the term "derived from" a designated protein (e.g. a MET antibody or antigen-binding fragment thereof) refers to the origin of the polypeptide. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least 3-5 amino acids, at least 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, e.g. affinity variants, wherein the variant CDR sequences maintain MET binding activity.

"Camelid-Derived"—In certain preferred embodiments, the MET antibody molecules of the invention comprise framework amino acid sequences and/or CDR amino acid sequences derived from a camelid conventional antibody raised by active immunisation of a camelid with a MET-derived antigen. However, MET antibodies comprising camelid-derived amino acid sequences may be engineered to comprise framework and/or constant region sequences derived from a human amino acid sequence (i.e. a human antibody) or other non-camelid mammalian species. For example, a human or non-human primate framework region, heavy chain portion, and/or hinge portion may be included in the subject MET antibodies. In one embodiment, one or more non-camelid amino acids may be present in the framework region of a "camelid-derived" MET antibody, e.g., a camelid framework amino acid sequence may comprise one or more amino acid mutations in which the corresponding human or non-human primate amino acid residue is present. Moreover, camelid-derived VH and VL domains, or humanised variants thereof, may be linked to the constant domains of human antibodies to produce a chimeric molecule, as extensively described elsewhere herein.

As used herein, a "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members.

As used herein, the term "heavy chain portion" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, an antibody or antigen binding fragment of the invention may comprise the Fc portion of an immunoglobulin heavy chain (e.g., a hinge portion, a CH2 domain, and a CH3 domain). In another embodiment, an antibody or antigen binding fragment of the invention may lack at least a portion of a constant domain (e.g., all or part of a CH2 domain). In certain embodiments, at least one, and preferably all, of the constant domains are derived from a human immunoglobulin heavy chain. For example, in one preferred embodiment, the heavy chain portion comprises a fully human hinge domain. In other preferred embodiments, the heavy chain portion comprises a fully human Fc portion (e.g., hinge, CH2 and CH3 domain sequences from a human immunoglobulin).

In certain embodiments, the constituent constant domains of the heavy chain portion are from different immunoglobulin molecules. For example, a heavy chain portion of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain portion may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant region domain (CL). Exemplary modifications include additions, deletions or substitutions of one or more amino acids in one or more domains.

As used herein, a "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric MET antibodies include fusion proteins comprising camelid-derived VH and VL domains, or humanised variants thereof, fused to the constant domains of a human antibody, e.g. human IgG1, IgG2, IgG3 or IgG4, or fused to the constant domains of a mouse antibody, e.g. mouse IgG1, IgG2a, IgG2b, IgG2c or IgG3.

As used herein, the terms "variable region" and "variable domain" are used interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20, 267-279, 2000). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20, 267-279, 2000). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20, 267-279, 2000).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1991) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, Md., 1991). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227, 799-817, 1992; Tramontano et al., J. Mol. Biol, 215, 175-182, 1990). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616, 1977, by Kabat et al., Sequences of Proteins of Immunological Interest, 5th Ed. Public Health Service, National Institutes of Health, Bethesda, Md., 1991, by Chothia et al., J. Mol. Biol. 196, 901-917, 1987, and by MacCallum et al., J. Mol. Biol. 262, 732-745, 1996, where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions.

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework region" or "FR region" includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As used herein, the term "hinge region" includes the portion of a heavy chain molecule that joins the CH1 domain to the CH2 domain. This hinge region comprises approximately residues and is flexible, thus allowing the two N-terminal antigen binding regions to move independently. Hinge regions can be subdivided into three distinct domains: upper, middle, and lower hinge domains (Roux et al., J. Immunol. 161, 4083-4090, 1998). MET antibodies comprising a "fully human" hinge region may contain one of the hinge region sequences shown in Table 2 below.

TABLE 2

Human hinge sequences.

| IgG | Upper hinge | Middle hinge | Lower hinge |
|---|---|---|---|
| IgG1 | EPKSCDKTHT (SEQ ID NO: 227) | CPPCP (SEQ ID NO: 228) | APELLGGP (SEQ ID NO: 229) |
| IgG3 | ELKTPLGDTTHT (SEQ ID NO: 230) | CPRCP $(EPKSCDTPPPCPRCP)_3$ (SEQ ID NO: 231) | APELLGGP (SEQ ID NO: 232) |
| IgG4 | ESKYGPP (SEQ ID NO: 233) | CPSCP (SEQ ID NO: 234) | APEFLGGP (SEQ ID NO: 235) |
| IgG42 | ERK (SEQ ID NO: 236) | CCVECPPPCP (SEQ ID NO: 237) | APPVAGP (SEQ ID NO: 238) |

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; Kabat et al., Sequences of Proteins of Immunological Interest, 5th Ed. Public Health Service, National Institutes of Health, Bethesda, Md. (1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to hMET and mMET). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding molecules have at least one binding site specific for hMET.

As used herein, the term "specificity" refers to the ability to bind (e.g., immunoreact with) a given target, e.g., hMET, mMET. A polypeptide may be monospecific and contain one or more binding sites which specifically bind a target or a polypeptide may be multispecific and contain two or more binding sites which specifically bind the same or different targets.

In one embodiment, an antibody of the invention is specific for more than one target. For example, in one embodiment, a multispecific binding molecule of the invention binds hMET and a second target molecule. In this context, the second target molecule is a molecule other than hMET or mMET.

The term "epitope" refers to the portion(s) of an antigen (e.g. human MET) that contact an antibody. Epitopes can be linear, i.e., involving binding to a single sequence of amino acids, or conformational, i.e., involving binding to two or more sequences of amino acids in various regions of the antigen that may not necessarily be contiguous. The antibodies provided herein may bind to different (overlapping or non-overlapping) epitopes within the extracellular domain of the human MET protein.

As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen; heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

The term "modified antibody" may also be used herein to refer to amino acid sequence variants of a MET antibody of the invention. It will be understood by one of ordinary skill in the art that a MET antibody of the invention may be modified to produce a variant MET antibody which varies in amino acid sequence in comparison to the MET antibody from which it was derived. For example, nucleotide or amino acid substitutions leading to conservative substitutions or changes at "non-essential" amino acid residues may be made (e.g., in CDR and/or framework residues). Amino acid substitutions can include replacement of one or more amino acids with a naturally occurring or non-natural amino acid.

As used herein, the term "humanising substitutions" refers to amino acid substitutions in which the amino acid residue present at a particular position in the VH or VL domain of a MET antibody of the invention (for example a camelid-derived MET antibody) is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of a MET antibody, defined herein.

As used herein the term "humanised variant" refers to a variant antibody which contains one or more "humanising substitutions" compared to a reference MET antibody, wherein a portion of the reference antibody (e.g. the VH domain and/or the VL domain or parts thereof containing at least one CDR) has an amino acid sequence derived from a non-human species, and the "humanising substitutions" occur within the amino acid sequence derived from a non-human species.

The term "germlined variant" is used herein to refer specifically to "humanised variants" in which the "humanising substitutions" result in replacement of one or more amino acid residues present at a particular position (s) in the VH or VL domain of a MET antibody of the invention (for example a camelid-derived MET antibody) with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably herein. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

As used herein, the term "affinity variant" refers to a variant antibody which exhibits one or more changes in amino acid sequence compared to a reference MET antibody of the invention, wherein the affinity variant exhibits an altered affinity for hMET and/or mMET in comparison to the reference antibody. Preferably the affinity variant will exhibit improved affinity for hMET and/or mMET, as compared to the reference MET antibody. The improvement may be apparent as a lower $K_D$ for hMET and/or for mMET, or a slower off-rate for hMET and/or for mMET. Affinity variants typically exhibit one or more changes in amino acid sequence in the CDRs, as compared to the reference MET antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

As used herein, antibodies having "high human homology" refers to antibodies comprising a heavy chain variable domain (VH) and a light chain variable domain (VL) which, taken together, exhibit at least 90% amino acid sequence identity to the closest matching human germline VH and VL sequences. Antibodies having high human homology may include antibodies comprising VH and VL domains of native non-human antibodies which exhibit sufficiently high % sequence identity to human germline sequences, including for example antibodies comprising VH and VL domains of camelid conventional antibodies, as well as engineered, especially humanised or germlined, variants of such antibodies and also "fully human" antibodies.

In one embodiment the VH domain of the antibody with high human homology may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and the closest matching human germline VH domain sequence may be 85% or greater, 90% or greater, 95% or greater, 97% or greater, or up to 99% or even 100%.

In one embodiment the VH domain of the antibody with high human homology may contain one or more (e.g. 1 to 10) amino acid sequence mis-matches across the framework regions FR1, FR2, FR3 and FR4, in comparison to the closest matched human VH sequence. In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and the closest matching human germline VL domain sequence may be 85% or greater 90% or greater, 95% or greater, 97% or greater, or up to 99% or even 100%.

In one embodiment the VL domain of the antibody with high human homology may contain one or more (e.g. 1 to 10) amino acid sequence mis-matches across the framework regions FR1, FR2, FR3 and FR4, in comparison to the closest matched human VL sequence.

Before analysing the percentage sequence identity between the antibody with high human homology and human germline VH and VL, the canonical folds may be determined, which allows the identification of the family of human germline segments with the identical combination of canonical folds for H1 and H2 or L1 and L2 (and L3). Subsequently the human germline family member that has the highest degree of sequence homology with the variable region of the antibody of interest is chosen for scoring the sequence homology. Procedures for determining the closest matching human germline, and determining sequence identity/homology, are well-known to the skilled person.

Antibodies with high human homology may comprise hypervariable loops or CDRs having human or human-like canonical fold structures. In one embodiment at least one hypervariable loop or CDR in either the VH domain or the VL domain of the antibody with high human homology may be obtained or derived from a VH or VL domain of a non-human antibody, for example a conventional antibody from a species of Camelidae, yet exhibit a predicted or actual canonical fold structure which is substantially identical to a canonical fold structure which occurs in human antibodies. In one embodiment, both H1 and H2 in the VH domain of the antibody with high human homology exhibit a predicted or actual canonical fold structure which is substantially identical to a canonical fold structure which occurs in human antibodies.

Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, e.g. a Camelidae species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, e.g. a Camelidae species, and form one of the following canonical fold combinations: 1-1, 1-2, 1-3, 1-6, 1-4, 2-1, 3-1 and 3-5. An antibody with high human homology may contain a VH domain which exhibits both high sequence identity/sequence homology with human VH, and which contains hypervariable loops exhibiting structural homology with human VH.

It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g. antibodies containing VH and VL domains which are derived from camelid conventional antibodies, especially antibodies containing humanised camelid VH and VL domains.

Thus, in one embodiment the VH domain of the MET antibody with high human homology may exhibit a sequence identity or sequence homology of 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain (e.g. derived from a Camelidae species, preferably llama), but form a combination of predicted or actual canonical fold structures which is the same as a canonical fold combination known to occur naturally in the same human VH domain.

In other embodiments, L1 and L2 in the VL domain of the antibody with high human homology are each obtained from a VL domain of a non-human species (e.g. a camelid-derived VL domain), and each exhibits a predicted or actual canonical fold structure which is substantially identical to a canonical fold structure which occurs in human antibodies. L1 and L2 in the VL domain of an antibody with high human homology may form a combination of predicted or actual canonical fold structures which is identical to a combination of canonical fold structures known to occur in a human germline VL domain. In non-limiting embodiments L1 and L2 in the VLambda domain of an antibody with high human homology (e.g. an antibody containing a camelid-derived VL domain or a humanised variant thereof) may form one of the following canonical fold combinations: 11-7, 13-7(A,B, C), 14-7(A,B), 12-11, 14-11 and 12-12 (as defined in Williams et al., J. Mol. Biol. 264, 220-232, 1996, and as shown on http://www.bioc.uzh.ch/antibody/Sequences/GermlinesA/Base_hVL.html). In non-limiting embodiments L1 and L2 in the Vkappa domain may form one of the following canonical fold combinations: 2-1, 3-1, 4-1 and 6-1 (as defined in Tomlinson et al., EMBO J. 14, 4628-4638, 1995 and as shown on http://www.bioc.uzh.ch/antibody/Sequences/Germlines/VBase_hVK.html). In a further embodiment, all three of L1, L2 and L3 in the VL domain of an antibody with high human homology may exhibit a substantially human structure. It is preferred that the VL domain of the antibody with high human homology exhibits both high sequence identity/sequence homology with human VL, and also that the hypervariable loops in the VL domain exhibit structural homology with human VL.

In one embodiment, the VL domain of a MET antibody with high human homology may exhibit a sequence identity of 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain.

It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings (e.g. camelid-derived VH/VL pairings) with maximal sequence and structural homology to human-encoded VH/VL pairings.

Procedures for evaluating camelid-derived (e.g. llama-derived) CDRs, VH domains or VL domains for the presence of human-like canonical fold structures are described in WO 2010/001251 and WO 2011/080350, the contents of which are incorporated herein in their entirety by reference.

As used herein, the term "affinity" or "binding affinity" should be understood based on the usual meaning in the art in the context of antibody binding, and reflects the strength and/or stability of binding between an antigen and a binding site on an antibody or antigen binding fragment thereof.

The anti-MET antibodies provided herein are characterised by high affinity binding to human MET (hMET), and also high affinity binding with mouse MET (mMET). Binding affinity for hMET and mMET may be assessed using standard techniques known to persons of skill in the art.

In one embodiment, binding affinity of a Fab clone comprising a defined VH/VL pairing may be assessed using surface plasmon resonance, e.g. using the Biacore™ system. Fab clones comprising VH/VL pairings of the antibodies and antigen binding fragments of the invention typically exhibit an off-rate for hMET measured by Biacore™ in the range of from $1\times10^{-3}$ to $1\times10^{-2}$ $s^{-1}$, optionally $1\times10^{-3}$ to $6\times10^{-3}$ $s^{-1}$. An off-rate within this range may be taken as an indication that the Fab, and a corresponding bivalent mAb, exhibit high affinity binding to hMET. Similarly, the Fab clones comprising VH/VL pairings of the antibodies, and antigen binding fragments of the invention typically exhibit an off-rate for mMET measured by Biacore™, as described in the accompanying examples, in the range of from $1\times10^{-3}$ to $1\times10^{-2}$ $s^{-1}$, optionally $1\times10^{-3}$ to $6\times10^{-3}$ $s^{-1}$. An off-rate within this range may be taken as an indication that the Fab, and a corresponding bivalent mAb, exhibit high affinity binding to mMET. Therefore, Fabs that exhibit off-rates for both human and murine MET falling within the stated ranges show high affinity binding for hMET, and high affinity binding for mMET—that is, the Fabs are cross-reactive between hMET and mMET. Bivalent mAbs comprising two Fabs that (individually) exhibit off-rates for human and murine MET within the stated ranges are also taken to exhibit high affinity binding to human MET and high affinity binding to murine MET.

Binding affinity may also be expressed as the dissociation constant for a particular antibody, or the $K_D$. The lesser the $K_D$ value, the stronger the binding interaction between an antibody and its target antigen. $K_D$ may be determined, for example, by combining the $K_{on}$ and $K_{off}$ rate determined by SPR measurement. Typically, antibodies and antigen binding fragments of the invention, when measured as mAbs, exhibit a $K_D$ for mMET and for hMET of less than 0.1 nMol/L.

Binding affinity to human and murine MET can also be assessed using a cell-based system as described in the accompanying examples, in which mAbs are tested for binding to mammalian cell lines that express MET, for example using ELISA or flow cytometry. High affinity for hMET or mMET may be indicated, for example, by an $EC_{50}$ of no more than 0.5 nM in an ELISA such as that described in Example 3.

As summarised above, the invention relates, at least in part, to antibodies, and antigen binding fragments thereof, that bind to hMET and mMET with high affinity. The properties and characteristics of the MET antibodies, and antibody fragments, according to the invention will now be described in further detail.

The high affinity hMET and mMET cross-reactive antibodies and antigen binding fragments described herein are MET agonists. As used herein, MET agonists induce (partially or fully) MET signalling when binding to the MET receptor. MET agonist antibodies and antigen binding fragments according to the invention are agonists of hMET and mMET. Agonist activity on binding of hMET or mMET by the antibodies described herein may be indicated by molecular and/or cellular responses that (at least partially) mimic the molecular and cellular responses induced upon homologous HGF-MET binding (i.e. human HGF binding hMET, mouse HGF binding mMET). Antibodies stimulating such a response are also referred to herein as "anti-MET agonists", "agonist antibodies" and grammatical variations thereof. Similarly, antibodies partially or fully stimulating such responses are referred to herein as "partial MET agonists" or "partial agonists", or "full MET agonists" or "full agonists", respectively. It is emphasised that antibodies and antigen binding fragments of the invention induce MET signalling in both human and mouse systems—that is, they are agonists of hMET and mMET. Thus the following discussion applies both to the response induced by binding of hMET by the antibodies and antigen binding fragments of the invention, and to the response induced by binding of mMET by the antibodies and antigen binding fragments of the invention.

MET agonism by antibodies and antigen binding fragments of the invention may be indicated by molecular responses such as phosphorylation of the MET receptor and/or cellular responses, for example those detectable in a cell scattering assay, an anti-apoptosis assay and/or a branching morphogenesis assay. These molecular and cellular responses are further described below:

(i) Phosphorylation of the MET receptor. In this context, a MET agonist antibody or antigen binding fragment phosphorylates MET when binding of the antibody or antigen binding fragment causes auto-phosphorylation of MET in the absence of receptor-ligand binding—that is, binding of the antibody or antigen binding fragment to human hMET results in phosphorylation of hMET in the absence of hHGF and binding of the antibody or antigen binding fragment to mMET results in phosphorylation of mMET in the absence of mHGF. Phosphorylation of MET may be determined by assays known in the art, for example Western Blotting or phospho-MET ELISA (as described in Example 6 and in Basilico et al., J Clin Invest. 124, 3172-3186, 2014). Antibodies and antigen binding fragments described herein may exhibit "high phosphorylation potency" or "low phosphorylation potency" for hMET and may exhibit "high phosphorylation potency" or "low phosphorylation potency" for mMET. In this context, an antibody or antigen binding fragment exhibits "high phosphorylation potency" when the antibody or fragment exhibits a potency for mMET with an $EC_{50}$ similar to HGF (<1 nM) and/or an $E_{MAX}$ of at least 80% (as a percentage of maximal HGF-induced activation) and exhibits a potency for hMET with an $EC_{50}$ similar to HGF (<1 nM) and/or an $E_{MAX}$ of at least 80% (as a percentage of maximal HGF-induced activation). An antibody or antigen binding fragment exhibits "low phosphorylation potency" when the antibody exhibits a potency for mMET with an $EC_{50}$ of 1 nM-5 nM and/or an $E_{MAX}$ of 60-80% (as a percentage of maximal HGF-induced activation) and exhibits a potency for hMET with an $EC_{50}$ of 1 nM-5 nM and/or an $E_{MAX}$ of 60-80% (as a percentage of maximal HGF-induced activation).

(ii) Inducing HGF-like cellular responses. MET agonism can be measured using assays such as the cell scattering assay, the anti-apoptosis assay and/or the branching morphogenesis assay described in the present Examples. In this context, MET agonist antibodies or antigen binding fragments according to the invention induce a response in cellular assays such as these that resembles (at least partially) the response observed following exposure to homologous HGF. For example, a MET agonist may be indicated by: an increase in cell scattering in response to the antibody compared to cells exposed to a control antibody (e.g. IgG1); a protective potency against drug-induced apoptosis with an $EC_{50}$ of less than 32 nM and/or an $E_{max}$ cellular viability of greater than 20% compared to untreated cells; and/or an increase in the number of branches per spheroid in cell spheroid preparations exposed to the antibody or antigen binding fragment.

Antibodies and antigen binding fragments described herein may "fully induce" or "partially induce" HGF-like cellular responses when contacted with a human cell and may "fully induce" or "partially induce" HGF-like cellular responses when contacted with a mouse cell, depending on the assay employed.

In this context, "full induction" of HGF-like cellular responses by an antibody or fragment may be measurable as:

- in a cell scattering assay, the antibody or antigen binding fragment induces an increase in cell scattering at least equivalent to 0.1 nM homologous HGF when the antibody concentration is 0.1-1 nM;
- in an anti-apoptosis assay, the antibody or antigen binding fragment exhibits an $EC_{50}$ no more than 1.1× that of HGF and/or an $E_{max}$ cellular viability of greater than 90% that observed for HGF; and/or
- in a branching morphogenesis assay, cells treated with the antibody or antigen binding fragment exhibit greater than 90% of the number of branches per spheroid induced by the same (non-zero) concentration of HGF.

In this context, if an antibody or antigen binding fragment does not "fully induce" HGF-like cellular responses as defined above, "partial induction" of HGF-like cellular responses may be measurable as:

- in a cell scattering assay, the antibody or antigen binding fragment induces a level of cell scattering at least 25% that induced by 0.1 nM homologous HGF when the antibody concentration is 1 nM or lower;
- in an anti-apoptosis assay, the antibody or antigen binding fragment exhibits an $EC_{50}$ no more than 7.0× that of HGF and/or an $E_{max}$ cellular viability of at least 50% that observed for HGF;
- in a branching morphogenesis assay, cells treated with the antibody or antigen binding fragment exhibit at least 25% the number of branches per spheroid induced by the same (non-zero) concentration of HGF.

As already described, antibodies and antigen binding fragments according to the invention are hMET agonists and mMET agonists. Thus, in embodiments wherein the antibodies induce (partially or fully) HGF-like cellular responses, the HGF-like cellular responses are (partially or fully) induced when the antibody or antigen binding fragment is contacted with a human cell and are (partially or fully) induced when the antibody or antigen binding fragment is contacted with a mouse cell.

Binding region mapping (Example 4) demonstrates that the anti-MET antibodies of the invention recognize epitopes of MET either in the PSI domain of MET or in the SEMA domain of MET. Therefore, in certain embodiments, the antibodies or antigen binding fragments of the invention recognize an epitope in the PSI domain of MET, preferably human MET. In certain alternative embodiments, the antibodies or antigen binding fragments of the invention recognize an epitope the SEMA domain of MET, preferably human MET.

In certain embodiments, antibodies or antigen binding fragments recognizing an epitope in the SEMA domain recognize an epitope located on a blade of the SEMA β-propeller. In certain embodiments, the epitope is located on blade 4 or 5 of SEMA β-propeller. In certain such embodiments, the epitope is located between amino acids 314-372 of human MET. In certain embodiments, the epitope is located on blades 1-4 or 1-3 of the SEMA β-propeller. In certain embodiments, the epitope is located between amino acids 27-313 of human MET, or between amino acids 27-225 of human MET.

In certain embodiments, antibodies or antigen binding fragments recognizing an epitope in the PSI domain of MET recognise an epitope located between amino acids 516-545 of MET, preferably human MET. In certain embodiments, antibodies or antigen binding fragments recognizing an epitope in the PSI domain of MET recognise an epitope located between amino acids 546-562 of MET, preferably human MET.

In certain aspects, the antibodies described herein recognize epitopes in the extracellular domain of MET that comprise one or more amino acid residues conserved across human and mouse MET. In preferred embodiments antibodies described herein recognize epitopes in the extracellular domain of MET that comprise one or more amino acid residues conserved across human MET, mouse MET, rat MET and simian (e.g. cynomolgus) MET.

In certain embodiments, antibodies of the invention recognize an epitope of human MET located in the region from amino acid residue 123 to residue 223 of human MET. In certain embodiments, antibodies of the invention recognize an epitope of human MET located in the region from amino acid residue 224 to residue 311 of human MET. In certain embodiments, antibodies of the invention recognize an epitope of human MET located in the region from amino acid residue 314 to residue 372 of human MET. In certain embodiments, antibodies of the invention recognize an epitope of human MET located in the region from amino acid residue 546 to residue 562 of human MET.

In certain embodiments antibodies or antigen binding fragments of the invention recognize an epitope of human MET comprising the amino acid residue Ile367. In certain embodiments antibodies or antigen binding fragments of the invention recognize an epitope of human MET comprising the amino acid residue Asp372 of human MET. In certain embodiments antibodies or antigen binding fragments of the invention recognize an epitope of human MET comprising the amino acid residues Ile367 and Asp372.

In certain such embodiments, antibodies or antigen binding fragments of the invention recognize an epitope of human MET located in the region from amino acid residue 314 to residue 372 of human MET, wherein the epitope comprises the amino acid residue Ile367. In certain such embodiments, antibodies or antigen binding fragments of the invention recognize an epitope of human MET located in the region from amino acid residue 314 to residue 372 of human MET, wherein the epitope comprises the amino acid residue Asp371. In certain such embodiments, antibodies or antigen binding fragments of the invention recognize an epitope of human MET located in the region from amino acid residue 314 to residue 372 of human MET, wherein the epitope comprises the amino acid residues Ile367 and Asp372.

In certain embodiments antibodies or antigen binding fragments of the invention bind an epitope of human MET comprising the amino acid residue Thr555 of human MET.

In certain such embodiments, antibodies or antigen binding fragments of the invention recognize an epitope of human MET located in the region from amino acid residue 546 to residue 562 of human MET, wherein the epitope comprises the amino acid residue Thr555.

It will be appreciated that an antibody or antigen binding fragment thereof can recognize an epitope made up of a number of amino acid residues. The epitope may be linear, conformational or a combination. Where an epitope is specified as being in a certain region of amino acids, the epitope may be formed of one or more amino acids in that region that are contacted by the antibody or fragment. Therefore, it will be appreciated that in certain embodiments of the invention, the antibodies or fragments thereof can recognize an epitope made up of multiple amino acid residues (consecutive or non-consecutive) within the region specified (e.g. from amino acid 314-372, or 546 to 562), provided the recognized epitope includes the specified amino acid residue (e.g. Ile367, Asp372, Thr555). Methods for determining the residues recognized as part of the epitope of an antibody are familiar to the skilled person and include, for example, those described in Examples 4 and 26.

As the anti-MET antibodies and antigen binding fragments of the invention bind epitopes overlapping or close to the binding domain recognised by HGF, the antibodies and antigen binding fragments are able to (at least partially) compete with HGF for binding of the homologous MET (i.e. compete with human HGF for hMET binding and compete with mouse HGF for mMET binding). That is, the antibodies or antigen binding fragments directly or indirectly prevent HGF from binding the homologous MET in a binding assay, for example an ELISA such as that described in Example 5. Therefore, in certain embodiments, the MET antibodies and antigen binding fragments of the invention compete with mouse and human HGF for binding of the homologous MET. An antibody or antigen binding fragment that competes with HGF in this way is also referred to herein as a “HGF competitor”. Assays to determine whether an antibody or antigen binding fragment competes with HGF for MET binding are well known to the skilled person—for example, in a competition ELISA an HGF competitor may exhibit an $IC_{50}$ of no more than 5 nM and/or an $I_{max}$ (maximum percentage competition at saturation) of at least 50%. Antibodies and antigen binding fragments of the invention compete with mouse HGF for mMET binding and human HGF for hMET binding.

An antibody or antigen binding fragment of the invention may “fully compete” or “partially compete” with HGF for homologous MET binding. In this context, a “full competitor” may be an antibody or antigen binding fragment that in a competition assay, for example an ELISA, exhibits an $IC_{50}$ of less than 2 nM and/or an $I_{max}$ of at least 90%. In certain embodiments, a “full competitor” exhibits an $IC_{50}$ of less than 1 nM and/or an $I_{max}$ of greater than 90%. A “partial competitor” may be an antibody or antigen binding fragment that in a competition assay, for example an ELISA, exhibits an $IC_{50}$ of 2-5 nM and/or an $I_{max}$ of 50-90%. The given values apply to competition with mouse HGF and human HGF for binding of the homologous MET.

As already described, the antibodies and antigen binding fragments of the invention are advantageous due to their ability to recognise both human and mouse MET. The antibodies or antigen binding fragments thereof described herein are particularly advantageous when they exhibit equivalent properties when binding to mMET and to hMET. This equivalence allows the antibodies to be analysed in pre-clinical murine models of disease with an expectation that the antibodies will exhibit the same or similar properties in a human context.

Therefore, in certain embodiments, the antibodies and binding fragments of the invention exhibit equivalent binding affinity for hMET and mMET. In this context, “equivalent binding affinity” is taken as meaning the affinity of the antibody or antigen binding fragment for hMET is 0.5-1.5 times the affinity of that antibody for mMET. In certain embodiments, antibodies and antigen binding fragments of the invention exhibit an affinity for hMET 0.8-1.2 times the affinity of that antibody or antigen binding fragment for mMET.

By way of clarification and example, antibodies or antigen binding fragments having equivalent affinity for mMET and hMET may, when measured as a Fab fragment, exhibit an off-rate for hMET that is 0.5-1.5 times that as the off-rate exhibited for mMET. For example, an antibody having equivalent affinity for mMET and hMET which exhibits an off-rate of $2.6\times10^{-3}$ $s^{-1}$ for mMET would exhibit an off-rate for hMET of $1.3\text{-}3.9\times10^{-3}$ $s^{-1}$. By way of further example, antibodies or antigen binding fragments having equivalent affinity for mMET and hMET may exhibit an $EC_{50}$ for hMET (determined for example by ELISA or flow cytometry) of 0.5-1.5 times the $EC_{50}$ of that antibody or fragment for mMET. For example, an antibody having equivalent affinity for mMET and hMET which exhibits an $EC_{50}$ for mMET of 0.1 nMol/L would exhibit an $EC_{50}$ for hMET of 0.05-0.15 nMol/L.

In certain embodiments, the antibodies and antigen binding fragments of the invention are equivalent agonists of mMET and of hMET. In this context, “equivalence” is taken as meaning the level of MET agonism induced upon binding of hMET is 0.5-1.5 times that of the level of signalling induced upon binding of mMET. In certain embodiments, antibodies and antigen binding fragments of the invention induce MET signalling upon binding of hMET 0.8-1.2 times that of the level of signalling induced upon binding of mMET.

In certain embodiments, the antibodies or antigen binding fragments of the invention are equivalent mMET and hMET agonists when measured by at least one assay of MET agonism described herein. For example, the antibodies or antigen binding fragments of the invention may induce equivalent phosphorylation of MET, exhibit equivalent protective efficacies against drug-induced apoptosis, and/or induce equivalent levels of branching in a branching morphogenesis assay. In certain embodiments, the antibodies or antigen binding fragments exhibit equivalent MET agonism when measured by all of the described assays.

By way of clarification, equivalent phosphorylation of MET by an antibody of the invention might be detectable as the $EC_{50}$ for that antibody for hMET being 0.5-1.5× the $EC_{50}$ for mMET. For example, if the $EC_{50}$ for mMET is 2.9 nM, that antibody would equivalently induce hMET phosphorylation if the $EC_{50}$ for hMET is in the range of 1.45-4.35 nM. Similarly, equivalent MET agonism indicated in an anti-apoptosis assay may be detectable as the $E_{max}$ in human cells being 0.5-1.5× the $E_{max}$ in mouse cells. For example, if the $E_{max}$ in mouse cells was 37.5%, that antibody would be an equivalent hMET agonist if the $E_{max}$ for human cells is in the range of 18.75-56.25%. Equivalent MET agonism indicated in a branching morphogenesis assay may be detectable as the number of branches observed following exposure of human cell spheroids to the antibody being 0.5-1.5× the number of branches observed following exposure of mouse cell spheroids to the same (non-zero) concentration of the antibody. For example, if the number of branches exhibited by mouse cells following exposure to 0.5 nM antibody was 14, that antibody would be an equivalent hMET agonist if the number of branches exhibited by human cells following exposure to 0.5 nM antibody is in the range of 7-21.

Similarly, equivalent agonism of hMET and mMET may be indicated by equivalent cell scattering. The nature of the output of such an assay means application of a 0.5-1.5 factor is not appropriate. In a cell scattering assay, equivalent agonism of hMET and mMET may be indicated by the cell scattering score for human cells exposed to an antibody being +/−1 the cell scattering score for mouse cells exposed to the same antibody at the same (non-zero) concentration. For example, if mouse cells exposed to 0.33 nM of an antibody exhibited a cell scattering score of 2, the antibody would be an equivalent agonist of hHGF if human cells exposed to 0.33 nM of the same antibody exhibited a cell scattering score of 1-3.

In certain embodiments, the antibodies and antigen binding fragments of the invention exhibit equivalent HGF competition between mMET and hMET. In this context, "equivalent HGF competition" is taken as meaning the level of competition exhibited by the antibody or antigen binding fragment with human HGF for hMET is 0.5-1.5 times the level of competition exhibited by the antibody or antigen binding fragment with mouse HGF for mMET. In certain embodiments, antibodies and antigen binding fragments of the invention exhibit a level for competition with human HGF 0.8-1.2 times the level of competition exhibited by that antibody or antigen binding fragment with mouse HGF for mMET.

By way of example, equivalent competition by an antibody with human HGF and mouse HGF might be detectable as the $IC_{50}$ for that antibody competing with human HGF-hMET binding being 0.5-1.5 times the $IC_{50}$ for that antibody competing with mouse HGF-mMET binding. For example, if the $IC_{50}$ for mHGF-mMET binding is 0.34 nM, an antibody competes with hHGF and mHGF equivalently if the $IC_{50}$ for hHGF-hMET binding is in the range of 0.17-0.51 nM.

In certain embodiments, the antibodies and antigen binding fragments of the invention are cross-reactive with rat MET and/or macaque MET. Cross-reactivity with one or both of rat and macaque MET has the advantage that toxicology studies can be conducted in rat and/or macaque model systems. In this regard, whether or not an antibody exhibits cross-reactivity with a cynomolgus or rat MET can be determined by ELISA, such as that described in the accompanying example 25.

The antibodies or antigen binding fragments thereof described herein may comprise at least one hypervariable loop or complementarity determining region obtained from a VH domain or a VL domain of a species in the family Camelidae. In particular, the antibody or antigen binding fragment may comprise VH and/or VL domains, or CDRs thereof, obtained by active immunisation of outbred camelids, e.g. llamas, with a human MET antigen.

By "hypervariable loop or complementarity determining region obtained from a VH domain or a VL domain of a species in the family Camelidae" is meant that hypervariable loop (HV) or CDR has an amino acid sequence which is identical, or substantially identical, to the amino acid sequence of a hypervariable loop or CDR which is encoded by a Camelidae immunoglobulin gene. In this context "immunoglobulin gene" includes germline genes, immunoglobulin genes which have undergone rearrangement, and also somatically mutated genes. Thus, the amino acid sequence of the HV or CDR obtained from a VH or VL domain of a Camelidae species may be identical to the amino acid sequence of a HV or CDR present in a mature Camelidae conventional antibody. The term "obtained from" in this context implies a structural relationship, in the sense that the HVs or CDRs of the MET antibody embody an amino acid sequence (or minor variants thereof) which was originally encoded by a Camelidae immunoglobulin gene. However, this does not necessarily imply a particular relationship in terms of the production process used to prepare the MET antibody.

Camelid-derived MET antibodies may be derived from any camelid species, including inter alia, llama, dromedary, alpaca, vicuna, guanaco or camel.

MET antibodies comprising camelid-derived VH and VL domains, or CDRs thereof, are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

Camelid-derived CDRs may comprise one of the CDR sequences shown in Tables 3 and 4 below.

In one embodiment the entire VH domain and/or the entire VL domain may be obtained from a species in the family Camelidae. In specific embodiments, the camelid-derived VH domain may comprise the amino acid sequence shown as SEQ ID NOs:155, 157, 159, 161, 163, 165, 167, 169, 171, 173, or 175, whereas the camelid-derived VL domain may comprise the amino acid sequence shown as SEQ ID NOs: 156, 158, 160, 162, 164, 166, 168, 170, 172, 174, or 176. The camelid-derived VH domain and/or the camelid-derived VL domain may then be subject to protein engineering, in which one or more amino acid substitutions, insertions or deletions are introduced into the camelid amino acid sequence. These engineered changes preferably include amino acid substitutions relative to the camelid sequence. Such changes include "humanisation" or "germlining" wherein one or more amino acid residues in a camelid-encoded VH or VL domain are replaced with equivalent residues from a homologous human-encoded VH or VL domain.

Isolated camelid VH and VL domains obtained by active immunisation of a camelid (e.g. llama) with a human MET antigen can be used as a basis for engineering MET antibodies according to the invention. Starting from intact camelid VH and VL domains, it is possible to engineer one or more amino acid substitutions, insertions or deletions which depart from the starting camelid sequence. In certain embodiments, such substitutions, insertions or deletions may be present in the framework regions of the VH domain and/or the VL domain. The purpose of such changes in primary amino acid sequence may be to reduce presumably unfavourable properties (e.g. immunogenicity in a human host (so-called humanization), sites of potential product heterogeneity and or instability (glycosylation, deamidation, isomerisation, etc.) or to enhance some other favourable property of the molecule (e.g. solubility, stability, bioavailability, etc.). In other embodiments, changes in primary amino acid sequence can be engineered in one or more of the hypervariable loops (or CDRs) of a Camelidae VH and/or VL domain obtained by active immunisation. Such changes may be introduced in order to enhance antigen binding affinity and/or specificity, or to reduce presumably unfavourable properties, e.g. immunogenicity in a human host (so-called humanization), sites of potential product heterogeneity and or instability, glycosylation, deamidation, isomerisation, etc., or to enhance some other favourable property of the molecule, e.g. solubility, stability, bioavailability, etc.

Thus, in one embodiment, the invention provides a variant MET antibody which contains at least one amino acid substitution in at least one framework or CDR region of either the VH domain or the VL domain in comparison to a camelid-derived VH or VL domain, examples of which include but are not limited to the camelid VH domains comprising the amino acid sequences shown as SEQ ID NOs:155, 157, 159, 161, 163, 165, 167, 169, 171, 173, or 175, and the camelid VL domains comprising the amino acid sequences show as SEQ ID NO: 156, 158, 160, 162, 164, 166, 168, 170, 172, 174, or 176.

In certain embodiments, there are provided "chimeric" antibody molecules comprising camelid-derived VH and VL domains (or engineered variants thereof) and one or more constant domains from a non-camelid antibody, for example human-encoded constant domains (or engineered variants thereof). In such embodiments it is preferred that both the VH domain and the VL domain are obtained from the same species of camelid, for example both VH and VL may be from llama (prior to introduction of engineered amino acid sequence variation). In such embodiments both the VH and the VL domain may be derived from a single animal, particularly a single animal which has been actively immunised with a human MET antigen.

The invention can, in certain embodiments, encompass chimeric camelid/human antibodies, and in particular chimeric antibodies in which the VH and VL domains are of fully camelid sequence (e.g. Llama or alpaca) and the remainder of the antibody is of fully human sequence. MET antibodies can include antibodies comprising "humanised" or "germlined" variants of camelid-derived VH and VL domains, or CDRs thereof, and camelid/human chimeric antibodies, in which the VH and VL domains contain one or more amino acid substitutions in the framework regions in comparison to camelid VH and VL domains obtained by active immunisation of a camelid with a human MET antigen. Such "humanisation" increases the % sequence identity with human germline VH or VL domains by replacing mis-matched amino acid residues in a starting Camelidae VH or VL domain with the equivalent residue found in a human germline-encoded VH or VL domain.

The invention can, in certain embodiments, encompass chimeric camelid/mouse antibodies, and in particular chimeric antibodies in which the VH and VL domains are of fully camelid sequence (e.g. Llama or alpaca) and the remainder of the antibody is of fully mouse sequence.

MET antibodies and antigen binding fragments of the invention may also be CDR-grafted antibodies in which CDRs (or hypervariable loops) derived from a camelid antibody, for example a camelid MET antibody raised by active immunisation with human MET protein, or otherwise encoded by a camelid gene, are grafted onto a human VH and VL framework, with the remainder of the antibody also being of fully human origin. Such CDR-grafted MET antibodies may contain CDRs having the amino acid sequences shown in Tables 3 and 4 below.

Camelid-derived MET antibodies include variants wherein the hypervariable loop(s) or CDR(s) of the VH domain and/or the VL domain are obtained from a conventional camelid antibody raised against human MET, but wherein at least one of said (camelid-derived) hypervariable loops or CDRs has been engineered to include one or more amino acid substitutions, additions or deletions relative to the camelid-encoded sequence. Such changes include "humanisation" of the hypervariable loops/CDRs. Camelid-derived HVs/CDRs which have been engineered in this manner may still exhibit an amino acid sequence which is "substantially identical" to the amino acid sequence of a camelid-encoded HV/CDR. In this context, "substantial identity" may permit no more than one, or no more than two amino acid sequence mis-matches with the camelid-encoded HV/CDR. Particular embodiments of the MET antibody may contain humanised variants of the CDR sequences shown in Tables 3 and 4.

Camelid (e.g. llama) conventional antibodies provide an advantageous starting point for the preparation of antibodies with utility as human therapeutic agents due to the following factors, discussed in U.S. Ser. No. 12/497,239 which is incorporated herein by reference:

1) High % sequence homology between camelid VH and VL domains and their human counterparts;

2) High degree of structural homology between CDRs of camelid VH and VL domains and their human counterparts (i.e. human-like canonical fold structures and human-like combinations of canonical folds).

The camelid (e.g. llama) platform also provides a significant advantage in terms of the functional diversity of the MET antibodies which can be obtained.

The utility of MET antibodies comprising camelid VH and/or camelid VL domains for human therapy can be improved still further by "humanisation" of natural camelid VH and VL domains, for example to render them less immunogenic in a human host. The overall aim of humanisation is to produce a molecule in which the VH and VL domains exhibit minimal immunogenicity when introduced into a human subject, whilst retaining the specificity and affinity of the antigen binding site formed by the parental VH and VL domains.

One approach to humanisation, so-called "germlining", involves engineering changes in the amino acid sequence of a camelid VH or VL domain to bring it closer to the germline sequence of a human VH or VL domain.

Determination of homology between a camelid VH (or VL) domain and human VH (or VL) domains is a critical step in the humanisation process, both for selection of camelid amino acid residues to be changed (in a given VH or VL domain) and for selecting the appropriate replacement amino acid residue(s).

An approach to germlining of camelid conventional antibodies has been developed based on alignment of a large number of novel camelid VH (and VL) domain sequences, typically somatically mutated VH (or VL) domains which are known to bind a target antigen, with human germline VH (or VL) sequences, human VH (and VL) consensus sequences, as well as germline sequence information available for llama pacos.

This procedure, described in WO 2011/080350, contents of which are incorporated by reference, can be applied to (i) select "camelid" amino acid residues for replacement in a camelid-derived VH or VL domain or a CDR thereof, and (ii) select replacement "human" amino acid residues to substitute in, when humanising any given camelid VH (or VL) domain. This approach can be used to prepare humanised variants of camelid-derived CDRs having the amino acid sequences shown in Tables 3 and 4 and also for germlining of camelid-derived VH and VL domains having the sequences shown in Table 5.

MET antibodies can take various different embodiments in which both a VH domain and a VL domain are present. The term "antibody" herein is used in the broadest sense and encompasses, but is not limited to, monoclonal antibodies (including full length monoclonal antibodies), polyclonal antibodies, multispecific antibodies (e.g., bispecific antibodies), so long as they exhibit the appropriate immunological specificity for a human MET protein and for a mouse MET protein. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

"Antibody fragments" comprise a portion of a full length antibody, generally the antigen binding or variable domain thereof. Examples of antibody fragments include Fab, Fab', F(ab')2, bi-specific Fab's, and Fv fragments, diabodies, linear antibodies, single-chain antibody molecules, a single chain variable fragment (scFv) and multispecific antibodies formed from antibody fragments (see Holliger and Hudson, Nature Biotechnol. 23:1126-1136, 2005, the contents of which are incorporated herein by reference).

In non-limiting embodiments, the MET antibodies provided herein may comprise CH1 domains and/or CL domains, the amino acid sequence of which is fully or substantially human. If the MET antibody is intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. Such antibodies may be of any human isotype, for example IgG1.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. Such antibodies may be of any human isotype, with human IgG4 and IgG1 being particularly preferred.

Also provided are MET antibodies comprising constant domains of "human" sequence which have been altered, by one or more amino acid additions, deletions or substitutions with respect to the human sequence, excepting those embodiments where the presence of a "fully human" hinge region is expressly required.

The presence of a "fully human" hinge region in the MET antibodies of the invention may be beneficial both to minimise immunogenicity and to optimise stability of the antibody.

The MET antibodies provided herein may be of any isotype. Antibodies intended for human therapeutic use will typically be of the IgA, IgD, IgE IgG, IgM type, often of the IgG type, in which case they can belong to any of the four sub-classes IgG1, IgG2a and b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

In non-limiting embodiments, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the MET antibody, it may be desirable to modify the antibody of the invention with respect to its binding properties to Fc receptors, for example to modulate effector function.

In certain embodiments, the MET antibodies may comprise an Fc region of a given antibody isotype, for example human IgG1, which is modified in order to reduce or substantially eliminate one or more antibody effector functions naturally associated with that antibody isotype. In non-limiting embodiments, the MET antibody may be substantially devoid of any antibody effector functions. In this context, "antibody effector functions" include one or more or all of antibody-dependent cellular cytotoxicity (ADCC), complement-dependent cytotoxicity (CDC) and antibody-dependent cellular phagocytosis (ADCP).

The amino acid sequence of the Fc portion of the MET antibody may contain one or more mutations, such as amino acid substitutions, deletions or insertions, which have the effect of reducing one or more antibody effector functions (in comparison to a wild type counterpart antibody not having said mutation). Several such mutations are known in the art of antibody engineering. Non-limiting examples, suitable for inclusion in the MET antibodies described herein, include the following mutations in the Fc domain of human IgG4 or human IgG1: N297A, N297Q, LALA (L234A, L235A), AAA (L234A, L235A, G237A) or D265A (amino acid residues numbering according to the EU numbering system in human IgG1).

Monoclonal antibodies or antigen-binding fragments thereof that "cross-compete" with the MET antibodies disclosed herein are those that bind human MET at site(s) that are identical to, or overlapping with, the site(s) at which the present MET antibodies bind and bind mouse MET at site(s) that are identical to, or overlapping with, the site(s) at which the present MET antibodies bind. Competing monoclonal antibodies or antigen-binding fragments thereof can be identified, for example, via an antibody competition assay. For example, a sample of purified or partially purified human MET can be bound to a solid support. Then, an antibody compound or antigen binding fragment thereof of the present invention and a monoclonal antibody or antigen-binding fragment thereof suspected of being able to compete with such invention antibody compound are added. One of the two molecules is labelled. If the labelled compound and the unlabelled compound bind to separate and discrete sites on MET, the labelled compound will bind to the same level whether or not the suspected competing compound is present. However, if the sites of interaction are identical or overlapping, the unlabelled compound will compete, and the amount of labelled compound bound to the antigen will be lowered. If the unlabelled compound is present in excess, very little, if any, labelled compound will bind. For purposes of the present invention, competing monoclonal antibodies or antigen-binding fragments thereof are those that decrease the binding of the present antibody compounds to MET by about 50%, about 60%, about 70%, about 80%, about 85%, about 90%, about 95%, or about 99%. Details of procedures for carrying out such competition assays are well known in the art and can be found, for example, in Harlow and Lane, Antibodies, A Laboratory Manual, Cold Spring Harbor Laboratory Press, Cold Spring Harbor, N.Y., 1988, 567-569, 1988, ISBN 0-87969-314-2. Such assays can be made quantitative by using purified antibodies. A standard curve is established by titrating one antibody against itself, i.e., the same antibody is used for both the label and the competitor. The capacity of an unlabelled competing monoclonal antibody or antigen-binding fragment thereof to inhibit the binding of the labelled molecule to the plate is titrated. The results are plotted, and the concentrations necessary to achieve the desired degree of binding inhibition are compared.

The invention also provides polynucleotide molecules encoding the MET antibodies of the invention, also expression vectors containing a nucleotide sequences which encode the MET antibodies of the invention operably linked to regulatory sequences which permit expression of the antigen binding polypeptide in a host cell or cell-free expression system, and a host cell or cell-free expression system containing this expression vector.

Polynucleotide molecules encoding the MET antibodies of the invention include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated". This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of a MET antibody according to the invention, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59-74, 1977); baby hamster kidney cells (BHK, ATCC CCL 10); Chinese hamster ovary cells/-DHFR (CHO, Urlaub et al., Proc. Natl. Acad. Sci. USA 77:4216, 1980); mouse sertoli cells (TM4; Mather, Biol. Reprod. 23:243-252, 1980); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumour (MMT 060562, ATCC CCL51); TRI cells (Mather et al., Annals N.Y. Acad. Sci. 383:44-68, 1982); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the definition of a "host cell".

In an important aspect, the invention also provides a method of producing a MET antibody of the invention which comprises culturing a host cell (or cell free expression system) containing polynucleotide (e.g. an expression vector) encoding the MET antibody under conditions which permit expression of the MET antibody, and recovering the expressed MET antibody. This recombinant expression process can be used for large scale production of MET antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

The MET antibodies provided herein have utility in therapy, in particular the therapeutic treatment of disease, in particular conditions that benefit from stimulation of MET function, including but not limited to degenerative diseases, inflammatory diseases, autoimmune diseases, metabolic diseases, transplantation-related disorders, and wound healing. In this regard, the MET antibodies provided herein are examples of a broader class of MET agonists, for example HGF, having therapeutic utility in the treatment of said conditions.

Hepatocytes express MET and are the principal target of HGF, which promotes their proliferation and protects them from apoptosis. The MET antibodies which induce MET signalling are shown herein (Examples 16 and 17) to protect hepatocytes in mouse models of liver damage, both acute liver damage and chronic damage. As already described herein, antibodies of the invention exhibit equivalent properties in a human system as in a mouse system and, thus, can be expected to confer similar protective effects in the context of human liver damage. Therefore, in one aspect the invention provides a method of treating or preventing liver damage in a human patient which comprises administering to a patient in need thereof a therapeutically effective amount of a MET antibody which induces MET signalling. In certain embodiments, the method is a method of treating or preventing acute liver damage. In certain embodiments, the method is a method of treating or preventing chronic liver damage. In certain embodiments, the antibody is an antibody as described herein.

Kidney epithelial cells express significant levels of MET and are sensitive to HGF stimulation. MET antibodies which induce MET signalling are shown herein (Example 18) to confer protection in a mouse model of acute kidney damage. As already described herein, antibodies of the invention exhibit equivalent properties in a human system as in a mouse system and, thus, can be expected to confer similar protective effects in the context of human kidney damage. Therefore, in one aspect the invention provides a method of treating or preventing kidney damage in a human patient which comprises administering to a patient in need thereof a therapeutically effective amount of a MET antibody which induces MET signalling. In certain embodiments, the method is a method of treating or preventing acute kidney damage. In certain embodiments, the antibody is an antibody as described herein.

It is also demonstrated herein (Examples 19 and 20) that administration of MET antibodies which induce MET signalling provides effective treatment in mouse models of inflammatory bowel disease (IBD), for example in ulcerative colitis. Therefore, in one aspect the invention provides a method of treating or preventing IBD in a human patient, which comprises administering to a patient in need thereof a therapeutically effective amount of a MET antibody which induces MET signalling. In certain embodiments, the method is a method of treating or preventing ulcerative colitis. In certain embodiments, the antibody is an antibody as described herein.

It is further demonstrated herein that administration of MET antibodies which induce MET signalling is able to restore metabolic function in diabetes, including both type I and type II diabetes (Examples 21 and 22). In particular, in a model of type I diabetes (Example 21), MET antibodies are shown to promote glucose uptake. Furthermore, administration of MET antibodies with insulin resulted in a synergistic effect on glucose uptake. In a model of type II diabetes (Example 22), MET antibodies are shown to normalise glucose control and to reduce insulin resistance. Therefore, in one aspect the invention provides a method of treating or preventing diabetes in a human patient, which comprises administering to a patient in need thereof a therapeutically effective amount of a MET antibody which induces MET signalling. In certain embodiments, the method is a method of treating or preventing type I diabetes. In certain such embodiments, the method further comprises the administration of insulin to the patient. In certain embodiments, the method is a method of treating type II diabetes. In certain embodiments, the antibody is an antibody as described herein.

It is further demonstrated herein that administration of MET antibodies which induce MET signalling is able to reduce the extent of fatty liver in a mouse model of non-alcoholic steatohepatitis (NASH) (Example 23). In particular, MET antibodies were able to reduce the number of fatty cells and the level of fibrosis. Therefore, in one aspect the invention provides a method of treating or preventing NASH in a human patient, which comprises administering to a patient in need thereof a therapeutically effective amount of a MET antibody which induces MET signalling. In certain embodiments, the antibody is an antibody as described herein.

It is further demonstrated herein that administration of MET antibodies which induce MET signalling is able to promote wound healing (Example 24). Moreover, MET antibodies were able to promote wound healing in diabetic mice, which exhibit impaired wound healing. Therefore, in one aspect the invention provides a method of promoting wound healing in a human patient, which comprises administering to a patient in need thereof a therapeutically effective amount of a MET antibody which induces MET signalling. In certain embodiments, the human patient has diabetes, optionally type I diabetes. In certain embodiments, the antibody is an antibody as described herein.

EXAMPLES

The invention will be further understood with reference to the following non-limiting experimental examples.

Example 1: Immunization of Llamas

Immunizations of llamas and harvesting of peripheral blood lymphocytes (PBLs) as well as the subsequent extraction of RNA and amplification of antibody fragments were performed as described (De Haard et al., J. Bact. 187:4531-4541, 2005). Two adult llamas (*Lama glama*) were immunized by intramuscular injection of a chimeric protein consisting of the extracellular domain (ECD) of human MET fused to the Fc portion of human IgG1 (MET-Fc; R&D Systems). Each llama received one injection per week for six weeks, for a total of six injections. Each injection consisted in 0.2 mg protein in Freund's Incomplete Adjuvant in the neck divided over two spots.

Blood samples of 10 ml were collected pre- and post-immunization to investigate the immune response. Approximately one week after the last immunization, 400 ml of blood was collected and PBLs were obtained using the Ficoll-Paque method. Total RNA was extracted by the phenol-guanidine thiocyanate method (Chomczynski et al., Anal. Biochem. 162:156-159, 1987) and used as template for random cDNA synthesis using the SuperScript™ III First-Strand Synthesis System kit (Life Technologies). Amplification of the cDNAs encoding the VH-CH1 regions of llama IgG1 and VL-CL domains (K and λ) and subcloning into the phagemid vector pCB3 was performed as described (de Haard et al., J Biol Chem. 274:18218-18230, 1999). The *E. coli* strain TG1 (Netherland Culture Collection of Bacteria) was transformed using recombinant phagemids to generate 4 different Fab-expressing phage libraries (one λ and one κ library per immunized llama). Diversity was in the range of $10^8$-$10^9$.

The immune response to the antigen was investigated by ELISA. To this end, we obtained the ECDs of human MET (UniProtKB #P08581; aa 1-932) and of mouse MET (UniProtKB #P16056.1; aa 1-931) by standard protein engineering techniques. Human or mouse MET ECD recombinant protein was immobilized in solid phase (100 ng/well in a 96-well plate) and exposed to serial dilutions of sera from llamas before (day 0) or after (day 45) immunization. Binding was revealed using a mouse anti-llama IgG1 (Daley et al., Clin. Vaccine Immunol. 12, 2005) and a HRP-conjugated donkey anti-mouse antibody (Jackson Laboratories). As shown in FIG. 1, both llamas displayed an immune response against human MET ECD. Consistent with the notion that the extracellular portion of human MET displays 87% homology with its mouse orthologue, a fairly good extent of cross-reactivity was also observed with mouse MET ECD.

Example 2: Selections and Screenings of Fabs Binding to Both Human and Mouse MET Fab-expressing phages from the libraries described above were produced according to standard phage display protocols. For selection, phages were first adsorbed to immobilized recombinant human MET ECD, washed, and then eluted using trypsin. After two cycles of selection with human MET ECD, two other cycles were performed in the same fashion using mouse MET ECD. In parallel, we also selected phages alternating a human MET ECD cycle with a mouse MET ECD cycle, for a total of four cycles. Phages selected by the two approaches were pooled together and then used to infect TG1 *E. coli*. Individual colonies were isolated and secretion of Fabs was induced using IPTG (Fermentas). The Fab-containing periplasmic fraction of bacteria was collected and tested for its ability to bind human and mouse MET ECD by Surface Plasmon Resonance (SPR). Human or mouse MET ECD was immobilized on a CM-5 chip using amine coupling in sodium acetate buffer (GE Healthcare). The Fab-containing periplasmic extracts were loaded into a BIACORE 3000 apparatus (GE Healthcare) with a flow rate of 30 μl/min. The Fab off-rates ($k_{off}$) were measured over a two minute period. Binding of Fabs to human and mouse MET was further characterized by ELISA using MET ECD in solid phase and periplasmic crude extract in solution. Because Fabs are engineered with a MYC flag, binding was revealed using HRP-conjugated anti-MYC antibodies (ImTec Diagnostics).

Fabs that bound to both human and mouse MET in both SPR and ELISA were selected and their corresponding phages were sequenced (LGC Genomics). Cross-reactive Fab sequences were divided into families based on VH CDR3 sequence length and content. VH families were given an internal number not based on IMTG (International Immunogenetics Information System) nomenclature. Altogether, we could identify 11 different human/mouse cross-reactive Fabs belonging to 8 VH families. The CDR and FR sequences of heavy chain variable regions are shown in Table 3. The CDR and FR sequences of light chain variable regions are shown in Table 4. The full amino acid sequences of heavy chain and light chain variable regions are shown in Table 5. The full DNA sequences of heavy chain and light chain variable regions are shown in Table 6.

TABLE 3

Framework regions and CDR sequences for VH domains of Fabs binding to both human and mouse MET.

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 76H10 | QLQLVESG GGLVQPGG SLRVSCTA SGFTFN | 1 | TYYMT | 2 | WVRQAPG KGLEWVS | 3 | DINSGGG TYYADSV KG | 4 | RFTISRDNAKNT LYLQMNSLKPED TALYYCVR | 5 | VRIWPVG YDY | 6 | WGQGTQ VTVSS | 7 |
| 71G3 | QVQLVESG GGLVQPGG SLRVSCAA SGFTFS | 8 | TYYMS | 9 | WVRQAPG KGLEWVS | 10 | DIRTDGG TYYADSV KG | 11 | RFTMSRDNAKNT LYLQMNSLKPED TALYYCAR | 12 | TRIFPSG YDY | 13 | WGQGTQ VTVSS | 14 |
| 71C3 | QLQLVESG GGLVQPGG SLRLSCAA SGFTFS | 15 | SHAMS | 16 | WVRQAPG KGLEWVS | 17 | AINSGGG STSYADS VKG | 18 | RFTISRDNAKNT LYLQMNSLKPED TAVYYCAK | 19 | ELRFDLA RYTDYEA WDY | 20 | WGQGTQ VTVSS | 21 |
| 71D4 | ELQLVESG GGLVQPGG SLRLSCAA SGFTFS | 22 | GYGMS | 23 | WVRQAPG KGLEWVS | 24 | DINSGGG STSYADS VKG | 25 | RFTISRDNAKNT LYLQMNSLKPED TAVYYCAK | 26 | DMRLYLA RYNDYEA WDY | 27 | WGQGTQ VTVSS | 28 |
| 71D6 | ELQLVESG GGLVQPGG SLRLSCAA SGFTFS | 29 | SYGMS | 30 | WVRQAPG KGLEWVS | 31 | AINSYGG STSYADS VKG | 32 | RFTISRDNAKNT LYLQMNSLKPED TAVYYCAK | 33 | EVRADLS RYNDYES YDY | 34 | WGQGTQ VTVSS | 35 |
| 71A3 | EVQLVESG GGLVQPGG SLRLSCAA SGFSFK | 36 | DYDIT | 37 | WVRQAPG KGLEWVS | 38 | TITSRSG STSYVDS VKG | 39 | RFTISGDNAKNT LYLQMNSLKPED TAVYYCAK | 40 | VYATTWD VGPLGYG MDY | 41 | WGKGTL VTVSS | 42 |
| 71G2 | EVQLQESG GGLVQPGG SLRLSCAA SGFTFS | 43 | IYDMS | 44 | WVRQAPG KGLEWVS | 45 | TINSDGS STSYVDS VKG | 46 | RFTISRDNAKNT LYLQMNSLKPED TAVYYCAK | 47 | VYGSTWD VGPMGYG MDY | 48 | WGKGTL VTVSS | 49 |
| 76G7 | QVQLVESG GNLVQPGG SLRLSCAA SGFTFS | 50 | NYYMS | 51 | WVRQAPG KGLEWVS | 52 | DIYSDGS TTWYSDS VKG | 53 | RFTISRDNAKNT LSLQMNSLKSED TAVYYCAR | 54 | VKIYPGG YDA | 55 | WGQGTQ VTVSS | 56 |

TABLE 3-continued

Framework regions and CDR sequences for VH domains of Fabs binding to both human and mouse MET.

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 71G12 | QVQLQESGGDLVQPGGSLRVSCVVSGFTFS | 57 | RYYMS | 58 | WVRQAPGKGLEWVS | 59 | SIDSYGYSTYYTDSVKG | 60 | RFTISRDNAKNTLYLQMNSLKPEDTALYYCAR | 61 | AKTTWSYDY | 62 | WGQGTQVTVSS | 63 |
| 74C8 | EVQLVESGGGLVQPGGSLRLSCAASGFTFR | 64 | NYHMS | 65 | WVRQVPGKGFEWIS | 66 | DINSAGGSTYYADSVKG | 67 | RFTISRDNAKNTLYLEMNSLKPEDTALYYCAR | 68 | VNVWGVNY | 69 | WGKGTLVSVSS | 70 |
| 72F8 | ELQLVESGGGLVQPGGSLRLSCAASGFTFS | 71 | NYVMS | 72 | WVRQAPGKGLEWVS | 73 | DTNSGGSTSYADSVKG | 74 | RFTISRDNAKNTLYLQMNSLKPEDTALYYCAR | 75 | SFFYGMNY | 76 | WGKGTQVTVSS | 77 |

TABLE 4

Framework regions and CDR sequences for VL domains of Fabs binding to both human and mouse MET.

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 76H10 | QAVVTQEPSLSVSPGGTVTLTC | 78 | GLSSGSVTTSNYPG | 79 | WFQQTPGQAPRTLIY | 80 | NTNNRHS | 81 | GVPSRFSGSISGNKAALTITGAQPEDEADYYC | 82 | SLYTGSYTTV | 83 | FGGGTHLTVL | 84 |
| 71G3 | QAVVTQEPSLSVSPGGTVTLTC | 85 | GLSSGSVTTSNYPG | 86 | WFQQTPGQAPRTLIY | 87 | NTNSRHS | 88 | GVPSRFSGSISGNKAALTIMGAQPEDEADYYC | 89 | SLYPGSTTV | 90 | FGGGTHLTVL | 91 |
| 71C3 | SYELTQPSALSVTLGQTAKITC | 92 | QGGSLGSSYAH | 93 | WYQQKPGQAPVLVIY | 94 | DDDSRPS | 95 | GIPERFSGSSSGGTATLTISGAQAEDEGDYYC | 96 | QSADSSGNAAV | 97 | FGGGTHLTVL | 98 |
| 71D4 | SSALTQPSALSVTLGQTAKITC | 99 | QGGSLGSSYAH | 100 | WYQQKPGQAPVLVIY | 101 | DDDSRPS | 102 | GIPERFSGSSSGGTATLTISGAQAEDEGDYYC | 103 | QSADSSGNAAV | 104 | FGGGTHLTVL | 105 |
| 71D6 | QPVLNQPSALSVTLGQTAKITC | 106 | QGGSLGARYAH | 107 | WYQQKPGQAPVLVIY | 108 | DDDSRPS | 109 | GIPERFSGSSSGGTATLTISGAQAEDEGDYYC | 110 | QSADSSGSV | 111 | FGGGTHLTVL | 112 |
| 71A3 | SYELTQPSALSVTLGQTAKITC | 113 | QGGSLGSSYAH | 114 | WYQQKPGQAPVLVIY | 115 | DDDSRPS | 116 | GIPERFSGSSSGGTATLTISGAQAEDEGDYYC | 117 | QSADSSGNAAV | 118 | FGGGTHLTVL | 119 |
| 71G2 | SSALTQPSALSVSLGQTARITC | 120 | QGGSLGSSYAH | 121 | WYQQKPGQAPVLVIY | 122 | GDDSRPS | 123 | GIPERFSGSSSGGTATLTISGAQAEDEDDYYC | 124 | QSTDSSGNTV | 125 | FGGGTRLTVL | 126 |
| 76G7 | QAGLTQPPSVSGSPGKTVTISC | 127 | AGNSSDVGYGNYVS | 128 | WYQQFPGMAPKLLIY | 129 | LVNKRAS | 130 | GITDRFSGSKSGNTASLTISGLQSEDEADYYC | 131 | ASYTGSNNIV | 132 | FGGGTHLTVL | 133 |
| 71G12 | EIVLTQSPSSVTASVGGKVTINC | 134 | KSSQSVFIASNQKTYLN | 135 | WYQQRPGQSPRLVIS | 136 | YASTRES | 137 | GIPDRFSGSGSTTDFTLTISSVQPEDAAVYYC | 138 | QQAYSHPT | 139 | FGQGTKVELK | 140 |
| 74C8 | QTVVTQEPSLSVSPGGTVTLTC | 141 | GLSSGSVTTSNYPG | 142 | WFQQTPGQAPRTLIY | 143 | NTNSRHS | 144 | GVPSRFSGSISGNKAALTITGAQPEDEADYYC | 145 | SLYPGSYTNV | 146 | FGGGTHLTVL | 147 |
| 72F8 | QSALTQPPSLSASPGSSVRLTC | 148 | TLSSGNNIGSYDIS | 149 | WYQQKAGSPPRYLLN | 150 | YYTDSRKHQDS | 151 | GVPSRFSGSKDASANAGLLLISGLQPEDEADYYC | 152 | SAYKSGSYRWV | 153 | FGGGTHVTVL | 154 |

TABLE 5

Variable domain amino acid sequences of Fabs binding to both human and mouse MET.

| CLONE | VH | SEQ ID NO. | VL | SEQ ID NO. |
|---|---|---|---|---|
| 76H10 | QLQLVESGGGLVQPGGSLRVSCTASGFTFNTYYMTWVRQAPGKGLEWVSDINSGGGTYYADSVKGRFTISRDNAKNTLYLQMNSLKPEDTALYYCVRVRIWPVGYDYWGQGTQVTVSS | 155 | QAVVTQEPSLSVSPGGTVTLTCGLSSGSVTTSNYPGWFQQTPGQAPRTLIYNTNNRHSGVPSRFSGSISGNKAALTITGAQPEDEADYYCSLYTGSYTTVFGGGTHLTVL | 156 |
| 71G3 | QVQLVESGGGLVQPGGSLRVSCAASGFTFSTYYMSWVRQAPGKGLEWVSDIRTDGGTYYADSVKGRFTMSRDNAKNTLYLQMNSLKPEDTALYYCARTRIFPSGYDYWGQGTQVTVSS | 157 | QAVVTQEPSLSVSPGGTVTLTCGLSSGSVTTSNYPGWFQQTPGQAPRTLIYNTNSRHSGVPSRFSGSISGNKAALTIMGAQPEDEADYYCSLYPGSTTVFGGGTHLTVL | 158 |
| 71C3 | QLQLVESGGGLVQPGGSLRLSCAASGFTFSSHAMSWVRQAPGKGLEWVSAINSGGGSTSYADSVKGRFTISRDNAKNTLYLQMNSLKPEDTAVYYCAKELRFDLARYTDYEAWDYWGQGTQVTVSS | 159 | SYELTQPSALSVTLGQTAKITCQGGSLGSSYAHWYQQKPGQAPVLVIYDDDSRPSGIPERFSGSSSGGTATLTISGAQAEDEGDYYCQSADSSGNAAVFGGGTHLTVL | 160 |
| 71D4 | ELQLVESGGGLVQPGGSLRLSCAASGFTFSGYGMSWVRQAPGKGLEWVSDINSGGGSTSYADSVKGRFTISRDNAKNTLYLQMNSLKPEDTAVYYCAKDMRLYLARYNDYEAWDYWGQGTQVTVSS | 161 | SSALTQPSALSVTLGQTAKITCQGGSLGSSYAHWYQQKPGQAPVLVIYDDDSRPSGIPERFSGSSSGGTATLTISGAQAEDEGDYYCQSADSSGNAAVFGGGTHLTVL | 162 |
| 71D6 | ELQLVESGGGLVQPGGSLRLSCAASGFTFSSYGMSWVRQAPGKGLEWVSAINSYGGSTSYADSVKGRFTISRDNAKNTLYLQMNSLKPEDTAVYYCAKEVRADLSRYNDYESYDYWGQGTQVTVSS | 163 | QPVLNQPSALSVTLGQTAKITCQGGSLGARYAHWYQQKPGQAPVLVIYDDDSRPSGIPERFSGSSSGGTATLTISGAQAEDEGDYYCQSADSSGSVFGGGTHLTVL | 164 |
| 71A3 | EVQLVESGGGLVQPGGSLRLSCAASGFSFKDYDITWVRQAPGKGLEWVSTITSRSGSTSYVDSVKGRFTISGDNAKNTLYLQMNSLKPEDTAVYYCAKVYATTWDVGPLGYGMDYWGKGTLVTVSS | 165 | SYELTQPSALSVTLGQTAKITCQGGSLGSSYAHWYQQKPGQAPVLVIYDDDSRPSGIPERFSGSSSGGTATLTISGAQAEDEGDYYCQSADSSGNAAVFGGGTHLTVL | 166 |
| 71G2 | EVQLQESGGGLVQPGGSLRLSCAASGFTFSIYDMSWVRQAPGKGLEWVSTINSDGSSTSYVDSVKGRFTISRDNAKNTLYLQMNSLKPEDTAVYYCAKVYGSTWDVGPMGYGMDYWGKGTLVTVSS | 167 | SSALTQPSALSVSLGQTARITCQGGSLGSSYAHWYQQKPGQAPVLVIYGDDSRPSGIPERFSGSSSGGTATLTISGAQAEDEDDYYCQSTDSSGNTVFGGGTRLTVL | 168 |
| 76G7 | QVQLVESGGNLVQPGGSLRLSCAASGFTFSNYYMSWVRQAPGKGLEWVSDIYSDGSTTWYSDSVKGRFTISRDNAKNTLSLQMNSLKSEDTAVYYCARVKIYPGGYDAWGQGTQVTVSS | 169 | QAGLTQPPSVSGSPGKTVTISCAGNSSDVGYGNYVSWYQQFPGMAPKLLIYLVNKRASGITDRFSGSKSGNTASLTISGLQSEDEADYYCASYTGSNNIVFGGGTHLTVL | 170 |
| 71G12 | QVQLQESGGDLVQPGGSLRVSCVVSGFTFSRYYMSWVRQAPGKGLEWVSSIDSYGYSTYYTDSVKGRFTISRDNAKNTLYLQMNSLKPEDTALYYCARAKTTWSYDYWGQGTQVTVSS | 171 | EIVLTQSPSSVTASVGGKVTINCKSSQSVFIASNQKTYLNWYQQRPGQSPRLVISYASTRESGIPDRFSGSGSTTDFTLTISSVQPEDAAVYYCQQAYSHPTFGQGTKVELK | 172 |
| 74C8 | EVQLVESGGGLVQPGGSLRLSCAASGFTFRNYHMSWVRQVPGKGFEWISDINSAGGSTYYADSVKGRFTISRDNAKNTLYLEMNSLKPEDTALYYCARVNVWGVNYWGKGTLVSVSS | 173 | QTVVTQEPSLSVSPGGTVTLTCGLSSGSVTTSNYPGWFQQTPGQAPRTLIYNTNSRHSGVPSRFSGSISGNKAALTITGAQPEDEADYYCSLYPGSYTNVFGGGTHLTVL | 174 |
| 72F8 | ELQLVESGGGLVQPGGSLRLSCAASGFTFSNYVMSWVRQAPGKGLEWVSDTNSGGSTSYADSVKGRFTISRDNAKNTLYLQMNSLKPEDTALYYCARSFFYGMNYWGKGTQVTVSS | 175 | QSALTQPPSLSASPGSSVRLTCTLSSGNNIGSYDISWYQQKAGSPPRYLLNYYTDSRKHQDSGVPSRFSGSKDASANAGLLLISGLQPEDEADYYCSAYKSGSYRWVFGGGTHVTVL | 176 |

TABLE 6

Variable domain nucleotide sequences of Fabs binding to both human and mouse MET.

| Clone | VH | SEQ ID NO. | VL | SEQ ID NO. |
|---|---|---|---|---|
| 76H10 | CAGTTGCAGCTGGTGGAGTCTGGGGGAGGCTTGGTGCAGCCTGGGGGGTCTCTGAGAGTTTCCTGTACAGCCTCTGGATTCACCTTCAATACCTACTACATGACCTGGGTCCGCCAGGCTCCAGGGAAGGGGCTCGAGTGGGTCTCAGATATTAATAGTGGTGGTGGTACATACTATGCAGACTCCGTGAAGGGCCGATTCACCATCTCCAGAGACAACGCCAAGAACACGCTATATCTGCAAATGAACAGCCTGAAACCTGAGGACACGGCCCTGTATTACTGTGTAAGAGTTCGTATTTGGCCAGTGGGATATGACTACTGGGGCCAGGGGACCCAGGTCACCGTTTCCTCA | 177 | CAGGCTGTGGTGACCCAGGAGCCGTCCCTGTCAGTGTCTCCAGGAGGGACGGTCACACTCACCTGCGGCCTCAGCTCTGGGTCTGTCACTACCAGTAACTACCCTGGTTGGTTCCAGCAGACACCGGGCCAGGCTCCACGCACTCTTATCTACAACACAAACAACCGCCACTCTGGGGTCCCCAGTCGCTTCTCCGGATCCATCTCTGGGAACAAAGCCGCCCTCACCATCACGGGGGCCCAGCCCGAGGACGAGGCCGACTATTACTGTTCTCTATATACTGGCAGTTACACTACTGTGTTCGGCGGAGGGACCCATCTGACCGTCCTG | 178 |
| 71G3 | CAGGTGCAGCTCGTGGAGTCTGGGGGAGGCTTGGTGCAGCCTGGGGGGTCTCTGAGAGTCTCCTGTGCAGCCTCTGGATTCACCTTCAGTACCTACTACATGAGCTGGGTCCGCCAGGCTCCAGGGAAGGGGCTCGAGTGGGTCTCAGATATTCGTACTGATGGTGGCACATACTATGCAGACTCCGTGAAGGGCCGATTCACCATGTCCAGAGACAACGCCAAGAACACGCTGTATCTACAAATGAACAGCCTGAAACCTGAGGACACGGCCCTGTATTACTGTGCAAGAACTCGAATTTTCCCCTCGGGGTATGACTACTGGGGCCAGGGGACCCAGGTCACCGTCTCCTCA | 179 | CAGGCTGTGGTGACCCAGGAGCCGTCCCTGTCAGTGTCTCCAGGAGGGACGGTCACACTCACCTGCGGCCTCAGCTCTGGGTCTGTCACTACCAGTAACTACCCTGGTTGGTTCCAGCAGACACCAGGCCAGGCTCCGCGCACTCTTATCTACAACACAAACAGCCGCCACTCTGGGGTCCCCAGTCGCTTCTCCGGATCCATCTCTGGGAACAAAGCCGCCCTCACCATCATGGGGGCCCAGCCCGAGGACGAGGCCGACTATTACTGTTCTCTGTACCCTGGTAGTACCACTGTGTTCGGCGGAGGGACCCATCTGACCGTCCTG | 180 |
| 71C3 | CAGTTGCAGCTGGTGGAGTCTGGGGGAGGCTTGGTGCAGCCTGGGGGGTCTCTGAGACTCTCCTGTGCAGCCTCTGGATTCACCTTCAGTAGCCATGCCATGAGCTGGGTCCGCCAGGCTCCAGGAAAGGGGCTCGAGTGGGTCTCAGCTATTAATAGTGGTGGTGGTAGCACAAGCTATGCAGACTCCGTGAAGGGCCGATTCACCATCTCCAGAGACAACGCCAAGAACACGCTGTACCTGCAAATGAACAGCCTGAAACCTGAGGACACGGCCGTGTATTACTGTGCAAAAGAGCTGAGATTCGACCTAGCAAGGTATACCGACTATGAGGCCTGGGACTACTGGGGCCAGGGGACCCAGGTCACCGTCTCCTCA | 181 | TCCTATGAGCTGACTCAGCCCTCCGCGCTGTCCGTAACCTTGGGACAGACGGCCAAGATCACCTGCCAAGGTGGCAGCTTAGGTAGCAGTTATGCTCACTGGTACCAGCAGAAGCCAGGCCAGGCCCCTGTGCTGGTCATCTATGATGATGACAGCAGGCCCTCAGGGATCCCTGAGCGGTTCTCTGGCTCCAGCTCTGGGGGCACAGCCACCCTGACCATCAGCGGGGCCCAGGCCGAGGACGAGGGTGACTATTACTGTCAGTCAGCAGACAGCAGTGGTAATGCTGCTGTGTTCGGCGGAGGGACCCATCTGACCGTCCTG | 182 |
| 71D4 | GAGTTGCAGCTGGTGGAGTCTGGGGGAGGCTTGGTGCAGCCTGGGGGGTCTCTGAGACTCTCCTGTGCAGCCTCTGGATTCACCTTCAGTGGCTATGGCATGAGCTGGGTCCGCCAGGCTCCAGGAAAGGGGCTCGAGTGGGTCTCAGATATTAATAGTGGTGGTGGTAGCACAAGCTATGCAGACTCCGTGAAGGGCCGATTCACCATCTCCAGAGACAACGCCAAGAACACGCTGTATCTGCAAATGAACAGCCTGAAACCTGAGGACACGGCCGTGTATTACTGTGCAAAAGATATGAGATTATACCTAGCAAGGTATAACGACTATGAGGCCTGGGACTACTGGGGCCAGGGGACCCAGGTCACCGTCTCCTCA | 183 | TCCTCTGCACTGACTCAGCCCTCCGCGCTGTCCGTAACCTTGGGACAGACGGCCAAGATCACCTGCCAAGGTGGCAGCTTAGGTAGCAGTTATGCTCACTGGTACCAGCAGAAGCCAGGCCAGGCCCCTGTGCTGGTCATCTATGATGATGACAGCAGGCCCTCAGGGATCCCTGAGCGGTTCTCTGGCTCCAGCTCTGGGGGCACAGCCACCCTGACCATCAGCGGGGCCCAGGCCGAGGACGAGGGTGACTATTACTGTCAGTCAGCAGACAGCAGTGGTAATGCTGCTGTGTTCGGCGGAGGGACCCATCTGACCGTCCTG | 184 |
| 71D6 | GAGTTGCAGCTGGTGGAGTCTGGGGGAGGCTTGGTGCAGCCTGGGGGGTCTCTGAGACTCTCCTGTGCAGCCTCTGGATTCACCTTCAGTAGCTATGGCATGAGCTGGGTCCGCCAGGCTCCAGGAAAGGGGCTCGAGTGGGTCTCAGCTATTAATAGTTATGGTGGTAGCACAAGCTATGCAGACTCCGTGAAGGGCCGATTCACCATCTCCAGAGACAACGCCAAGAACACGCTGTATCTGCAAATGAACAGCCTGAAACCTGAGGACACGGCCGTGTATTACTGTGCAAAAGAAGTGCGGGCCGACCTAAGCCGCTATAACGACTATGAGTCGTATGACTACTGGGGCCAGGGGACCCAGGTCACCGTCTCCTCA | 185 | CAGCCGGTGCTGAATCAGCCCTCCGCGCTGTCCGTAACCTTGGGACAGACGGCCAAGATCACCTGCCAAGGTGGCAGCTTAGGTGCGCGTTATGCTCACTGGTACCAGCAGAAGCCAGGCCAGGCCCCTGTGCTGGTCATCTATGATGATGACAGCAGGCCCTCAGGGATCCCTGAGCGGTTCTCTGGCTCCAGCTCTGGGGGCACAGCCACCCTGACCATCAGCGGGGCCCAGGCCGAGGACGAGGGTGACTATTACTGTCAGTCAGCAGACAGCAGTGGTTCTGTGTTCGGCGGAGGGACCCATCTGACCGTCCTG | 186 |
| 71A3 | GAGGTGCAGCTCGTGGAGTCTGGGGGAGGCTTGGTGCAGCCTGGGGGGTCTCTGAGACTCTCCTGTGCAGCCTCTGGATTCAGCTTCAAGGACTATGACATAACCTGGGTCCGCCAGGCTCCGGGAAAGGGGCTCGAGTGGGTCTCAACTATTACTAGTCGTAGTGGTAGCACAAGCTATGTAGACTCCGTAAAGGGCCGATTCACCATCTCCGGAGACAACGCCAAGAACACGCTGTATCTGCAAATGAACAGCCTGAAACCTGAGGACACGGCCGTGTATTACTGTGCAAAAGTTTACGCGACTACCTGGGACGTCGGCCCTCTGGGCTACGGCATGGACTACTGGGGCAAGGGGACCCTGGTCACCGTCTCCTCA | 187 | TCCTATGAGCTGACTCAGCCCTCCGCGCTGTCCGTAACCTTGGGACAGACGGCCAAGATCACCTGCCAAGGTGGCAGCTTAGGTAGCAGTTATGCTCACTGGTACCAGCAGAAGCCAGGCCAGGCCCCTGTGCTGGTCATCTATGATGATGACAGCAGGCCCTCAGGGATCCCTGAGCGGTTCTCTGGCTCCAGCTCTGGGGGCACAGCCACCCTGACCATCAGCGGGGCCCAGGCCGAGGACGAGGGTGACTATTACTGTCAGTCAGCAGACAGCAGTGGTAATGCTGCTGTGTTCGGCGGAGGGACCCATCTGACCGTCCTG | 188 |

TABLE 6-continued

Variable domain nucleotide sequences of Fabs binding to both human and mouse MET.

| Clone | VH | SEQ ID NO. | VL | SEQ ID NO. |
|---|---|---|---|---|
| 71G2 | GAGGTGCAGCTGCAGGAGTCGGGGGGAGGCTTGGTGCA<br>GCCTGGGGGGTCTCTGAGACTCTCCTGTGCAGCCTCTG<br>GATTCACCTTCAGTATATATGACATGAGCTGGGTCCGC<br>CAGGCTCCAGGAAAGGGGCTCGAGTGGGTCTCAACTAT<br>TAATAGTGATGGTAGTAGCACAAGCTATGTAGACTCCG<br>TGAAGGGCCGATTCACCATCTCCAGAGACAACGCCAAG<br>AACACGCTGTATCTGCAAATGAACAGCCTGAAACCTGA<br>GGACACGGCCGTGTATTACTGTGCGAAAGTTTACGGTA<br>GTACCTGGGACGTCGGCCCTATGGGCTACGGCATGGAC<br>TACTGGGGCAAAGGGACCCTGGTCACTGTCTCCTCA | 189 | TCCTCTGCACTGACTCAGCCCTCCGCGCTGTCCGTGTC<br>CTTGGGACAGACGGCCAGGATCACCTGCCAAGGTGGCA<br>GCTTAGGTAGCAGTTATGCTCACTGGTACCAGCAGAAG<br>CCAGGCCAGGCCCCTGTGCTGGTCATCTATGGTGATGA<br>CAGCAGGCCCTCAGGGATCCCTGAGCGGTTCTCTGGCT<br>CCAGCTCTGGGGGCACAGCCACCCTGACCATCAGCGGG<br>GCCCAGGCCGAGGACGAGGATGACTATTACTGTCAGTC<br>AACAGACAGCAGTGGTAATACTGTGTTCGGCGGAGGGA<br>CCCGACTGACCGTCCTG | 190 |
| 76G7 | CAGGTGCAGCTGGTGGAGTCTGGGGGAAACTTGGTGCA<br>GCCTGGGGGTTCTCTGAGACTCTCCTGTGCAGCCTCTG<br>GATTCACCTTCAGTAACTACTACATGAGCTGGGTCCGC<br>CAGGCTCCAGGGAAGGGGCTGGAATGGGTGTCCGATAT<br>TTATAGTGACGGTAGTACCACATGGTATTCAGACTCCG<br>TCAAGGGCCGATTCACCATCTCCAGAGACAACGCCAAG<br>AACACGCTGTCTCTGCAAATGAACAGTCTGAAATCTGA<br>GGACACGGCCGTCTATTACTGTGCGCGCGTGAAGATCT<br>ATCCGGGGGGGTATGACGCCTGGGGCCAGGGGACCCAG<br>GTCACCGTCTCCTCA | 191 | CAGGCAGGGCTGACTCAGCCTCCCTCCGTGTCTGGGTC<br>TCCAGGAAAGACGGTCACCATCTCCTGTGCAGGAAACA<br>GCAGTGATGTTGGGTATGGAAACTATGTCTCCTGGTAC<br>CAGCAGTTCCCAGGAATGGCCCCCAAACTCCTGATATA<br>TCTCGTCAATAAACGGGCCTCAGGGATCACTGATCGCT<br>TCTCTGGCTCCAAGTCAGGCAACACGGCCTCCCTGACC<br>ATCTCTGGGCTCCAGTCTGAGGACGAGGCTGATTATTA<br>CTGTGCCTCATATACAGGTAGCAACAATATCGTGTTCG<br>GCGGAGGGACCCATCTAACCGTCCTC | 192 |
| 71G12 | CAGGTGCAGCTGCAGGAGTCGGGGGGAGACTTGGTGCA<br>GCCTGGGGGGTCTCTGAGAGTCTCCTGTGTAGTCTCTG<br>GATTCACCTTCAGTCGCTACTACATGAGCTGGGTCCGC<br>CAGGCTCCAGGGAAGGGGCTCGAGTGGGTCTCATCTAT<br>TGATAGTTATGGTTACAGCACATACTATACAGACTCCG<br>TGAAGGGCCGATTCACCATCTCCAGAGACAACGCCAAG<br>AACACGCTGTATCTGCAAATGAACAGCCTGAAACCTGA<br>GGACACGGCCCTGTATTACTGTGCAAGAGCGAAAACGA<br>CTTGGAGTTATGACTACTGGGGCCAGGGGACCCAGGTC<br>ACCGTCTCCTCA | 193 | GAAATTGTGTTGACGCAGTCTCCCAGCTCCGTGACTGC<br>ATCTGTAGGAGGGAAGGTCACTATCAACTGTAAGTCCA<br>GCCAGAGCGTCTTCATAGCTTCTAATCAGAAAACCTAC<br>TTAAACTGGTACCAGCAGAGACCTGGACAGTCTCCGAG<br>GTTGGTCATCAGCTATGCGTCCACCCGTGAATCGGGGA<br>TCCCTGATCGATTCAGCGGCAGTGGGTCCACAACAGAT<br>TTCACTCTCACGATCAGCAGTGTCCAGCCTGAAGATGC<br>GGCCGTGTATTACTGTCAGCAGGCTTATAGCCATCCAA<br>CGTTCGGCCAGGGGACCAAGGTGGAACTCAAA | 194 |
| 74C8 | GAGGTGCAGCTCGTGGAGTCTGGGGGAGGCTTGGTGCA<br>ACCTGGGGGTTCTCTGAGACTCTCCTGTGCAGCCTCTG<br>GATTCACCTTCAGGAATTACCACATGAGTTGGGTCCGC<br>CAGGTTCCAGGGAAGGGGTTCGAGTGGATCTCAGATAT<br>TAATAGTGCAGGTGGTAGCACATACTATGCAGACTCCG<br>TGAAGGGCCGATTCACCATCTCCAGAGACAACGCCAAG<br>AACACGCTGTATCTGGAAATGAACAGCCTGAAACCTGA<br>GGACACGGCCCTGTATTACTGTGCAAGAGTCAACGTCT<br>GGGGGGTGAACTACTGGGGCAAAGGGACCCTGGTCAGC<br>GTCTCCTCA | 195 | CAGACTGTGGTGACTCAGGAGCCGTCCCTGTCAGTGTC<br>TCCAGGAGGGACGGTCACACTCACCTGCGGCCTCAGCT<br>CTGGGTCTGTCACTACCAGTAACTACCCTGGTTGGTTC<br>CAGCAGACACCAGGCCAGGCTCCACGCACTCTTATCTA<br>CAACACAAACAGCCGCCACTCTGGGGTCCCCAGTCGCT<br>TCTCCGGATCCATCTCTGGGAACAAAGCCGCCCTCACC<br>ATCACGGGGGCCCAGCCCGAGGACGAGGCCGACTATTA<br>CTGTTCTCTGTACCCTGGTAGTTACACTAATGTGTTCG<br>GCGGAGGGACCCATCTGACCGTCCTG | 196 |
| 72F8 | GAGTTGCAGCTGGTGGAGTCTGGGGGAGGCTTGGTGCA<br>GCCTGgGGGGTCTCTGAGACTCTcCTGTGCAGCCTCTG<br>GATTCACCTTCAGCAACTATGTCATGAGCTGGGTCCGC<br>CAGGCTCCAGGAAAGGGGCTCGAGTGGGTCTCAGATAC<br>TAATAGTGGTGGTAGCACAAGCTATGCAGACTCCGTGA<br>AGGGCCGATTCACCATCTCTAGAGACAACGCCAAGAAC<br>ACGCTGTATTTGCAAATGAACAGCCTGAAACCTGAGGA<br>CACGGCATTGTATTACTGTGCGAGATCATTTTTCTACG<br>GCATGAACTACTGGGGCAAAGGGACCCAGGTCACCGTG<br>TCCTCA | 197 | CAGTCTGCCCTGACTCAGCCGCCCTCCCTCTCTGCATC<br>TCCGGGATCATCTGTCAGACTCACCTGCACCCTGAGCA<br>GTGGAAACAATATTGGCAGCTATGACATAAGTTGGTAC<br>CAGCAGAAGGCAGGGAGCCCTCCCCGGTACCTCCTGAA<br>CTACTACACCGACTCACGCAAGCACCAGGACTCCGGGG<br>TCCCGAGCCGCTTCTCTGGGTCCAAAGATGCCTCGGCC<br>AACGCAGGGCTTCTGCTCATCTCTGGGCTTCAGCCCGA<br>GGACGAGGCTGACTATTACTGTTCTGCATACAAGAGTG<br>GTTCTTACCGTTGGGTGTTCGGCGGAGGGACGCACGTG<br>ACCGTCCTG | 198 |

The various Fab families and their ability to bind human and mouse MET are shown in Table 7.

TABLE 7

Fabs binding to both human MET (hMET) and mouse MET (mMET). Fabs are grouped in families based on their VH CDR3 sequence. Binding of Fabs to human and mouse MET ECD was determined by Surface Plasmon Resonance (SPR) and by ELISA. SPR values represent the koff ($s^{-1}$). ELISA values represent the Optical Density (OD) at 450 nm (AU, arbitrary units). Both SPR and ELISA were performed using crude periplasmic extracts. Fab concentration in the extract was not determined. Values are the mean of three independent measurements.

| | | | SPR ($K_{off}$; $s^{-1}$) | | ELISA ($OD_{450}$; AU) | |
|---|---|---|---|---|---|---|
| Fab | VH | VL | hMET | mMET | hMET | mMET |
| 76H10 | VH 1 | Lambda | 5.68E−03 | 5.44E−03 | 3.704 | 3.697 |
| 71G3 | VH 2 | Lambda | 1.42E−03 | 1.41E−03 | 3.462 | 3.443 |
| 71D6 | VH 3a | Lambda | 2.94E−03 | 2.67E−03 | 3.261 | 3.072 |
| 71C3 | VH 3b | Lambda | 2.25E−03 | 2.58E−03 | 1.650 | 1.643 |
| 71D4 | VH 3c | Lambda | 2.17E−03 | 2.38E−03 | 0.311 | 0.307 |
| 71A3 | VH 4 | Lambda | 4.92E−03 | 4.74E−03 | 0.581 | 0.524 |
| 71G2 | VH 4 | Lambda | 1.21E−03 | 1.48E−03 | 0.561 | 0.543 |
| 76G7 | VH 5 | Lambda | 4.32E−03 | 4.07E−03 | 3.199 | 3.075 |
| 71G12 | VH 6 | Kappa | 2.28E−03 | 2.55E−03 | 0.450 | 0.420 |

TABLE 7-continued

Fabs binding to both human MET (hMET) and mouse MET (mMET). Fabs are grouped in families based on their VH CDR3 sequence. Binding of Fabs to human and mouse MET ECD was determined by Surface Plasmon Resonance (SPR) and by ELISA. SPR values represent the koff ($s^{-1}$). ELISA values represent the Optical Density (OD) at 450 nm (AU, arbitrary units). Both SPR and ELISA were performed using crude periplasmic extracts. Fab concentration in the extract was not determined. Values are the mean of three independent measurements.

| | | | SPR ($K_{off}$; $s^{-1}$) | | ELISA ($OD_{450}$; AU) | |
|---|---|---|---|---|---|---|
| Fab | VH | VL | hMET | mMET | hMET | mMET |
| 74C8 | VH 9 | Lambda | 3.48E−03 | 3.70E−03 | 2.976 | 2.924 |
| 72F8 | VH 10 | Lambda | 4.96E−03 | 4.58E−03 | 3.379 | 3.085 |

Example 3: Chimerization of Fabs into mAbs

The cDNAs encoding the VH and VL (κ or λ) domains of selected Fab fragments were engineered into two separate pUPE mammalian expression vectors (U-protein Express) containing the cDNAs encoding CH1, CH2 and CH3 of human IgG1 or the human CL (κ or λ), respectively. The full amino acid sequences of llama-human chimeric antibody heavy chain and light chain is shown in Table 8.

TABLE 8

Full heavy chain and light chain amino acid sequences of llama-human chimeric mAbs binding to both human and mouse MET.

| Clone | Heavy chain (VH-CH1-CH2-CH3) | SEQ ID NO. | Light chain (VL-CL) | SEQ ID NO. |
|---|---|---|---|---|
| 76H10 | QLQLVESGGGLVQPGGSLRVSCTASGFTFNTYYMTWVRQAPGKGLEWVSDINSGGGTYYADSVKGRFTISRDNAKNTLYLQMNSLKPEDTALYYCVRVRIWPVGYDYWGQGTQVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTSEVFVPQSRKVI | 199 | QAVVTQEPSLSVSPGGTVTLTCGLSSGSVTTSNYPGWFQQTPGQAPRTLIYNTNNRHSGVPSRFSGSISGNKAALTITGAQPEDEADYYCSLYTGSYTTVFGGGTHLTVLQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 200 |
| 71G3 | QVQLVESGGGLVQPGGSLRVSCAASGFTFSTYYMSWVRQAPGKGLEWVSDIRTDGGTYYADSVKGRFTMSRDNAKNTLYLQMNSLKPEDTALYYCARTRIFPSGYDYWGQGTQVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTSEVFVPQSRKVI | 201 | QAVVTQEPSLSVSPGGTVTLTCGLSSGSVTTSNYPGWFQQTPGQAPRTLIYNTNSRHSGVPSRFSGSISGNKAALTIMGAQPEDEADYYCSLYPGSTTVFGGGTHLTVLQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 202 |
| 71C3 | QLQLVESGGGLVQPGGSLRLSCAASGFTFSSHAMSWVRQAPGKGLEWVSAINSGGGSTSYADSVKGRFTISRDNAKNTLYLQMNSLKPEDTAVYYCAKELRFDLARYTDYEAWDYWGQGTQVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTSEVFVPQSRKVI | 203 | SYELTQPSALSVTLGQTAKITCQGGSLGSSYAHWYQQKPGQAPVLVIYDDDSRPSGIPERFSGSSSGGTATLTISGAQAEDEGDYYCQSADSSGNAAVFGGGTHLTVLQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 204 |

TABLE 8-continued

Full heavy chain and light chain amino acid sequences of llama-human chimeric mAbs binding to both human and mouse MET.

| Clone | Heavy chain (VH-CH1-CH2-CH3) | SEQ ID NO. | Light chain (VL-CL) | SEQ ID NO. |
|---|---|---|---|---|
| 71D4 | ELQLVESGGGLVQPGGSLRLSCAASGFTFSGYGMSWVRQAPGKGLEWV<br>SDINSGGGSTSYADSVKGRFTISRDNAKNTLYLQMNSLKPEDTAVYYC<br>AKDMRLYLARYNDYEAWDYWGQGTQVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPS<br>DIAVEWESNGQPENNYKTTPPVLDSDGSFFLYSKLTVDKSRWQQGNVF<br>SCSVMHEALHNHYTSEVFVPQSRKVI | 205 | SSALTQPSALSVTLGQTAKITCQGGSLGSSYAH<br>WYQQKPGQAPVLVIYDDDSRPSGIPERFSGSSS<br>GGTATLTISGAQAEDEGDYYCQSADSSGNAAVF<br>GGGTHLTVLQPKAAPSVTLFPPSSEELQANKAT<br>LVCLISDFYPGAVTVAWKADSSPVKAGVETTTP<br>SKQSNNKYAASSYLSLTPEQWKSHRSYSCQVTH<br>EGSTVEKTVAPTECS | 206 |
| 71D6 | ELQLVESGGGLVQPGGSLRLSCAASGFTFSSYGMSWVRQAPGKGLEWV<br>SAINSYGGSTSYADSVKGRFTISRDNAKNTLYLQMNSLKPEDTAVYYC<br>AKEVRADLSRYNDYESYDYWGQGTQVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPS<br>DIAVEWESNGQPENNYKTTPPVLDSDGSFFLYSKLTVDKSRWQQGNVF<br>SCSVMHEALHNHYTSEVFVPQSRKVI | 207 | QPVLNQPSALSVTLGQTAKITCQGGSLGARYAH<br>WYQQKPGQAPVLVIYDDDSRPSGIPERFSGSSS<br>GGTATLTISGAQAEDEGDYYCQSADSSGSVFGG<br>GTHLTVLQPKAAPSVTLFPPSSEELQANKATLV<br>CLISDFYPGAVTVAWKADSSPVKAGVETTTPSK<br>QSNNKYAASSYLSLTPEQWKSHRSYSCQVTHEG<br>STVEKTVAPTECS | 208 |
| 71A3 | EVQLVESGGGLVQPGGSLRLSCAASGFSFKDYDITWVRQAPGKGLEWV<br>STITSRSGSTSYVDSVKGRFTISGDNAKNTLYLQMNSLKPEDTAVYYC<br>AKVYATTWDVGPLGYGMDYWGKGTLVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPS<br>DIAVEWESNGQPENNYKTTPPVLDSDGSFFLYSKLTVDKSRWQQGNVF<br>SCSVMHEALHNHYTSEVFVPQSRKVI | 209 | SYELTQPSALSVTLGQTAKITCQGGSLGSSYAH<br>WYQQKPGQAPVLVIYDDDSRPSGIPERFSGSSS<br>GGTATLTISGAQAEDEGDYYCQSADSSGNAAVF<br>GGGTHLTVLQPKAAPSVTLFPPSSEELQANKAT<br>LVCLISDFYPGAVTVAWKADSSPVKAGVETTTP<br>SKQSNNKYAASSYLSLTPEQWKSHRSYSCQVTH<br>EGSTVEKTVAPTECS | 210 |
| 71G2 | EVQLQESGGGLVQPGGSLRLSCAASGFTFSIYDMSWVRQAPGKGLEWV<br>STINSDGSSTSYVDSVKGRFTISRDNAKNTLYLQMNSLKPEDTAVYYC<br>AKVYGSTWDVGPMGYGMDYWGKGTLVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPS<br>DIAVEWESNGQPENNYKTTPPVLDSDGSFFLYSKLTVDKSRWQQGNVF<br>SCSVMHEALHNHYTSEVFVPQSRKVI | 211 | SSALTQPSALSVSLGQTARITCQGGSLGSSYAH<br>WYQQKPGQAPVLVIYGDDSRPSGIPERFSGSSS<br>GGTATLTISGAQAEDEDDYYCQSTDSSGNTVFG<br>GGTRLTVLQPKAAPSVTLFPPSSEELQANKATL<br>VCLISDFYPGAVTVAWKADSSPVKAGVETTTPS<br>KQSNNKYAASSYLSLTPEQWKSHRSYSCQVTHE<br>GSTVEKTVAPTECS | 212 |
| 76G7 | QVQLVESGGNLVQPGGSLRLSCAASGFTFSNYYMSWVRQAPGKGLEWV<br>SDIYSDGSTTWYSDSVKGRFTISRDNAKNTLSLQMNSLKSEDTAVYYC<br>ARVKIYPGGYDAWGQGTQVTVSSASTKGPSVFPLAPSSKSTSGGTAAL<br>GCLVKDYFPEPVTVSWNSGALTSGVHTFPAVLQSSGLYSLSSVVTVPS<br>SSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHE<br>ALHNHYTSEVFVPQSRKVI | 213 | QAGLTQPPSVSGSPGKTVTISCAGNSSDVGYGN<br>YVSWYQQFPGMAPKLLIYLVNKRASGITDRFSG<br>SKSGNTASLTISGLQSEDEADYYCASYTGSNNI<br>VFGGGTHLTVLQPKAAPSVTLFPPSSEELQANK<br>ATLVCLISDFYPGAVTVAWKADSSPVKAGVETT<br>TPSKQSNNKYAASSYLSLTPEQWKSHRSYSCQV<br>THEGSTVEKTVAPTECS | 214 |
| 71G12 (kappa) | QVQLQESGGDLVQPGGSLRVSCVVSGFTFSRYYMSWVRQAPGKGLEWV<br>SSIDSYGYSTYYTDSVKGRFTISRDNAKNTLYLQMNSLKPEDTALYYC<br>ARAKTTWSYDYWGQGTQVTVSSASTKGPSVFPLAPSSKSTSGGTAALG<br>CLVKDYFPEPVTVSWNSGALTSGVHTFPAVLQSSGLYSLSSVVTVPSS<br>SLGTQTYICNVNHKPSNTKVDKKVEPKSCDKTHTCPPCPAPELLGGPS<br>VFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKT<br>ISKAKGQPREPQVYTLPPSRDELTKNQVSLTCLVKGFYPSDIAVEWES<br>NGQPENNYKTTPPVLDSDGSFFLYSKLTVDKSRWQQGNVFSCSVMHEA<br>LHNHYTSEVFVPQSRKVI | 215 | EIVLTQSPSSVTASVGGKVTINCKSSQSVFIAS<br>NQKTYLNWYQQRPGQSPRLVISYASTRESGIPD<br>RFSGSGSTTDFTLTISSVQPEDAAVYYCQQAYS<br>HPTFGQGTKVELKRTVAAPSVFIFPPSDEQLKS<br>GTASVVCLLNNFYPREAKVQWKVDNALQSGNSQ<br>ESVTEQDSKDSTYSLSSTLTLSKADYEKHKVYA<br>CEVTHQGLSSPVTKSFNRGEC | 216 |
| 74C8 | EVQLVESGGGLVQPGGSLRLSCAASGFTFRNYHMSWVRQVPGKGFEWI<br>SDINSAGGSTYYADSVKGRFTISRDNAKNTLYLEMNSLKPEDTALYYC<br>ARVNVWGVNYWGKGTLVSVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKKVEPKSCDKTHTCPPCPAPELLGGPSV<br>FLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTI | 217 | QTVVTQEPSLSVSPGGTVTLTCGLSSGSVTTSN<br>YPGWFQQTPGQAPRTLIYNTNSRHSGVPSRFSG<br>SISGNKAALTITGAQPEDEADYYCSLYPGSYTN<br>VFGGGTHLTVLQPKAAPSVTLFPPSSEELQANK<br>ATLVCLISDFYPGAVTVAWKADSSPVKAGVETT<br>TPSKQSNNKYAASSYLSLTPEQWKSHRSYSCQV<br>THEGSTVEKTVAPTECS | 218 |

TABLE 8-continued

Full heavy chain and light chain amino acid sequences of llama-human chimeric mAbs binding to both human and mouse MET.

| Clone | Heavy chain (VH-CH1-CH2-CH3) | SEQ ID NO. | Light chain (VL-CL) | SEQ ID NO. |
|---|---|---|---|---|
| | SKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTSEVFVPQSRKVI | | | |
| 72F8 | ELQLVESGGGLVQPGGSLRLSCAASGFTFSNYVMSWVRQAPGKGLEWV SDTNSGGSTSYADSVKGRFTISRDNAKNTLYLQMNSLKPEDTALYYCA RSFFYGMNYWGKGTQVTVSSASTKGPSVFPLAPSSKSTSGGTAALGCL VKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTSEVFVPQSRKVI | 219 | QSALTQPPSLSASPGSSVRLTCTLSSGNNIGSY DISWYQQKAGSPPRYLLNYYTDSRKHQDSGVPS RFSGSKDASANAGLLLISGLQPEDEADYYCSAY KSGSYRWVFGGGTHVTVLQPKAAPSVTLFPPSS EELQANKATLVCLISDFYPGAVTVAWKADSSPV KAGVETTTPSKQSNNKYAASSYLSLTPEQWKSH RSYSCQVTHEGSTVEKTVAPTECS | 220 |

Production (by transient transfection of mammalian cells) and purification (by protein A affinity chromatography) of the resulting chimeric llama-human IgG1 molecules was outsourced to U-protein Express. Binding of chimeric mAbs to MET was determined by ELISA using hMET or mMET ECD in solid phase and increasing concentrations of antibodies (0-20 nM) in solution. Binding was revealed using HRP-conjugated anti-human Fc antibodies (Jackson Immuno Research Laboratories). This analysis revealed that all chimeric llama-human antibodies bound to human and mouse MET with picomolar affinity, displaying an $EC_{50}$ comprised between 0.06 nM and 0.3 nM. Binding capacity ($E_{MAX}$) varied from antibody to antibody, possibly due to partial epitope exposure in the immobilized antigen, but was similar in the human and mouse setting. $EC_{50}$ and $E_{MAX}$ values are shown in Table 9.

TABLE 9

Binding of chimeric mAbs to human and mouse MET as determined by ELISA using immobilized MET ECD in solid phase and increasing concentrations (0-20 nM) of antibodies in solution. $EC_{50}$ values are expressed as nMol/L. $E_{MAX}$ values are expressed as Optical Density (OD) at 450 nm (AU, arbitrary units).

| | hMET | | mMET | |
|---|---|---|---|---|
| mAb | $EC_{50}$ | $E_{MAX}$ | $EC_{50}$ | $E_{MAX}$ |
| 76H10 | 0.090 | 2.669 | 0.062 | 2.662 |
| 71G3 | 0.067 | 2.835 | 0.057 | 2.977 |
| 71D6 | 0.026 | 2.079 | 0.049 | 2.009 |
| 71C3 | 0.203 | 2.460 | 0.293 | 2.238 |
| 71D4 | 0.207 | 1.428 | 0.274 | 1.170 |
| 71A3 | 0.229 | 2.401 | 0.176 | 2.730 |
| 71G2 | 0.112 | 3.094 | 0.101 | 3.168 |
| 76G7 | 0.128 | 2.622 | 0.103 | 2.776 |
| 71G12 | 0.106 | 3.076 | 0.127 | 2.973 |
| 74C8 | 0.090 | 0.994 | 0.116 | 0.896 |
| 72F8 | 0.064 | 2.779 | 0.048 | 2.903 |

We also analysed whether chimeric anti-MET antibodies bound to native human and mouse MET in living cells. To this end, increasing concentrations of antibodies (0-100 nM) were incubated with A549 human lung carcinoma cells (American Type Culture Collection) or MLP29 mouse liver precursor cells (a gift of Prof. Enzo Medico, University of Torino, Strada Provinciale 142 km 3.95, Candiolo, Torino, Italy; Medico et al., Mol Biol Cell 7, 495-504, 1996), which both express physiological levels of MET. Antibody binding to cells was analysed by flow cytometry using phycoerythrin-conjugated anti-human IgG1 antibodies (eBioscience) and a CyAn ADP analyser (Beckman Coulter). As a positive control for human MET binding, we used a commercial mouse anti-human MET antibody (R&D Systems) and phycoerythrin-conjugated anti-mouse IgG1 antibodies (eBioscience). As a positive control for mouse MET binding we used a commercial goat anti-mouse MET antibody (R&D Systems) and phycoerythrin-conjugated anti-goat IgG1 antibodies (eBioscience). All antibodies displayed dose-dependent binding to both human and mouse cells with an $EC_{50}$ varying between 0.2 nM and 2.5 nM. Consistent with the data obtained in ELISA, maximal binding ($E_{MAX}$) varied depending on antibody, but was similar in human and mouse cells. These results indicate that the chimeric llama-human antibodies recognize membrane-bound MET in its native conformation in both human and mouse cellular systems. $EC_{50}$ and $E_{MAX}$ values are shown in Table 10.

TABLE 10

Binding of chimeric mAbs to human and mouse cells as determined by flow cytometry using increasing concentrations (0-50 nM) of antibodies. $EC_{50}$ values are expressed as nMol/L. $E_{MAX}$ values are expressed as % relative to control.

| | Human cells (A549) | | Mouse cells (MLP29) | |
|---|---|---|---|---|
| mAb | $EC_{50}$ | $E_{MAX}$ | $EC_{50}$ | $E_{MAX}$ |
| 76H10 | 2.345 | 130.2 | 1.603 | 124.3 |
| 71G3 | 0.296 | 116.9 | 0.214 | 116.2 |
| 71D6 | 0.259 | 112.7 | 0.383 | 121.2 |
| 71C3 | 0.572 | 106.5 | 0.585 | 115.1 |
| 71D4 | 0.371 | 107.2 | 0.498 | 94.8 |
| 71A3 | 0.514 | 160.8 | 0.811 | 144.2 |
| 71G2 | 0.604 | 144.4 | 0.688 | 129.9 |
| 76G7 | 2.298 | 121.2 | 2.371 | 114.8 |
| 71G12 | 2.291 | 109.9 | 2.539 | 121.2 |
| 74C8 | 0.235 | 85.7 | 0.208 | 73.8 |
| 72F8 | 0.371 | 156.3 | 0.359 | 171.6 |

Example 4: Receptor Regions Responsible for Antibody Binding

In order to map the receptor regions recognized by antibodies binding to both human and mouse MET (herein after referred to as human/mouse equivalent anti-MET antibodies), we measured their ability to bind to a panel of engineered proteins derived from human MET generated as described (Basilico et al, J Biol. Chem. 283, 21267-21227, 2008). This panel included (FIG. 2): the entire MET ECD (Decoy MET); a MET ECD lacking IPT domains 3 and 4 (SEMA-PSI-IPT 1-2); a MET ECD lacking IPT domains 1-4 (SEMA-PSI); the isolated SEMA domain (SEMA); a fragment containing IPT domains 3 and 4 (IPT 3-4). Engineered MET proteins were immobilized in solid phase and exposed to increasing concentrations of chimeric antibodies (0-50 nM) in solution. Binding was revealed using HRP-conjugated anti-human Fc antibodies (Jackson Immuno Research Laboratories). As shown in Table 11, this analysis revealed that 7 mAbs recognize an epitope within the SEMA domain, while the other 4 recognize an epitope within the PSI domain.

TABLE 11

Binding of human/mouse equivalent anti-MET antibodies to the panel of MET deletion mutants described in FIG. 2. The MET domain responsible for antibody binding is indicated in the last column to the right.

| mAb | Decoy MET | SEMA-PSI-IPT 1-2 | SEMA-PSI | SEMA | IPT 3-4 | Binding domain |
|---|---|---|---|---|---|---|
| 76H10 | + | + | + | − | − | PSI |
| 71G3 | + | + | + | − | − | PSI |
| 71D6 | + | + | + | + | − | SEMA |
| 71C3 | + | + | + | + | − | SEMA |
| 71D4 | + | + | + | + | − | SEMA |
| 71A3 | + | + | + | + | − | SEMA |
| 71G2 | + | + | + | + | − | SEMA |

TABLE 11-continued

Binding of human/mouse equivalent anti-MET antibodies to the panel of MET deletion mutants described in FIG. 2. The MET domain responsible for antibody binding is indicated in the last column to the right.

| mAb | Decoy MET | SEMA-PSI-IPT 1-2 | SEMA-PSI | SEMA | IPT 3-4 | Binding domain |
|---|---|---|---|---|---|---|
| 76G7 | + | + | + | − | − | PSI |
| 71G12 | + | + | + | − | − | PSI |
| 74C8 | + | + | + | + | − | SEMA |
| 72F8 | + | + | + | + | − | SEMA |

To more finely map the regions of MET responsible for antibody binding, we exploited the absence of cross-reactivity between our antibodies and llama MET (the organism used for generating these immunoglobulins). To this end, we generated a series of llama-human and human-llama chimeric MET proteins spanning the entire MET ECD as described (Basilico et al., J Clin Invest. 124, 3172-3186, 2014). Chimeras (FIG. 3) were immobilized in solid phase and then exposed to increasing concentrations of mAbs (0-20 nM) in solution. Binding was revealed using HRP-conjugated anti-human Fc antibodies (Jackson Immuno Research Laboratories). This analysis unveiled that 5 SEMA-binding mAbs (71D6, 71C3, 71D4, 71A3, 71G2) recognize an epitope localized between aa 314-372 of human MET, a region that corresponds to blades 4-5 of the 7-bladed SEMA β-propeller (Stamos et al., EMBO J. 23, 2325-2335, 2004). The other 2 SEMA-binding mAbs (74C8, 72F8) recognize an epitope localized between aa 123-223 and 224-311, respectively, corresponding to blades 1-3 and 1-4 of the SEMA β-propeller. The PSI-binding mAbs (76H10, 71G3, 76G7, 71G12) did not appear to display any significant binding to any of the two PSI chimeras. Considering the results presented in Table 11, these antibodies probably recognize an epitope localized between aa 546 and 562 of human MET. These results are summarized in Table 12.

TABLE 12

Mapping of the epitopes recognized by human/mouse equivalent anti-MET antibodies as determined by ELISA. Human MET ECD (hMET) or llama MET ECD (lMET) as well as the llama-human MET chimeric proteins described in FIG. 3 (CH1-7) were immobilized in solid phase and then exposed to increasing concentrations of mAbs.

| mAb | hMET | lMET | CH1 | CH2 | CH3 | CH4 | CH5 | CH6 | CH7 | Epitope (aa) |
|---|---|---|---|---|---|---|---|---|---|---|
| 76H10 | + | − | + | + | + | + | + | − | − | 546-562 |
| 71G3 | + | − | + | + | + | + | + | − | − | 546-562 |
| 71D6 | + | − | + | + | + | − | − | + | + | 314-372 |
| 71C3 | + | − | + | + | + | − | − | + | + | 314-372 |
| 71D4 | + | − | + | + | + | − | − | + | + | 314-372 |
| 71A3 | + | − | + | + | + | − | − | + | + | 314-372 |
| 71G2 | + | − | + | + | + | − | − | + | + | 314-372 |
| 76G7 | + | − | + | + | + | + | + | − | − | 546-562 |
| 71G12 | + | − | + | + | + | + | + | − | − | 546-562 |
| 74C8 | + | − | + | − | − | − | − | + | + | 123-223 |
| 72F8 | + | − | + | + | − | − | − | + | + | 224-311 |

Example 5: HGF Competition Assays

The above analysis suggests that the epitopes recognized by some of the human/mouse equivalent anti-MET antibodies may overlap with those engaged by HGF when binding to MET (Stamos et al., EMBO J. 23, 2325-2335, 2004; Merchant et al., Proc Natl Acad Sci USA 110, E2987-2996, 2013; Basilico et al., J Clin Invest. 124, 3172-3186, 2014). To investigate along this line, we tested the competition between mAbs and HGF by ELISA. Recombinant human and mouse HGF (R&D Systems) were biotinylated at the N-terminus using NHS-LC-biotin (Thermo Scientific). MET-Fc protein, either human or mouse (R&D Systems), was immobilized in solid phase and then exposed to 0.3 nM biotinylated HGF, either human or mouse, in the presence of increasing concentrations of antibodies (0-120 nM). HGF binding to MET was revealed using HRP-conjugated streptavidin (Sigma-Aldrich). As shown in Table 13, this analysis allowed to divide human/mouse equivalent anti-MET mAbs into two groups: full HGF competitors (71D6, 71C3, 71D4, 71A3, 71G2), and partial HGF competitors (76H10, 71G3, 76G7, 71G12, 74C8, 72F8).

TABLE 13

Ability of human/mouse equivalent anti-MET antibodies to compete with HGF for binding to MET as determined by ELISA. A MET-Fc chimeric protein (either human or mouse) was immobilized in solid phase and exposed to a fixed concentration of biotinylated HGF (either human or mouse), in the presence of increasing concentrations of antibodies. HGF binding to MET was revealed using HRP-conjugated streptavidin. Antibody-HGF competition is expressed as $IC_{50}$ (the concentration that achieves 50% competition) and $I_{MAX}$ (the maximum % competition reached at saturation).

| | hHGF on hMET | | mHGF on mMET | |
|---|---|---|---|---|
| mAb | $IC_{50}$ (nM) | $I_{MAX}$ (%) | $IC_{50}$ (nM) | $I_{MAX}$ (%) |
| 76H10 | 1.86 | 64.22 | 2.01 | 62.71 |
| 71G3 | 0.49 | 63.16 | 0.53 | 62.87 |
| 71D6 | 0.29 | 98.34 | 0.34 | 90.54 |
| 71C3 | 1.42 | 93.64 | 1.56 | 89.23 |
| 71D4 | 0.34 | 95.62 | 0.40 | 91.34 |
| 71A3 | 0.51 | 93.37 | 0.54 | 87.74 |
| 71G2 | 0.23 | 97.84 | 0.26 | 91.86 |
| 76G7 | 1.47 | 69.42 | 1.56 | 62.52 |
| 71G12 | 3.87 | 51.39 | 4.05 | 50.67 |
| 74C8 | 0.43 | 76.89 | 0.49 | 71.55 |
| 72F8 | 0.45 | 77.34 | 0.52 | 72.79 |

As a general rule, SEMA binders displaced HGF more effectively than PSI binders. In particular, those antibodies that recognize an epitope within blades 4 and 5 of the SEMA β-propeller were the most potent HGF competitors (71D6, 71C3, 71D4, 71A3, 71G2). This observation is consistent with the notion that SEMA blade 5 contains the high affinity binding site for the α-chain of HGF (Merchant et al., Proc Natl Acad Sci USA 110, E2987-2996, 2013). The PSI domain has not been shown to participate directly with HGF, but it has been suggested to function as a 'hinge' regulating the accommodation of HGF between the SEMA domain and the IPT region (Basilico et al., J Clin Invest. 124, 3172-3186, 2014). It is therefore likely that mAbs binding to PSI (76H10, 71G3, 76G7, 71G12) hamper HGF binding to MET by interfering with this process or by steric hindrance, and not by direct competition with the ligand. Finally, blades 1-3 of the SEMA β-propeller have been shown to be responsible for low-affinity binding of the β-chain of HGF, which plays a central role in MET activation but only partially contributes to the HGF-MET binding strength (Stamos et al., EMBO J. 23, 2325-2335, 2004). This could explain why mAbs binding to that region of MET (74C8, 72F8) are partial competitors of HGF.

Example 6: MET Activation Assays

Due to their bivalent nature, immunoglobulins directed against receptor tyrosine kinases may display receptor agonistic activity, mimicking the effect of natural ligands. To investigate along this line, we tested the ability of human/mouse equivalent anti-MET antibodies to promote MET auto-phosphorylation in a receptor activation assay. A549 human lung carcinoma cells and MLP29 mouse liver precursor cells were deprived of serum growth factors for 48 hours and then stimulated with increasing concentrations (0-5 nM) of antibodies or recombinant HGF (A549 cells, recombinant human HGF, R&D Systems; MLP29 cells, recombinant mouse HGF, R&D Systems). After 15 minutes of stimulation, cells were washed twice with ice-cold phosphate buffered saline (PBS) and then lysed as described (Longati et al., Oncogene 9, 49-57, 1994). Protein lysates were resolved by electrophoresis and then analysed by Western blotting using antibodies specific for the phosphorylated form of MET (tyrosines 1234-1235), regardless of whether human or mouse (Cell Signaling Technology). The same lysates were also analysed by Western blotting using anti-total human MET antibodies (Invitrogen) or anti-total mouse MET antibodies (R&D Systems). This analysis revealed that all human/mouse equivalent antibodies display MET agonistic activity. As shown in FIG. 4, some antibodies promoted MET auto-phosphorylation to an extent comparable to that of HGF (71G3, 71D6, 71C3, 71D4, 71A3, 71G2, 74C8). Some others (76H10, 76G7, 71G12, 72F8) were less potent, and this was particularly evident at the lower antibody concentrations. No clear correlation between MET activation activity and HGF-competition activity was observed.

To obtain more quantitative data, the agonistic activity of antibodies was also characterized by phospho-MET ELISA. To this end, A549 and MLP29 cells were serum-starved as above and then stimulated with increasing concentrations (0-25 nM) of mAbs. Recombinant human (A549) or mouse (MLP29) HGF was used as control. Cells were lysed and phospho-MET levels were determined by ELISA as described (Basilico et al., J Clin Invest. 124, 3172-3186, 2014). Briefly, 96 well-plates were coated with mouse anti-human MET antibodies or rat anti-mouse MET antibodies (both from R&D Systems) and then incubated with cell lysates. After washing, captured proteins were incubated with biotin-conjugated anti-phospho-tyrosine antibodies (Thermo Fisher), and binding was revealed using HRP-conjugated streptavidin (Sigma-Aldrich).

The results of this analysis are consistent with the data obtained by Western blotting. As shown in Table 14, 71G3, 71D6, 71C3, 71D4, 71A3, 71G2 and 74C8 potently activated MET, while 76H10, 76G7, 71G12 and 72F8 caused a less pronounced effect. In any case, all antibodies displayed a comparable effect in human and in mouse cells.

TABLE 14

Agonistic activity of human/mouse equivalent anti-MET antibodies in human and mouse cells as measured by ELISA. A549 human lung carcinoma cells and MLP29 mouse liver precursor cells were serum-starved and then stimulated with increasing concentrations of mAbs. Recombinant human HGF (hHGF; A549) or mouse HGF (mHGF; MLP29) was used as control. Cell lysates were analysed by ELISA using anti-total MET antibodies for capture and anti-phospho-tyrosine antibodies for revealing. Agonistic activity is expressed as $EC_{50}$ (nM) and $E_{MAX}$ (% HGF activity).

| | A549 cells | | MLP29 cells | |
|---|---|---|---|---|
| mAb | $EC_{50}$ (nM) | $E_{MAX}$ (%) | $EC_{50}$ (nM) | $E_{MAX}$ (%) |
| 76H10 | 1.77 | 61.23 | 2.91 | 64.10 |
| 71G3 | 0.41 | 95.72 | 0.37 | 97.81 |
| 71D6 | 0.32 | 101.57 | 0.21 | 114.56 |
| 71C3 | 0.35 | 86.19 | 0.33 | 98.85 |
| 71D4 | 0.59 | 84.63 | 0.51 | 95.34 |
| 71A3 | 0.31 | 86.56 | 0.26 | 95.95 |
| 71G2 | 0.37 | 101.35 | 0.25 | 109.87 |
| 76G7 | 1.86 | 62.34 | 1.19 | 71.45 |
| 71G12 | 2.48 | 70.61 | 2.01 | 75.39 |
| 74C8 | 0.52 | 87.63 | 0.41 | 102.15 |
| 72F8 | 1.51 | 69.74 | 0.79 | 66.82 |
| HGF | 0.19 | 100.00 | 0.23 | 100.00 |

Example 7: Scatter Assay

To evaluate whether the agonistic activity of human/mouse equivalent anti-MET antibodies could translate into biological activity, we performed scatter assays with both human and mouse epithelial cells. To this end, HPAF-II human pancreatic adenocarcinoma cells (American Type Culture Collection) and MLP29 mouse liver precursor cells were stimulated with increasing concentrations of recombinant HGF (human or mouse; both from R&D Systems) and cell scattering was determined 24 hours later by microscopy as described previously (Basilico et al., J Clin Invest. 124, 3172-3186, 2014). This preliminary analysis revealed that HGF-induced cell scattering is linear until it reaches saturation at approximately 0.1 nM in both cell lines. Based on these HGF standard curves, we elaborated a scoring system ranging from 0 (total absence of cell scattering in the absence of HGF) to 4 (maximal cell scattering in the presence of 0.1 nM HGF). HPAF-II and MLP29 cells were stimulated with increasing concentrations of human/mouse equivalent anti-MET antibodies, and cell scattering was determined 24 hours later using the scoring system described above. As shown in Table 15, this analysis revealed that all mAbs tested promoted cell scattering in both the human and the mouse cell systems, with substantially overlapping results on both species. 71D6 and 71G2 displayed the very same activity as HGF; 71G3 and 71A3 were just slightly less potent than HGF; 71C3 and 74C8 required a substantially higher concentration in order to match the activity of HGF; 71D4, 76G7, 71G12 and 72F8 did not reach saturation in this assay.

TABLE 15

Biological activity of human/mouse equivalent anti-MET antibodies as measured in a cell-based scatter assay. HPAF-II human pancreatic adenocarcinoma cells and MLP29 mouse liver precursor cells were stimulated with increasing concentrations of human/mouse equivalent anti-MET antibodies, and cell scattering was determined 24 hours later using the scoring system described in the text (0, absence of cell scattering; 4, maximal cell scattering).

| | mAb concentration (nM) | | | | | | | | |
|---|---|---|---|---|---|---|---|---|---|
| mAb | 9.000 | 3.000 | 1.000 | 0.333 | 0.111 | 0.037 | 0.012 | 0.004 | 0.001 |
| HPAF-II human pancreatic adenocarcinoma cells | | | | | | | | | |
| 76H10 | 3 | 2 | 1 | 0 | 0 | 0 | 0 | 0 | 0 |
| 71G3 | 4 | 4 | 4 | 4 | 3 | 2 | 1 | 0 | 0 |
| 71D6 | 4 | 4 | 4 | 4 | 4 | 3 | 2 | 1 | 0 |
| 71C3 | 4 | 4 | 3 | 2 | 1 | 0 | 0 | 0 | 0 |
| 71D4 | 2 | 2 | 1 | 0 | 0 | 0 | 0 | 0 | 0 |
| 71A3 | 4 | 4 | 4 | 4 | 3 | 3 | 2 | 0 | 0 |
| 71G2 | 4 | 4 | 4 | 4 | 4 | 3 | 2 | 1 | 0 |
| 76G7 | 3 | 2 | 1 | 0 | 0 | 0 | 0 | 0 | 0 |
| 71G12 | 3 | 2 | 2 | 1 | 0 | 0 | 0 | 0 | 0 |
| 74C8 | 4 | 4 | 3 | 3 | 2 | 1 | 0 | 0 | 0 |
| 72F8 | 3 | 2 | 1 | 0 | 0 | 0 | 0 | 0 | 0 |
| hHGF | 4 | 4 | 4 | 4 | 4 | 3 | 2 | 1 | 0 |
| IgG1 | 0 | 0 | 0 | 0 | 0 | 0 | 0 | 0 | 0 |
| MLP29 mouse liver precursor cells | | | | | | | | | |
| 76H10 | 3 | 2 | 1 | 0 | 0 | 0 | 0 | 0 | 0 |
| 71G3 | 4 | 4 | 4 | 4 | 2 | 1 | 0 | 0 | 0 |
| 71D6 | 4 | 4 | 4 | 4 | 4 | 3 | 2 | 1 | 0 |
| 71C3 | 4 | 4 | 3 | 2 | 1 | 0 | 0 | 0 | 0 |
| 71D4 | 2 | 2 | 1 | 0 | 0 | 0 | 0 | 0 | 0 |
| 71A3 | 4 | 4 | 4 | 4 | 3 | 3 | 2 | 0 | 0 |
| 71G2 | 4 | 4 | 4 | 4 | 4 | 2 | 1 | 0 | 0 |
| 76G7 | 3 | 2 | 1 | 0 | 0 | 0 | 0 | 0 | 0 |
| 71G12 | 3 | 2 | 2 | 1 | 0 | 0 | 0 | 0 | 0 |
| 74C8 | 4 | 4 | 3 | 3 | 2 | 1 | 0 | 0 | 0 |
| 72F8 | 3 | 2 | 1 | 0 | 0 | 0 | 0 | 0 | 0 |
| mHGF | 4 | 4 | 4 | 4 | 4 | 3 | 2 | 1 | 0 |
| IgG1 | 0 | 0 | 0 | 0 | 0 | 0 | 0 | 0 | 0 |

Example 8: Protection Against Drug-Induced Apoptosis

Several lines of experimental evidence indicate that HGF display a potent anti-apoptotic effect on MET-expressing cells (reviewed by Nakamura et al., J Gastroenterol Hepatol. 26 Suppl 1, 188-202, 2011). To test the potential anti-apoptotic activity of human/mouse equivalent anti-MET antibodies, we performed cell-based drug-induced survival assays. MCF10A human mammary epithelial cells (American Type Culture Collection) and MLP29 mouse liver precursor cells were incubated with increasing concentrations of staurosporine (Sigma Aldrich). After 48 hours, cell viability was determined by measuring total ATP concentration using the Cell Titer Glo kit (Promega) with a Victor X4 multilabel plate reader (Perkin Elmer). This preliminary analysis revealed that the drug concentration that induced about 50% cell death is 60 nM for MCF10A cells and 100 nM for MLP29 cells. Next, we incubated MCF10A cells and MLP29 cells with the above determined drug concentrations in the presence of increasing concentrations (0-32 nM) of anti-MET mAbs or recombinant HGF (human or mouse; both from R&D Systems). Cell viability was determined 48 hours later as described above. The results of this analysis, presented in Table 16, suggest that human/mouse equivalent antibodies protected human and mouse cells against staurosporine-induced cell death to a comparable extent. While some mAbs displayed a protective activity similar or superior to that of HGF (71G3, 71D6, 71G2), other molecules displayed only partial protection (76H10, 71C3, 71D4, 71A3, 76G7, 71G12, 74C8, 72F8), either in the human or in the mouse cell system.

TABLE 16

Biological activity of human/mouse equivalent anti-MET antibodies as measured by a cell-based drug-induced apoptosis assay. MCF10A human mammary epithelial cells and MLP29 mouse liver precursor cells were incubated with a fixed concentration of staurosporine in the the presence of increasing concentrations of anti-MET mAbs or recombinant HGF (human or mouse), and total ATP content was determined 48 hours later. Cell viability was calculated as % total ATP content relative to cells treated with neither staurosporine nor antibodies, and is expressed as $EC_{50}$ and $E_{MAX}$.

| | MCF10A cells | | MLP29 cells | |
|---|---|---|---|---|
| mAb | $EC_{50}$ (nM) | $E_{MAX}$ (%) | $EC_{50}$ (nM) | $E_{MAX}$ (%) |
| 76H10 | >32.00 | 22.75 | >32.00 | 27.21 |
| 71G3 | 5.04 | 65.23 | 4.85 | 62.28 |
| 71D6 | 1.48 | 66.81 | 0.95 | 68.33 |
| 71C3 | 31.87 | 50.16 | 31.03 | 51.32 |
| 71D4 | 30.16 | 51.71 | 29.84 | 52.13 |
| 71A3 | <0.50 | 71.70 | <0.50 | 70.54 |
| 71G2 | 1.06 | 64.85 | 1.99 | 58.29 |
| 76G7 | 25.41 | 51.93 | 30.08 | 50.16 |
| 71G12 | >32.00 | 39.35 | >32.00 | 39.73 |
| 74C8 | >32.00 | 41.74 | >32.00 | 37.52 |
| 72F8 | >32.00 | 35.79 | >32.00 | 43.81 |
| HGF | 4.57 | 59.28 | 5.35 | 58.65 |

Example 9: Branching Morphogenesis Assay

As discussed in the Background section, HGF is a pleiotropic cytokine which promotes the harmonic regulation of independent biological activities, including cell proliferation, motility, invasion, differentiation and survival. The cell-based assay that better recapitulates all of these activities is the branching morphogenesis assay, which replicates the formation of tubular organs and glands during embryogenesis (reviewed by Rosário and Birchmeier, Trends Cell Biol. 13, 328-335, 2003). In this assay, a spheroid of epithelial cells is seeded inside a 3D collagen matrix and is stimulated by HGF to sprout tubules which eventually form branched structures. These branched tubules resemble the hollow structures of epithelial glands, e.g. the mammary gland, in that they display a lumen surrounded by polarized cells. This assay is the most complete HGF assay that can be run in vitro.

In order to test whether human/mouse equivalent anti-MET antibodies displayed agonistic activity in this assay, we seeded LOC human kidney epithelial cells (Michieli et al. Nat Biotechnol. 20, 488-495, 2002) and MLP29 mouse liver precursor cells in a collagen layer as described (Hultberg et al., Cancer Res. 75, 3373-3383, 2015), and then exposed them to increasing concentrations of mAbs or recombinant HGF (human or mouse, both from R&D Systems). Branching morphogenesis was followed over time by microscopy, and colonies were photographed after 5 days. Representative images are shown in FIG. 5. Quantification of branching morphogenesis activity was obtained by counting the number of branches for each spheroid. As shown in Table 17, all antibodies tested induced dose-dependent formation of branched tubules. However, consistent with the data obtained in MET auto-phosphorylation assays and cell scattering assays, 71D6, 71A3 and 71G2 displayed the most potent agonistic activity, similar or superior to that of recombinant HGF.

TABLE 17

Branching morphogenesis assay. Cell spheroids preparations of LOC human kidney epithelial cells or MLP29 mouse liver precursor cells were seeded in a collagen layer and then incubated with increasing concentrations (0, 0.5, 2.5 and 12.5 nM) of mAbs or recombinant HGF (LOC, human HGF; MLP29, mouse HGF). Branching morphogenesis was followed over time by microscopy, and colonies were photographed after 5 days. Branching was quantified by counting the number of branches for each spheroid (primary branches plus secondary branches).

| mAb | 0 nM | 0.5 nM | 2.5 nM | 12.5 nM |
|---|---|---|---|---|
| LOC cells | | | | |
| 76H10 | 3.3 ± 1.5 | 7.3 ± 0.6 | 11.7 ± 1.5 | 16.7 ± 1.5 |
| 71G3 | 3.0 ± 1.0 | 13.7 ± 1.5 | 19.0 ± 2.6 | 22.3 ± 2.1 |
| 71D6 | 3.0 ± 1.0 | 29.0 ± 2.0 | 29.0 ± 2.6 | 32.7 ± 1.5 |
| 71C3 | 3.3 ± 0.6 | 8.7 ± 1.5 | 12.7 ± 2.1 | 15.7 ± 2.1 |
| 71D4 | 3.0 ± 1.0 | 9.0 ± 2.6 | 15.7 ± 1.2 | 18.7 ± 1.5 |
| 71A3 | 3.0 ± 1.7 | 24.0 ± 4.6 | 30.3 ± 3.2 | 31.3 ± 1.5 |
| 71G2 | 3.7 ± 1.5 | 25.3 ± 2.1 | 29.3 ± 3.5 | 31.7 ± 3.5 |
| 76G7 | 2.7 ± 0.6 | 6.7 ± 0.6 | 13.3 ± 4.2 | 16.3 ± 5.7 |
| 71G12 | 3.3 ± 0.6 | 7.0 ± 2.6 | 15.3 ± 5.5 | 16.0 ± 4.6 |
| 74C8 | 3.0 ± 1.0 | 10.3 ± 4.2 | 17.0 ± 4.6 | 18.7 ± 4.9 |
| 72F8 | 3.3 ± 1.5 | 9.0 ± 3.5 | 12.3 ± 2.1 | 16.0 ± 3.0 |
| hHGF | 3.0 ± 1.0 | 18.0 ± 2 | 27.7 ± 2.5 | 20.3 ± 2.1 |
| MLP29 cells | | | | |
| 76H10 | 0.3 ± 0.6 | 10.7 ± 4.0 | 14.3 ± 3.2 | 24.7 ± 6.0 |
| 71G3 | 0.3 ± 0.6 | 24.7 ± 4.5 | 34.3 ± 5.5 | 29.3 ± 8.0 |
| 71D6 | 1.3 ± 1.2 | 32.7 ± 3.5 | 39.0 ± 7.5 | 41.3 ± 8.0 |
| 71C3 | 0.3 ± 0.6 | 11.7 ± 3.5 | 15.7 ± 6.5 | 24.7 ± 6.5 |
| 71D4 | 0.7 ± 1.2 | 16.0 ± 2.6 | 14.7 ± 4.5 | 21.7 ± 5.5 |
| 71A3 | 0.7 ± 0.6 | 30.3 ± 2.1 | 42.0 ± 6.2 | 42.7 ± 8.0 |
| 71G2 | 1.0 ± 1.0 | 34.0 ± 2.6 | 46.3 ± 4.7 | 45.0 ± 7.0 |
| 76G7 | 0.3 ± 0.6 | 14.7 ± 2.1 | 18.7 ± 4.5 | 24.7 ± 6.5 |
| 71G12 | 1.0 ± 1.0 | 14.0 ± 2.6 | 14.7 ± 5.5 | 22.7 ± 6.0 |
| 74C8 | 0.7 ± 0.6 | 17.3 ± 2.5 | 15.3 ± 6.0 | 22.3 ± 9.0 |
| 72F8 | 1.0 ± 1.0 | 12.7 ± 3.1 | 11.7 ± 3.5 | 18.7 ± 2.5 |
| mHGF | 0.7 ± 1.2 | 32.3 ± 4.0 | 43.7 ± 4.2 | 36.0 ± 7.2 |

Example 10: Human-Mouse Equivalent Agonistic Anti-MET Antibodies Offer Ample Opportunity to Modulate MET Activity Based on the biochemical and biological assays described thus far, we made a comprehensive analysis aimed at comparing antibody functions. The performance of the various mAbs measured in the assays conducted is summarized in Table 18. By analysing this table it emerges that human-mouse equivalent agonistic anti-MET antibodies display a wide array of biochemical and biological activities, offering ample opportunity to modulate MET activity in a custom fashion. Depending on the translational or clinical application of choice, antibodies can be selected among those identified that fully or partially compete with HGF, that potently or mildly cause MET activation, that strongly or weekly promote cell invasiveness, or that vigorously or softly antagonize apoptosis. From this perspective, agonistic antibodies are much more versatile and plastic compared to HGF, as they allow for more graduated response to be induced compared to the on-or-off nature of HGF.

From a pharmacological viewpoint, the possibility of eliciting selective biological activities downstream MET can be quite useful. For example, certain applications in the field of oncology benefit of ligands that disassociate the trophic properties of HGF from its pro-invasive activity (Michieli et al., Nat Biotechnol. 20, 488-495, 2002). Other applications in the field of hepatology ideally require factors that protect hepatocytes against apoptosis without promoting cell invasion (Takahara et al., Hepatology, 47, 2010-2025, 2008). In yet other applications in the field of muscular dystrophy, differentiation of myoblasts into myocytes requires shutdown of HGF-induced proliferation on one hand and protection against differentiation-associated apoptosis on the other (Cassano et al., PLoS One 3, e3223, 2008). In all these applications and in other similar cases, one could envision to employ partial agonistic mAbs that displace endogenous HGF on one hand and elicit mild MET activation on the other, thus enhancing certain biological activities of HGF while reducing others.

Conversely, diverse applications in the field of regenerative medicine require potent pro-survival signals and rapid tissue repair in order to prevent irreversible cellular damage or degeneration. For example, this situation is found in the case of sudden liver failure, acute kidney injury, or severe pancreatitis (reviewed by Nakamura et al., J Gastroenterol Hepatol. 26 Suppl 1, 188-202, 2011). In all these applications and in other similar cases, one would prefer to employ full agonistic mAbs that push as potently as possible tissue healing and regeneration. HGF competition does not really play a role in this case because fully agonistic mAbs are as potent—if not more potent—than HGF and can reach pharmacological concentrations logarithms higher than the physiological levels at which the endogenous ligand is found.

In yet other pathological situations that involve non-canonical, less characterized functions of HGF, such as those that involve the immune system (inflammatory diseases, auto-immune disorders, transplantation-related complications), the hematopoietic system (stem cell mobilization, hematopoiesis) and the nervous system (nerve growth, neuronal degeneration), the role of the HGF/MET pathway is still poorly studied. While several lines of experimental evidence suggest that recombinant HGF or HGF gene therapy ameliorate these disorders in preclinical models (reviewed by Nakamura et al., J Gastroenterol Hepatol. 26 Suppl 1, 188-202, 2011), we do not have enough information for determining whether all functions of HGF or only part of them are beneficial. For these therapeutic applications as well, the possibility of finely tuning MET activity with a highly diverse panel of MET-agonistic antibodies is potentially advantageous compared to HGF (without mentioning the numerous pharmacological problems implicit in the use of recombinant HGF as a drug discussed in the Summary of the Invention section).

In conclusion, we suggest that all human-mouse equivalent anti-MET antibodies identified can be potentially useful for therapeutic application, whether fully or partially competing with HGF, and whether fully or partially activating the MET receptor.

TABLE 18

Major biochemical and biological characteristics of human/mouse equivalent anti-MET antibodies. This table summarizes the ability of each mAb to bind to purified MET ECD (ELISA), to recognize native MET on MET-expressing cells (FACS), to compete with HGF for MET binding (HGF competition), to activate MET in receptor auto-phosphorylation assays (MET activation), to promote cell scattering (Scatter assay), to protect cells against drug-induced apoptosis (Survival assay), and to promote branching morphogenesis of epithelial cell spheroids (Branching morphogenesis). For each assay, the score is based on the relative activity of any given mAb with respect to the other antibodies (+, lower 50%; ++, upper 50%). Since all antibodies displayed similar activities in human and mouse systems, only one score per assay is shown.

| | | Biochemical activity | | | Biological activity | | | |
|---|---|---|---|---|---|---|---|---|
| mAb | VH | ELISA | FACS | HGF comp. | MET activ. | Scatt. Assay | Surv. Assay | Bran. morph. |
| 76H10 | 1 | ++ | + | + | + | + | + | + |
| 71G3 | 2 | ++ | ++ | + | ++ | ++ | ++ | ++ |
| 71D6 | 3a | ++ | ++ | ++ | ++ | ++ | ++ | ++ |
| 71C3 | 3b | + | ++ | ++ | ++ | ++ | + | + |
| 71D4 | 3c | + | ++ | ++ | ++ | + | + | + |
| 71A3 | 4 | + | ++ | ++ | ++ | ++ | ++ | ++ |
| 71G2 | 4 | ++ | ++ | ++ | ++ | ++ | ++ | ++ |
| 76G7 | 5 | ++ | + | + | + | + | + | + |
| 71G12 | 6 | ++ | + | + | + | + | + | + |
| 74C8 | 9 | + | ++ | + | + | ++ | + | + |
| 72F8 | 10 | ++ | ++ | + | ++ | + | + | + |

Example 11: Constant Region Swapping does not Alter the Biochemical and Biological Features of Human/Mouse Equivalent Antibodies Since the aim of the invention is to generate and identify agonistic anti-MET antibodies that work equally well in human and mouse systems, we sought to determine whether swapping of the human heavy chain and light chain constant regions with the corresponding mouse constant regions affected the major biochemical and biological activities of a representative panel of antibodies. To this end, we selected 3 representative molecules from the panel of human/mouse equivalent antibodies (71G3, partial competitor of HGF and partial agonist in biological assays; 71D6 and 71G2, full competitors of HGF and full agonists in biological assays). The VH and VL regions of 71G3, 71D6 and 71G2 were mounted onto mouse IgG1/A antibody frames. The sequences of all mouse immunoglobulin variants are available in public databases such as the ImMunoGeneTics information system (www.imgt.org). Fusion with the desired variable regions can be achieved by standard genetic engineering procedures. The full amino acid sequences of the heavy chain and light chains of the generated llama-mouse chimeric antibodies are shown in Table 19.

TABLE 19

Full heavy chain and light chain amino acid sequences of llama-mouse chimeric mAbs binding to both human and mouse MET.

| Clone | Heavy chain (VH-CH1-CH2-CH3) | SEQ ID NO. | Light chain (VL-CL) | SEQ ID NO. |
|---|---|---|---|---|
| 71G3 | QVQLVESGGGLVQPGGSLRVSCAASGFT<br>FSTYYMSWVRQAPGKGLEWVSDIRTDGG<br>TYYADSVKGRFTMSRDNAKNTLYLQMNS<br>LKPEDTALYYCARTRIFPSGYDYWGQGT<br>QVTVSSAKTTPPSVYPLAPGSAAQTNSM<br>VTLGCLVKGYFPEPVTVTWNSGSLSSGV<br>HTFPAVLQSDLYTLSSSVTVPSSPRPSE<br>TVTCNVAHPASSTKVDKKIVPRDCGCKP<br>CICTVPEVSSVFIFPPKPKDVLTITLTP<br>KVTCVVVDISKDDPEVQFSWFVDDVEVH<br>TAQTQPREEQFNSTFRSVSELPIMHQDW<br>LNGKEFKCRVNSAAFPAPIEKTISKTKG<br>RPKAPQVYTIPPPKEQMAKDKVSLTCMI<br>TDFFPEDITVEWQWNGQPAENYKNTQPI<br>MNTNGSYFVYSKLNVQKSNWEAGNTFTC<br>SVLHEGLHNHHTEKSLSHSPGK | 221 | QAVVTQEPSLSVSPGGTVT<br>LTCGLSSGSVTTSNYPGWF<br>QQTPGQAPRTLIYNTNSRH<br>SGVPSRFSGSISGNKAALT<br>IMGAQPEDEADYYCSLYPG<br>STTVFGGGTHLTVLGQPKS<br>SPSVTLFPPSSEELETNKA<br>TLVCTITDFYPGVVTVDWK<br>VDGTPVTQGMetETTQPSK<br>QSNNKYMetASSYLTLTAR<br>AWERHSSYSCQVTHEGHTV<br>EKSLSRADCS | 222 |
| 71D6 | ELQLVESGGGLVQPGGSLRLSCAASGFT<br>FSSYGMSWVRQAPGKGLEWVSAINSYGG<br>STSYADSVKGRFTISRDNAKNTLYLQMN<br>SLKPEDTAVYYCAKEVRADLSRYNDYES<br>YDYWGQGTQVTVSSAKTTPPSVYPLAPG<br>SAAQTNSMVTLGCLVKGYFPEPVTVTWN<br>SGSLSSGVHTFPAVLQSDLYTLSSSVTV<br>PSSPRPSETVTCNVAHPASSTKVDKKIV<br>PRDCGCKPCICTVPEVSSVFIFPPKPKD<br>VLTITLTPKVTCVVVDISKDDPEVQFSW<br>FVDDVEVHTAQTQPREEQFNSTFRSVSE<br>LPIMHQDWLNGKEFKCRVNSAAFPAPIE<br>KTISKTKGRPKAPQVYTIPPPKEQMAKD<br>KVSLTCMITDFFPEDITVEWQWNGQPAE<br>NYKNTQPIMNTNGSYFVYSKLNVQKSNW<br>EAGNTFTCSVLHEGLHNHHTEKSLSHSP<br>GK | 223 | QPVLNQPSALSVTLGQTAK<br>ITCQGGSLGARYAHWYQQK<br>PGQAPVLVIYDDDSRPSGI<br>PERFSGSSSGGTATLTISG<br>AQAEDEGDYYCQSADSSGS<br>VFGGGTHLTVLGQPKSSPS<br>VTLFPPSSEELETNKATLV<br>CTITDFYPGVVTVDWKVDG<br>TPVTQGMetETTQPSKQSN<br>NKYMetASSYLTLTARAWE<br>RHSSYSCQVTHEGHTVEKS<br>LSRADCS | 224 |
| 71G2 | EVQLQESGGGLVQPGGSLRLSCAASGFT<br>FSIYDMSWVRQAPGKGLEWVSTINSDGS<br>STSYVDSVKGRFTISRDNAKNTLYLQMN<br>SLKPEDTAVYYCAKVYGSTWDVGPMGYG<br>MDYWGKGTLVTVSSAKTTPPSVYPLAPG<br>SAAQTNSMVTLGCLVKGYFPEPVTVTWN<br>SGSLSSGVHTFPAVLQSDLYTLSSSVTV<br>PSSPRPSETVTCNVAHPASSTKVDKKIV<br>PRDCGCKPCICTVPEVSSVFIFPPKPKD<br>VLTITLTPKVTCVVVDISKDDPEVQFSW<br>FVDDVEVHTAQTQPREEQFNSTFRSVSE<br>LPIMHQDWLNGKEFKCRVNSAAFPAPIE<br>KTISKTKGRPKAPQVYTIPPPKEQMAKD<br>KVSLTCMITDFFPEDITVEWQWNGQPAE<br>NYKNTQPIMNTNGSYFVYSKLNVQKSNW<br>EAGNTFTCSVLHEGLHNHHTEKSLSHSP<br>GK | 225 | SSALTQPSALSVSLGQTAR<br>ITCQGGSLGSSYAHWYQQK<br>PGQAPVLVIYGDDSRPSGI<br>PERFSGSSSGGTATLTISG<br>AQAEDEDDYYCQSTDSSGN<br>TVEGGGIRLTVLGQPKSSP<br>SVTLFPPSSEELETNKATL<br>VCTITDFYPGVVTVDWKVD<br>GTPVTQGMetETTQPSKQS<br>NNKYMetASSYLTLTARAW<br>ERHSSYSCQVTHEGHTVEK<br>SLSRADCS | 226 |

Production and purification of recombinant immunoglobulins can be obtained by transient transfection in mammalian cells and affinity chromatography, respectively, following well established protocols. Thereafter, we compared the biochemical and biological activities of 71G3, 71D6 and 71G2 in the mouse format with those of the same antibodies in the human format.

We evaluated the ability of the antibodies to bind to purified human or mouse MET ECD by ELISA, to recognize native MET on human or mouse cells by FACS, to induce scattering of human and mouse epithelial cells, and to promote branching morphogenesis in collagen. The results of this analysis, summarized in Table 20, reveal that swapping the human with the mouse constant regions does not substantially affect any of the properties analysed.

TABLE 20

Constant region swapping does not alter the biochemical and biological features of human/mouse equivalent antibodies. Three representative agonistic antibodies (71G3, 71D6 and 71G2) in either mouse or human format were subjected to several in vitro assays aimed at characterizing their major biochemical and biological properties.

| | 71G3 | | 71D6 | | 71G2 | |
|---|---|---|---|---|---|---|
| Assay (measure unit) | Human IgG1/λ | Mouse IgG1/λ | Human IgG1/λ | Mouse IgG1/λ | Human IgG1/λ | Mouse IgG1/λ |
| hMET ELISA ($EC_{50}$, nM) | 0.061 ± 0.024 | 0.067 ± 0.026 | 0.032 ± 0.015 | 0.038 ± 0.014 | 0.109 ± 0.038 | 0.113 ± 0.023 |
| mMET ELISA ($EC_{50}$, nM) | 0.059 ± 0.035 | 0.062 ± 0.028 | 0.036 ± 0.022 | 0.036 ± 0.025 | 0.101 ± 0.029 | 0.109 ± 0.021 |
| A549 FACS ($E_{MAX}$, % CTR) | 110.5 ± 15.3 | 115.7 ± 17.2 | 115.2 ± 9.7 | 121.9 ± 11.4 | 137.0 ± 19.1 | 141.7 ± 12.5 |
| MLP29 FACS ($E_{MAX}$, % CTR) | 112.5 ± 11.3 | 109.7 ± 13.2 | 120.4 ± 14.1 | 118.6 ± 15.8 | 130.7 ± 18.3 | 127.7 ± 12.1 |
| A549 MET act. ($E_{MAX}$, % HGF) | 94.3 ± 9.8 | 90.8 ± 8.9 | 103.7 ± 7.9 | 98.3 ± 9.5 | 105.5 ± 9.6 | 101.5 ± 8.2 |
| MLP29 MET act. ($E_{MAX}$, % HGF) | 96.8 ± 8.8 | 91.9 ± 8.4 | 110.5 ± 8.5 | 103.4 ± 7.9 | 109.7 ± 9.8 | 102.5 ± 4.7 |
| LOC br. m. (branch n.) | 22.3 ± 2.1 | 20.8 ± 3.5 | 32.7 ± 1.5 | 30.4 ± 3.7 | 31.7 ± 3.5 | 29.8 ± 4.1 |
| MLP29 br. m. (branch n.) | 29.3 ± 8.0 | 30.1 ± 7.3 | 41.3 ± 8.0 | 39.5 ± 6.1 | 45.0 ± 7.0 | 41.2 ± 6.3 |

Example 12: Comparison with Prior Art Antibodies: Human-Mouse Cross-Reactivity As discussed in detail in the Background section, a few other studies have already described agonistic anti-MET antibodies that mimic HGF activity, at least partially. At the time of writing, these include: (i) the 3D6 mouse anti-human MET antibody (U.S. Pat. No. 6,099,841); (ii) the 5D5 mouse anti-human MET antibody (U.S. Pat. No. 5,686,292); (iii) the NO-23 mouse anti-human MET antibody (U.S. Pat. No. 7,556,804 B2); (iv) the B7 human naïve anti-human MET antibody (U.S. Patent Application No. 2014/0193431 A1); (v) the DO-24 mouse anti-human MET antibody (Prat et al., Mol Cell Biol. 11, 5954-5962, 1991; Prat et al., J Cell Sci. 111, 237-247, 1998); and (vi) the DN-30 mouse anti-human MET antibody (Prat et al., Mol Cell Biol. 11, 5954-5962, 1991; Prat et al., J Cell Sci. 111, 237-247, 1998).

We obtained all prior art agonistic anti-MET antibodies as follows. The 3D6 hybridoma was purchased from the American Type Culture Collection (Cat. No. ATCC-HB-12093). The 3D6 antibody was purified from the hybridoma conditioned medium by standard affinity chromatography protocols.

The cDNA encoding the variable regions of the 5D5 antibody, the bivalent progenitor of the antagonistic anti-MET antibody Onartuzumab (Merchant et al., Proc Natl Acad Sci USA 110, E2987-2996, 2013), were synthesized based on the VH and VL sequences published in U.S. Pat. No. 7,476,724 B2. The obtained DNA fragments were fused with mouse constant IgG1/A domains and produced as bivalent monoclonal antibodies by standard protein engineering protocols.

The NO-23 antibody was obtained from Prof. Maria Prat, University of Novara, Italy (inventor of NO-23; U.S. Pat. No. 7,556,804 B2). The NO-23 antibody can also be obtained by requesting the corresponding hybridoma to the international depositary authority Interlab Cell Line Collection (ICLC) at the Advanced Biotechnology Center (ABC) in Genova, Italy (Clone No. ICLC 03001).

The cDNA encoding the variable regions of the B7 antibody were synthesized based on the VH and VL sequences published in US Patent Application No. 2014/0193431 A1. The obtained DNA fragments were fused with mouse constant IgG1/A domains and produced as bivalent monoclonal antibodies as described above.

The DO-24 and DN-30 antibodies were obtained from Prof. Maria Prat, University of Novara, Italy (who first identified and characterized DO-24 and DN-30; Prat et al., Mol Cell Biol. 11, 5954-5962, 1991; Prat et al., J Cell Sci. 111, 237-247, 1998). The DO-24 antibody, now discontinued, has been commercially available for years from Upstate Biotechnology. The DN-30 antibody can also be obtained by requesting the corresponding hybridoma to the international depositary authority Interlab Cell Line Collection (ICLC) at the Advanced Biotechnology Center (ABC) in Genoa, Italy (Clone No. ICLC PD 05006).

Because the vast majority of animal models of human diseases employ the mouse as a host, cross-reactivity with the mouse antigen is an essential pre-requisite for an antibody the biological activity of which needs to be validated in pre-clinical systems. Since all antibodies of the prior art were generated in a mouse (except for B7 that was identified using a human naïve phage library), it is unlikely that these molecules display cross-reactivity with mouse MET. Even if a minor cross-reactivity with self-antigens is in principle possible, these interactions have normally a very low affinity.

As detailed in U.S. Pat. No. 6,099,841, the 3D6 antibody does not bind to mouse MET and the inventors had to use ferrets and minks to demonstrate that their antibody has in vivo activity. It is clear that these animal models do not represent ideal systems for modelling human diseases nor their use in preclinical medicine has been established. Furthermore, the inventors do not provide any quantitative data relative to the difference in antibody affinity and activity between human systems and ferret or mink systems.

The 5D5 antibody and its derivatives were explicitly shown not to bind to mouse MET (Merchant et al., Proc Natl Acad Sci USA 110, E2987-2996, 2013). No information is available about its cross-reactivity with other preclinical species.

Likewise, U.S. Patent Application No. 2014/0193431 A1 provides no information relative to cross-reactivity of the B7 antibody with mouse MET or that of other species.

U.S. Pat. No. 7,556,804 B2 claims that the NO-23 antibody cross-reacts with mouse, rat and dog MET, but no quantitative experimental evidence is provided in support of this statement. The inventors use a single saturating dose of NO-23 to immuno-precipitate MET from lysates of mouse, rats, human or dog cells, and then incubate the immuno-precipitated proteins with radioactive $^{32}$P-ATP. After radiolabeling, the incorporated $^{32}$P-ATP is visualized by autoradiography. This method is extremely sensitive and by no mean quantitative; it is not possible to tell to what percentage of cross-reactivity the bands on the gel correspond to.

Similarly, the DO-24 antibody is suggested to cross-react with mouse MET because a DO-24-containing Matrigel pellet promotes blood vessel recruitment when implanted in the abdominal cavity of a mouse (Prat et al., J Cell Sci. 111, 237-247, 1998). However, this could also be due to increased inflammation and no direct evidence that DO-24 interacts with mouse MET is provided. In a different study, a single saturating dose of DO-24 (20 nM) is shown to cause auto-phosphorylation of MET in the rat cardiac muscle cell line H9c2 and in the mouse cardiac muscle cell line HL-5 (Pietronave et al., Am J Physiol Heart Circ Physiol. 298, H1155-65, 2010; FIG. 1). In the same experiment, a much lower dose of recombinant HGF (0.5 nM) is shown to cause MET phosphorylation to a comparable extent. As the authors themselves acknowledge in the Discussion section, these results suggest that DO-24 is dramatically less potent than HGF in these rodent cell lines. Since DO-24 is claimed by the same authors to be a full agonistic mAb that matches HGF activity in human cell models (Prat et al., J Cell Sci. 111, 237-247, 1998), then it should be concluded that DO-24 does not elicit the same efficacy or potency in human and in mouse cells. Furthermore, it should be noted that the experiments shown by Pietronave et al. are not quantitative and are not useful to extract information on the degree of cross-reactivity that occurs between DO-24 and mouse or rat MET, the measurement of which would require a head-to-head dose-response study, like the one that we did (see below). In a third work, a mixture of the DO-24 and DN-30 antibodies is used to immuno-precipitate MET from mouse mesenchymal stem cell lysates (Forte et al., Stem Cells. 24, 23-33, 2006). Both the presence of DN-30 and the assay type (immuno-precipitation from cell lysates) prevent to obtain precise information on the ability of DO-24 to interact with native mouse MET. In conclusion, no experimental evidence whatsoever exists that the DO-24 antibody elicits comparable biological responses in human and in mouse cells.

Finally, the DN-30 antibody was explicitly shown not to interact with mouse MET (Prat et al., J Cell Sci. 111, 237-247, 1998; and suppl. material of Petrelli et al., Proc Natl Acad Sci USA 103, 5090-9095, 2006).

In order to directly determine whether—and to what extent—the prior art agonistic anti-MET antibodies cross-reacted with mouse MET, and to compare them to our human/mouse equivalent anti-MET antibodies, we performed an ELISA assay. Since all prior art antibodies were obtained or engineered with a mouse IgG/A format, we employed the mouse IgG/A version of 71G3, 71D6 and 71G2. Human or mouse MET ECD was immobilized in solid phase (100 ng/well in a 96-well plate) and exposed to increasing concentrations of antibodies (0-40 nM) in solution. Binding was revealed using HRP-conjugated anti-mouse Fc antibodies (Jackson Immuno Research Laboratories). As shown in Table 21, this analysis revealed that, while the prior art antibodies bound to human MET with a $K_D$ ranging from 0.059 nM (B7) to 4.935 nM (3D6), none of them displayed any affinity for mouse MET, even at a concentration as high as 40 nM. Among the antibodies tested, only 71G3, 71D6 and 71G2 bound to both human and mouse MET, and they did so with indistinguishable affinities and capacities. The entire binding profile of all antibodies is shown in FIG. 6.

TABLE 21

Binding affinity and capacity of anti-MET antibodies for human and mouse MET as determined by ELISA. Affinity is expressed as $EC_{50}$ (nMol/L). Capacity is expressed as $E_{MAX}$ (optical density at 450 nm; n.c., not converged). See FIG. 6 for the entire binding profiles.

| | hMET | | mMET | |
|---|---|---|---|---|
| mAb | $EC_{50}$ | $E_{MAX}$ | $EC_{50}$ | $E_{MAX}$ |
| 71G3 | 0.058 | 3.107 | 0.059 | 3.065 |
| 71D6 | 0.042 | 2.688 | 0.044 | 2.941 |
| 71G2 | 0.098 | 2.857 | 0.091 | 2.963 |
| 3D6 | 4.935 | 3.208 | >40.000 | n.c. |
| 5D5 | 0.197 | 3.162 | >40.000 | n.c. |
| B7 | 0.059 | 3.272 | >40.000 | n.c. |
| NO-23 | 0.063 | 3.106 | >40.000 | n.c. |
| DO-24 | 0.761 | 3.321 | >40.000 | n.c. |
| DN-30 | 0.067 | 3.064 | >40.000 | n.c. |

Example 13: Comparison with Prior Art Antibodies: MET Auto-Phosphorylation

In order to compare the agonistic activity of the prior art antibodies with that of human/mouse equivalent anti-MET antibodies, we performed a MET auto-phosphorylation experiment using both human and mouse cells. A549 human lung carcinoma cells and MLP29 mouse liver precursor cells were deprived of serum growth factors for 48 hours and then stimulated with increasing concentrations of antibodies (0-25 nM). After 15 minutes of stimulation, cells were washed twice with ice-cold phosphate buffered saline (PBS) and then lysed as described (Longati et al., Oncogene 9, 49-57, 1994). Phospho-MET levels were determined by ELISA as described (Basilico et al., J Clin Invest. 124, 3172-3186, 2014) using anti-MET antibodies for capture (R&D Systems) and anti-phospho tyrosines for revealing (R&D Systems).

This analysis revealed two major differences between prior art antibodies and the human/mouse equivalent anti-MET antibodies described in the present document. First, consistent with the results obtained in binding experiments, only 71G3, 71D6 and 71G2 could promote MET auto-phosphorylation in both human and mouse cells. The prior art antibodies, including DO-24 and NO-23, induced MET activation in human cells only; no activity on mouse cells could be detected in the system that we analyzed. Second, all prior art antibodies invariably displayed lower agonistic activity compared to 71G3, 71D6 and 71G2. The most agonistic prior art mAbs were 5D5 and B7, which displayed an activity slightly lower than 71G3, 71D6 and 71G2. The least agonistic prior art mAb was 3D6. The other molecules displayed intermediate activity. The results of this analysis are shown in FIG. 7.

Example 14: Comparison with Prior Art Antibodies: Branching Morphogenesis

In order to compare the biological activity of prior art antibodies with that of human/mouse equivalent anti-MET antibodies, we performed a branching morphogenesis assay. This assay recapitulates all the relevant biological activities of HGF including cell proliferation, scattering, differentiation and survival. LOC human kidney epithelial cells and MLP29 mouse liver precursor cells were seeded in a collagen layer as described above and then incubated with increasing concentrations of mAbs or recombinant HGF (human or mouse, both from R&D Systems). Branching morphogenesis was followed over time by microscopy, and colonies were photographed after 5 days. Quantification of branching morphogenesis activity was achieved by counting the number of branched tubules sprouting from each spheroid and is shown in Table 22. Representative images of spheroids are shown in FIG. 8 (LOC cells) and in FIG. 9 (MLP29 cells).

TABLE 22

Branching morphogenesis assay. Cell spheroids preparations of LOC human kidney epithelial cells or MLP29 mouse liver precursor cells were seeded in a collagen layer and then incubated with increasing concentrations (0, 0.04, 0.2, 1, and 5 nM) of mAbs or recombinant human HGF (LOC) or mouse HGF (MLP29). Branching morphogenesis was followed over time by microscopy, and colonies were photographed after 5 days. Branching was quantified by counting the number of branches for each spheroid (primary branches plus secondary branches).

| mAb | 0 nM | 0.04 nM | 0.2 nM | 1 nM | 5 nM |
|---|---|---|---|---|---|
| LOC cells | | | | | |
| 71G3 | 2.7 ± 0.6 | 9.0 ± 1.0 | 13.3 ± 1.5 | 17.7 ± 1.5 | 20.7 ± 1.2 |
| 71D6 | 2.3 ± 0.6 | 18.7 ± 3.2 | 29.3 ± 2.5 | 30.7 ± 2.1 | 30.3 ± 1.2 |
| 71G2 | 2.7 ± 1.5 | 22.3 ± 2.3 | 26.3 ± 2.1 | 30.0 ± 2.0 | 30.3 ± 3.5 |
| 3D6 | 2.3 ± 0.6 | 4.0 ± 1.0 | 7.0 ± 1.0 | 10.7 ± 1.5 | 19.3 ± 4.2 |
| 5D5 | 4.3 ± 1.5 | 15.7 ± 1.5 | 18.3 ± 1.5 | 21.3 ± 2.1 | 27.7 ± 1.5 |
| B7 | 3.3 ± 1.5 | 8.7 ± 1.5 | 13.3 ± 1.5 | 19.7 ± 1.5 | 24.0 ± 2.0 |
| NO-23 | 3.3 ± 1.2 | 6.0 ± 1.0 | 7.0 ± 1.0 | 8.7 ± 1.2 | 8.7 ± 1.5 |
| DO-24 | 3.3 ± 2.1 | 8.0 ± 1.0 | 12.0 ± 1.0 | 12.3 ± 1.2 | 17.7 ± 2.1 |
| DN-30 | 3.3 ± 0.6 | 6.3 ± 1.5 | 8.3 ± 1.5 | 9.7 ± 1.5 | 10.3 ± 1.5 |
| hHGF | 4.7 ± 1.5 | 10.7 ± 1.5 | 16.7 ± 1.5 | 28.3 ± 3.5 | 24.7 ± 7.6 |
| MLP29 cells | | | | | |
| 71G3 | 0.3 ± 0.6 | 19.3 ± 1.5 | 23.7 ± 2.1 | 32.7 ± 2.5 | 28.7 ± 1.2 |
| 71D6 | 0.7 ± 0.6 | 21.0 ± 2.0 | 32.0 ± 1.0 | 42.7 ± 5.5 | 37.0 ± 2.0 |
| 71G2 | 0.0 ± 0.0 | 15.0 ± 1.7 | 36.0 ± 4.6 | 50.7 ± 5.5 | 48.0 ± 3.6 |
| 3D6 | 0.3 ± 0.6 | 0.7 ± 0.6 | 0.7 ± 0.6 | 0.7 ± 0.6 | 0.7 ± 0.6 |
| 5D5 | 1.0 ± 1.0 | 0.7 ± 1.2 | 0.3 ± 0.6 | 1.3 ± 1.5 | 1.0 ± 1.0 |
| B7 | 0.3 ± 0.6 | 0.7 ± 0.6 | 0.3 ± 0.6 | 1.3 ± 1.5 | 0.7 ± 1.2 |
| NO-23 | 0.7 ± 1.2 | 0.3 ± 0.6 | 0.7 ± 0.6 | 1.0 ± 1.0 | 0.7 ± 0.6 |
| DO-24 | 1.0 ± 1.0 | 0.7 ± 1.2 | 0.7 ± 0.6 | 0.7 ± 1.2 | 0.7 ± 1.2 |
| DN-30 | 0.7 ± 0.6 | 0.3 ± 0.6 | 1.0 ± 1.0 | 0.7 ± 0.6 | 0.7 ± 0.6 |
| mHGF | 0.3 ± 0.6 | 26.0 ± 4.4 | 34.0 ± 5.0 | 46.0 ± 2.6 | 37.0 ± 2.0 |

The data presented lead to the following observations. In human cells, 71D6, 71G2 and 5D5 displayed an activity comparable to that of human HGF; 71G3, 3D6, B7 and DO-24 behaved as partial agonists; NO-23 and DN-30 displayed very little agonistic activity. In mouse cells, only 71G3, 71D6 and 71G2 effectively induced the formation of branched tubules; all the other antibodies—consistent with their inability to bind to mouse MET in ELISA—did not induce branching morphogenesis at all.

We conclude that the prior art antibodies, in contrast to human/mouse equivalent anti-MET antibodies, elicit different biological activities in human and mouse systems.

Example 15: Plasma Half-Life of Human/Mouse Equivalent Anti-MET Antibodies

Next, we moved the selected human/mouse equivalent anti-MET antibodies forward to in vivo studies. As a preliminary analysis, we determined their peak and trough levels in mice. To this end, we injected affinity purified 71G3, 71D6 and 71G2 (in their mouse IgG/A format) into 7 week-old female BALB/c mice (Charles River) by i.p. injection. A single bolus of 1 mg/kg or 10 mg/kg was injected and blood samples were taken from the tail vein at 3, 6, 12 and 24 hours post-injection. Blood samples were processed and antibody concentration in plasma was determined by ELISA. Standard 96-well plates were coated with human MET ECD (100 ng/well) as described in Example 1 and then exposed to increasing dilutions of mouse plasma to capture anti-MET antibodies. After repeated washing with PBS, the presence of anti-MET antibodies was revealed using a HRP-conjugated donkey anti-mouse antibody (Jackson Laboratories). To quantify bound antibody, we set up a standard curve of purified 71G3, 71D6 and 71G2 in the same conditions.

The results of this analysis are shown in FIG. 10. The antibody concentrations in plasma were similar for all the antibodies tested and directly proportional to the amount of protein injected. After 24 hours, antibody concentration in plasma was approximately 15 nM for the 1 mg/kg bolus and 250 nM for the 10 mg/kg bolus. Considering that the agonistic activity of these antibodies in the most demanding assay (the branching morphogenesis assay) reaches saturation at a concentration of 5 nM or lower, we can safely conclude that the plasma levels of antibodies obtained by i.p. injection are relevant from a biologic viewpoint with boluses as low as 1 mg/kg.

Furthermore, we also calculated the plasma half-life of injected antibodies. This was achieved by transforming the antibody concentration to natural logarithm (Ln), fitting the data into a line and then calculating the slope of the line. This analysis led to estimate that the half-lives of 71G3, 71D6 and 71G2 are very similar and correspond approximately to 3 days for the 1 mg/kg bolus and 9 days for the 10 mg/kg bolus. This is a significantly higher stability compared to that of recombinant HGF which has been reported to have a half-life of 2.4 minutes in rodents (Ido et al., Hepatol Res. 30, 175-181, 2004). The whole panel of plasma stability data is summarized in Table 23.

These data suggest that human/mouse equivalent anti-MET antibodies could advantageously substitute recombinant HGF in all clinical applications that require systemic administration of HGF.

TABLE 23

Plasma stability of human/mouse equivalent antibodies. A single bolus (1 mg/kg or 10 mg/kg) of affinity purified 71G3, 71D6 and 71G2 was administered to 7 week-old female BALB/c mice by i.p. injection. Blood samples were taken from the tail vein at 3, 6, 12 and 24 hours post-injection, and antibody concentration in plasma was determined by ELISA. Plasma half-life was calculated by linear fitting of the natural logarithm transforms of antibody concentrations.

| | 1 mg/kg bolus | | 10 mg/kg bolus | |
|---|---|---|---|---|
| mAb | Conc. after 24 h (nM) | Plasma half-life (days) | Conc. after 24 h (nM) | Plasma half-life (days) |
| 71G3 | 16.6 ± 1.6 | 2.917 | 251.7 ± 24.0 | 9.025 |
| 71D6 | 15.6 ± 1.6 | 3.040 | 246.9 ± 44.3 | 10.697 |
| 71G2 | 18.1 ± 0.6 | 3.282 | 262.2 ± 17.6 | 9.025 |

Example 16: In Vivo Activity: Protection Against Acute Liver Damage

Hepatocytes express MET and are the principal target of HGF, which promotes their proliferation and protects them against apoptosis (reviewed by Nakamura et al., J Gastroenterol Hepatol. 1, 188-202, 2011). We therefore tested whether human/mouse equivalent agonistic anti-MET antibodies displayed protective activity in mouse models of acute liver failure. To this end, we injected a single dose of $CCl_4$ (0.2 ml of a 10% solution in olive oil; both from Sigma-Aldrich) into the subcutaneous compartment of 7 week-old female BALB/c mice (Charles River). Soon after $CCl_4$ injection, mice were randomized into 4 arms of 6 mice each which received a single bolus of purified 71G3, 71D6, 71G2 or vehicle only (PBS). Antibodies were administered by i.p. injection at a dose of 5 mg/kg. Blood samples were taken at different times post-injection (0, 12, 24 and 48 hours). An additional, fifth control arm contained 6 mice that received no $CCl_4$ or antibody and were sacrificed at the end of the experiment. At autopsy, blood and livers were collected for analysis. Plasma levels of the hepatic markers aspartate transaminase (AST), alanine aminotransferase (ALT) and bilirubin (BIL) were determined by standard clinical biochemistry methods. Livers were embedded in paraffin and processed for histological analysis using standard protocols.

As shown in FIG. 11, $CCl_4$ injection in control mice caused a rapid and dramatic increase in the levels of all three blood parameters analysed, which reached a peak 12-24 hours post-intoxication. In the control arm, $CCl_4$ injection caused AST, ALT and bilirubin levels to rise 286, 761 and 13 times, respectively. In all antibody arms, these increases were significantly reduced (71G3, 53%, 62%, and 46%; 71D6, 37%, 34% and 48%; 71G2, 50%, 39% and 54%, respectively). The most potent antibody in terms of hepatic protection was 71D6.

Histological examination of livers at autopsy revealed that $CCl_4$ caused marked tissue damage around the central vein of each hepatic module, characterized by eosinophilic staining and a large cytoplasm, typical of suffering hepatocytes. Cell-cell interactions appeared loose allowing for infiltration of red blood cells leaking from the damaged vessels. In the antibody-treated arms, these peri-central damaged areas were smaller and displayed less signs of sufferance, as evidenced by a less eosinophilic staining, normal cytoplasm size and decreased blood cell infiltration. Representative images of liver sections stained with hematoxylin and eosin are shown in FIG. 12.

These results suggest that human/mouse equivalent agonistic anti-MET antibodies could be used in the clinic to treat acute disorders of the liver characterized by rapid development of hepatic dysfunction, which typically lead to abnormal liver biochemical values, jaundice, coagulopathy, cerebral edema and encephalopathy. These pathological conditions include—but are not limited to—paracetamol overdose, idiosyncratic reactions to medications (e.g. tetracycline), drug abuse (ecstasy, cocaine), viral infections (hepatitis A, B, E).

Example 17: In Vivo Activity: Protection Against Chronic Liver Damage

We also tested whether human/mouse equivalent agonistic anti-MET antibodies displayed therapeutic effects in a mouse model of chronic liver damage. In fact, HGF is known to have anti-fibrotic activity in the liver (reviewed by Matsumoto and Nakamura, Ciba Found Symp. 212, 198-211; discussion 211-214, 1997). To this end, 7 week-old female BALB/c mice (Charles River) were chronically exposed to $CCl_4$ for several weeks. The first week, mice were injected subcutaneously for two times with 0.1 ml of a 5% solution of $CCl_4$ in olive oil (both from Sigma-Aldrich). The following weeks, the dose of $CCl_4$ was increased (0.1 ml of a 10% solution in olive oil), while the frequency of injection was maintained unchanged (twice a week). Soon after the first injection, mice were randomized into 4 arms of 7 mice each which received treatment with purified 71G3, 71D6, 71G2 or vehicle only (PBS), respectively. Antibodies were administered three times a week by i.p. injection at a dose of 1 mg/kg. An additional, fifth control arm contained 7 mice that received no $CCl_4$ or antibody and served as healthy control. Mice were sacrificed after 6 weeks of chronic $CCl_4$ intoxication. At autopsy, blood and livers were collected for analysis. Plasma levels of the hepatic markers aspartate transaminase (AST) and alanine aminotransferase (ALT) were determined by standard clinical biochemistry methods. Livers were embedded in paraffin and processed for histological analysis using standard protocols.

As shown in FIG. 13, chronic exposure to $CCl_4$ in control mice led to impaired liver function as determined by higher AST and ALT plasma levels. In contrast to the acute model which causes a sharp but transient burst in liver marker levels, chronic $CCl_4$ intoxication induced a more moderate increase of AST and ALT levels, approximately 5 times compared to untreated mice. Remarkably, antibody treatment could completely prevent the increase in AST concentration, actually lowering it below the basal levels. Antibodies could also significantly prevent the burst in ALT levels, although not as spectacularly as observed for AST.

Liver sections were stained by various techniques aimed at detecting fibrotic tissue, including Masson's trichrome, Picro Sirius red and anti-alpha smooth muscle actin ($\alpha$-SMA) antibodies. Staining with hematoxylin and eosin was also performed in order to examine general histology architecture. This analysis revealed that chronic $CCl_4$ treatment caused the formation of a remarkable amount of fibrotic tissues in the inter-lobular space, specifically characterized by positivity to Picro Sirius red and anti-alpha smooth muscle actin ($\alpha$-SMA) antibody staining. The fibrotic tissue formed a sort of 'ribbon' that linked the portal triads, evidencing the hexagonal shape of the hepatic units. Remarkably, liver sections derived from animals who received both $CCl_4$ and agonistic anti-MET antibodies displayed much milder fibrosis in terms of staining intensity, and the fibrotic area appeared confined to the peri-portal space. Representative images of liver sections stained with Picro Sirius red and anti-$\alpha$-SMA antibodies are shown in FIG. 14 and FIG. 15, respectively.

These data suggest that human/mouse equivalent agonistic anti-MET antibodies could be used in the clinic to treat pathological conditions associated with chronic liver damage, characterized by progressive destruction and regeneration of the liver parenchyma and leading to cirrhosis and fibrosis. Agonistic anti-MET antibodies may be used to reduce or prevent fibrosis, leading to restoration of liver architecture and function. They may also be used to suppress inflammation and immune reaction, often aggravating chronic liver diseases.

Example 18: In Vivo Activity: Protection Against Acute Kidney Damage

Kidney epithelial cells express significant levels of MET and are very sensitive to HGF stimulation (reviewed by Mizuno et al. Front Biosci. 13, 7072-7086, 2008). Therefore, we tested whether human/mouse equivalent agonistic anti-MET antibodies displayed protective effects in a mouse model of acute kidney failure. To this end, we induced tubular damage in 7 week-old female BALB/c mice (Charles River) by i.p. injection of a single bolus of $HgCl_2$ (3 mg/kg). Soon after $HgCl_2$ intoxication, mice were randomized into 4 arms which were subjected to treatment with 71G3, 71D6, 71G2 or vehicle only (PBS). Antibodies were administered by i.p. injection every 24 hours at a dose of 10 mg/kg. Each arm comprised 6 mice that were sacrificed 72 hours after $HgCl_2$ injection. At autopsy, blood and kidneys were collected for analysis. Blood urea nitrogen (BUN) and creatinine (CRE) plasma levels were determined by standard clinical biochemistry methods. Kidneys were processed for histological analysis using standard protocols.

As shown in FIG. 16, $HgCl_2$ injection in control mice caused a sharp increase in the levels of BUN and CRE. In the control arm, BUN and CRE increased 6 and 12 times, respectively. In all antibody arms, these increases were significantly reduced (71G3, 52%, and 54%; 71D6, 39% and 30%; 71G2, 45% and 44%, respectively). The most potent antibody in terms of kidney protection was 71D6.

Histological examination of kidneys revealed that $HgCl_2$ caused a widespread tubular damage characterized by proximal tubule dilatation, atrophy and necrosis. The glomerular structures collapsed and detached from the surrounding stroma, substantially incrementing the peri-glomerular space. In the antibody-treated arms, proximal tubule cells were less necrotic and the histological architecture of glomeruli appeared intact. Representative images of kidney sections stained with hematoxylin and eosin are shown in FIG. 17.

We propose that human/mouse equivalent agonistic anti-MET antibodies may be used in the clinic to treat pathological conditions associated with acute kidney failure, which may be caused for example by ischemic or nephrotoxic injury, hypovolemic shock, obstruction of the urinary collection system, atherosclerosis, sepsis, diabetes mellitus, autoimmune diseases, or rhabdomyolysis. Agonistic anti-MET antibodies may be useful to prevent or reverse acute renal failure, protect tubular epithelial cells from apoptosis, accelerate epithelial cell regeneration and restore kidney function.

Example 19: In Vivo Activity: Protection Against Acute Colonic Damage, Reduction of Inflammation and Promotion of Regeneration in a Mouse Model of Ulcerative Colitis It is well established that intestinal epithelial cells express MET and that HGF plays a pivotal role in the homeostasis and regeneration of the gastro-enteric tract (reviewed by Nakamura et al., J Gastroenterol Hepatol. 1, 188-202, 2011). We therefore tested whether human/mouse equivalent agonistic anti-MET antibodies could promote gut protection and regeneration in a mouse model of ulcerative colitis. To this end, we exposed 7 week-old female BALB/c mice (Charles River) to dextran sodium sulphate (DSS) in the drinking water for 10 days. On day 10, DSS treatment was interrupted and mice were put back on normal water. Starting from day 1, mice were randomized into 7 arms of 7 mice each which received treatment with 71G3, 71D6, 71G2 (at a dose of 1 mg/kg or 5 mg/kg) or vehicle only (PBS). Antibodies were administered three times a week by i.p. injection. An additional, eighth control arm contained 7 mice that received no DSS or antibody and served as healthy control. Mice were sacrificed on day 12, i.e. 2 days after DSS administration was interrupted. At autopsy, colons were collected, washed through, and their length was determined using a ruler. Following measurement, colons were embedded in paraffin and processed for histological analysis.

During the whole course of the experiment, mouse weight was monitored on a regular basis, and the clinical symptoms of ulcerative colitis were assessed by determining fecal blood, rectal bleeding and stool consistency. Quantification was achieved using a standard scoring system used in pre-clinical models (Kim et al., J Vis Exp. 60, pii: 3678, 2012): each parameter scored from 0 (absence of the symptom) to 3 (maximal manifestation of the symptom). Scores relative to the single parameters were summed together to give rise to the Disease Activity Index (DAI) ranging from 0 to 9.

As shown in FIG. 18, exposure to DSS in the PBS arm caused a weight loss of up to 25%; the DAI increased to a score of 4 or higher; and the length of the colon was reduced by up to 40%. Remarkably, all antibodies analyzed reversed these effects in a dose-dependent fashion, displaying significant activity already at the lower dose tested. 71D6 was the most potent antibody: after a transient decline, it brought body weight back at normal values, comparable to those observed in the PBS group; it curbed the DAI increase, substantially inhibiting all the clinical symptoms; and it prevented colon shortage, limiting it to negligible variations.

Colon sections were stained with hematoxylin and eosin and examined by microscopy. As shown in FIG. 19, DSS administration caused profound damage to the colonic mucosa. The epithelial layer appeared eroded and infiltrated with lymphocytes. The colonic mucosa was disseminated with cryptic abscess sites and was heavily colonized by foamy macrophages, responsible for tissue destruction. Perivisceral lymph nodes appeared enlarged. The muciparous glands were characterized by atrophy and displayed marked mucinous depletion, which was substituted with inflammatory infiltrate including foamy macrophages, lymphocytes and neutrophils. Several ulcers were visibly invaded by granulocytic or macrophage exudate, leading to the total disappearance of the glandular component. Remarkably, mice treated with both DSS and agonistic anti-MET antibodies displayed much milder symptoms of degeneration and inflammation. Specifically, elements of acute inflammation were absent, including macrophages and granulocytes; the mucosa appeared only marginally injured, displaying sparse glandular distortion and rarefaction; mucin secretion was restored, and erosions and ulcers were completely absent. Although these protective effects were dose-dependent in all antibody groups, they were already evident at 1 mg/kg, indicating that the concentrations of antibodies reached with this dose are very close to saturation (see plasma stability in Example 15). In this model as well, the most effective antibody appeared to be 71D6.

Example 20: In Vivo Activity: Protection Against Acute Colonic Damage, Reduction of Inflammation and Immune Suppression in a Mouse Model of Inflammatory Bowel Disease Prompted by the above results, we also tested whether agonistic anti-MET antibodies displayed a therapeutic effect in a more specific mouse model of inflammatory bowel disease. To this end, we induced acute colon injury in 7 week-old female C57BL/6 mice (Charles River) by intrarectal injection of 2,4,6-trinitrobenzenesulfonic acid (TNBS) dissolved in ethanol. The TNBS/ethanol combination is known to induce colorectal inflammation through both immunological and erosive processes (reviewed by Jones-Hall and Grisham, Pathophysiology 21, 267-288, 2014). TNBS dissolved in 50% ethanol was administered by enema at a dose of 5 mg/mouse. Soon after TNBS administration, mice were randomized into 4 arms of 6 mice each which received treatment with purified 71G3, 71D6, 71G2 or vehicle only (PBS). Antibodies were administered every second day by i.p. injection at a dose of 1 mg/kg. An additional, fifth control arm contained 6 mice that received no TNBS or antibody and served as healthy control. Mouse weight was monitored daily. Mice were sacrificed 5 days after TNBS administration. At autopsy, colons were collected and measured as described above. Following measurement, colons were embedded in paraffin and processed for histological analysis.

As shown in FIG. 20, exposure to TNBS caused a weight loss of approximately 15% and reduced colon length by more than 20%. These effects, although more moderate compared to those caused by DSS, were significantly different from those observed in all antibody arms. In fact, treatment with 71G3, 71D6 and 71G2 inhibited TNBS-induced weight loss and colon shortening almost completely, making the antibody-treated animals hardly distinguishable from the healthy control mice.

Colon sections were stained with hematoxylin and eosin and examined by microscopy. As shown in FIG. 21, TNBS administration caused the onset of the typical signs of lymphocytic colitis, characterized by enlarged peri-visceral lymph nodes, appearance of lymphocytic aggregation in the sub-mucosa and mucosa, and increased lymphocyte infiltration. Several full-depth ulcers were visible, associated with stromal hyper-proliferation and infiltration by lymphocytes and neutrophils. All these pathological processes were strongly inhibited in the agonistic anti-MET antibodies arms, which displayed reduced lymphocytic infiltration and reduced mucosal damage. Even where lymphocytes were present, they were not associated with muciparous depletion or epithelial injury.

These results and the data reported in the previous example indicate that human/mouse equivalent agonistic anti-MET antibodies may be employed in the clinic to treat pathological conditions associated with ulcerative colitis or more in general with an inflammatory bowel disease. Treatment with agonistic anti-MET antibodies may reduce intestinal lesions, promote epithelial cell proliferation and reduce inflammatory cell infiltration, thus improving the clinical course of the disease.

Example 21: In Vivo Activity: Promotion of Glucose Uptake and Cooperation with Insulin in a Mouse Model of Type I Diabetes HGF has been reported to promote insulin-dependent glucose uptake in cultured mouse skeletal muscle cells (Perdomo et al., J Biol Chem. 283, 13700-13706, 2008). We therefore tested whether our agonistic anti-MET antibodies could reduce high blood glucose levels in a mouse model of type I diabetes. To this end, we induced pancreatic β-cell degeneration in 7 week-old female BALB/c mice (Charles River) by i.p. injection of streptozotocin (STZ; Sigma Aldrich). STZ was injected at a dose of 40 mg/kg every day for 5 consecutive days. One week after the last injection, blood glucose levels under fasting conditions were determined using standard glucose strips (GIMA). At this time, STZ-treated mice displayed a mean basal glycemy two times higher compared to untreated mice (240 mg/dL vs. 120 mg/dL). Mice were randomized into 4 arms of 7 mice each based on basal glycemy, which received treatment with purified 71G3, 71D6, 71G2 or vehicle only (PBS), respectively. Antibodies were administered two times a week by i.p. injection at a dose of 1 mg/kg. An additional, fifth control arm contained 7 mice that received no STZ or antibody and served as healthy control. Blood glucose concentration in fasting conditions was monitored over time for 5 weeks. At the end of week 5, we performed a glucose tolerance test (GTT) and an insulin tolerance test (ITT). A GTT consists in administering glucose to a fasting animal by oral gavage and then measuring blood glucose levels at different time points. An ITT consists in administering insulin to a partially fasting animal by i.p or i.v. injection and then measuring blood glucose levels at different time points.

As shown in FIG. 22A, basal blood glucose levels in STZ-treated mice continued to increase for the whole duration of the experiment. This is due to chronic pancreas inflammation, which progressively aggravates organ injury. In contrast, antibody-treated animals displayed steadily decreasing glycemic levels which eventually reached a plateau after the second week of treatment. Antibody administration did not completely normalize glycemy but lowered it by up to 25%, thus bringing it about half way between the levels observed in STZ-treated mice and in control mice. Considering that in this model hyperglycemy is due to the absence of β-cell-derived insulin, we wondered whether lower glucose levels in the antibody arms was due to increased insulin levels. However, ELISA assays on blood samples revealed that this is not the case (not shown). In a GTT, mice receiving antibody treatment—while starting from lower blood glucose levels—failed to display a normal glucose uptake curve (FIG. 22B). In contrast, antibody-treated mice did display a more rapid response to insulin in an ITT (FIG. 22C). Fifteen minutes after insulin injection, glucose blood levels in mice subjected to chronic antibody treatment dropped to approximately 30-40% relative to time zero, which is significantly less than what observed in both STZ-treated mice and control animals (FIG. 22D). These results suggest that agonistic anti-MET antibodies promote glucose uptake in the absence of insulin. They also suggest that agonistic anti-MET antibodies and insulin, when both are present, cooperate in mediating glucose uptake.

This hypothesis was tested in cell-based assays using mouse skeletal muscle cells. C2C12 mouse myoblast cells (obtained from American Tissue Type Collection) were induced to differentiate into myocytes as recommended by the provider and then incubated with human/mouse equivalent agonistic anti-MET antibodies (71G3, 71D6, 71G2). After 24 hours, antibody-treated cells were divided into 3 arms, which were subjected to acute stimulation with 0 nM, 100 nM or 1000 nM human recombinant insulin (Sigma Aldrich) for 1 hour in the presence of the fluorescent glucose analogue 2-(N-(7-Nitrobenz-2-oxa-1,3-diazol-4-yl)Amino)-2-Deoxyglucose (2-NBDG; Life Technologies). 2-NBDG uptake was determined by flow cytometry.

As shown in FIG. 23, 71G3, 71D6 and 71G2 promoted glucose uptake in a dose-dependent fashion. Combination of insulin and agonistic anti-MET antibodies resulted in a co-operative effect and promoted higher glucose uptake compared to both insulin alone and antibodies alone. These data are consistent with the finding that HGF and insulin co-operate in regulating glucose metabolism in cultured cells (Fafalios et al. Nat Med. 17, 1577-1584, 2011), and confirm our hypothesis that agonistic anti-MET antibodies are capable of enhancing both insulin-independent and -dependent glucose uptake.

Example 22: In Vivo Activity: Blood Glucose Level Normalization and Insulin Resistance Overcoming in a Mouse Model of Type II Diabetes Prompted by the observation that human/mouse equivalent agonistic anti-MET antibodies could cooperate with insulin in promoting glucose uptake, we tested their therapeutic potential in a mouse model of type II diabetes. Type II diabetes mellitus is characterized by high blood glucose levels, hyperinsulinemia, and insulin resistance. One of the most characterized mouse models of type II diabetes is represented by db/db mice, a C57BLKS/J strain bearing a point mutation in the leptin receptor gene lepr. This mutation results in loss of satiety sense and thus in unlimited feeding, leading to obesity and the above mentioned type II diabetes clinical hallmarks (reviewed by Wang et al. Curr Diabetes Rev. 10, 131-145, 2014).

Female db/db mice were obtained from Charles River (JAX™ Mice Strain BKS.Cg-Dock$^{7m}$+/+Lepr$^{db}$J) at the age of 7 weeks. One week later, animals were randomized into 4 arms of 5 mice each, which received treatment with purified 71G3, 71D6, 71G2 or vehicle only (PBS), respectively. Antibodies were administered two times a week by i.p. injection at a dose of 1 mg/kg. Blood glucose concentration in fasting conditions was monitored every 14 days for 8 weeks. After 7 weeks of treatment, i.e. when mice were 15 weeks old, a glucose tolerance test (GTT) and an insulin tolerance test (ITT) were performed.

As shown in FIG. 24, the mean basal blood glucose concentration in the PBS arm at the time of randomization was approximately 230 mg/dL, which definitely corresponds to diabetic levels.

These values tended to increase over time and at the end of the experiment, i.e. 8 weeks later, the mean blood glucose concentration in the PBS arm was approximately 330 mg/dL. In contrast, in the arms receiving antibody treatment, basal glycemy in fasting conditions decreased constantly over time. At the end of the experiment, the mean blood glucose concentration in the 71G3, 71D6 and 71G2 arms was 173 mg/dL, 138 mg/dL and 165 mg/dL, respectively.

After 7 weeks of treatment, i.e. when mice were 15 weeks old, we tested their acute response to glucose and insulin challenge. It should be kept in mind that these mice, in contrast to mice treated with STZ (see example 21), are hyperinsulinemic and display high blood glucose levels because they are insulin-resistant. In fact, when challenged with glucose in a GTT, mice of the PBS arm failed to display a normal glucose uptake profile. All mice showed a sharp increase in glycemy that remained elevated for the whole duration of the test. Symmetrically, when subjected to an ITT, the same mice showed a paradoxical response to insulin, displaying a slight and transient increase in glucose levels. This paradoxical response is a hallmark of insulin resistance, at least in pre-clinical models.

Mice of the antibody arms, while starting from lower basal levels, also did not display a normal glucose uptake profile in a GTT, thus suggesting that agonistic anti-MET antibodies are unable to neutralize an acute burst in blood glucose levels. However, remarkably, antibody treatment did dramatically improve response to insulin in an ITT, reversing the paradoxical effect observed in the PBS arm and making the ITT profile look more similar to that displayed by non-diabetic mice (C57BLKS/J; Charles River). We conclude that long-term treatment with agonistic anti-MET antibodies ameliorates type II diabetes in db/db mice and partially overcomes insulin resistance.

Based on these results and those presented in the previous example, we suggest that human/mouse equivalent agonistic anti-MET antibodies may be used in the clinic to treat pathological conditions associated with high blood glucose levels. These may include type I diabetes mellitus, type II diabetes mellitus, or other diabetes-like pathologies that are characterized by high glucose and/or insulin resistance (e.g. metabolic syndrome).

Example 23: In Vivo Activity: Fatty Liver Amelioration in a Mouse Model of Non-Alcoholic Steatohepatitis Targeted genetic deletion of MET in the liver has been shown to lead to the development of severe non-alcoholic steatohepatitis (NASH) in mice (Kroy et al. J Hepatol. 61, 883-890, 2014). In an independent study (Kosone et al., Am J Physiol Gastrointest Liver Physiol. 293, G204-210, 2007), HGF ameliorated high fat diet-induced fatty liver in mice by activating microsomal triglyceride transfer protein (MTP) and apolipoprotein B (ApoB), thus minimizing fatty acid storage.

Hyperinsulinemic db/db mice are also widely used as a model of NASH and, more in general, of fatty liver diseases. On a normal diet, these mice accumulate a remarkable amount of lipids in their hepatocytes, leading to liver steatosis, fibrosis and chronic liver failure. This condition can be further aggravated by putting mice on a high fat diet (reviewed by Anstee and Goldin, Int J Exp Pathol. 87, 1-16, 2006).

Prompted by the above observations and considerations, we tested whether human/mouse equivalent agonistic anti-MET antibodies could ameliorate moderate hepatic steatosis in db/db mice kept on a normal diet. To this end, we obtained female db/db mice as described above. When animals were 8 weeks old, they were randomized into 4 arms of 6 mice each, which received treatment with purified 71G3, 71D6, 71G2 or vehicle only (PBS), respectively. Antibodies were administered two times a week by i.p. injection at a dose of 1 mg/kg. After 8 weeks of treatment, mice were sacrificed and subjected to autopsy. Livers were extracted, embedded in paraffin and processed for histological examination. Blood was collected for analysis of hepatic function markers.

Liver sections were stained with hematoxylin and eosin or with Picro Sirius red to highlight fibrosis. As shown in FIG. 25, livers from the PBS arm displayed a remarkable steatosis, typically concentrated around the central veins. Hepatocytes appeared dramatically enlarged and full of lipids. Fatty hepatocytes were mixed together with normal hepatocytes, and steatosis occupied up to 60% of the peri-central space. In contrast, livers from antibody-treated animals contained remarkably less fatty cells and appeared overall quite normal. As shown in FIG. 26, Picro Sirius red staining evidenced a moderate peri-portal fibrosis in the PBS group, characterized by thickening of the stromal layer around the hepatic triads (portal vein, hepatic artery and bile duct), sometimes expanding into the interlobular space. Remarkably, liver sections from all the antibody arms displayed a much lower fibrosis—if any. Analysis of the liver function markers AST and ALT in the plasma confirmed these observations (see FIG. 27). In fact, animals treated with agonistic anti-MET antibodies displayed exceptionally low plasma concentrations of AST and ALT, about 2.5 times lower than the PBS group and 2 times lower than the mean AST and ALT levels in normal mice.

These data suggest that human/mouse equivalent agonistic anti-MET antibodies could be used in the clinic to treat NASH or other pathological conditions associated with fatty liver. Agonistic anti-MET antibodies may be used to inhibit lipid accumulation in the hepatocytes, preventing or reversing hepatosteatosis, and suppressing the vicious cycle that occurs between fatty acid accumulation and macrophage infiltration. Chronic inflammation invariably leads to deposition of extracellular matrix. Therefore, agonistic anti-MET antibodies can also be employed to reduce steatosis-associated fibrosis.

Example 24: In Vivo Activity: Wound Healing in Diabetic Mice

A clinically relevant complication of diabetes is represented by increased ulceration and impaired healing of wounds. Since HGF has been implicated in wound healing (Nakamura et al., J Gastroenterol Hepatol. 1, 188-202, 2011), we sought to determine whether human/mouse equivalent anti-MET antibodies could promote the healing of wounds in a diabetic background. To this end, we obtained db/db diabetic mice as described above. At the age of 8 weeks, we subjected animals to anaesthesia and then cut a 0.8 cm-wide circular wound in the right posterior flank using a circular punch blade for skin biopsies (GIMA). The entire epidermal layer was removed. The day after surgery, mice were randomized into 4 arms that received treatment with purified 71G3, 71D6 and 71G2 or vehicle only (PBS). Antibodies were delivered every second day by i.p injection at a dose of 5 mg/kg. Wound diameter was measured every day using a caliper.

As shown in FIG. 28, antibody treatment significantly accelerated wound closure and re-epithelization. While the control arm repaired the experimental wound at an average rate of 5% per day, this value increased to 8% in the 71G3 arm, to 12% in the 71D6 arm, and to 11% in the 71G2 arm.

We suggest that human/mouse equivalent agonistic anti-MET antibodies could be used in the clinic to treat diabetes-associated ulcers and wounds that typically display impaired healing. Diabetes-associated sores represent an unmet medical need. In the United States, diabetes is the leading cause of non-traumatic lower extremity amputations. Agonistic anti-MET antibodies may be used to accelerate healing, improve re-epithelization and promote vascularization of high blood glucose-induced sores.

Example 25: Cross-Reactivity with *Rattus norvegicus* and *Macaca fascicularis* MET Since the vast majority of animal models of human diseases employ the mouse as a host, cross-reactivity with the mouse antigen is a pre-requisite for an antibody that needs to be validated in pre-clinical systems. This was the rationale that prompted us to identify human-mouse equivalent anti-MET antibodies. However, some pre-clinical procedures are conducted preferably in larger rodents or in primates (e.g. organ transplantation and other experimental practices requiring complex surgical interventions). Furthermore, pharmacodynamics and pharmacokinetics studies are preferably conducted in higher vertebrates, typically rats and monkeys. Finally and most importantly, toxicological assessment of therapeutic antibodies are ideally performed in monkeys, or alternatively—if this is not possible—in two different species of rodents. Therefore, cross-reactivity with rat and monkey is also ideally desired.

To this end, we investigated whether our human/mouse equivalent anti-MET antibodies cross-reacted with MET from other species, including rat (*Rattus norvegicus*) and cynomolgus monkey (*Macaca fascicularis*). Rat MET ECD (NCBI #NP_113705.1; aa 1-931) and monkey MET ECD (NCBI #XP_005550635.2; aa 1-948) were obtained by standard protein engineering techniques. Human and mouse MET ECD were used as controls. A restricted panel of antibodies representative of both SEMA binders (71D6, 71C3, 71D4, 71A3, 71G2) and PSI binders (76H10, 71G3) was selected. The 5D5 prior art antibody was used as control. MET ECD proteins were immobilized in solid phase (100 ng/well in a 96-well plate) and exposed to increasing concentrations (0-40 nM) of antibodies (with human constant regions) in solution. Binding was revealed using HRP-conjugated anti-human Fc antibodies (Jackson Immuno Research Laboratories). As shown in FIG. 29, all human/mouse equivalent antibodies tested bound to human, mouse, rat and simian MET with similar affinity and capacity, while 5D5 bound to human and simian MET only. We conclude that the 71D6, 71C3, 71D4, 71A3, 71G2, 76H10 and 71G3 antibodies bind with similar affinity and capacity to human MET, mouse MET, rat MET and simian MET, at least as determined by ELISA.

Example 26: Fine Epitope Mapping

In order to finely map the epitopes of MET recognized by human/mouse equivalent anti-MET antibodies we pursued the following strategy. We reasoned that, if an antibody generated in llamas and directed against human MET cross-reacts with mouse MET, then this antibody probably recognizes a residue (or several residues) that is (or are) conserved between *H. sapiens* and *M. musculus* but not among *H. sapiens, M. musculus* and *L. glama*. The same reasoning can be extended to *R. norvegicus* and *M. fascicularis.*

To investigate along this line, we aligned and compared the amino acid sequences of human (UniProtKB #P08581; aa 1-932), mouse (UniProtKB #P16056.1; aa 1-931), rat (NCBI #NP_113705.1; aa 1-931), cynomolgus monkey (NCBI #XP 005550635.2; aa 1-948) and llama MET (GenBank #KF042853.1; aa 1-931) among each other (FIG. 30). With reference to Table 12, we concentrated our attention within the regions of MET responsible for binding to the 71D6, 71C3, 71D4, 71A3 and 71G2 antibodies (aa 314-372 of human MET) and to the 76H10 and 71G3 antibodies (aa 546-562 of human MET). Within the former region of human MET (aa 314-372) there are five residues that are conserved in human and mouse MET but not in llama MET (Ala 327, Ser 336, Phe 343, Ile 367, Asp 372). These amino acids are indicated with a black box and the progressive numbers 1-5 in FIG. 30. Of these, four residues are also conserved in rat and cynomolgus monkey MET (Ala 327, Ser 336, Ile 367, Asp 372). Within the latter region of human MET (aa 546-562) there are three residues that are conserved in human and mouse MET but not in llama MET (Arg 547, Ser 553, Thr 555). These amino acids are indicated with a black box and the progressive numbers 6-8 in FIG. 30. Of these, two residues are also conserved in rat and cynomolgus monkey MET (Ser 553 and Thr 555).

Using human MET as a template, we mutagenized each of these residues in different permutations, generating a series of MET mutants that are fully human except for specific residues, which are llama. A schematic representation of the mutants is shown in FIG. 31. Next, we tested the affinity of selected SEMA-binding mAbs (71D6, 71C3, 71D4, 71A3, 71G2) and PSI-binding mAbs (76H10 and 71G3) for these MET mutants by ELISA. To this end, the various MET proteins were immobilized in solid phase (100 ng/well in a 96-well plate) and then exposed to increasing concentrations of antibodies (0-50 nM) solution. As the antibodies used were in their human constant region format, binding was revealed using HRP-conjugated anti-human Fc secondary antibody (Jackson Immuno Research Laboratories). Wild-type human MET was used as positive control. The results of this analysis are presented in Table 24.

TABLE 24

The epitopes of MET responsible for agonistic antibody binding represent residues conserved among *H. sapiens*, *M. musculus*, *R. norvegicus*, *M. fascicularis* but not among the same species and *L. glama*. The relevance of residues conserved among human, mouse, rat, cynomolgus monkey but not llama MET for binding to agonistic mAbs was tested by ELISA. Wild-type (WT) or mutant (MT) human MET ECD was immobilized in solid phase and exposed to increasing concentrations of mAbs in solution. Binding was revealed using anti-human Fc secondary antibodies. All binding values were normalized to the WT protein and are expressed as % binding ($E_{MAX}$) compared to WT MET. Each mutant (A-L) contained at least 2 of the mutations (1-8) showed in FIG. 31.

| | | mAb binding (% WT MET ECD) | | | | | | |
|---|---|---|---|---|---|---|---|---|
| | | SEMA BINDERS | | | | | PSI BINDERS | |
| MT | MUTATIONS | 71D6 | 71C3 | 71D4 | 71A3 | 71G2 | 76H10 | 71G3 |
| WT | — | 100.0 | 100.0 | 100.0 | 100.0 | 100.0 | — | — |
| A | 1, 2, 3 | 103.3 | 99.8 | 114.5 | 116.8 | 92.1 | — | — |
| B | 4, 5 | 0.0 | 0.0 | 0.0 | 0.0 | 0.0 | — | — |
| C | 1, 2, 3, 4, 5 | 0.0 | 0.0 | 0.0 | 0.0 | 0.0 | — | — |
| D | 1, 2 | 128.0 | 101.8 | 119.6 | 127.9 | 113.5 | — | — |
| E | 2, 3, 4 | 43.6 | 59.6 | 57.2 | 65.4 | 41.4 | — | — |
| F | 2, 4, 5 | 0.0 | 0.0 | 0.0 | 0.0 | 0.0 | — | — |
| G | 3, 4, 5 | 0.0 | 0.0 | 0.0 | 0.0 | 0.0 | — | — |
| H | 2, 4 | 38.6 | 61.6 | 58.7 | 76.7 | 40.2 | — | — |
| I | 6, 7, 8 | — | — | — | — | — | 100.0 | 100.0 |
| J | 6, 7 | — | — | — | — | — | 89.0 | 91.2 |
| K | 6, 8 | — | — | — | — | — | 0.0 | 0.0 |
| L | 7, 8 | — | — | — | — | — | 0.0 | 0.0 |

The results presented above provide a definite and clear picture of the residues relevant for binding to our agonistic antibodies.

All the SEMA binders tested (71D6, 71C3, 71D4, 71A3, 71G2) appear to bind to the same epitope that contains 2 key amino acids conserved in human, mouse, cynomolgus and rat MET but not in llama MET lying within blade 5 of the SEMA β-propeller: Ile 367 and Asp 372. In fact, mutation of Ala 327, Ser 336 or Phe 343 did not affect binding at all; mutation of Ile 367 partially impaired binding; mutation of Ile 367 and Asp 372 completely abrogated binding. We conclude that both Ile 367 and Asp 372 of human MET are crucial for binding to the SEMA-directed antibodies tested. These two residues are indicated with an "S" (for SEMA) in FIG. 30.

Also the PSI binders tested (76H10, 71G3) appear to bind to the same epitope. In contrast to the SEMA epitope, however, the PSI epitope contains only one key amino acid also conserved in human, mouse, cynomolgus and rat MET but not in llama MET: Thr 555. In fact, mutation of Arg 547 or Ser 553 did not affect binding at all, while mutation of Thr 555 completely abrogated it. We conclude that Thr 555 represents the crucial determinant for binding to the PSI-directed antibodies tested. This residue is indicated with a "P" (for PSI) in FIG. 30.

Example 27: Uniqueness of Human/Mouse Equivalent Agonistic Antibodies

The fine epitope mapping results presented in Example 26 provide a molecularly detailed demonstration that the agonistic antibodies presented by this invention possess unique features not shared by any of the prior art molecules. This uniqueness is best understood by performing the following analysis.

For most of the prior art antibodies discussed in Examples 12-14 there is no information available on the precise epitopes that they recognize on MET. However, we know that these epitopes must be different than the ones recognized by our antibodies because none of the prior art molecules cross-reacts with mouse MET. An illuminating example of this diversity is provided by 5D5/Onartuzumab, the only prior art anti-MET antibody annotated with detailed molecular information on its interaction with MET. 5D5/Onartuzumab recognizes 4 different residues that lie within blade 5 of the SEMA β-propeller, very close to the amino acids responsible for interacting with our SEMA-binding antibodies (Merchant et al., Proc Natl Acad Sci USA 110, E2987-2996, 2013). These residues, indicated with an "0" (for Onartuzumab) in FIG. 30, correspond to Gln 328, Arg 331, Leu 337 and Asn 338.

It is interesting to note that none of these residues is conserved between *H. sapiens* and *M. musculus*. This is fully consistent with the notion that 5D5/Onartuzumab was generated using a mouse as host, and explains why it does not cross-react with mouse MET (Merchant et al., vedi supra, and our data presented in FIG. 6 and FIG. 29). Furthermore, none of these residues is conserved either between *H. sapiens* and *R. norvegicus*, but all of them are conserved between *H. sapiens* and *M. fascicularis*. This explains why 5D5/Onartuzumab does not bind to rat MET but it does bind to cynomolgus monkey MET (FIG. 29).

In contrast to 5D5/Onartuzumab and to all other prior art molecules discussed here, our human/mouse equivalent antibodies were generated using a llama as host and were explicitly screened for their ability to cross-react with both human and mouse MET. Since most of the few amino acids that are conserved between *H. sapiens* and *M. musculus* but not among *H. sapiens, M. musculus* and *L. glama* (indicated in a black box in FIG. 30) are also conserved in *R. norvegicus* and *M. fascicularis*, chance determined that the selected antibodies are also cross-reactive with rat and monkey.

In conclusion, both the immunization strategy and the screening design make the antibodies of this invention unique. On one hand, the species used for immunization (*L. glama*) is sufficiently distant from *H. sapiens, M. musculus, R. norvegicus* and *M. fascicularis* to guarantee the existence of enough mismatches among the amino acid sequences of llama MET compared to MET from the other species (see FIG. 30). These mismatches are crucial, because an immunized host cannot raise antibodies against an epitope that it recognizes as 'self'. On the other hand, the human/mouse double screening protocol forces the selection of those antibodies that recognize epitopes conserved between these two species. This step is also essential because without two-species panning one would simply select the antibodies that are most represented or display higher affinity, but are not necessarily cross-reactive. The introduction of both these criteria (the fifth species and the 'double dipping' protocol) allowed us to identify antibodies with new, unique features.

REFERENCES

Anstee Q M and Goldin R D, Int J Exp Pathol. 87, 1-16, 2006

Basilico C et al, J Biol. Chem. 283:21267-21227, 2008

Basilico C et al., J Clin Invest. 124, 3172-3186, 2014

Cassano M et al., PLoS One 3, e3223, 2008

Chomczynski P et al., Anal. Biochem. 162:156-159, 1987

Daley L P et al., Clin. Vaccine Immunol. 12, 2005 de Haard H et al., J Biol Chem. 274:18218-18230, 1999

De Haard H et al., J. Bact. 187:4531-4541, 2005
Fafalios A et al. Nat Med. 17, 1577-1584, 2011
Forte G et al., Stem Cells. 24, 23-33, 2006
Hultberg A et al., Cancer Res. 75, 3373-3383, 2015
Ido A et al., Hepatol Res. 30, 175-181, 2004
Jones-Hall Y L and Grisham M B, Pathophysiology 21, 267-288, 2014
Kim J J et al., J Vis Exp. 60, pii: 3678, 2012
Kosone T et al., Am J Physiol Gastrointest Liver Physiol. 293, G204-210, 2007
Kroy D C et al. J Hepatol. 61, 883-890, 2014
Longati P et al., Oncogene 9, 49-57, 1994
Matsumoto K and Nakamura T, Ciba Found Symp. 212, 198-214, 1997
Medico E et al., Mol Biol Cell 7, 495-504, 1996
Merchant Metal., Proc Natl Acad Sci USA 110, E2987-2996, 2013
Michieli P et al. Nat Biotechnol. 20, 488-495, 2002
Mizuno S et al. Front Biosci. 13, 7072-7086, 2008
Nakamura T et al., J Gastroenterol Hepatol. 26 Suppl 1, 188-202, 2011
Perdomo G et al., J Biol Chem. 283, 13700-13706, 2008
Petrelli A et al., Proc Natl Acad Sci USA 103, 5090-9095, 2006
Pietronave S et al., Am J Physiol Heart Circ Physiol. 298, H1155-65, 2010
Prat M et al., Mol Cell Biol. 11, 5954-5962, 1991
Prat M et al., J Cell Sci. 111, 237-247, 1998
Rosário M and Birchmeier W, Trends Cell Biol. 13, 328-335, 2003
Stamos J et al., EMBO J. 23, 2325-2335, 2004
Takahara et al., Hepatology, 47, 2010-2025, 2008
Wang B et al. Curr Diabetes Rev. 10, 131-145, 2014

The invention claimed is:

1. An antibody or antigen binding fragment which comprises:

a heavy chain variable domain comprising H-CDR1, H-CDR2 and H-CDR3, and a light chain variable domain comprising L-CDR1, L-CDR2 and L-CDR3, wherein:

H-CDR1 comprises the amino acid sequence shown as SEQ ID NO:30,

H-CDR2 comprises the amino acid sequence shown as SEQ ID NO:32,

H-CDR3 comprises the amino acid sequence shown as SEQ ID NO:34,

L-CDR1 comprises the amino acid sequence shown as SEQ ID NO: 107,

L-CDR2 comprises the amino acid sequence shown as SEQ ID NO: 109, and

L-CDR3 comprises the amino acid sequence shown as SEQ ID NO: 111; and wherein the antibody or antigen binding fragment binds human MET protein comprising the amino acid sequence of SEQ ID NO: 239.

2. The antibody or antigen binding fragment according to claim 1, wherein the heavy chain variable domain comprises the amino acid sequence of SEQ ID NO: 163, or a sequence at least 90%, 95%, 97% or 99% identical thereto, and the light chain variable domain comprises the amino acid sequence of SEQ ID NO: 164, or a sequence at least 90%, 95%, 97% or 99% identical thereto.

3. A pharmaceutical composition comprising an antibody or antigen binding fragment according to claim 1 and at least one pharmaceutically acceptable carrier or excipient.

* * * * *